US012516316B2

(12) United States Patent
Zhu et al.

(10) Patent No.: US 12,516,316 B2
(45) Date of Patent: Jan. 6, 2026

(54) HIGH FIDELITY RESTRICTION ENDONUCLEASES

(71) Applicant: New England Biolabs, Inc., Ipswich, MA (US)

(72) Inventors: Zhenyu Zhu, Beverly, MA (US); Aine Quimby, Newton, NH (US); Shuang-Yong Xu, Lexington, MA (US); Shengxi Guan, Stoneham, MA (US); Hua Wei, Ipswich, MA (US); Penghua Zhang, Lexington, MA (US); Dapeng Sun, Arlington, MA (US); Siu-Hong Chan, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 18/750,621

(22) Filed: Jun. 21, 2024

(65) Prior Publication Data

US 2024/0352447 A1 Oct. 24, 2024

Related U.S. Application Data

(62) Division of application No. 17/227,799, filed on Apr. 12, 2021, now Pat. No. 12,054,707, which is a division of application No. 16/567,332, filed on Sep. 11, 2019, now abandoned, which is a division of application No. 15/882,603, filed on Jan. 29, 2018, now Pat. No. 10,450,559, which is a division of application No. 14/972,844, filed on Dec. 17, 2015, now abandoned, which is a division of application No. 13/736,406, filed on Jan. 8, 2013, now Pat. No. 9,249,396, which is a division of application No. 12/172,963, filed on Jul. 14, 2008, now Pat. No. 8,372,619, said application No. 14/972,844 is a division of application No. 12/172,963, filed on Jul. 14, 2008, now Pat. No. 8,372,619.

(60) Provisional application No. 60/959,203, filed on Jul. 12, 2007.

(51) Int. Cl.

| | |
|---|---|
| ***C12N 15/10*** | (2006.01) |
| ***C12N 9/16*** | (2006.01) |
| ***C12N 9/22*** | (2006.01) |

(52) U.S. Cl.

CPC .......... *C12N 15/1058* (2013.01); *C12N 9/16* (2013.01); *C12N 9/22* (2013.01); *C12N 15/1034* (2013.01); *C12N 15/1086* (2013.01)

(58) Field of Classification Search

CPC ........ C12N 15/1058; C12N 9/16; C12N 9/22; C12N 15/1034; C12N 15/1086; C12Q 1/44

See application file for complete search history.

(56) References Cited

U.S. PATENT DOCUMENTS

| | | | |
|---|---|---|---|
| 5,663,067 | A | 9/1997 | Xu et al. |
| 6,723,546 | B2 | 4/2004 | Zhu et al. |
| 8,372,619 | B2 | 2/2013 | Zhu et al. |
| 2005/0158834 | A1 | 7/2005 | Xu et al. |
| 2009/0029376 | A1 | 1/2009 | Zhu et al. |

FOREIGN PATENT DOCUMENTS

| | | | | |
|---|---|---|---|---|
| WO | WO 2007/097778 A2 | 8/2007 | | |
| WO | WO-2009009797 A2 * | 1/2009 | ......... | C12N 15/1034 |

OTHER PUBLICATIONS

Witkowski et al. (Biochemistry 38:11643-11650, 1999) (Year: 1999).*
Tang et al. (Phil Trans R Soc B 368:20120318, 1-10, 2013) (Year: 2013).*
Seffernick et al. (J. Bacteriol. 183(8):2405-2410, 2001) (Year: 2001).*
Sadowski et al. (Current Opinion in Structural Biology 19:357-362, 2009) (Year: 2009).*
McKane et al Genetics 139 35-43 1993.
Danna et al PNAS 68 2913-2917 1971.
Nasri et al NAR 14 811-821 1986.
New England Biolabs Catalog and Technical Reference Oct. 2009.
Velculescu et al Science 270 484-487 1995.
Roberts et al NAR 31 1805-1812 2003.
Heitman Genet Eng 15 57-108 1993.
Roberts PNAS 102 5905-5908 2005.
Raleigh et al Bac Genomes Phys Struct Analysis 78-92 1998.
Roberts et al NAR 33 D230-232 2005.
Kelly et al JMB 51 393-409 1970.
Polisky et al PNAS 72 3310-3314 1975.
Walker et al PNAS 89 392-396 1992.
Arber Science 205 361-365 1979.
Carlson et al Mol Microbiol 27 671-676 1998.
Zhu et al J. Mol. Biol 337 573-583, 2004.
Genbank Accession No. AAR96018.1.
Branden et al Introduction to Protein Structure, 247, 1991.

(Continued)

*Primary Examiner* — Manjunath N Rao
*Assistant Examiner* — Erica Nicole Jones-Foster
(74) *Attorney, Agent, or Firm* — New England Biolabs, Inc

(57) ABSTRACT

Compositions and methods are provided for enzymes with altered properties that involve a systematic approach to mutagenesis and a screening assay that permits selection of the desired proteins. Embodiments of the method are particularly suited for modifying specific properties of restriction endonucleases such as star activity. The compositions includes restriction endonucleases with reduced star activity as defined by an overall fidelity index improvement factor.

4 Claims, 49 Drawing Sheets

Specification includes a Sequence Listing.

(56) References Cited

OTHER PUBLICATIONS

Sadowski et al Current Opinion in Structural Biology 19 357-362 2009.
Seffernick et al Journal of Bacteriology 183 8 2405-2410 2001.
Tang et al Advanced Materials Research 602 1309-1312 2012.
Witkowski et al Biochemistry 38 11643-11650 1999.

* cited by examiner

BamHI(E86P)

1 HOUR

BamHI(E86P)

14 HOURS

BamHI-HF(E163A/E167T)

NEB2

BamHI-HF(E163A/E167T)

NEB1

COMPARISON OF
BamHI-HF AND WT BamHI

COMPARISON OF
BamHI-HF AND WT BamHI

EcoRI

K62E IN NEB4

EcoRI

K62A IN NEB4

EcoRI

WT IN EcoRI BUFFER

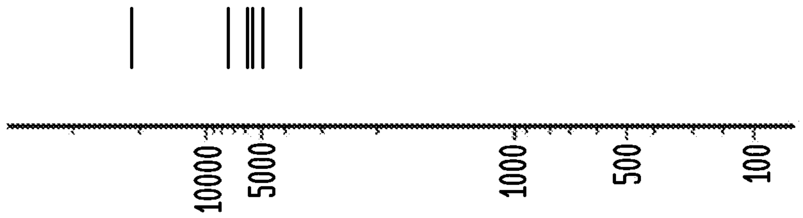
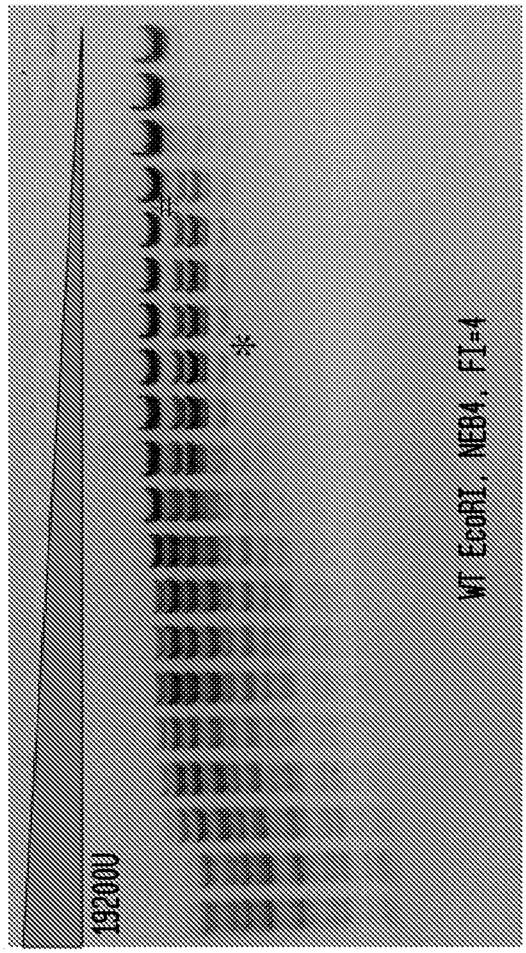
FIG. 8A
COMPARISON OF
EcoRI-HF AND WT EcoRI
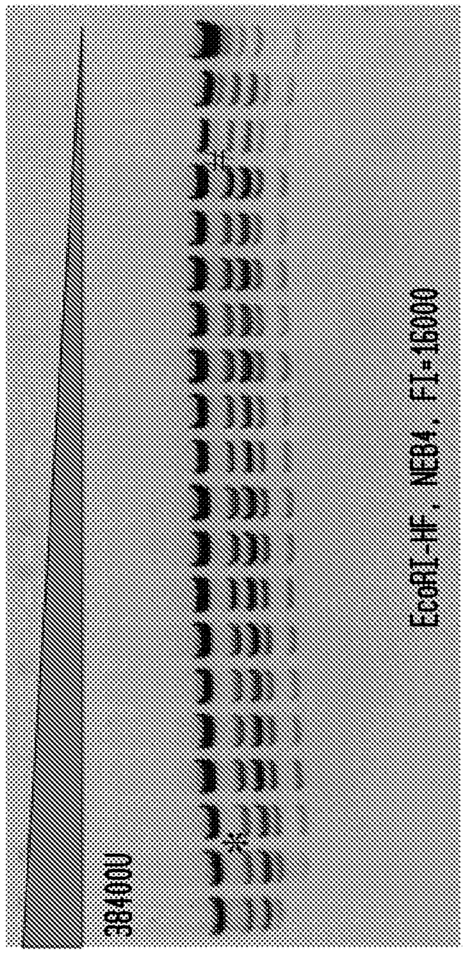
FIG. 8B
COMPARISON OF
EcoRI-HF AND WT EcoRI ScaI COMBINATION OF MUTATIONS

NEB2, 5% GLYCEROL

ScaI COMBINATION OF MUTATIONS

NEB2, 37% GLYCEROL

ScaI COMPARISON OF ScaI-HF AND WT ScaI

ScaI COMPARISON OF ScaI-HF AND WT ScaI

ScaI COMPARISON OF ScaI-HF AND WT ScaI

ScaI COMPARISON OF ScaI-HF AND WT ScaI

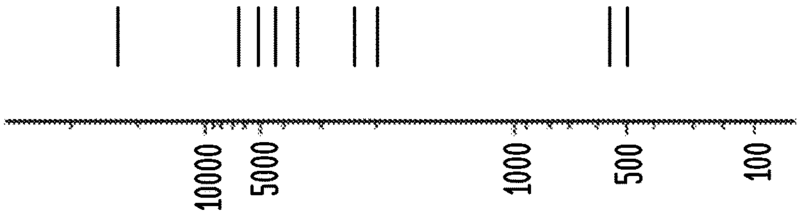
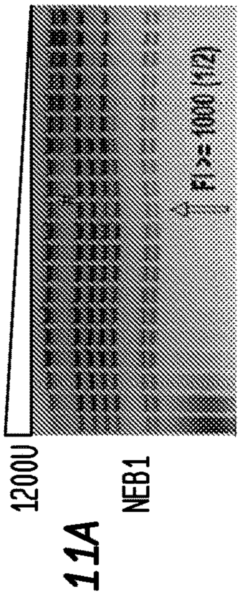
1200U NEB1
FIG. 11A
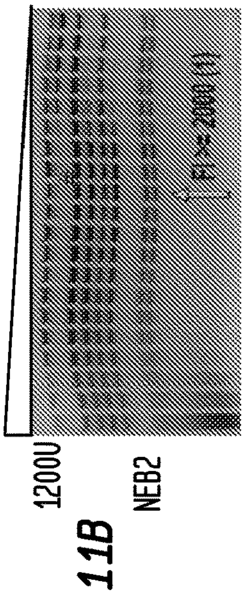
1200U NEB2
FIG. 11B
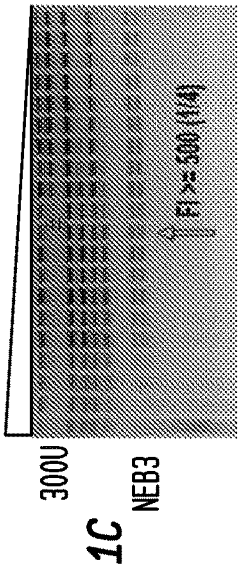
300U NEB3
FIG. 11C
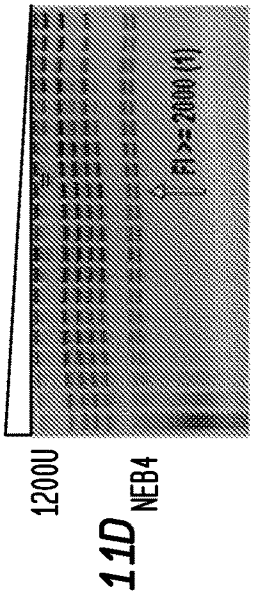
1200U NEB4
FIG. 11D
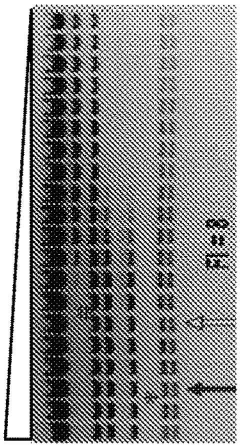
19.2U NEB1
FIG. 11E
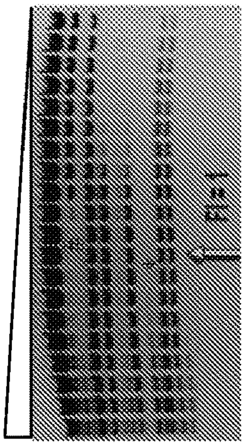
150U NEB2
FIG. 11F
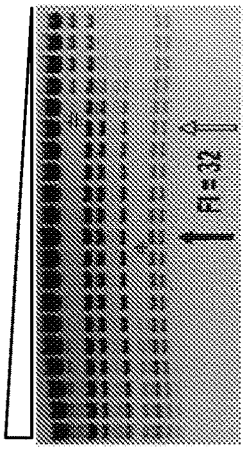
9600U NEB3
FIG. 11G
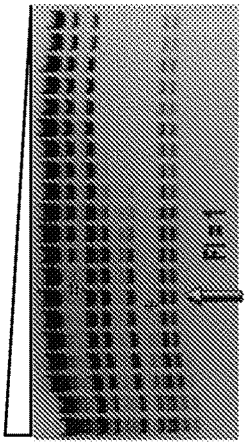
38.4U NEB4
FIG. 11H

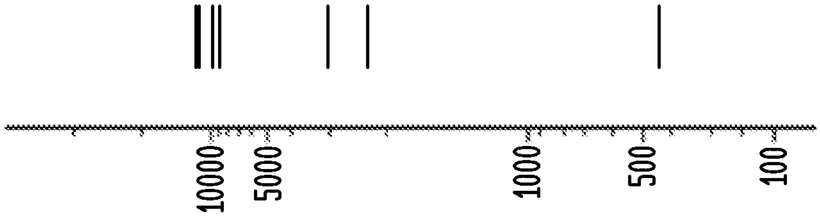
FIG. 12A
19200U
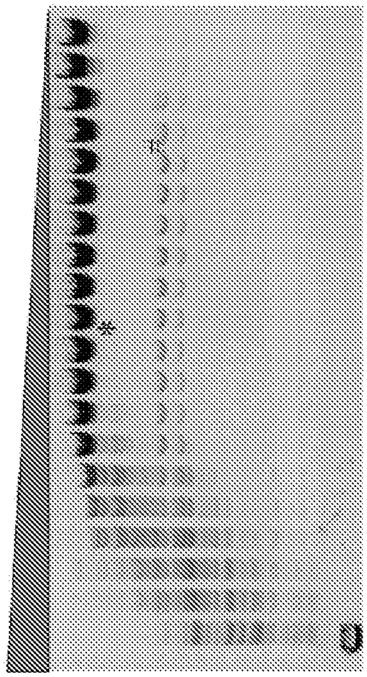
WT SphI
FIG. 12B
143600U
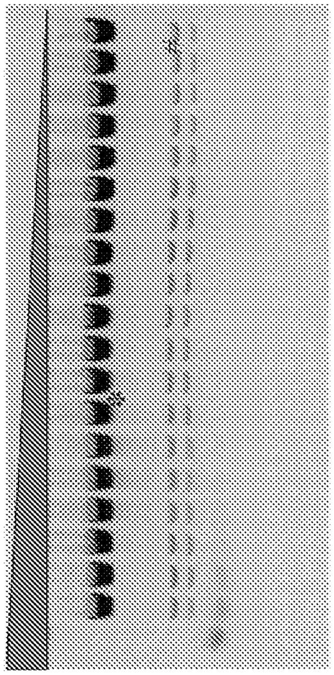
SphI-HF

NEB4

NEB3

WT PvuII

NEB4

NEB3

PvuII-HF

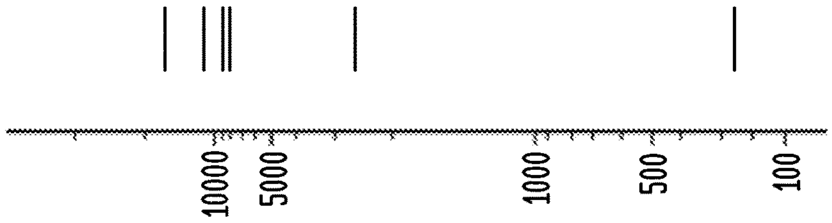
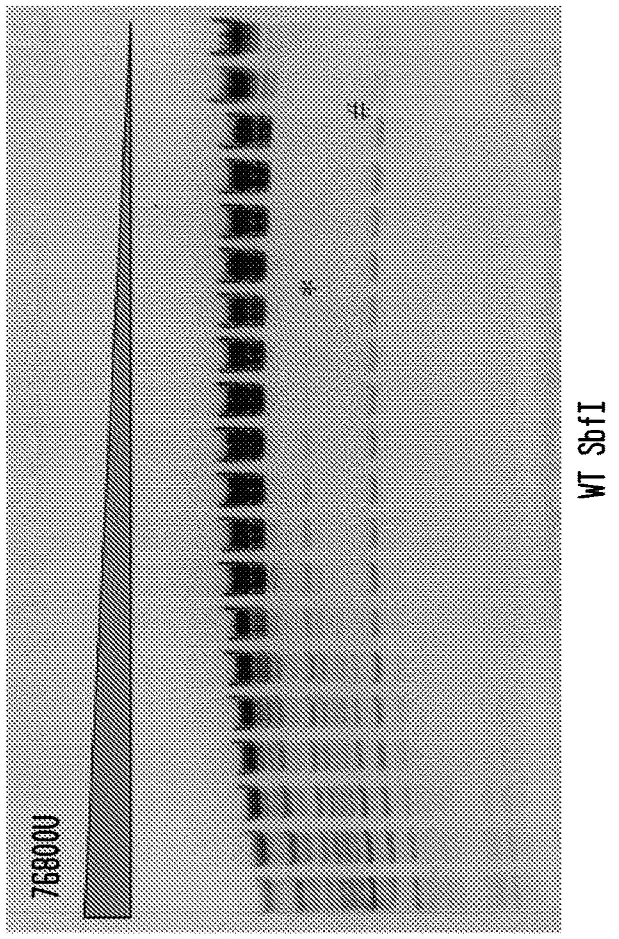
FIG. 22A
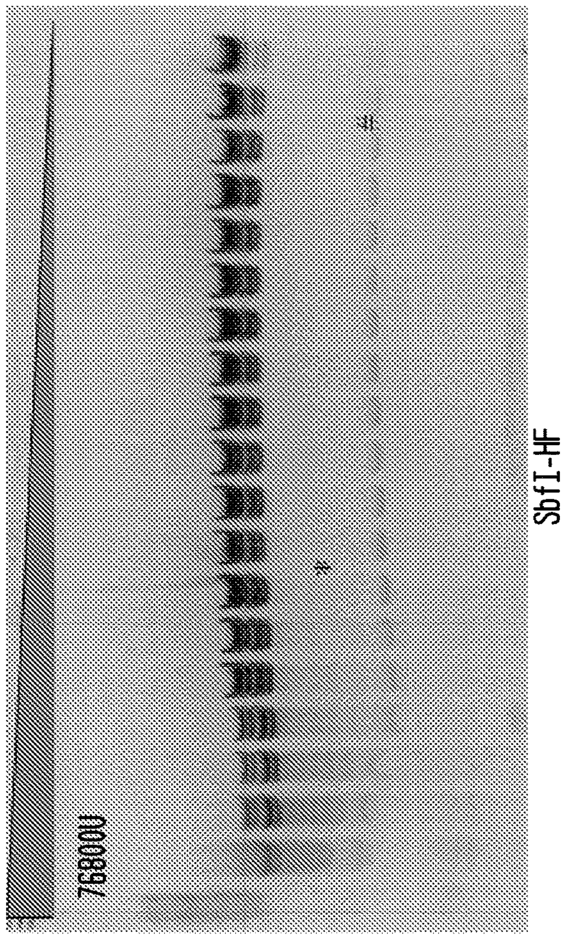
FIG. 22B

NEB2

NEB1

EagI-HF

NEB2

NEB1

WT EagI

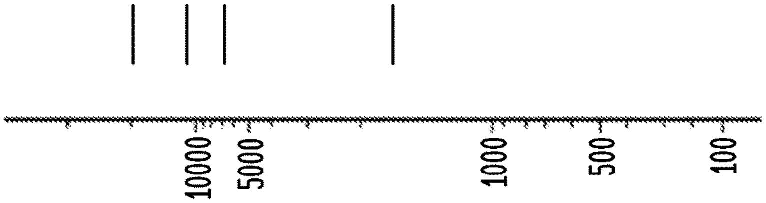
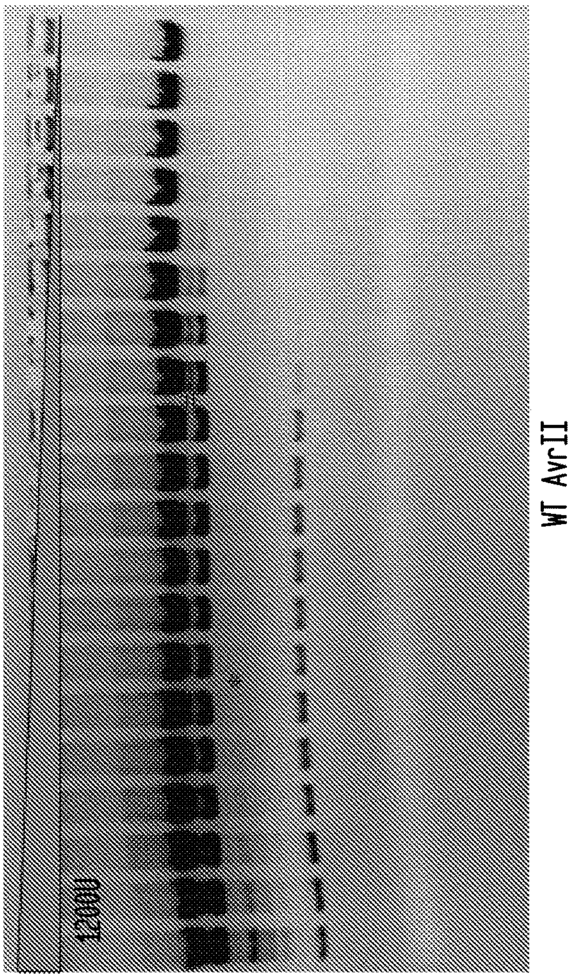
FIG. 25A
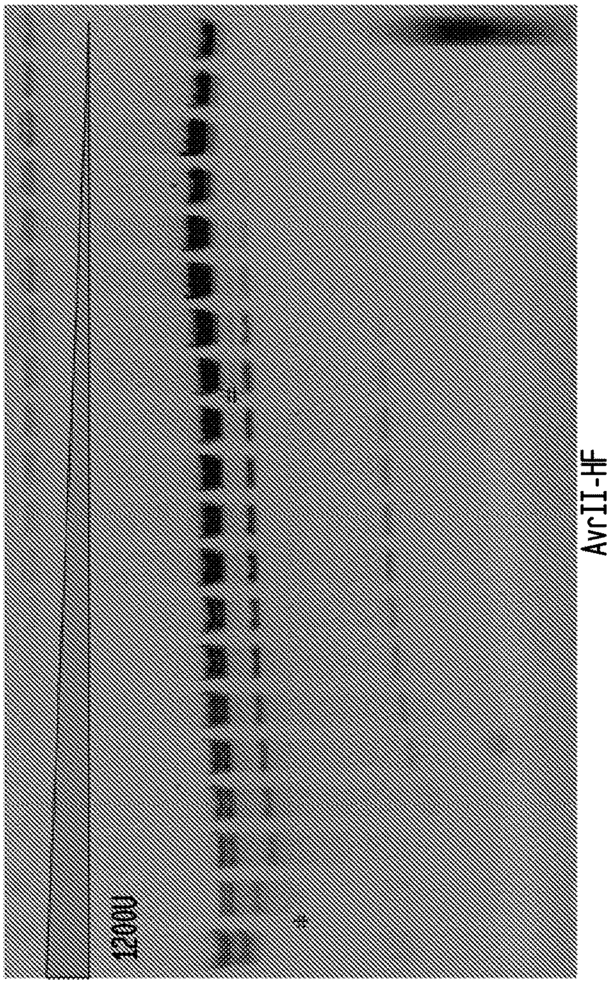
FIG. 25B

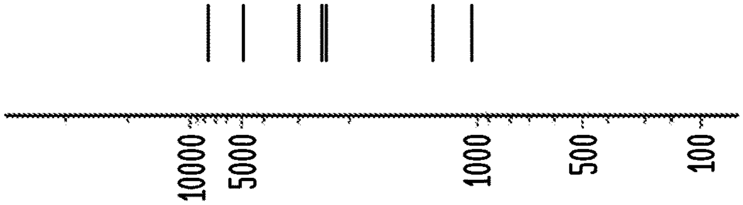
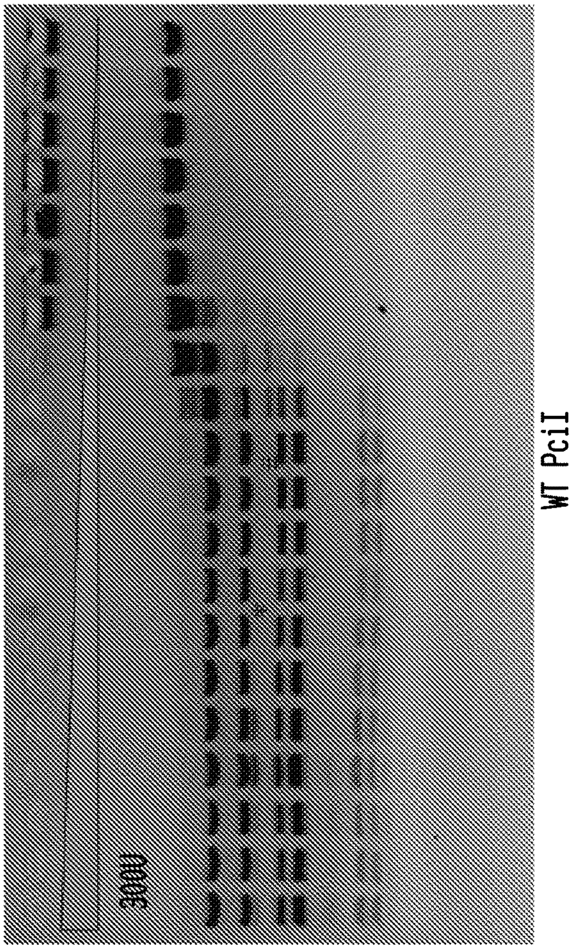
WT PciI
FIG. 27A
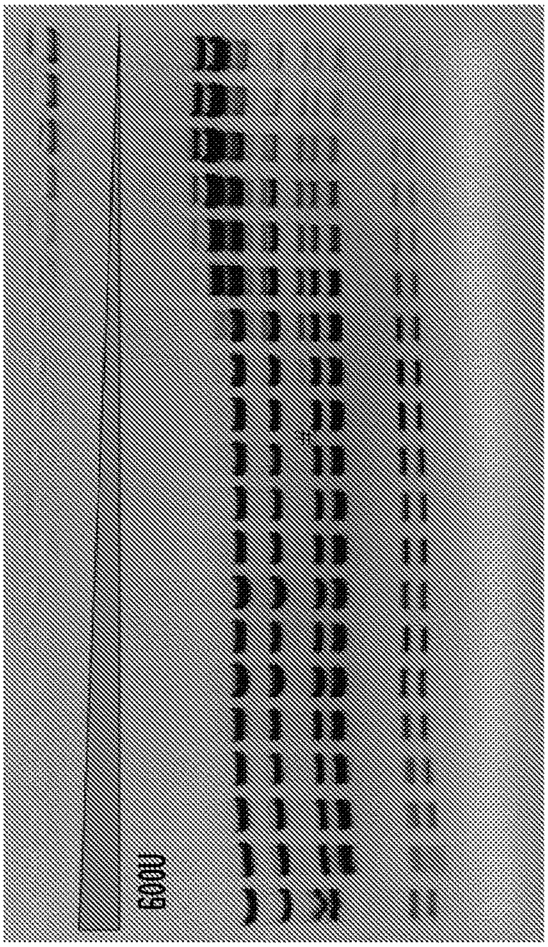
PciI-HF
FIG. 27B

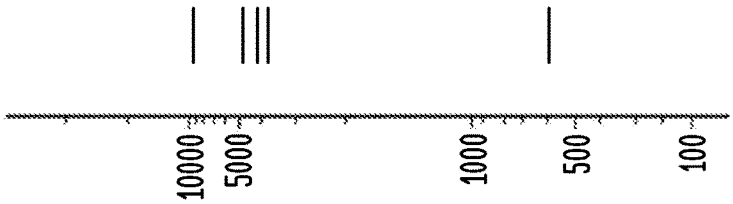
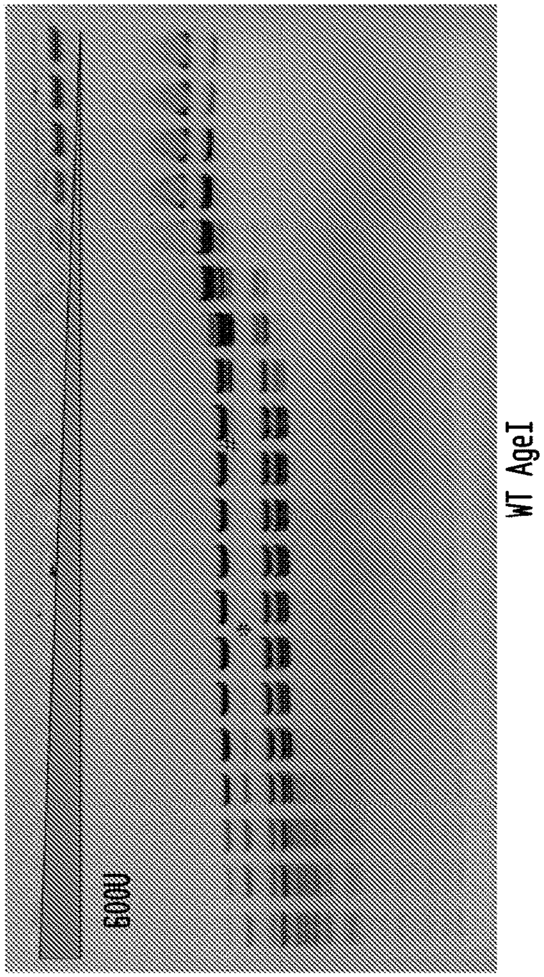
FIG. 29A
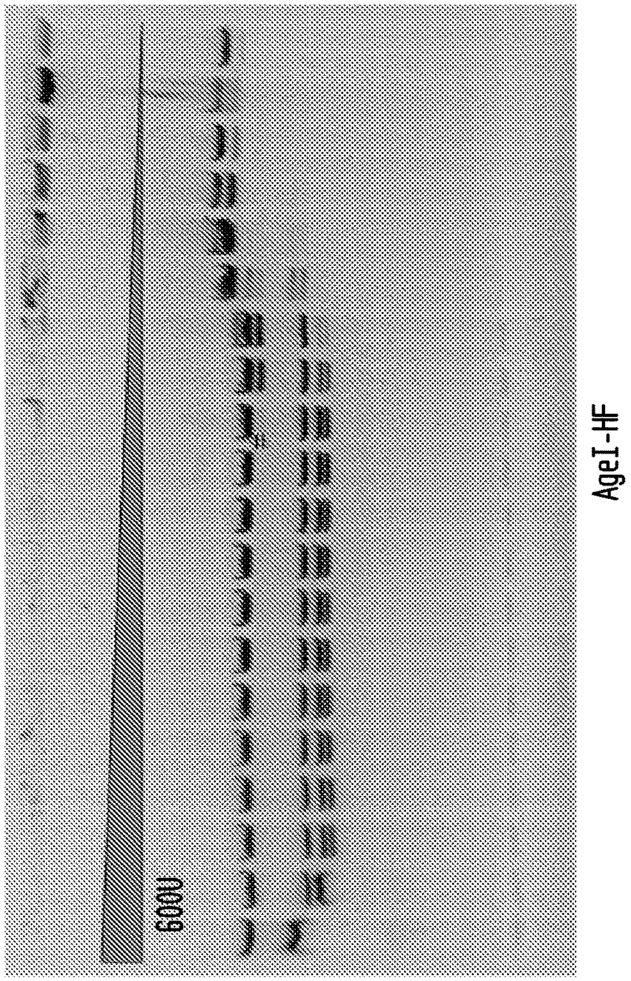
FIG. 29B

FIG. 31A

SEQ ID NO:1

```
   1 ATGATCAAGT ACTTGGGTAG CAAGCGGACG CTCGTGCCCG TCCTCGGTGA
  51 CATCGCTTCG GCCTCTGAAG CAACAGAGGC GGTTGACCTG TTCACTGGCA
 101 CGACGCGTGT GGCGCAAGAG TTCAAGCGTC GCGGGCTTCG AGTTCTTGCT
 151 AACGACATAG CGACGTACTC CGAGGTTTTA GCCCAGTGCT ATATCGCCAC
 201 CAACGGCCAG GAAGTTGACC GCCGTGCGCT CGAGGCCGCT CTGGCGGAGC
 251 TGAACGCCTT GCCCGGCGAA CCTGGATACT TCACGGAAAC CTTCTGTGAG
 301 GCTTCTCGCT ACTTCCAGCC CAAGAACGGG GCTCGGGTGG ATGCAATCAG
 351 GAATGCGATC GACGACCGGT ACGCGGACTC ATGGATGCGA CCGATCCTCC
 401 TCACGAGCTT GATGCTTGCG GCCGACCGCG TCGACTCCAC TACCGGAGTG
 451 CAGATGGCTT ACCTGAAGCA GTGGGCCGCG CGTGCGCACA ATGATCTAGA
 501 GTTGCGGCTT CCAGACCTAA TCGCAGGTGA CGGTGACGCT GCTCGTGAGG
 551 ATGCGGTGAC TCTCGCACAA GAGCTGCCTC GCGTCCAGCT GATGTACCTT
 601 GATCCTCCCT ATAACCAGCA CAGGTACTTC ACCAACTACC ATATTTGGGA
 651 GACCCTGATT CGTTGGGATG CCCCTGAGAG TTATGGGATC GCCTGTAAGC
 701 GCATTGACTC TCGAGATGAT GCCACCAAGA GCCCCTATAA TATGAAGCGG
 751 CGAATGCCCG ACGAGATGCG TCGCCTGCTG ATGACCATCA AGGCGGACCT
 801 CGCGGTTGTA TCTTACAACA ATGAGTCGTG GATTGATCCG GAGACGATGA
 851 TGTCGACCCT GCGCGATGCG GGATATGAGG ACGTGCGTCT GCTCGCTTTC
 901 GACTATAAGC GCTACGTTGG GGCTCAAATC GGGATCTACA ATCCCTCCGG
 951 GGAAAAGGTC GGTCGTGTGA GTCACCTCCG AAACATCGAG TATCTCTTTC
1001 TTGCGGGACC AACGGAGCGC GTTGAGGTGT GCGCCGCGAG TGTTGAACAC
1051 CGAGCACTAC CCAAGGAACC GGAACTCACC GCGTTCTAG
```

FIG. 31B

SEQ ID NO:2

```
MIKYLGSKRT LVPVLGDIAS
ASEATEAVDL FTGTTRVAQE
FKRRGLRVLA NDIATYSEVL
AQCYIATNGQ EVDRRALEAA
LAELNALPGE PGYFTETFCE
ASRYFQPKNG ARVDAIRNAI
DDRYADSWMR PILLTSLMLA
ADRVDSTTGV QMAYLKQWAA
RAHNDLELRL PDLIAGDGDA
AREDAVTLAQ ELPRVQLMYL
DPPYNQHRYF TNYHIWETLI
RWDAPESYGI ACKRIDSRDD
ATKSPYNMKR RMPDEMRRLL
MTIKADLAVV SYNNESWIDP
ETMMSTLRDA GYEDVRLLAF
DYKRYVGAQI GIYNPSGEKV
GRVSHLRNIE YLFLAGPTER
VEVCAASVEH RALPKEPELT
AF
```

*FIG. 32*

SEQ ID NO:3

```
TTGGAGAATT TTTTGAATAA TTTAGATATT AAAACCTTAG GGCAGGTTTT CACCCCTAAA
AAGATAGTGG ATTTCATGCT CACTCTCAAG CACAATCATG GGAGTGTTTT AGAGCCAAGC
GCGGGCGATG GGAGTTTTTT AAAGCGCTTA AAAAAGGCTG TAGGGATTGA AATCGATCCT
AAAATCTGCC CTAAAAATGC CCTTTGCATG GACTTTTTTG ACTACCCTTT AGAAAATCAA
TTTGACACGA TTATTGGCAA TCCGCCCTAT GTCAAGCACA AGGATATTGC GCCAAGCACG
AAAGAAAAAC TCCATTACAG CCTTTTTGAT GAAAGGAGTA ATCTATACTT GTTTTTCATA
GAAAAAGCGA TCAAGCATTT AAAGCCTAAA GGCGAATTGA TTTTCATCAC CCCAAGGGAT
TTTTTAAAAT CCACTTCTAG CGTGAAATTA AACGAATGGA TTTACAAAGA AGGCACGATA
ACGCATTTTT TTGAATTAGG CGATCAAAAG ATTTTCCCAA ACGCCATGCC TAATTGCGTG
ATTTTTCGTT TTTGTAAAGG TGATTTCAGT AGAATCACCA ACGATGGTTT GCAATTTGTG
TGCAAAAAAG GCATTTTGTA TTTCCTCAAC CAATCTTACA CGCAAAAATT AAGCGAGGTT
TTTAAGGTTA AGGTGGGGGC AGTGAGCGGG TGCGATAAGA TTTTTAAAAA TGAAACATAC
GGGAATTTAG AATTTGTCAC CTCAATCACC AAAAGAACCA ATGTTTTAGA AAAAATGGTT
TTTGTCAATA AACCTAATGA TTATTTACTC CAGCATAAAG ACAGCTTGAT GCAAAGAAAG
ATTAAAAAAT TCAATGAAAG TAATTGGTTT GAATGGGGGA GGATGCATCA CATATCCCCT
AAAAAACGCA TTTATGTTAA CGCCAAAACG CGCCAAAAAA ACCCCTTTTT CATCCACCAA
TGCCCTAATT ATGACGGCTC TATTTTAGCG CTATTCCCTT ATAACCAAAA TTTGGATTTA
CAAAACCTCT GCGATAAACT CAACGCTATC AACTGGCAAG AATTAGGCTT TGTGTGCGGC
GGGCGTTTTT TGTTTTCGCA GCGCTCTTTA GAAAACGCCC TTTTGCCTAA AGACTTTTTA
AATTAG
```

*FIG. 33A*

SEQ ID NO:4

ATGGGTAAAT CTGAATTAAG TGGAAGATTA AATTGGCAAG CATTGGCTGG ATTAAAAGCT AGTGGTGCTG
AACAAAACTT ATATAACGTG TTTAACGCTG TTTTTGAAGG AACTAAATAC GTTTTATACG AGAAGCCAAA
GCACCTTAAA AATCTATACG CTCAAGTAGT CTTACCTGAT GATGTTATTA AAGAAATTTT TAATCCTTTA
ATTGATTTAT CAACTACTCA ATGGGGTGTT TCTCCAGATT TCGCAATAGA AAATACAGAA ACGCATAAAA
TTCTTTTTGG TGAAATTAAA AGACAAGATG GATGGGTAGA AGGTAAAGAT CCTAGTGCTG GCAGGGGTAA
TGCACATGAG AGATCTTGTA AATTATTTAC TCCTGGATTA TTAAAAGCTT ATAGAACAAT TGGTGGAATT
AACGATGAAG AGATATTGCC ATTCTGGGTT GTATTCGAAG GTGATATAAC ACGAGATCCC AAAAGAGTAA
GAGAAATTAC TTTCTGGTAT GACCACTATC AAGATAATTA TTTCATGTGG CGACCAAATG AATCAGGCGA
AAAATTAGTT CAACACTTCA ATGAAAAATT AAAAAAATAT TTAGATTAA

*FIG. 33B*

SEQ ID NO:5

MGKSELSGRL NWQALAGLKA SGAEQNLYNV FNAVFEGTKY VLYEKPKHLK NLYAQVVLPD DVIKEIFNPL
IDLSTTQWGV SPDFAIENTE THKILFGEIK RQDGWVEGKD PSAGRGNAHE RSCKLFTPGL LKAYRTIGGI
NDEEILPFWV VFEGDITRDP KRVREITFWY DHYQDNYFMW RPNESGEKLV QHFNEKLKKY LD

FIG. 34A

SEQ ID NO:6

ATGGCTATTA CATTATGTGA CATAAATGGT TGTAGACTTG AGAGAGGACA TACTGGTAAA CATAATAAAT TTCCTGAATT
TGTATGGACT TCTCAATTTA ATAAAAAAGA TATTGATAAG GTCAATAAAG CAGGATATGC AACACCAAGA GGTGGGGACA
AAGGAGCCTA TCAGAACCAT GTTTACAGAA ATAATAAAGT AATTATTCCT TTTGAAAGGT TGGAAAATGT TAATTTAAAT
AACTATCAAG ATGGATATGT TATTAGGTTA TTCCCTAATC AGTACTTTGA ATCAGCCGGG GTAGTTAAGC CGGAATTCTT
ACAACCAAAT TCATTTGTTA AAGTTGGGGA CAATGCATTT ATTTTATATC GCACACATTC ATCTTTTGAG GAATTACCTC
CTCTACCAGA CTGGGAGGTT AGACATCTAA AAAAGAACGG TAATATAGTT ACCAGAAGAA GTAAGGACGT AATCGATGCT
GGACATTATG TCTTACGATT ATCATCAATT AGTAACAAAA AAGAAAGAAA AGAGGGCCCT CCTCAAGGTA TTTTTGCACC
TGAATATGCA AATGCAGAGA CTAATTATCT GTCAAAAGCA TTTTTAGCCT GGTTAATTAT TAAAACTCAA AATAGTCCGT
ATAATGAAGA ACAATTCCAA CACTTAAGAG CGATCTTAAT TAGTCATAAT CTCATCAATA TTTCTCAACT TGAAGAAAAG
GCTATTCTAA AGAATGGTAT CACATGCTGC CCTTTATGCG AGCAAATTAT TTTTTACGAA CAGCTACACG AAATGGTTTC
TTTTGAAGGT GCGTCTGGCC TTGCGAATTC ACAAGAACAG GTTGAGGGTG CAACTAGGTC AACATCAGTT AATTTATTCC
ATATGGTACC ATTAGTATAT GAAACCTTGG AACACAAACC TGATCAAATA GCATGGGGCC ATGCCATTTG TAATACTAGA
CTTGGTCAAA GAGAGTGCCT GCCTCTTAGT AGACTAAAAC AAGAAGGTAC GCCCGTTGGT CTTCTTGATG AAGATTCGAA
TCTTGAAGTA TTAGGATGGA TTAGTAAAGA TAAGCAATTT ATTCGTACAG AAAATGGGGA AGTTTGGATT AAAATTACAG
ATATTGAATT TAACGATGAC TTTGAAGAAT AA

FIG. 34B

SEQ ID NO:7

MAITLCDING CRLERGHTGK HNKFPEFVWT SQFNKKDIDK VNKAGYATPR GGDKGAYQNH VYRNNKVIIP
FERLENVNLN NYQDGYVIRL FPNQYFESAG VVKPEFLQPN SFVKVGDNAF ILYRTHSSFE ELPPLPDWEV
RHLKKNGNIV TRRSKDVIDA GHYVLRLSSI SNKKERKEGP PQGIFAPEYA NAETNYLSKA FLAWLIIKTQ
NSPYNEEQFQ HLRAILISHN LINISQLEEK AILKNGITCC PLCEQIIFYE QLHEMVSFEG ASGLANSQEQ
VEGATRSTSV NLFHMVPLVY ETLEHKPDQI AWGHAICNTR LGQRECLPLS RLKQEGTPVG LLDEDSNLEV
LGWISKDKQF IRTENGEVWI KITDIEFNDD FEE

FIG. 35A

SEQ ID NO:8

ATGATTTTTG CTGATATTGA ATTTGAAAAA GAACTTTTTT CAGCTGCTAA TAAATTAAGG GGAAAAATTG CTCCAAGTGA
GTATAAGCAT TATGTTTTGC CTTTGATATT CCTTAGATAT TTATCTCTTA AATACCAACA AAGAAGGAAT GAAATTCAAC
AACAGATAAA TGATTCAAGG GATCACAAGA AAAATCAAGA TGAAGTGTTA AAGATATTGG AAGACAGGAC TGAATACACC
AAAGTAAATG TTTTCTATAT TCCTGAAAAA GCTAGTTGGG AATACTTATT GAAAAATTCC GAAAATGATA AAATTAAAGA
AATGATAGAT TCAGCTATGG AAATACTGGA AAATGAATAT GACGAGTTAA AAGGTGTTTT GCCAAAGATA TATAAAAACT
CAAATATACC GAATGAAGTT ATTAGTGATT TACTAAAACT ATTTTCTCAA GAAGTATTTT CAGCACATGA TGGAAGAAAT
GTTGATTTAT TGGGGAGAGT TTATGAATAC TTTATAAGTA ATTTTGCTAC TACAGAAGGT ACTAGAGGTG GTGAATATTT
TACACCGTCT TCAATCGTAA AATTATTGGT AGCAATGCTA GAGCCCATTA AAGGTACAGT TTATGATCCG GCCTGTGGGA
CAGGAGGAAT GTTTATTCAG TCTAATAAAT ATAGAGAAAA TAATCATAAC TTGTGTTTTG TAGGCCAGGA ACAAAACGAG
CTTACTATCA AATTGGCTAA AATGAATGGA ATTCTACATG GAATAAATCC TGAAATTAGA CAAGGTGATT CATTATTAAA
TGACCGTTAT CCAGAATTGA AAGCTGAAAT TGTAATATCT AATCCACCGT TTAATATGAA GGATTGGGGA GCTGAACGCC
TGCCACTTAA TGATAAGCGA TTAATAGGAC CGGTAACAAA CAGTAATGCA AATTACATGT GGATACAGCA TTTTCTATAC
CATTTAAAAG ATGGTGGTTT AGCAGGATTT GTTATTGCTA ATGGAGCTTT GACTAGTAAT CTGGCTGCTG AAAAAATTGT
AAGGAAACAC TTAATAGACA ATGATTATGT AGATTGTGTT GTTCAATTAC CTGAAAAAAT GTTCTTTGGT ACTGGCATTC
CAAGTGCTTT AGTGTTTTTA AGTAAGAATC GAAATGGAAG TAACGGCCAT GCCAAAAGAG AAAAAGAGGT TCTATTTATT
GATGCAAGCG ATAAGGGAAC ATTAGTGGGT AAAAAGAATA AAATATTTTT AGATGATGAA ATAAAAGAAA TTGCAGATTT
ATATCATTCA TTTAAATTTT TAAATGATAA TGATTATAAC CATAGTGGTT TTTACAAAAA GGTTAACATT GAAAAAATCG
TGGAAAATGA TTATAAATTA ACTCCAACTC TCTATGTAGG TGTAAAGGAA GAGACTGAAA TGGAGAAGCC ATTTAGAGAA
ATGATAATAG AATATAAAGC GATATTAGAG CAACAATTTG AAGAATCAAA CAAACTACAG CAGAAAATAT TAAAGAATTT
AGAGGGATTA TTATGA

FIG. 35B

SEQ ID NO:9

MIFADIEFEK ELFSAANKLR GKIAPSEYKH YVLPLIFLRY LSLKYQQRRN EIQQQINDSR DHKKNQDEVL KILEDRTEYT
KVNVFYIPEK ASWEYLLKNS ENDKIKEMID SAMEILENEY DELKGVLPKI YKNSNIPNEV ISDLLKLFSQ EVFSAHDGRN
VDLLGRVYEY FISNFATTEG TRGGEYFTPS SIVKLLVAML EPIKGTVYDP ACGTGGMFIQ SNKYRENNHN LCFVGQEQNE
LTIKLAKMNG ILHGINPEIR QGDSLLNDRY PELKAEIVIS NPPFNMKDWG AERLPLNDKR LIGPVTNSNA NYMWIQHFLY
HLKDGGLAGF VIANGALTSN LAAEKIVRKH LIDNDYVDCV VQLPEKMFFG TGIPSALVFL SKNRNGSNGH AKREKEVLFI
DASDKGTLVG KKNKIFLDDE IKEIADLYHS FKFLNDNDYN HSGFYKKVNI EKIVENDYKL TPTLYVGVKE ETEMEKPFRE
MIIEYKAILE QQFEESNKLQ QKILKNLEGL L

FIG. 36A
SEQ ID NO:10

ATGAAAAGTA CTTTGAAGGA ATATAAATTG GGTGATATTA CCGAAGTCGT TAATGGTGCC ACTCCTTCAA
CTAAAAAGCC TGAGTACTAT GAAAATGGTA CAATTCCATG GATTACTCCT AAAGATTTAT CAGGCTATTA
CTTTAAATAT ATATCTCATG GTGAACGTAA TATAACAGAG CTTGGTCTAA GAAATAGTTC AGCTAAGTTG
TTACCAAAAG GAACTGTATT ATTTTCCTCA AGAGCCCCAA TAGGATACGT AGCAATAGCT GATAATTGGT
TAACTACGAA CCAGGGATTT AAAAGTTTTA TATGTAATGA GGAGATTATT TACAATGAAT ACCTTTATTA
TTTTCTTATT GCTAAAAGGG ATTTTATTGA AACATTTGCG AATGGGAGTA CGTTTAAAGA GCTTTCATCA
ACTTCTGCAA AGAATATACC AATCAATCTT CCTAGTTTAG AAGAGCAAAA GAAGATTGTG ACAATTTTAG
GGGATTTGGA TAGAAAGATA GAATTAAATT ATAAAATTAT TGAAAGCTTA GAAAAAATAG CAGAAAGAAC
ATATAAATAT TGGTTTGTCG ATGAATTAAA TCAAGATGAA CAGCACATCC GTAATGGATG GGAAACTGCT
AAAATTGGCG ATGTGGTGGA ACTTTTGGGA GGGGGAACCC CTAAAACTTC GGAAAGTAAG TATTGGGAAG
ATGGAGATAT TAATTGGTTT ACTCCTTCAG ATTTAACAAA AACTAGACAG CTTTTTGTAC GTGATTCTCA
AAGAAAAATA ACAATTGATG GACTTAATAA CAGTGCAGCG AAATTAATTC CCCCTTATTC CTTGTTAATG
TCAAGTAGAG CTACAATTGG CGAGTTGGCA ATTAATCAAG AATCTGCTAC TACAAATCAA GGGTTTATTG
TATTAATACC AAATGAAAAA ATTTCTATTT ACCAATTATA CTTTTGGGCT AAACTTAATA AGAGCAAAAT
TATTTCAATG GCAAATGGTA GTACTTTTAA AGAAATTAGT AAGCGGGATT TTAAATCTTT GGAGATAATA
TTACCAAAAA ATATAGACAC TTTTAATTCA ATTATGCAAG ATTATTTTAG GAAAATTGAG GAGTTAATTG
ATGAAATAAA AATCTTAAAA ACCGCAAGAG ATAATTTAAT TCCAAAACTT ATAAAATGA

FIG. 36B
SEQ ID NO:11

MKSTLKEYKL GDITEVVNGA TPSTKKPEYY ENGTIPWITP KDLSGYYFKY ISHGERNITE
LGLRNSSAKL LPKGTVLFSS RAPIGYVAIA DNWLTTNQGF KSFICNEEII YNEYLYYFLI
AKRDFIETFA NGSTFKELSS TSAKNIPINL PSLEEQKKIV TILGDLDRKI ELNYKIIESL
EKIAERTYKY WFVDELNQDE QHIRNGWETA KIGDVVELLG GGTPKTSESK YWEDGDINWF
TPSDLTKTRQ LFVRDSQRKI TIDGLNNSAA KLIPPYSLLM SSRATIGELA INQESATTNQ
GFIVLIPNEK ISIYQLYFWA KLNKSKIISM ANGSTFKEIS KRDFKSLEII LPKNIDTFNS
IMQDYFRKIE ELIDEIKILK TARDNLIPKL IK

FIG. 37A

SEQ ID NO:12

ATGAAACAGT TTGCAGATCC TTTTGAAAGA AGATTCCTTG ATGCAATTGA ACATCATCTT GATGGAATTT
CTGAGAAAAT AAAAAAAGAC TTTACACACA AAAACTTTTT AAAAGAATTG AATGGCCTTA AAGGTGATAA
AGTCTATCAT GACTTAGGCT TTGATACCGC TGAATATACT CTGGTACGTC TTATAGGAAG AATGAGCATA
AGCGTTGGGA GAAGGCTGGG GGAGATATAC GATAAAGTCC CTCGTTATGT TGCTGCCGCG CGATTTGGTC
TTCAACCAAA TCAAATTGCA GAAGTATTTG ATGGTCTTGA GTTAGATATA GCTTTGCGCA ATAGCCTTTT
GTCAGATGAT GATAAAATTC ACATAAAAAA AATAACTGAA AAGATGTCAG GCGAAACATA CTCGGGAATC
GGAATCGAAA TTCGTTATAA CTTTAATCCA AATGACAGTT CCCGTTTAAG AAAAGACGTC GATGTAGCTT
CTAAATTGTC GGCCGCGGGG TTATTTCCTG TTTATTTAAT ATTTAGCTCT CTCAGTCCTA GGAATGATGC
AATAGCCCGT CTTAAAAGAG GGGGATGGAG CTTTAAACAG GGGCAGGAAG CCTTAGACTT CCTTACCGAA
CTTTTAGGAG TGGATATTGG GTCTGTTTTA TCTGACCCAA TAATAGCCGC AGAAACTAGG GAGAAAACAT
CAAAAATTAT GAAGTCTATA TTTGAATCAG AGGCATTCCA ATCTGTTATA CCGGGAGAGT GGAGTAAACT
ATAG

FIG. 37B

SEQ ID NO:13

MKQFADPFER RFLDAIEHHL DGISEKIKKD FTHKNFLKEL NGLKGDKVYH DLGFDTAEYT LVRLIGRMSI
SVGRRLGEIY DKVPRYVAAA RFGLQPNQIA EVFDGLELDI ALRNSLLSDD DKIHIKKITE KMSGETYSGI
GIEIRYNFNP NDSSRLRKDV DVASKLSAAG LFPVYLIFSS LSPRNDAIAR LKRGGWSFKQ GQEALDFLTE
LLGVDIGSVL SDPIIAAETR EKTSKIMKSI FESEAFQSVI PGEWSKL

FIG. 38A

SEQ ID NO:14

ATGACAAATT TTTCGCACTC AGCTCTAACG AGCTACGATC TTCTCGGGCA TGAAATTGTC CAAGATTCTG
AAGCTGTTAG CTCGGGTCCA TATCTGGTCA GCTATGACCC GATCCCTGTA CGTCGGTCTA CATTCCTAGC
TGGACTGTCA GAGAACGTTC ACTCGTGGTT TCGTCTCACA CCAAGTTTCG GACCGGATCT AGTTCGAACA
ATCATCAAAC AGATGAATCT TGCGCCGCAC TCACACATCC ATGACCCTTT CTCAGGAGCC GGGACTACCG
CGATTGAGGC TTCGTTAGAG GGCTATGAAG CAAGCTGCGT AGAAGTTAAT CCGTTTCTCT ACTTCGTGGG
GAAAACATCC ATAGATTGGT CTATCAATGC TGATGATGCT GCAGCGCAGC TAGAAAGCAT TAAAAATAAA
TATTATAGCA TGTCTGCAAC CGCTACTTTG GATAACATAG CCGACCTAGG AATAGATATA CCAAAAATAC
ACAATATTCA TCGGTGGTGG AGAAACGATG TTCTTAAAGA TATATTAGTC CTAAAATCTT CTATCAGATC
TTGCACACAA GATAAGTATT GTTCCTTTTT TGAGCTAGCC CTAGCTGCAG TTCTCGTTCC AGATTTGACA
AATGTAACGC TAGGAAAACT ACAACTGCAC TTTGTAAACA AAGACGATAA AGAGATAAAC GTCTGGCCTA
CATATGAATC TCATGCAAAA AAAATGATTC ACGACTTGTC ATTAATTAAT AAGCAAAATT TCGAATTTTT
GCCCAAGATT ATTTATGGTG ATTCAACTCA AAAATCAACA TTTAGCGAGG TGGCAGGGAT AGATGCTATA
ATAACATCCC CTCCGTACCC TAATAGGTAC AGCTATATTT GGAATACTCG CCCTCACCTG TACATTCTTG
ATATGATTTC CGAAGCAAAA GAGGCTTCGC AAATAGATCG TAGAACGATT GGTGGAACAT GGGGGACAGC
AACTTCCGAA TTAGGAAAGG GTATATTTTC TCCAATCAAT GCTGTAGTCA AAGACGCGCT TGAAGGGGTT
CACGAAAGAA TCGCCGGTTC CGATCAACTC ATGGCAAACT ATGTAACTCA TTATTTTAAT CGGCTCTTTT
TACATATAGA AGCTATAAAA CCATCACTTA ATCCAAAAGC AAAGCTTGCT TATGTTGTTG GGAACTCTTG
GATTAAGGGC GAATATGTAG CCACTGACGT AATCTTAGCA AAAATTATCG AAGGGGCTTT GCCAGGCTCA
TCAATTGATG GTCTTCATCG TTTCCGTCGC CGGAACAGTG GAAAGAATCT CTTTGAAACT ATAGTTTACT
CCACTCTCCC GGTATAA

FIG. 38B

SEQ ID NO:15

MTNFSHSALT SYDLLGHEIV QDSEAVSSGP YLVSYDPIPV RRSTFLAGLS ENVHSWFRLT PSFGPDLVRT
IIKQMNLAPH SHIHDPFSGA GTTAIEASLE GYEASCVEVN PFLYFVGKTS IDWSINADDA AAQLESIKNK
YYSMSATATL DNIADLGIDI PKIHNIHRWW RNDVLKDILV LKSSIRSCTQ DKYCSFFELA LAAVLVPDLT
NVTLGKLQLH FVNKDDKEIN VWPTYESHAK KMIHDLSLIN KQNFEFLPKI IYGDSTQKST FSEVAGIDAI
ITSPPYPNRY SYIWNTRPHL YILDMISEAK EASQIDRRTI GGTWGTATSE LGKGIFSPIN AVVKDALEGV
HERIAGSDQL MANYVTHYFN RLFLHIEAIK PSLNPKAKLA YVVGNSWIKG EYVATDVILA KIIEGALPGS
SIDGLHRFRR RNSGKNLFET IVYSTLPV

FIG. 39

SEQ ID NO:17

>M1.EarI CTCTTC 1245 nt

GTGAATCAGA AAAATGAAAA ATCATTTATG CGTTTGCAAT CAACCTTTAG CGGTGGCAAA
GGTAGTCCAA TGCATGATTG GTACCCATAT TTAGAGGGTT ATTCTCCCGA ATTTGTGAAA
TGCTTGATTT CACGATTTGC TCCTAAAGCC AAAACAATTT TAGATCCATT TTGTGGCTCT
GGAACAACAG CCATTGTTTC CGTTTTAGAG GGTTTAAATA ATTACTATTG CGAAGTAAAC
CCTTTATGCC AATATATTAT TGAAACTAAA CTAATAGCTT TAACATTAAG CGAAGAAGAA
AAAACAAAAT TAGTAAATGA ACTTTATTCT ATTTCTAATG AAATAACTAA TGTACTCAAA
CCTTCTGCAA CCGAGACAGA TCTAGAGAAA TCATTTAAAT CCGTTTTTGG TAATACGAAA
TTTTTTGAGG ATCACATATT TAAAGATATA CTTAGTTATC AATGTTACAT TAGCTCTATC
GAAGATGAAA ATCTTAAGAG ACTTCTGACA ATAGCAGGGA TTAGATCGTT AATCCCTTCC
TCGTTATTGG TAAGACGAGG TGATTTACGA TTCAAGACAC AAAAAGAATT AGAGAAAGGC
AACCAGGGCT TTCGCTTTCA TGTACAAAAA AGCTTAGAAT TAATTGCCAG TGATTTATTA
GACATTACGG AAGGTAGTGG TTTAGCTACC TTCTTATGTG ATGATGCCAA AGAAATATCT
GGGAATAACC TGATTGATGC TGTAATAACA AGCCCGCCAT ATTTAAATGG CACAAATTAT
TTTAGAAATA CTAAAATTGA ACTTTGGTTT ATAGGGAAAT TAAAGACCAA ATCAGATCTA
AGACATTATA GGGATTTAGC TATTACCAGT GGTATTAACG ATGTAACTAA AGGTAAAAGC
TTATCTTCAA ATAATACTAT TATCTCAGAA ATACCATTAT TATCTGAATG TATTAAAGAA
CTAAGCATAA AAGAGTATGA TAGTCGTATT TCAATGATGG TTGAAAACTA CTTTTGGGAC
ATGTTCAAAT TCTTATCAAA ACTCCCAAAA TTACTAACTA ATGATGCGAC TATCTGTATA
GATTTAGGTG ATTCTGTTTA TTGTAACGTC TACATCCCTA CACAAGATAT TTTGAAAGAA
ATGATGTCAA AGTTAGGTTT TGAAGAGAAC GAAAGGGTCA TTCTTCGTGA ACGAAAATCC
CGCAATGGAA CAAAGTTAGT CCAGACTGTT CAGGTTTTTA AATGA

FIG. 40

SEQ ID NO:18

>M2.EarI CTCTTC 1140 nt

ATGAAAAATA AATATTTTAG TAAAAAATGG GAGCAATTCA AGAAAGAATT ACCCCATCAA
TCAGGTGAAA TGGTAAAGAG AAATTGGGGC CATAACTGGC ACTCTATGTG TTCATACCAA
GGGAAACTTA AACCATCAAT AGCTAGATCT TTAATTGATA CATTCATGCC ATCAAGTAAG
GGACGTATAT TAGATGTCTT CTCAGGTGTT GGCACCATTC CTTTCGAAGC AAGATTACTT
GGTCATACTG CATATGGATT TGATATTAGT CCAGCAGCAG TTAATATTTC ACGCGCAAAA
CTAGAAGTTA TAAGTAAAAA TGAAATCCAA GAGGTAATTA ATAAATTATC TGATTTTATT
GAGCAAAACA AAAATTCAAT AGATTATAAC GAACATAATT TAATAAGGTT TAATGGTTCA
ATTGAATCCT ATTTTCATCC TGAAACTTTT AAGGAAATAC TGTGTGCTCG TAAATTCTTT
TTAATAAAAG GTGAATTAAA TGCATCTGAA TCGTTAGTAC AGTCATGTTT ATTACATATT
TTACATGGTA ATCGTCCGTA TGCATTGAGT AGAAAGTCCC ATCCTATTAC ACCTTTCGCG
CCTACTGGAG ATTTTATATA CAGTAATTTA GTTATAAAGT TAATCAAAAA AGTTGAAAGA
GTCTTGCAAA ATTCTGATGG TATCCCAGAT ACTGGCAGCA AAGTATTTTA TCAGGACTCT
ACAAAAAGTT GGCCTGAAGA AGTAAATAAT TTAGATGCAA TTATAACATC ACCTCCATTT
TATGATAGTA CCCGTTTCTA TTCAGCAAAT TGGATGCGAT TATGGTTTTC TGGTTGGGAA
AAAGATGACT TCCAAACGAA GCCAAAAGAT TTTGTGGACG AAACTCAGAA AAAAAGCTTT
GAAATATATG ATAATATATT CAAACAATCT CAACAATGCT TAAAAAAAGA TGGCGTTTTT
TTAATGCACG TTGGCAAAAG TAAAAAAAGT GATATGGCAG GACAAATTGC TAAAATTGGT
AGTAATTATC TTAGCCTTAT AGATATATTT GACGAAAGTG TTGAACATTG CGAAAGTCAC
GGAATTAAAG ACAAAGGCAC GACAACCCAT CATCAGTACC TTGTCTTTAC GAAAGATTAG

WT KpnI

KpnI D16N/E132A/D148E

FIG. 44A

>AgeI ACCGGT 272 aa (SEQ ID NO:79)

MRLDLDFGRG LVAHVMLDNV SEEQYQQISD YFVPLVNKPK LKSRDAIGQA
FVMATEVCPD ANPSDLWHHV LYRIYIREKI GTDPSQSWVR TSGEAFEVAL
VERYNPVLAR HGIRLTALFK GQKGLALTRM GVADRVGSRK VDVMIEKQGG
GRSPDAEGFG VVGGIHAKVS LAERVSDDIP ASRIMMGEGL LSVLSTLDVK
SFPPPHGDLV NRGELGTPDR PSDKRNYIEG HGDFSACFSY NLRTPPSNAT
TPSGRHIYVS ASLVRTTSSP TT

>AvrII CCTAGG 358 aa (SEQ ID NO:80)

MEEDLDLSEN IEAASAELTT LYQVAADAMK DYIEIYLALS KQSDGFSNIN
NLDLTSRNRR LVVIHGLSLE LDPDTSTPEE IKREAERMLA IALDTESAIT
AGVYEKMRLF ASSLVDQLFE QTDELNSLSS EYLSANPGFL PFFQQLAGLR
SKSELKREVG NASDNSISKA VAERILERII RNLRIRTFSK EKLLQAVEPT
LEGIVRDLVG KVLLENIVAD ALSDLQVPFM RESEYQSLKG VIYDFRADFV
IPDAQNPIAF IEVRKSSTRH ASLYAKDKMF SAINWKGKNK RLLGILVVEG
PWTRETLRVM ANVFDYVTPL TRVSQVAEAI RAYLDGDKTR LKWLVNFSIE
EADHDNIT

>AvrII CCTAGG 1077 nt (SEQ ID NO:110)

ATGGAAGAAG ACCTTGATTT ATCTGAAAAT ATCGAAGCTG CATCTGCGGA
GCTTACGACT CTTTATCAGG TAGCTGCTGA TGCTATGAAA GATTATATTG
AAATCTATCT TGCGCTGAGT AAACAGTCTG ATGGGTTTTC AAATATTAAC
AATCTTGACT TAACTTCTCG TAACAGGCGT TTGGTAGTTA TACATGGACT
TTCGTTAGAG TTAGATCCAG ATACTTCGAC TCCAGAGGAA ATTAAACGTG
AAGCTGAACG AATGCTAGCG ATAGCTCTTG ATACAGAGTC AGCAATTACG
GCAGGAGTAT ATGAAAAAAT GCGTCTCTTC GCAAGCTCTT TAGTAGATCA
GCTATTTGAA CAAACGGATG AACTTAATTC ATTATCATCG GAATATTTGT
CAGCAAATCC AGGATTTTTG CCGTTTTTCC AGCAGTTGGC GGGGCTTAGA
AGTAAATCAG AGTTAAAGAG AGAAGTAGGA AATGCCTCTG ACAATAGTAT
TTCTAAAGCG GTTGCAGAGA GAATATTAGA GCGCATTATA CGTAACTTGA
GAATTCGCAC TTTTTCCAAA GAGAAACTAT TACAAGCTGT TGAGCCTACT
TTAGAAGGAA TAGTCAGGGA TCTCGTAGGA AAAGTGTTAT TGGAAAATAT
AGTTGCTGAT GCTTTATCTG ATTTACAAGT TCCTTTCATG CGTGAATCAG
AGTATCAAAG CCTTAAAGGA GTGATTTATG ATTTCCGCGC TGATTTTGTG
ATACCAGACG CACAAAATCC AATTGCTTTT ATCGAGGTGC GAAAAAGCTC
TACACGACAT GCGTCACTCT ATGCCAAGGA TAAGATGTTT TCAGCGATTA
ATTGGAAAGG AAAAAATAAA AGGCTTTTGG GTATTTTGGT TGTGGAAGGA
CCTTGGACAA GAGAAACTCT TCGCGTCATG GCAAATGTGT TTGATTACGT
TACACCTTTA ACTCGTGTTT CCCAAGTTGC AGAAGCTATC AGAGCATATC
TAGATGGGGA TAAAACGAGA CTGAAGTGGT TAGTTAATTT CAGTATTGAA
GAAGCAGACC ACGACAACAT AACCTAA

FIG. 44B

>BsmBI CGTCTC 530 aa (SEQ ID NO:81)

MAKYGRGKFL PHQNYIDYMH FIVNHKNYSG MPNAIGEDGR INWQVSSGKT
TSFYEYYQAR FEWWEKKADE LNLPGTGNSN KRFSLAARLI HPTGQRPCRL
CGKYQYVGYM YVSHNLYKRW SKITGREDLF FKKQNIIEAA NIFKSIMGEQ
ALINELTTIF PERKDYFNRL PNIEDFFVSS SHIKNNGNYI SPGFMANPPD
RLDGFHDYGI CCRKEKDPGR HDDNMRLYNH DRRAFMWWSE GDWALADALY
NKAGAGKCAD PDCQKEVEKI SPDHVGPISC GFKQIPFFKP LCASCNSAKN
RRFSYQDVKE LLKYENYTGD SVASWQVRAL WDNCKHLVKN DDDSKLLSNL
MRSLQDYYLR SLYKLFSNGF AHLLSYFLTP EYAHYKITFE GLNTSTLEYE
RYYKTFKKTK STSSLAARIV RIAFEELEIY NSKDINERKL IKFDTSSWEK
DFENIISYAT KNLSLDEEAS KWNKVLTDKN LSSTEKDKKI SSLLEDKNYE
VYKKQFYILK DLLVEHFNKI GEQIAKDYMK

>BspQI GCTCTTC 430 aa (SEQ ID NO:16)

1 MRRLAKNSRN DSYLSNRDYQ EIVRENTTTI SFPLKEKHTL TLTKKIGLNQ 50
51 TAGFGGWFFP DSPCLLTVTV LSSFGTKVTS KTFSLSKDWN RVGLAWINEH 100
101 SSDTMSIVLE FSDVEIVHTW GLTCDVFNVH ELIIDAIEDQ NKLIDVLNQE 150
151 HLSPETYYLN HDSDTDLIEN LESTEEIKIV NQSQKQISLK KCCYCQRYMP 200
201 VNILVRSNSS FHKHKSKKTG FQNECRACKK WRINNSFNPV RTKDQLHESA 250
251 VITREKKILL KEPEILQKIK NRNNGEGLKS IIWKKFDKKC FNCEKELTIE 300
301 EVRLDHTRPL AYLWPIDEHA TCLCEKCNNT KHDMFPIDFY QGDEDKLRRL 350
351 ARITGLDYES LVKRDVNEVE LARIINNIED FATNVEARTF RSIRNKVKEV 400
401 RPDTDLFEIL KSKNINLYNE LQYELLTRKD 430

>BspQI GCTCTTC 1293 nt (SEQ ID NO:101)

ATGAGACGAT TAGCAAAAAA TTCACGGAAC GACAGTTATT TAAGTAATAG
GGATTACCAG GAAATCGTGA GGGAAAATAC CACTACAATA TCGTTTCCCT
TAAAAGAAAA ACATACTCTG ACTTTAACGA AAAAAATAGG GCTAAATCAG
ACTGCTGGAT TCGGAGGATG GTTTTTCCCT GATTCACCAT GTTTATTAAC
AGTAACTGTA CTATCCTCTT TCGGTACAAA GGTAACTTCT AAAACCTTTA
GCCTTTCTAA AGATTGGAAT CGTGTTGGGC TTGCTTGGAT TAACGAGCAT
TCGAGTGACA CCATAAGCAT TGTCCTAGAG TTTAGTGATG TGGAAATAGT
TCATACATGG GGACTTACAT GTGATGTTTT TAATGTCCAT GAATTAATTA
TTGATGCTAT AGAAGATCAA AATAAACTAA TAGACGTGCT AAATCAAGAA
CATTTATCTC CTGAAACATA TTATTTAAAC CATGACTCTG ATACTGATTT
AATTGAGAAT TTGGAATCTA CAGAAGAGAT AAAGATAGTT AACCAAAGCC
AAAAGCAAAT CTCTTTAAAA AAATGCTGTT ATTGTCAACG TTATATGCCT
GTGAACATAT TAGTTCGTTC AAATTCATCA TTTCATAAAC ACAAGAGTAA
GAAAACTGGT TTTCAAAATG AATGTCGGGC TTGTAAGAAG TGGAGAATAA
ATAATTCATT CAATCCAGTC AGAACAAAAG ACCAACTACA TGAATCAGCA
GTTATTACAC GTGAAAAAAA AATATTACTT AAAGAACCTG AAATATTACA
GAAAATCAAA AATAGAAATA ACGGTGAGGG CTTAAAAAGT ATTATATGGA

FIG. 44C

AAAAATTTGA TAAAAAATGC TTTAATTGTG AAAAAGAATT AACCATTGAA
GAGGTACGCC TAGACCATAC AAGACCACTT GCTTATCTGT GGCCTATCGA
TGAACACGCA ACTTGTTTAT GTGAAAAATG CAACAATACA AAACATGATA
TGTTTCCTAT CGATTTTTAT CAAGGGGACG AAGACAAATT AAGACGTTTA
GCTAGAATTA CGGGGTTAGA TTATGAATCT CTAGTTAAGA GGGACGTAAA
TGAAGTTGAA CTTGCAAGAA TAATCAATAA CATTGAAGAC TTTGCAACTA
ATGTAGAGGC ACGTACTTTT CGCTCAATAA GAAATAAAGT AAAAGAAGTA
CGTCCCGATA CTGACCTATT TGAAATTCTT AAATCTAAAA ATATTAATTT
ATATAATGAA CTTCAATATG AACTTCTTAC CCGTAAGGAT TAA

>EagI CGGCCG 301 aa (SEQ ID NO:82)

MKKRRDLVEV FGYNPMDLSP EVRALWNLGA CPFLNKECIK INHDQTIIYG
TCSVTSPYGD VIICPNRLYA NDYETLHKVS RDAFGDDVPF LTYSNFIKYR
ATYKDCIVAL GKNSGKEVQV GRALSMDWVL VRITDGELKE YVGVEIQSID
ITGNYRDAWH AYKNLKPIDI IDNLPTSQHG LNWANVHKRL IPQIIRKGVV
YSRSNYVKKG LYFILPEIVY NKFEDVIGAD IPLLKTQTNK SITVHTYSLG
EPAANGEQRK LISEREIIFD LDEFSKRFTT GPNLPKGDDL DAVIKKALGM
M

>EcoRI GAATTC 277 aa (SEQ ID NO:83)

MSNKKQSNRL TEQHKLSQGV IGIFGDYAKA HDLAVGEVSK LVKKALSNEY
PQLSFRYRDS IKKTEINEAL KKIDPDLGGT LFVSNSSIKP DGGIVEVKDD
YGEWRVVLVA EAKHQGKDII NIRNGLLVGK RGDQDLMAAG NAIERSHKNI
SEIANFMLSE SHFPYVLFLE GSNFLTENIS ITRPDGRVVN LEYNSGILNR
LDRLTAANYG MPINSNLCIN KFVNHKDKSI MLQAASIYTQ GDGREWDSKI
MFEIMFDIST TSLRVLGRDL FEQLTSK

>EcoRV GATATC 245 aa (SEQ ID NO:84)

MSLRSDLINA LYDENQKYDV CGIISAEGKI YPLGSDTKVL STIFELFSRP
IINKIAEKHG YIVEEPKQQN HYPDFTLYKP SEPNKKIAID IKTTYTNKEN
EKIKFTLGGY TSFIRNNTKN IVYPFDQYIA HWIIGYVYTR VATRKSSLKT
YNINELNEIP KPYKGVKVFL QDKWVIAGDL AGSGNTTNIG SIHAHYKDFV
EGKGIFDSED EFLDYWRNYE RTSQLRNDKY NNISEYRNWI YRGRK

>HindIII AAGCTT 300 aa (SEQ ID NO:85)

MKKSALEKLL SLIENLTNQE FKQATNSLIS FIYKLNRNEV IELVRSIGIL
PEAIKPSSTQ EKLFSKAGDI VLAKAFQLLN LNSKPLEQRG NAGDVIALSK
EFNYGLVADA KSFRLSRTAK NQKDFKVKAL SEWREDKDYA VLTAPFFQYP
TTKSQIFKQS LDENVLLFSW EHLAILLQLD LEETNIFPFE QLWNFPKKQS
KKTSVSDAEN NFMRDFNKYF MDLFKIDKDT LNQLLQKEIN FIEERSLIEK
EYWKKQINII KNFTREEAIE ALLKDINMSS KIETIDSFIK GIKSNDRLYL

FIG. 44D

>HpaI GTTAAC 254 aa (SEQ ID NO:86)

MKYEEINFKV PVESPYYPNY SQCVIERIYS ILRNQKDMGD DRIIINTNLK
KGLPLENINK IAGPMIEAWA EEVFSGIRDN RDNQYNLINV EAQERLGISD
IILQFQVNNN VITGNVDVKA TSNDIPDSGK SPNITSFSRI RTAYVKDPNF
IFIILSIKHS VYVKRNEYTN LMDGIMQIID FNVYDLKYIS DSDISYNPAL
GTGQIQIKDI HYVSSQKRTT WQMCQLLDLK YLRSKKRTIE QFYNEAKRNK
WIKD

>KpnI GGTACC 218 aa (SEQ ID NO:87)

MDVFDKVYSD DNNSYDQKTV SQRIEALFLN NLGKVVTRQQ IIRAATDPKT
GKQPENWHQR LSELRTDKGY TILSWRDMKV LAPQEYIMPH ATRRPKAAKR
VLPTKETWEQ VLDRANYSCE WQEDGQHCGL VEGDIDPIGG GTVKLTPDHM
TPHSIDPATD VNDPKMWQAL CGRHQVMKKN YWDSNNGKIN VIGILQSVNE
KQKNDALEFL LNYYGLKR

>NcoI CCATGG 288 aa (SEQ ID NO:88)

MATAPGHLLG QIIGNVMEEA LKPVLQEMAD RHDLYLDSKG LRPGVRSGAL
VTWTDDLGNN HDLDFVLERG GSATKAGNPA AFIEAAWRRY TKHSKAKAQE
IQGAVLPVLA AWNNVKPTPA AVVAGQWTAP SLQQMRSNGF VVLHLHFPTT
AQVFGGNGIN IEGTGEGTPD AFWQQQCDAY TSKSEADKDS LATALRTAHA
QEFRTFVAEL ERRVVRAIDY VVVTPLHGHG SQYTSIENAI EAVRTYSCGE
ESAPFLRFEI RISYTNGDVI QATFGSSSDA IEFLDTFN

>NheI GCTAGC 328 aa (SEQ ID NO:89)

MSSYHDDLNI LNVDFNHLRL TELIKLADQA EPFYLWVEKI FRQVSGRADS
LETIIEVEER VVLKMAILTC FTSDEKELPK LFNGVGVPYP HIKACYFFFA
WLVRDAATQR LDPLIREAFT QLKSIHPQMK KTELESEIFS QLLVNYRNEL
IHFSWPVIRE VLISRLEGSR RAARGSYLEL FVRTALAQSI TYFYKIYGNY
GKFLDVKIHD KPLKVKNRTY DVVAELIGNN HNTQYLILPV KTRETQGGGH
AHLFTRDIEQ SNNDIRELYP NAVIAPVIIA ENWSDTEKDL ENVGYNDIFH
FSVNPNRFAG FSDVEQIRLN RLVERILL

FIG. 44E

>NotI GCGGCCGC 383 aa (SEQ ID NO:90)

MRSDTSVEPE GANFIAEFFG HRVYPEVVST EAARNDQATG TCPFLTAAKL
VETSCVKAET SRGVCVVNTA VDNERYDWLV CPNRALDPLF MSAASRKLFG
YGPTEPLQFI AAPTLADQAV RDGIREWLDR GVHVVAYFQE KLGGELSISK
TDSSPEFSFD WTLAEVESIY PVPKIKRYGV LEIQTMDFHG SYKHAVGAID
IALVEGIDFH GWLPTPAGRA ALSKKMEGPN LSNVFKRTFY QMAYKFALSG
HQRCAGTGFA IPQSVWKSWL RHLANPTLID NGDGTFSLGD TRNDSENAWI
FVFELDPDTD ASPRPLAPHL EIRVNVDTLI DLALRESPRA ALGPSGPVAT
FTDKVEARML RFWPKTRRRR STTPGGQRGL FDA

>PstI CTGCAG 326 aa (SEQ ID NO:91)

MKELKLKEAK EILKALGLPP QQYNDRSGWV LLALANIKPE DSWKEAKAPL
LPTVSIMEFI RTEYGKDYKP NSRETIRRQT LHQFEQARIV DRNRDLPSRA
TNSKDNNYSL NQVIIDILHN YPNGNWKELI QQFLTHVPSL QELYERALAR
DRIPIKLLDG TQISLSPGEH NQLHADIVHE FCPRFVGDMG KILYIGDTAS
SRNEGGKLMV LDSEYLKKLG VPPMSHDKLP DVVVYDEKRK WLFLIEAVTS
HGPISPKRWL ELEAALSSCT VGKVYVTAFP TRTEFRKNAA NIAWETEVWI
ADNPDHMVHF NGDRFLGPHD KKPELS

>PvuII CAGCTG 157 aa (SEQ ID NO:92)

MSHPDLNKLL ELWPHIQEYQ DLALKHGIND IFQDNGGKLL QVLLITGLTV
LPGREGNDAV DNAGQEYELK SINIDLTKGF STHHHMNPVI IAKYRQVPWI
FAIYRGIAIE AIYRLEPKDL EFYYDKWERK WYSDGHKDIN NPKIPVKYVM
EHGTKIY

FIG. 44F

>SacI GAGCTC 358 aa (SEQ ID NO:93)

MGITIKKSTA EQVLRKAYEA AASDDVFLED WIFLATSLRE VDAPRTYTAA
LVTALLARAC DDRVDPRSIK EKYDDRAFSL RTLCHGVVVP MSVELGFDLG
ATGREPINNQ PFFRYDQYSE IVRVQTKARP YLDRVSSALA RVDEEDYSTE
ESFRALVAVL AVCISVANKK QRVAVGSAIV EASLIAETQS FVVSGHDVPR
KLQACVAAGL DMVYSEVVSR RINDPSRDFP GDVQVILDGD PLLTVEVRGK
SVSWEGLEQF VSSATYAGFR RVALMVDAAS HVSLMSADDL TSALERKYEC
IVKVNESVSS FLRDVFVWSP RDVHSILSAF PEAMYRRMIE IEVREPELDR
WAEIFPET

>SalI GTCGAC 315 aa (SEQ ID NO:94)

MINADKPHRW NDDVQASVRL YNQWFLDAAP KAYRDTRQLT IDEVEQAFQR
TANMTSITPE VLKAHPKTLA TLRMSTAPPI ARDRLVGLSH GSKSLLDTME
KGKLPPRMKG DVLDTHLAKM CAVLTDLLDL DLFHWYPTGE PAEPRQRELA
ATVVADRLCG AIADPIVRNA QERRQLALIE EWLLARGYTK KTHSASLPLN
TMQPGTFSFR QNVVVGSDLP VNIPVDAVIQ PHTPHSHKLP ILIEAKSAGD
FTNTNKRRKE EATKIHQLQL KYGNEISLTL FLCGYFNTGY LGYSAAEGLD
WVWEHRIDDL EAAGA

>SapI GCTCTTC 432 aa (SEQ ID NO:95)

MRRLATQRRE DAYKSNRDYQ TVHEAQSLRV NSTDDDNLSL FLLKDISPRE
DSKNIVGFGG FVKPEIATTM ALTLTTDIDK QIKSVPLSSN WNRISIVAKF
ASNPSVSITL GFDQTPWVDF WGINSDDIGL SFVSDAVPLE MSMIDSIHIA
PETLYLDHSS ACLLDIDPVE STRFKTGHGD PLSLKKCSYC GRLLPIDLER
PGKLSFHKHR AKITNHQNEC RSCKKWRINN SFNPMRTIDQ LNESALITRE
RKIFLQEPEI LQEIKDRTGA GLKSQVWERF HRKCFNCRKD LKLSEVQLDH
TRPLAYLWPI DEHATCLCAQ CNNTKKDRFP VDFYSEQQIR ELSDICGLPY
QDLCARSLNL DQLDRIERNI AEFSKEWDVR TFASTARRIS EVYPARDLFE
TLKKESESAY NKIIEKLKER PDALLDEALP LD

>SbfI CCTGCAGG 323 aa (SEQ ID NO:96)

MNSSDGIDGT VASIDTARAL LKRFGFDAQR YNVRSAVTLL ALAGLKPGDR
WVDSTTPRLG VQKIMDWSGE HWAKPYATGS REDFRKKTLR QWVDNGFAVL
NADNLNIATN SQLNEYCLSD EALQALRAYG TEGFEESLVV FLDEASKAVK
ARAEALQAAM ISVDLPGGEE FLLSPAGQNP LLKKMVEEFV PRFAPRSTVL
YLGDTRGKHS LFEREIFEEV LGLTFDPHGR MPDLILHDEV RGWLFLMEAV
KSKGPFDEER HRSLQELFVT PSAGLIFVNC FENRESMRQW LPELAWETEA
WVAEDPDHLI HLNGSRFLGP YER

FIG. 44G

>ScaI AGTACT 227 aa (SEQ ID NO:97)

MINDQLPRWV REARVGTRTG GPAMRPKTSD SPYFGWDSED WPEVTRQLLS
EQPLSGDTLV DAVLASWESI FESRLGSGFH IGTQIRPTPQ IMGFLLHALI
PLELANGDPS WRADLNSSEK DLVYQPDHKY SIEMKTSSHK DQIFGNRSFG
VENPGKGKKA KDGYYVAVNF EKWSDAPGRL PRIRTIRYGW LDHTDWVAQK
SQTGQQSSLP AVVSNTQLLA IHTGGQR

>SphI GCATGC 235 aa (SEQ ID NO:98)

MTSKDPIVLS ADQIAWLRQL KMSKRAALVR DYILEYGAVT TGKLAELGYS
HPPRAARDLK DAGAGVVTIM VKGPDGRRMA SYAFNGKANE DGAGRVVIPK
AFGEALKRAH GGKCAVCYGD FSERELQCDH RVPFAIAGDK PKLVQEDFMP
LCASDNRAKS WSCENCPNWE LKDEDTCRSC FWASPENYTH VSTRPERRIN
LLFQGDEVEI FDALKNAAAN EGVSLTEATK RKLAD

>SspI AATATT 281 aa (SEQ ID NO:99)

MSKAAYQDFT KRFSLLIKKH PNLITMTLSN IFTMRLIGNK THGDLAEIAI
SEFINQYMYD FKSIHVGKDL YRAKSKEEDI TVENEITKEK FPISLKAYGD
GPLQLSTDKN FLMYPLLEEI GAFINAKEKI EEIFANEAFS CFSEINVLPL
IYDEKRQRCN ILVFDAARAR AETAYIRKET EGSGRKHPAY RFFDKNKNYI
CEVRYGNAAA NALQRGLWTN TKNATSFFDS VTNGWVDYSH NLVLVKLLSH
ALVSSRKGHE AALEEIKKDI LQLKQTNGIN V

SEQUENCE LISTING

```
Sequence total quantity: 106
SEQ ID NO: 1           moltype = DNA  length = 1089
FEATURE                Location/Qualifiers
source                 1..1089
                       mol_type = other DNA
                       organism = Micrococcus luteus
SEQUENCE: 1
atgatcaagt acttgggtag caagcggacg ctcgtgcccg tcctcggtga catcgcttcg  60
gcctctgaag caacagaggc ggttgacctg ttcactggca cgacgcgtgt ggcgcaagag  120
ttcaagcgtc gcgggcttcg agttcttgct aacgacatag cgacgtactc cgaggtttta  180
gcccagtgct atatcgccac caacggccag gaagttgacc gccgtgcgct cgaggccgct  240
ctggcggagc tgaacgcctt gcccggcgaa cctggatact tcacggaaac cttctgtgag  300
gcttctcgct acttccagcc caagaacggg gctcgggtgg atgcaatcag gaatgcgatc  360
gacgaccggt acgcggactc atggatgcga ccgatcctcc tcacgagctt gatgcttgcg  420
gccgaccgcg tcgactccac taccggagtg cagatggctt acctgaagca gtgggccgcg  480
cgtgcgcaca atgatctaga gttgcggctt ccagacctaa tcgcaggtga cggtgacgct  540
gctcgtgagg atgcggtgac tctcgcacaa gagctgcctc gcgtccagct gatgtacctt  600
gatcctccct ataaccagca caggtacttc accaactacc atatttggga gaccctgatt  660
cgttgggatg cccctgagag ttatgggatc gcctgtaagc gcattgactc tcgagatgat  720
gccaccaaga gcccctataa tatgaagcgg cgaatgcccg acgagatgcg tcgcctgctg  780
atgaccatca aggcggacct cgcggttgta tcttacaaca atgagtcgtg gattgatccg  840
gagacgatga tgtcgaccct gcgcgatgcg ggatatgagg acgtgcgtct gctcgctttc  900
gactataagc gctacgttgg ggctcaaatc gggatctaca atccctccgg ggaaaaggtc  960
ggtcgtgtga gtcacctccg aaacatcgag tatctctttc ttgcgggacc aacggagcgc  1020
gttgaggtgt gcgccgcgag tgttgaacac cgagcactac ccaaggaacc ggaactcacc  1080
gcgttctag                                                          1089

SEQ ID NO: 2           moltype = AA  length = 362
FEATURE                Location/Qualifiers
source                 1..362
                       mol_type = protein
                       organism = Micrococcus luteus
SEQUENCE: 2
MIKYLGSKRT LVPVLGDIAS ASEATEAVDL FTGTTRVAQE FKRRGLRVLA NDIATYSEVL  60
AQCYIATNGQ EVDRRALEAA LAELNALPGE PGYFTETFCE ASRYFQPKNG ARVDAIRNAI  120
DDRYADSWMR PILLTSLMLA ADRVDSTTGV QMAYLKQWAA RAHNDLELRL PDLIAGDGDA  180
AREDAVTLAQ ELPRVQLMYL DPPYNQHRYF TNYHIWETLI RWDAPESYGI ACKRIDSRDD  240
ATKSPYNMKR RMPDEMRRLL MTIKADLAVV SYNNESWIDP ETMMSTLRDA GYEDVRLLAF  300
DYKRYVGAQI GIYNPSGEKV GRVSHLRNIE YLFLAGPTER VEVCAASVEH RALPKEPELT  360
AF                                                                 362

SEQ ID NO: 3           moltype = DNA  length = 1146
FEATURE                Location/Qualifiers
source                 1..1146
                       mol_type = other DNA
                       organism = Helicobacter pylori
SEQUENCE: 3
ttggagaatt ttttgaataa tttagatatt aaaaccttag ggcaggtttt cacccctaaa  60
aagatagtgg atttcatgct cactctcaag cacaatcatg ggagtgtttt agagccaagc  120
gcgggcgatg ggagtttttt aaagcgctta aaaaaggctg tagggattga aatcgatcct  180
aaaatctgcc ctaaaaatgc cctttgcatg gacttttttg actacccttt agaaaatcaa  240
tttgacacga ttattggcaa tccgccctat gtcaagcaca aggatattgc gccaagcacg  300
aaagaaaaac tccattacag cctttttgat gaaaggagta atctatactt gtttttcata  360
gaaaaagcga tcaagcattt aaagcctaaa ggcgaattga ttttcatcac cccaagggat  420
tttttaaaat ccacttctag cgtgaaatta aacgaatgga tttacaaaga aggcacgata  480
acgcattttt ttgaattagg cgatcaaaag attttcccaa acgccatgcc taattgcgtg  540
atttttcgtt tttgtaaagg tgatttcagt agaatcacca acgatggttt gcaatttgtg  600
tgcaaaaaag gcattttgta tttcctcaac caatcttaca cgcaaaaatt aagcgaggtt  660
tttaaggtta aggtgggggc agtgagcggg tgcgataaga tttttaaaaa tgaaacatac  720
```

```
gggaatttag aatttgtcac ctcaatcacc aaaagaacca atgttttaga aaaaatggtt  780
tttgtcaata aacctaatga ttatttactc cagcataaag acagcttgat gcaaagaaag  840
attaaaaaat tcaatgaaag taattggttt gaatgggggga ggatgcatca catatcccct  900
aaaaaacgca tttatgttaa cgccaaaacg cgccaaaaaa accccttttt catccaccaa  960
tgccctaatt atgacggctc tattttagcg ctattccctt ataaccaaaa tttggattta  1020
caaaacctct gcgataaact caacgctatc aactggcaag aattaggctt tgtgtgcggc  1080
gggcgttttt tgttttcgca gcgctcttta gaaaacgccc ttttgcctaa agacttttta  1140
aattag                                                              1146

SEQ ID NO: 4          moltype = DNA  length = 609
FEATURE               Location/Qualifiers
source                1..609
                      mol_type = other DNA
                      organism = Mycoplasma fermentans
SEQUENCE: 4
atgggtaaat ctgaattaag tggaagatta aattggcaag cattggctgg attaaaagct  60
agtggtgctg aacaaaactt atataacgtg tttaacgctg tttttgaagg aactaaatac  120
gttttatacg agaagccaaa gcaccttaaa aatctatacg ctcaagtagt cttacctgat  180
gatgttatta aagaaatttt taatccttta attgatttat caactactca atggggtgtt  240
tctccagatt tcgcaataga aaatacagaa acgcataaaa ttctttttgg tgaaattaaa  300
agacaagatg gatgggtaga aggtaaagat cctagtgctg gcaggggtaa tgcacatgag  360
agatcttgta aattatttac tcctggatta ttaaaagctt atagaacaat tggtggaatt  420
aacgatgaag agatattgcc attctgggtt gtattcgaag gtgatataac acgagatccc  480
aaaagagtaa gagaaattac tttctggtat gaccactatc aagataatta tttcatgtgg  540
cgaccaaatg aatcaggcga aaaattagtt caacacttca atgaaaaatt aaaaaaatat  600
ttagattaa                                                           609

SEQ ID NO: 5          moltype = AA  length = 202
FEATURE               Location/Qualifiers
source                1..202
                      mol_type = protein
                      organism = Mycoplasma fermentans
SEQUENCE: 5
MGKSELSGRL NWQALAGLKA SGAEQNLYNV FNAVFEGTKY VLYEKPKHLK NLYAQVVLPD  60
DVIKEIFNPL IDLSTTQWGV SPDFAIENTE THKILFGEIK RQDGWVEGKD PSAGRGNAHE  120
RSCKLFTPGL LKAYRTIGGI NDEEILPFWV VFEGDITRDP KRVREITFWY DHYQDNYFMW  180
RPNESGEKLV QHFNEKLKKY LD                                            202

SEQ ID NO: 6          moltype = DNA  length = 1152
FEATURE               Location/Qualifiers
source                1..1152
                      mol_type = other DNA
                      organism = Bacillus stearothermophilus
SEQUENCE: 6
atggctatta cattatgtga cataaatggt tgtagacttg agagaggaca tactggtaaa  60
cataataaat ttcctgaatt tgtatggact tctcaattta ataaaaaaga tattgataag  120
gtcaataaag caggatatgc aacaccaaga ggtggggaca aaggagccta tcagaaccat  180
gtttacagaa ataataaagt aattattcct tttgaaaggt tggaaaatgt taatttaaat  240
aactatcaag atggatatgt tattaggtta ttccctaatc agtactttga atcagccggg  300
gtagttaagc cggaattctt acaaccaaat tcatttgtta aagttgggga caatgcattt  360
attttatatc gcacacattc atcttttgag gaattacctc ctctaccaga ctgggaggtt  420
agacatctaa aaaagaacgg taatatagtt accagaagaa gtaaggacgt aatcgatgct  480
ggacattatg tcttacgatt atcatcaatt agtaacaaaa aagaaagaaa agagggccct  540
cctcaaggta tttttgcacc tgaatatgca aatgcagaga ctaattatct gtcaaaagca  600
tttttagcct ggttaattat taaaactcaa aatagtccgt ataatgaaga acaattccaa  660
cacttaagag cgatcttaat tagtcataat ctcatcaata tttctcaact tgaagaaaag  720
gctattctaa agaatggtat cacatgctgc cctttatgcg agcaaattat tttttacgaa  780
cagctacacg aaatggtttc ttttgaaggt gcgtctggcc ttgcgaattc acaagaacag  840
gttgagggtg caactaggtc aacatcagtt aatttattcc atatggtacc attagtatat  900
gaaaccttgg aacacaaacc tgatcaaata gcatggggcc atgccatttg taatactaga  960
cttggtcaaa gagagtgcct gcctcttagt agactaaaac aagaaggtac gcccgttggt  1020
cttcttgatg aagattcgaa tcttgaagta ttaggatgga ttagtaaaga taagcaattt  1080
attcgtacag aaaatgggga agtttggatt aaaattacag atattgaatt taacgatgac  1140
tttgaagaat aa                                                       1152

SEQ ID NO: 7          moltype = AA  length = 383
FEATURE               Location/Qualifiers
source                1..383
                      mol_type = protein
                      organism = Bacillus stearothermophilus
SEQUENCE: 7
MAITLCDING CRLERGHTGK HNKFPEFVWT SQFNKKDIDK VNKAGYATPR GGDKGAYQNH  60
VYRNNKVIIP FERLENVNLN NYQDGYVIRL FPNQYFESAG VVKPEFLQPN SFVKVGDNAF  120
ILYRTHSSFE ELPPLPDWEV RHLKKNGNIV TRRSKDVIDA GHYVLRLSSI SNKKERKEGP  180
PQGIFAPEYA NAETNYLSKA FLAWLIIKTQ NSPYNEEQFQ HLRAILISHN LINISQLEEK  240
AILKNGITCC PLCEQIIFYE QLHEMVSFEG ASGLANSQEQ VEGATRSTSV NLFHMVPLVY  300
ETLEHKPDQI AWGHAICNTR LGQRECLPLS RLKQEGTPVG LLDEDSNLEV LGWISKDKQF  360
IRTENGEVWI KITDIEFNDD FEE                                           383
```

```
SEQ ID NO: 8           moltype = DNA  length = 1536
FEATURE                Location/Qualifiers
source                 1..1536
                       mol_type = other DNA
                       organism = Bacillus stearothermophilus
SEQUENCE: 8
atgatttttg ctgatattga atttgaaaaa gaactttttt cagctgctaa taaattaagg  60
ggaaaaattg ctccaagtga gtataagcat tatgttttgc ctttgatatt ccttagatat  120
ttatctctta aataccaaca aagaaggaat gaaattcaac aacagataaa tgattcaagg  180
gatcacaaga aaaatcaaga tgaagtgtta aagatattgg aagacaggac tgaatacacc  240
aaagtaaatg ttttctatat tcctgaaaaa gctagttggg aatacttatt gaaaaattcc  300
gaaaatgata aaattaaaga aatgatagat tcagctatgg aaatactgga aaatgaatat  360
gacgagttaa aaggtgtttt gccaaagata tataaaaact caaatatacc gaatgaagtt  420
attagtgatt tactaaaact attttctcaa gaagtatttt cagcacatga tggaagaaat  480
gttgatttat tggggagagt ttatgaatac tttataagta attttgctac tacagaaggt  540
actagaggtg gtgaatattt tacaccgtct tcaatcgtaa aattattggt agcaatgcta  600
gagcccatta aaggtacagt ttatgatccg gcctgtggga caggaggaat gtttattcag  660
tctaataaat atagagaaaa taatcataac ttgtgttttg taggccagga acaaaacgag  720
cttactatca aattggctaa aatgaatgga attctacatg gaataaatcc tgaaattaga  780
caaggtgatt cattattaaa tgaccgttat ccagaattga aagctgaaat tgtaatatct  840
aatccaccgt ttaatatgaa ggattgggga gctgaacgcc tgccacttaa tgataagcga  900
ttaataggac cggtaacaaa cagtaatgca aattacatgt ggatacagca ttttctatac  960
catttaaaag atggtggttt agcaggattt gttattgcta atggagcttt gactagtaat  1020
ctggctgctg aaaaaattgt aaggaaacac ttaatagaca atgattatgt agattgtgtt  1080
gttcaattac ctgaaaaaat gttctttggt actggcattc caagtgcttt agtgttttta  1140
agtaagaatc gaaatggaag taacggccat gccaaaagag aaaaagaggt tctatttatt  1200
gatgcaagcg ataagggaac attagtgggt aaaaagaata aaatattttt agatgatgaa  1260
ataaaagaaa ttgcagattt atatcattca tttaaatttt taaatgataa tgattataac  1320
catagtggtt tttacaaaaa ggttaacatt gaaaaaatcg tggaaaatga ttataaatta  1380
actccaactc tctatgtagg tgtaaaggaa gagactgaaa tggagaagcc atttagagaa  1440
atgataatag aatataaagc gatattagag caacaatttg aagaatcaaa caaactacag  1500
cagaaaatat taaagaattt agagggatta ttatga                            1536

SEQ ID NO: 9           moltype = AA  length = 511
FEATURE                Location/Qualifiers
REGION                 1..511
                       note = misc_feature - protein sequence for M.BstXI
source                 1..511
                       mol_type = protein
                       organism = Bacillus stearothermophilus
SEQUENCE: 9
MIFADIEFEK ELFSAANKLR GKIAPSEYKH YVLPLIFLRY LSLKYQQRRN EIQQQINDSR  60
DHKKNQDEVL KILEDRTEYT KVNVFYIPEK ASWEYLLKNS ENDKIKEMID SAMEILENEY  120
DELKGVLPKI YKNSNIPNEV ISDLLKLFSQ EVFSAHDGRN VDLLGRVYEY FISNFATTEG  180
TRGGEYFTPS SIVKLLVAML EPIKGTVYDP ACGTGGMFIQ SNKYRENNHN LCFVGQEQNE  240
LTIKLAKMNG ILHGINPEIR QGDSLLNDRY PELKAEIVIS NPPFNMKDWG AERLPLNDKR  300
LIGPVTNSNA NYMWIQHFLY HLKDGGLAGF VIANGALTSN LAAEKIVRKH LIDNDYVDCV  360
VQLPEKMFFG TGIPSALVFL SKNRNGSNGH AKREKEVLFI DASDKGTLVG KKNKIFLDDE  420
IKEIADLYHS FKFLNDNDYN HSGFYKKVNI EKIVENDYKL TPTLYVGVKE ETEMEKPFRE  480
MIIEYKAILE QQFEESNKLQ QKILKNLEGL L                                 511

SEQ ID NO: 10          moltype = DNA  length = 1179
FEATURE                Location/Qualifiers
misc_feature           1..1179
                       note = DNA sequence of S.BstXI
source                 1..1179
                       mol_type = other DNA
                       organism = Bacillus stearothermophilus
SEQUENCE: 10
atgaaaagta ctttgaagga atataaattg ggtgatatta ccgaagtcgt taatggtgcc  60
actccttcaa ctaaaaagcc tgagtactat gaaaatggta caattccatg gattactcct  120
aaagatttat caggctatta ctttaaatat atatctcatg gtgaacgtaa tataacagag  180
cttggtctaa gaaatagttc agctaagttg ttaccaaaag gaactgtatt attttcctca  240
agagccccaa taggatacgt agcaatagct gataattggt taactacgaa ccagggattt  300
aaaagtttta tatgtaatga ggagattatt tacaatgaat acctttatta ttttcttatt  360
gctaaaaggg attttattga aacatttgcg aatgggagta cgtttaaaga gctttcatca  420
acttctgcaa agaatatacc aatcaatctt cctagtttag aagagcaaaa gaagattgtg  480
acaattttag ggggatttgga tagaaagata gaattaaatt ataaaattat tgaaagctta  540
gaaaaaatag cagaaagaac atataaatat tggtttgtcg atgaattaaa tcaagatgaa  600
cagcacatcc gtaatggatg ggaaactgct aaaattggcg atgtggtgga acttttggga  660
gggggaaccc ctaaaacttc ggaaagtaag tattgggaag atggagatat taattggttt  720
actccttcag atttaacaaa aactagacag ctttttgtac gtgattctca aagaaaaata  780
acaattgatg gacttaataa cagtgcagcg aaattaattc ccccttattc cttgttaatg  840
tcaagtagag ctacaattgg cgagttggca attaatcaag aatctgctac tacaaatcaa  900
gggtttattg tattaatacc aaatgaaaaa atttctattt accaattata cttttgggct  960
aaacttaata agagcaaaat tatttcaatg gcaaatggta gtacttttaa agaaattagt  1020
aagcgggatt ttaaatcttt ggagataata ttaccaaaaa atatagacac ttttaattca  1080
attatgcaag attattttag gaaaattgag gagttaattg atgaaataaa aatcttaaaa  1140
accgcaagag ataatttaat tccaaaactt ataaaatga                         1179
```

```
SEQ ID NO: 11          moltype = AA  length = 392
FEATURE                Location/Qualifiers
REGION                 1..392
                       note = misc_feature - protein sequence for S.BstXI
source                 1..392
                       mol_type = protein
                       organism = Bacillus stearothermophilus
SEQUENCE: 11
MKSTLKEYKL GDITEVVNGA TPSTKKPEYY ENGTIPWITP KDLSGYYFKY ISHGERNITE  60
LGLRNSSAKL LPKGTVLFSS RAPIGYVAIA DNWLTTNQGF KSFICNEEII YNEYLYYFLI  120
AKRDFIETFA NGSTFKELSS TSAKNIPINL PSLEEQKKIV TILGDLDRKI ELNYKIIESL  180
EKIAERTYKY WFVDELNQDE QHIRNGWETA KIGDVVELLG GGTPKTSESK YWEDGDINWF  240
TPSDLTKTRQ LFVRDSQRKI TIDGLNNSAA KLIPPYSLLM SSRATIGELA INQESATTNQ  300
GFIVLIPNEK ISIYQLYFWA KLNKSKIISM ANGSTFKEIS KRDFKSLEII LPKNIDTFNS  360
IMQDYFRKIE ELIDEIKILK TARDNLIPKL IK                               392

SEQ ID NO: 12          moltype = DNA  length = 770
FEATURE                Location/Qualifiers
source                 1..770
                       mol_type = other DNA
                       organism = Planococcus citreus
SEQUENCE: 12
atgaaacagt ttgcagatcc ttttgaaaga agattccttg atgcaattga acatcatctt  60
gatggaattt ctgagaaaat aaaaaaagac tttacacaca aaaacttttt aaaagaattg  120
aatggcctta aaggtgataa agtctatcat gacttaggct ttgataccgc tgaatatact  180
ctggtacgtc ttataggaag aatgagcata agcgttggga gaaggctggg ggagatatac  240
gataaagtcc ctcgttatgt tgctgccgcg cgatttggtc ttcaaccaaa tcaaattgca  300
gaagtatttg atggtcttga gttagatata gctttgcgca atagcctttt gtcagatgat  360
gataaaattc acataaaaaa aataactgaa aagatgtcag gcgaaacata ctcgggaatc  420
ggaatcgaaa ttcgttataa ctttaatcca aatgacagtt cccgtttaag aaaagacgtc  480
gatgtagctt ctaaattgtc ggccgcgggg ttatttcctg tttatttaat atttagctct  540
ctcagtccta ggaatgatgc aatagcccgt cttaaaagag ggggatggag ctttaaacag  600
gggcaggaag ccttagactt ccttaccgaa cttttaggag tggatattgg gtctgtttta  660
tctgacccaa taatagccgc agaaactagg gagaaaacat caaaaattat gaagtctata  720
tttgaatcag aggcattcca atctgttata ccgggagagt ggagtaaact             770

SEQ ID NO: 13          moltype = AA  length = 257
FEATURE                Location/Qualifiers
source                 1..257
                       mol_type = protein
                       organism = Planococcus citreus
SEQUENCE: 13
MKQFADPFER RFLDAIEHHL DGISEKIKKD FTHKNFLKEL NGLKGDKVYH DLGFDTAEYT  60
LVRLIGRMSI SVGRRLGEIY DKVPRYVAAA RFGLQPNQIA EVFDGLELDI ALRNSLLSDD  120
DKIHIKKITE KMSGETYSGI GIEIRYNFNP NDSSRLRKDV DVASKLSAAG LFPVYLIFSS  180
LSPRNDAIAR LKRGGWSFKQ GQEALDFLTE LLGVDIGSVL SDPIIAAETR EKTSKIMKSI  240
FESEAFQSVI PGEWSKL                                                257

SEQ ID NO: 14          moltype = DNA  length = 1347
FEATURE                Location/Qualifiers
misc_feature           1..1347
                       note = DNA sequence for M.PciI
source                 1..1347
                       mol_type = other DNA
                       organism = Planococcus citreus
SEQUENCE: 14
atgacaaatt tttcgcactc agctctaacg agctacgatc ttctcgggca tgaaattgtc  60
caagattctg aagctgttag ctcgggtcca tatctggtca gctatgaccc gatccctgta  120
cgtcggtcta cattcctagc tggactgtca gagaacgttc actcgtggtt tcgtctcaca  180
ccaagtttcg gaccggatct agttcgaaca atcatcaaac agatgaatct tgcgccgcac  240
tcacacatcc atgacccttt ctcaggagcc gggactaccg cgattgaggc ttcgttagag  300
ggctatgaag caagctgcgt agaagttaat ccgtttctct acttcgtggg gaaaacatcc  360
atagattggt ctatcaatgc tgatgatgct gcagcgcagc tagaaagcat taaaaataaa  420
tattatagca tgtctgcaac cgctactttg gataacatag ccgacctagg aatagatata  480
ccaaaaatac acaatattca tcggtggtgg agaaacgatg ttcttaaaga tatattagtc  540
ctaaaatctt ctatcagatc ttgcacacaa gataagtatt gttccttttt tgagctagcc  600
ctagctgcag ttctcgttcc agatttgaca aatgtaacgc taggaaaact acaactgcac  660
tttgtaaaca aagacgataa agagataaac gtctggccta catatgaatc tcatgcaaaa  720
aaaatgattc acgacttgtc attaattaat aagcaaaatt tcgaattttt gcccaagatt  780
atttatggtg attcaactca aaaatcaaca tttagcgagg tggcagggat agatgctata  840
ataacatccc ctccgtaccc taataggtac agctatattt ggaatactcg ccctcacctg  900
tacattcttg atatgatttc cgaagcaaaa gaggcttcgc aaatagatcg tagaacgatt  960
ggtggaacat gggggacagc aacttccgaa ttaggaaagg gtatattttc tccaatcaat  1020
gctgtagtca aagacgcgct tgaaggggtt cacgaaagaa tcgccggttc cgatcaactc  1080
atggcaaact atgtaactca ttattttaat cggctctttt tacatataga agctataaaa  1140
ccatcactta atccaaaagc aaagcttgct tatgttgttg ggaactcttg gattaagggc  1200
gaatatgtag ccactgacgt aatcttagca aaaattatcg aaggggcttt gccaggctca  1260
tcaattgatg gtcttcatcg tttccgtcgc cggaacagtg gaaagaatct ctttgaaact  1320
```

```
atagtttact ccactctccc ggtataa                                    1347

SEQ ID NO: 15          moltype = AA  length = 448
FEATURE                Location/Qualifiers
REGION                 1..448
                       note = misc_feature - Protein sequence for M.PciI
source                 1..448
                       mol_type = protein
                       organism = Planococcus citreus
SEQUENCE: 15
MTNFSHSALT SYDLLGHEIV QDSEAVSSGP YLVSYDPIPV RRSTFLAGLS ENVHSWFRLT  60
PSFGPDLVRT IIKQMNLAPH SHIHDPFSGA GTTAIEASLE GYEASCVEVN PFLYFVGKTS  120
IDWSINADDA AAQLESIKNK YYSMSATATL DNIADLGIDI PKIHNIHRWW RNDVLKDILV  180
LKSSIRSCTQ DKYCSFFELA LAAVLVPDLT NVTLGKLQLH FVNKDDKEIN VWPTYESHAK  240
KMIHDLSLIN KQNFEFLPKI IYGDSTQKST FSEVAGIDAI ITSPPYPNRY SYIWNTRPHL  300
YILDMISEAK EASQIDRRTI GGTWGTATSE LGKGIFSPIN AVVKDALEGV HERIAGSDQL  360
MANYVTHYFN RLFLHIEAIK PSLNPKAKLA YVVGNSWIKG EYVATDVILA KIIEGALPGS  420
SIDGLHRFRR RNSGKNLFET IVYSTLPV                                   448

SEQ ID NO: 16          moltype = AA  length = 430
FEATURE                Location/Qualifiers
source                 1..430
                       mol_type = protein
                       organism = Bacillus sphaericus
SEQUENCE: 16
MRRLAKNSRN DSYLSNRDYQ EIVRENTTTI SFPLKEKHTL TLTKKIGLNQ TAGFGGWFFP  60
DSPCLLTVTV LSSFGTKVTS KTFSLSKDWN RVGLAWINEH SSDTMSIVLE FSDVEIVHTW  120
GLTCDVFNVH ELIIDAIEDQ NKLIDVLNQE HLSPETYYLN HDSDTDLIEN LESTEEIKIV  180
NQSQKQISLK KCCYCQRYMP VNILVRSNSS FHKHKSKKTG FQNECRACKK WRINNSFNPV  240
RTKDQLHESA VITREKKILL KEPEILQKIK NRNNGEGLKS IIWKKFDKKC FNCEKELTIE  300
EVRLDHTRPL AYLWPIDEHA TCLCEKCNNT KHDMFPIDFY QGDEDKLRRL ARITGLDYES  360
LVKRDVNEVE LARIINNIED FATNVEARTF RSIRNKVKEV RPDTDLFEIL KSKNINLYNE  420
LQYELLTRKD                                                       430

SEQ ID NO: 17          moltype = DNA  length = 1245
FEATURE                Location/Qualifiers
source                 1..1245
                       mol_type = other DNA
                       organism = Enterobacter aerogenes
SEQUENCE: 17
gtgaatcaga aaaatgaaaa atcatttatg cgtttgcaat caacctttag cggtggcaaa  60
ggtagtccaa tgcatgattg gtacccatat ttagagggtt attctcccga atttgtgaaa  120
tgcttgattt cacgatttgc tcctaaagcc aaaacaattt tagatccatt ttgtggctct  180
ggaacaacag ccattgtttc cgttttagag ggtttaaata attactattg cgaagtaaac  240
cctttatgcc aatatattat tgaaactaaa ctaatagctt taacattaag cgaagaagaa  300
aaaacaaaat tagtaaatga actttattct atttctaatg aaataactaa tgtactcaaa  360
ccttctgcaa ccgagacaga tctagagaaa tcatttaaat ccgtttttgg taatacgaaa  420
ttttttgagg atcacatatt taaagatata cttagttatc aatgttacat tagctctatc  480
gaagatgaaa atcttaagag acttctgaca atagcaggga ttagatcgtt aatcccttcc  540
tcgttattgg taagacgagg tgatttacga ttcaagacac aaaaagaatt agagaaaggc  600
aaccagggct ttcgctttca tgtacaaaaa agcttagaat taattgccag tgatttatta  660
gacattacgg aaggtagtgg tttagctacc ttcttatgtg atgatgccaa agaaatatct  720
gggaataacc tgattgatgc tgtaataaca agcccgccat atttaaatgg cacaaattat  780
tttagaaata ctaaaattga actttggttt atagggaaat taaagaccaa atcagatcta  840
agacattata gggatttagc tattaccagt ggtattaacg atgtaactaa aggtaaaagc  900
ttatcttcaa ataatactat tatctcagaa ataccattat tatctgaatg tattaaagaa  960
ctaagcataa aagagtatga tagtcgtatt tcaatgatgg ttgaaaacta cttttgggac  1020
atgttcaaat tcttatcaaa actcccaaaa ttactaacta atgatgcgac tatctgtata  1080
gatttaggtg attctgttta ttgtaacgtc tacatcccta cacaagatat tttgaaagaa  1140
atgatgtcaa agttaggttt tgaagagaac gaaagggtca ttcttcgtga acgaaaatcc  1200
cgcaatggaa caaagttagt ccagactgtt caggttttta aatga                 1245

SEQ ID NO: 18          moltype = DNA  length = 1140
FEATURE                Location/Qualifiers
source                 1..1140
                       mol_type = other DNA
                       organism = Enterobacter aerogenes
SEQUENCE: 18
atgaaaaata aatattttag taaaaaatgg gagcaattca agaaagaatt accccatcaa  60
tcaggtgaaa tggtaaagag aaattggggc cataactggc actctatgtg ttcataccaa  120
gggaaactta aaccatcaat agctagatct ttaattgata cattcatgcc atcaagtaag  180
ggacgtatat tagatgtctt ctcaggtgtt ggcaccattc ctttcgaagc aagattactt  240
ggtcatactg catatggatt tgatattagt ccagcagcag ttaatatttc acgcgcaaaa  300
ctagaagtta taagtaaaaa tgaaatccaa gaggtaatta ataaattatc tgattttatt  360
gagcaaaaca aaaattcaat agattataac gaacataatt taataaggtt taatggttca  420
attgaatcct attttcatcc tgaaactttt aaggaaatac tgtgtgctcg taaattcttt  480
ttaataaaag gtgaattaaa tgcatctgaa tcgttagtac agtcatgttt attacatatt  540
ttacatggta atcgtccgta tgcattgagt agaaagtccc atcctattac acctttcgcg  600
cctactggag attttatata cagtaattta gttataaagt taatcaaaaa agttgaaaga  660
```

```
gtcttgcaaa attctgatgg tatcccagat actggcagca aagtatttta tcaggactct  720
acaaaaagtt ggcctgaaga agtaaataat ttagatgcaa ttataacatc acctccattt  780
tatgatagta cccgtttcta ttcagcaaat tggatgcgat tatggttttc tggttgggaa  840
aaagatgact tccaaacgaa gccaaaagat tttgtggacg aaactcagaa aaaaagcttt  900
gaaatatatg ataatatatt caaacaatct caacaatgct taaaaaaaga tggcgttttt  960
ttaatgcacg ttggcaaaag taaaaaaagt gatatggcag gacaaattgc taaaattggt  1020
agtaattatc ttagccttat agatatattt gacgaaagtg ttgaacattg cgaaagtcac  1080
ggaattaaag acaaaggcac gacaacccat catcagtacc ttgtctttac gaaagattag  1140

SEQ ID NO: 19          moltype = AA  length = 213
FEATURE                Location/Qualifiers
source                 1..213
                       mol_type = protein
                       organism = Bacillus amyloliquefaciens
SEQUENCE: 19
MEVEKEFITD EAKELLSKDK LIQQAYNEVK TSICSPIWPA TSKTFTINNT EKNCNGVVPI  60
KELCYTLLED TYNWYREKPL DILKLEKKKG GPIDVYKEFI ENSELKRVGM EFETGNISSA  120
HRSMNKLLLG LKHGEIDLAI ILMPIKQLAY YLTDRVTNFE ELEPYFELTE GQPFIFIGFN  180
AEAYNSNVPL IPKGSDGMSK RSIKKWKDKV ENK                               213

SEQ ID NO: 20          moltype = AA  length = 194
FEATURE                Location/Qualifiers
source                 1..194
                       mol_type = protein
                       organism = Oceanospirillum kriegii
SEQUENCE: 20
MKIKRIEVLI NNGSVPGIPM ILNEIQDAIK TVSWPEGNNS FVINPVRKGN GVKPIKNSCM  60
RHLHQKGWAL EHPVRIKAEM RPGPLDAVKM IGGKAFALEW ETGNISSSHR AINKMVMGML  120
ERVIIGGVLI LPSRDMYNYL TDRVGNFREL EPYFSVWRQF NLKDAYLAIV EIEHDSVDAQ  180
VSLIPKGTDG RAIR                                                    194

SEQ ID NO: 21          moltype = AA  length = 180
FEATURE                Location/Qualifiers
REGION                 1..180
                       note = MISC_FEATURE - Residues 1-180 correspond to residues
                        22-201 of the protein sequence of BamHI (seq id no. 19)
source                 1..180
                       mol_type = protein
                       organism = Bacillus amyloliquefaciens
SEQUENCE: 21
IQQAYNEVKT SICSPIWPAT SKTFTINNTE KNCNGVVPIK ELCYTLLEDT YNWYREKPLD  60
ILKLEKKKGG PIDVYKEFIE NSELKRVGME FETGNISSAH RSMNKLLLGL KHGEIDLAII  120
LMPIKQLAYY LTDRVTNFEE LEPYFELTEG QPFIFIGFNA EAYNSNVPLI PKGSDGMSKR  180

SEQ ID NO: 22          moltype = AA  length = 177
FEATURE                Location/Qualifiers
REGION                 1..177
                       note = MISC_FEATURE - Residues 1-177 correspond to residues
                        18-194 of the protein sequence of OkrAI (seq id no. 20)
source                 1..177
                       mol_type = protein
                       organism = Oceanospirillum kriegii
SEQUENCE: 22
IPMILNEIQD AIKTVSWPEG NNSFVINPVR KGNGVKPIKN SCMRHLHQKG WALEHPVRIK  60
AEMRPGPLDA VKMIGGKAFA LEWETGNISS SHRAINKMVM GMLERVIIGG VLILPSRDMY  120
NYLTDRVGNF RELEPYFSVW RQFNLKDAYL AIVEIEHDSV DAQVSLIPKG TDGRAIR     177

SEQ ID NO: 23          moltype = DNA  length = 38
FEATURE                Location/Qualifiers
misc_feature           1..38
                       note = primer
source                 1..38
                       mol_type = other DNA
                       organism = synthetic construct
SEQUENCE: 23
attcaacaag catacaatgc agttaaaaca tctattgt                          38

SEQ ID NO: 24          moltype = DNA  length = 39
FEATURE                Location/Qualifiers
misc_feature           1..39
                       note = primer
source                 1..39
                       mol_type = other DNA
                       organism = synthetic construct
SEQUENCE: 24
acaaatagat gttttaactg cattgtatgc ttgttgaat                         39

SEQ ID NO: 25          moltype = DNA  length = 39
FEATURE                Location/Qualifiers
```

```
misc_feature           1..39
                       note = primer
source                 1..39
                       mol_type = other DNA
                       organism = synthetic construct
SEQUENCE: 25
caagcataca atgaagttgc aacatctatt tgttcacct                         39

SEQ ID NO: 26          moltype = DNA  length = 39
FEATURE                Location/Qualifiers
misc_feature           1..39
                       note = primer
source                 1..39
                       mol_type = other DNA
                       organism = synthetic construct
SEQUENCE: 26
aggtgaacaa atagatgttg caacttcatt gtatgcttg                         39

SEQ ID NO: 27          moltype = DNA  length = 39
FEATURE                Location/Qualifiers
misc_feature           1..39
                       note = primer
source                 1..39
                       mol_type = other DNA
                       organism = synthetic construct
SEQUENCE: 27
acgattaaca acaccgaagc aaattgtaac ggtgtagta                         39

SEQ ID NO: 28          moltype = DNA  length = 40
FEATURE                Location/Qualifiers
misc_feature           1..40
                       note = primer
source                 1..40
                       mol_type = other DNA
                       organism = synthetic construct
SEQUENCE: 28
acgattaaca acaccgaagc aaattgtaac ggtgtagtat                        40

SEQ ID NO: 29          moltype = DNA  length = 39
FEATURE                Location/Qualifiers
misc_feature           1..39
                       note = primer
source                 1..39
                       mol_type = other DNA
                       organism = synthetic construct
SEQUENCE: 29
aacggtgtag taccaattgc agaactatgt tacacctta                         39

SEQ ID NO: 30          moltype = DNA  length = 39
FEATURE                Location/Qualifiers
misc_feature           1..39
                       note = primer
source                 1..39
                       mol_type = other DNA
                       organism = synthetic construct
SEQUENCE: 30
taaggtgtaa catagttctg caattggtac tacaccgtt                         39

SEQ ID NO: 31          moltype = DNA  length = 39
FEATURE                Location/Qualifiers
misc_feature           1..39
                       note = primer
source                 1..39
                       mol_type = other DNA
                       organism = synthetic construct
SEQUENCE: 31
aacccccttg atatacttgc acttgaaaag aaaaaaggt                         39

SEQ ID NO: 32          moltype = DNA  length = 39
FEATURE                Location/Qualifiers
misc_feature           1..39
                       note = primer
source                 1..39
                       mol_type = other DNA
                       organism = synthetic construct
SEQUENCE: 32
acctttttc ttttcaagtg caagtatatc aaggggttt                          39

SEQ ID NO: 33          moltype = DNA  length = 36
```

```
FEATURE                Location/Qualifiers
misc_feature           1..36
                       note = primer
source                 1..36
                       mol_type = other DNA
                       organism = synthetic construct
SEQUENCE: 33
gatatactta aacttgcaaa gaaaaaaggt ggtccg                    36

SEQ ID NO: 34          moltype = DNA  length = 39
FEATURE                Location/Qualifiers
misc_feature           1..39
                       note = primer
source                 1..39
                       mol_type = other DNA
                       organism = synthetic construct
SEQUENCE: 34
cggaccacct tttttctttg caagtttaag tatatcaag                 39

SEQ ID NO: 35          moltype = DNA  length = 39
FEATURE                Location/Qualifiers
misc_feature           1..39
                       note = primer
source                 1..39
                       mol_type = other DNA
                       organism = synthetic construct
SEQUENCE: 35
atacttaaac ttgaaaaggc aaaaggtggt ccgattgat                 39

SEQ ID NO: 36          moltype = DNA  length = 40
FEATURE                Location/Qualifiers
misc_feature           1..40
                       note = primer
source                 1..40
                       mol_type = other DNA
                       organism = synthetic construct
SEQUENCE: 36
atcaatcgga ccaccttttg ccttttcaa gtttaagtat                 40

SEQ ID NO: 37          moltype = DNA  length = 39
FEATURE                Location/Qualifiers
misc_feature           1..39
                       note = primer
source                 1..39
                       mol_type = other DNA
                       organism = synthetic construct
SEQUENCE: 37
ggtccgattg atgtttatgc agagttcata gaaaacagt                 39

SEQ ID NO: 38          moltype = DNA  length = 39
FEATURE                Location/Qualifiers
misc_feature           1..39
                       note = primer
source                 1..39
                       mol_type = other DNA
                       organism = synthetic construct
SEQUENCE: 38
actgttttct atgaactctg cataaacatc aatcggacc                 39

SEQ ID NO: 39          moltype = DNA  length = 37
FEATURE                Location/Qualifiers
misc_feature           1..37
                       note = primer
source                 1..37
                       mol_type = other DNA
                       organism = synthetic construct
SEQUENCE: 39
atagaaaaac agtgaacttg cacgtgtagg tatggaa                   37

SEQ ID NO: 40          moltype = DNA  length = 39
FEATURE                Location/Qualifiers
misc_feature           1..39
                       note = primer
source                 1..39
                       mol_type = other DNA
                       organism = synthetic construct
SEQUENCE: 40
aaattccata cctacacgtg caagttcact gttttctat                 39
```

```
SEQ ID NO: 41          moltype = DNA  length = 39
FEATURE                Location/Qualifiers
misc_feature           1..39
                       note = primer
source                 1..39
                       mol_type = other DNA
                       organism = synthetic construct
SEQUENCE: 41
ggaaatatta gttctgccgc acgttcaatg aacaaactt                        39

SEQ ID NO: 42          moltype = DNA  length = 39
FEATURE                Location/Qualifiers
misc_feature           1..39
                       note = primer
source                 1..39
                       mol_type = other DNA
                       organism = synthetic construct
SEQUENCE: 42
aagtttgttc attgaaacgt gcggcagaac taatattcc                        39

SEQ ID NO: 43          moltype = DNA  length = 39
FEATURE                Location/Qualifiers
misc_feature           1..39
                       note = primer
source                 1..39
                       mol_type = other DNA
                       organism = synthetic construct
SEQUENCE: 43
aatattagtt ctgcccacgc atcaatgaac aaacttcta                        39

SEQ ID NO: 44          moltype = DNA  length = 39
FEATURE                Location/Qualifiers
misc_feature           1..39
                       note = primer
source                 1..39
                       mol_type = other DNA
                       organism = synthetic construct
SEQUENCE: 44
tagaagtttg ttcattgatg cgtgggcaga actaatatt                        39

SEQ ID NO: 45          moltype = DNA  length = 42
FEATURE                Location/Qualifiers
misc_feature           1..42
                       note = primer
source                 1..42
                       mol_type = other DNA
                       organism = synthetic construct
SEQUENCE: 45
gcccaccgtt caatgaacgc acttctatta ggattaaaac at                    42

SEQ ID NO: 46          moltype = DNA  length = 42
FEATURE                Location/Qualifiers
misc_feature           1..42
                       note = primer
source                 1..42
                       mol_type = other DNA
                       organism = synthetic construct
SEQUENCE: 46
atgttttaat cctaatagaa gtgcggtcat tgaacggtgg gc                    42

SEQ ID NO: 47          moltype = DNA  length = 39
FEATURE                Location/Qualifiers
misc_feature           1..39
                       note = primer
source                 1..39
                       mol_type = other DNA
                       organism = synthetic construct
SEQUENCE: 47
attatcctta tgcctattgc acaattggcc tattatctt                        39

SEQ ID NO: 48          moltype = DNA  length = 39
FEATURE                Location/Qualifiers
misc_feature           1..39
                       note = primer
source                 1..39
                       mol_type = other DNA
                       organism = synthetic construct
SEQUENCE: 48
aagataatag gccaattgtg caataggcat aaggataat                        39
```

```
SEQ ID NO: 49          moltype = DNA  length = 39
FEATURE                Location/Qualifiers
misc_feature           1..39
                       note = primer
source                 1..39
                       mol_type = other DNA
                       organism = synthetic construct
SEQUENCE: 49
ttggcctatt atcttacagc acgtgttacc aatttcgag                         39

SEQ ID NO: 50          moltype = DNA  length = 39
FEATURE                Location/Qualifiers
misc_feature           1..39
                       note = primer
source                 1..39
                       mol_type = other DNA
                       organism = synthetic construct
SEQUENCE: 50
ctcgaaattg gtaacacgtg ctgtaagata ataggccaa                         39

SEQ ID NO: 51          moltype = DNA  length = 39
FEATURE                Location/Qualifiers
misc_feature           1..39
                       note = primer
source                 1..39
                       mol_type = other DNA
                       organism = synthetic construct
SEQUENCE: 51
gcctattatc ttacagatgc agttaccaat ttcgaggaa                         39

SEQ ID NO: 52          moltype = DNA  length = 39
FEATURE                Location/Qualifiers
misc_feature           1..39
                       note = primer
source                 1..39
                       mol_type = other DNA
                       organism = synthetic construct
SEQUENCE: 52
ttcctcgaaa ttggtaactg catctgtaag ataataggc                         39

SEQ ID NO: 53          moltype = DNA  length = 39
FEATURE                Location/Qualifiers
misc_feature           1..39
                       note = primer
source                 1..39
                       mol_type = other DNA
                       organism = synthetic construct
SEQUENCE: 53
cgtgttacca atttcgaggc attagaacct tattttgaa                         39

SEQ ID NO: 54          moltype = DNA  length = 39
FEATURE                Location/Qualifiers
misc_feature           1..39
                       note = primer
source                 1..39
                       mol_type = other DNA
                       organism = synthetic construct
SEQUENCE: 54
ttcaaaataa ggttctaatg cctcgaaatt ggtaacacg                         39

SEQ ID NO: 55          moltype = DNA  length = 39
FEATURE                Location/Qualifiers
misc_feature           1..39
                       note = primer
source                 1..39
                       mol_type = other DNA
                       organism = synthetic construct
SEQUENCE: 55
accaatttcg aggaattagc accttatttt gaacttact                         39

SEQ ID NO: 56          moltype = DNA  length = 39
FEATURE                Location/Qualifiers
misc_feature           1..39
                       note = primer
source                 1..39
                       mol_type = other DNA
                       organism = synthetic construct
SEQUENCE: 56
```

```
agtaagttca aaataaggtg ctaattcctc gaaattggt                  39

SEQ ID NO: 57           moltype = DNA  length = 42
FEATURE                 Location/Qualifiers
misc_feature            1..42
                        note = primer
source                  1..42
                        mol_type = other DNA
                        organism = synthetic construct
SEQUENCE: 57
ccttattttg aacttactgc aggacaacca tttattttta tt              42

SEQ ID NO: 58           moltype = DNA  length = 42
FEATURE                 Location/Qualifiers
misc_feature            1..42
                        note = primer
source                  1..42
                        mol_type = other DNA
                        organism = synthetic construct
SEQUENCE: 58
aataaaaata aatggttgtg ctgcagtaag ttcaaaataa gg              42

SEQ ID NO: 59           moltype = DNA  length = 45
FEATURE                 Location/Qualifiers
misc_feature            1..45
                        note = primer
source                  1..45
                        mol_type = other DNA
                        organism = synthetic construct
SEQUENCE: 59
tttattttta ttggatttaa tgctgcagct tataattcta atgtc           45

SEQ ID NO: 60           moltype = DNA  length = 45
FEATURE                 Location/Qualifiers
misc_feature            1..45
                        note = primer
source                  1..45
                        mol_type = other DNA
                        organism = synthetic construct
SEQUENCE: 60
gacattagaa ttataagctg cagcattaaa tccaataaaa ataaa           45

SEQ ID NO: 61           moltype = DNA  length = 39
FEATURE                 Location/Qualifiers
misc_feature            1..39
                        note = primer
source                  1..39
                        mol_type = other DNA
                        organism = synthetic construct
SEQUENCE: 61
aatgtccctt taattcccgc aggttctgac ggtatgtca                  39

SEQ ID NO: 62           moltype = DNA  length = 39
FEATURE                 Location/Qualifiers
misc_feature            1..39
                        note = primer
source                  1..39
                        mol_type = other DNA
                        organism = synthetic construct
SEQUENCE: 62
tgacataccg tcagaacctg cgggaattaa agggacatt                  39

SEQ ID NO: 63           moltype = DNA  length = 39
FEATURE                 Location/Qualifiers
misc_feature            1..39
                        note = primer
source                  1..39
                        mol_type = other DNA
                        organism = synthetic construct
SEQUENCE: 63
ttaattccca aaggttctgc aggtatgtca aaacgctca                  39

SEQ ID NO: 64           moltype = DNA  length = 39
FEATURE                 Location/Qualifiers
misc_feature            1..39
                        note = primer
source                  1..39
                        mol_type = other DNA
                        organism = synthetic construct
```

```
SEQUENCE: 64
tgagcgtttt gacatacctg cagaaccttt gggaattaa                         39

SEQ ID NO: 65           moltype = DNA  length = 39
FEATURE                 Location/Qualifiers
misc_feature            1..39
                        note = primer
source                  1..39
                        mol_type = other DNA
                        organism = synthetic construct
SEQUENCE: 65
tctgacggta tgtcaaaagc atcaattaag aaatggaaa                         39

SEQ ID NO: 66           moltype = DNA  length = 39
FEATURE                 Location/Qualifiers
misc_feature            1..39
                        note = primer
source                  1..39
                        mol_type = other DNA
                        organism = synthetic construct
SEQUENCE: 66
tttccatttc ttaattgatg cttttgacat accgtcaga                         39

SEQ ID NO: 67           moltype = DNA  length = 54
FEATURE                 Location/Qualifiers
misc_feature            1..54
                        note = primer
source                  1..54
                        mol_type = other DNA
                        organism = synthetic construct
SEQUENCE: 67
ggtggtgcat gcggaggtaa ataaatggaa gtagaaaaag agtttattac tgat        54

SEQ ID NO: 68           moltype = DNA  length = 51
FEATURE                 Location/Qualifiers
misc_feature            1..51
                        note = primer
source                  1..51
                        mol_type = other DNA
                        organism = synthetic construct
SEQUENCE: 68
ggtggtggta ccctatttgt tttcaacttt atctttccat ttcttaattg a           51

SEQ ID NO: 69           moltype = DNA  length = 39
FEATURE                 Location/Qualifiers
misc_feature            1..39
                        note = primer
misc_feature            19..21
                        note = n=a, c, g or t
source                  1..39
                        mol_type = other DNA
                        organism = synthetic construct
SEQUENCE: 69
caagcataca atgaagttnn nacatctatt tgttcacct                         39

SEQ ID NO: 70           moltype = DNA  length = 39
FEATURE                 Location/Qualifiers
misc_feature            1..39
                        note = primer
misc_feature            19..21
                        note = n=a. c. g or t
source                  1..39
                        mol_type = other DNA
                        organism = synthetic construct
SEQUENCE: 70
aggtgaacaa atagatgtnn naacttcatt gtatgcttg                         39

SEQ ID NO: 71           moltype = DNA  length = 37
FEATURE                 Location/Qualifiers
misc_feature            1..37
                        note = primer
misc_feature            16..18
misc_feature            16..18
                        note = n=a, c, g, or t
source                  1..37
                        mol_type = other DNA
                        organism = synthetic construct
SEQUENCE: 71
gatatactta aacttnnnaa gaaaaaaagg tggtccg                           37
```

```
SEQ ID NO: 72          moltype = DNA  length = 39
FEATURE                Location/Qualifiers
misc_feature           1..39
                       note = primer
misc_feature           19..21
misc_feature           19..21
                       note = n=a, c, g, or t
source                 1..39
                       mol_type = other DNA
                       organism = synthetic construct
SEQUENCE: 72
cggaccacct tttttcttnn naagtttaag tatatcaag                          39

SEQ ID NO: 73          moltype = DNA  length = 54
FEATURE                Location/Qualifiers
misc_feature           1..54
                       note = primer
source                 1..54
                       mol_type = other DNA
                       organism = synthetic construct
SEQUENCE: 73
ggtggtgcat gcggaggtaa ataaatgtct aataaaaaac agtcaaatag gcta         54

SEQ ID NO: 74          moltype = DNA  length = 39
FEATURE                Location/Qualifiers
misc_feature           1..39
                       note = primer
source                 1..39
                       mol_type = other DNA
                       organism = synthetic construct
SEQUENCE: 74
ggtggtggta cctcacttag atctaagctg ttcaaacaa                          39

SEQ ID NO: 75          moltype = AA  length = 267
FEATURE                Location/Qualifiers
REGION                 1..267
                       note = MISC_FEATURE - Amino acid residues 1-267 correspond
                        to residues 4-270 of the protein sequence of EcoRI
source                 1..267
                       mol_type = protein
                       organism = Escherichia coli
SEQUENCE: 75
KKQSNRLTEQ HKLSQGVIGI FGDYAKAHDL AVGEVSKLVK KALSNEYPQL SFRYRDSIKK  60
TEINEALKKI DPDLGGTLFV SNSSIKPDGG IVEVKDDYGE WRVVLVAEAK HQGKDIINIR  120
NGLLVGKRGD QDLMAAGNAI ERSHKNISEI ANFMLSESHF PYVLFLEGSN FLTENISITR  180
PDGRVVNLEY NSGILNRLDR LTAANYGMPI NSNLCINKFV NHKDKSIMLQ AASIYTQGDG  240
REWDSKIMFE IMFDISTTSL RVLGRDL                                      267

SEQ ID NO: 76          moltype = AA  length = 265
FEATURE                Location/Qualifiers
REGION                 1..265
                       note = MISC_FEATURE - amino acid residues 1-265 correspond
                        to residues 10-274 of the protein sequence of RsrI
source                 1..265
                       mol_type = protein
                       organism = Rhodopseudomonas sphaeroides
SEQUENCE: 76
KGQALRLGIQ QELGGGPLSI FGAAAQKHDL SIREVTAGVL TKLAEDFPNL EFQLRTSLTK  60
KAINEKLRSF DPRLGQALFV ESASIRPDGG ITEVKDRHGN WRVILVGESK HQGNDVEKIL  120
AGVLQGKAKD QDFMAAGNAI ERMHKNVLEL RNYMLDEKHF PYVVFLQGSN FATESFEVTR  180
PDGRVVKIVH DSGMLNRIDR VTASSLSREI NQNYCENIVV RAGSFDHMFQ IASLYCKAAP  240
WTAGEMAEAM LAVAKTSLRI IADDL                                        265

SEQ ID NO: 77          moltype = DNA  length = 39
FEATURE                Location/Qualifiers
misc_feature           1..39
                       note = primer
source                 1..39
                       mol_type = other DNA
                       organism = synthetic construct
SEQUENCE: 77
gattgggtgg cgcagaaatt tcaaacgggc cagcagtcg                          39

SEQ ID NO: 78          moltype = DNA  length = 39
FEATURE                Location/Qualifiers
misc_feature           1..39
                       note = primer
source                 1..39
```

```
                          mol_type = other DNA
                          organism = synthetic construct
SEQUENCE: 78
cgactgctgg cccgtttgaa atttctgcgc cacccaatc                          39

SEQ ID NO: 79             moltype = AA  length = 272
FEATURE                   Location/Qualifiers
source                    1..272
                          mol_type = protein
                          organism = Agrobacterium gelatinovorum
SEQUENCE: 79
MRLDLDFGRG LVAHVMLDNV SEEQYQQISD YFVPLVNKPK LKSRDAIGQA FVMATEVCPD  60
ANPSDLWHHV LYRIYIREKI GTDPSQSWVR TSGEAFEVAL VERYNPVLAR HGIRLTALFK  120
GQKGLALTRM GVADRVGSRK VDVMIEKQGG GRSPDAEGFG VVGGIHAKVS LAERVSDDIP  180
ASRIMMGEGL LSVLSTLDVK SFPPPHGDLV NRGELGTPDR PSDKRNYIEG HGDFSACFSY  240
NLRTPPSNAT TPSGRHIYVS ASLVRTTSSP TT                                272

SEQ ID NO: 80             moltype = AA  length = 358
FEATURE                   Location/Qualifiers
source                    1..358
                          mol_type = protein
                          organism = Anabaena variabilis
SEQUENCE: 80
MEEDLDLSEN IEAASAELTT LYQVAADAMK DYIEIYLALS KQSDGFSNIN NLDLTSRNRR  60
LVVIHGLSLE LDPDTSTPEE IKREAERMLA IALDTESAIT AGVYEKMRLF ASSLVDQLFE  120
QTDELNSLSS EYLSANPGFL PFFQQLAGLR SKSELKREVG NASDNSISKA VAERILERII  180
RNLRIRTFSK EKLLQAVEPT LEGIVRDLVG KVLLENIVAD ALSDLQVPFM RESEYQSLKG  240
VIYDFRADFV IPDAQNPIAF IEVRKSSTRH ASLYAKDKMF SAINWKGKNK RLLGILVVEG  300
PWTRETLRVM ANVFDYVTPL TRVSQVAEAI RAYLDGDKTR LKWLVNFSIE EADHDNIT    358

SEQ ID NO: 81             moltype = AA  length = 530
FEATURE                   Location/Qualifiers
source                    1..530
                          mol_type = protein
                          organism = Bacillus stearothermophilus
SEQUENCE: 81
MAKYGRGKFL PHQNYIDYMH FIVNHKNYSG MPNAIGEDGR INWQVSSGKT TSFYEYYQAR  60
FEWWEKKADE LNLPGTGNSN KRFSLAARLI HPTGQRPCRL CGKYQYVGYM YVSHNLYKRW  120
SKITGREDLF FKKQNIIEAA NIFKSIMGEQ ALINELTTIF PERKDYFNRL PNIEDFFVSS  180
SHIKNNGNYI SPGFMANPPD RLDGFHDYGI CCRKEKDPGR HDDNMRLYNH DRRAFMWWSE  240
GDWALADALY NKAGAGKCAD PDCQKEVEKI SPDHVGPISC GFKQIPFFKP LCASCNSAKN  300
RRFSYQDVKE LLKYENYTGD SVASWQVRAL WDNCKHLVKN DDDSKLLSNL MRSLQDYYLR  360
SLYKLFSNGF AHLLSYFLTP EYAHYKITFE GLNTSTLEYE RYYKTFKKTK STSSLAARIV  420
RIAFEELEIY NSKDINERKL IKFDTSSWEK DFENIISYAT KNLSLDEEAS KWNKVLTDKN  480
LSSTEKDKKI SSLLEDKNYE VYKKQFYILK DLLVEHFNKI GEQIAKDYMK             530

SEQ ID NO: 82             moltype = AA  length = 301
FEATURE                   Location/Qualifiers
source                    1..301
                          mol_type = protein
                          organism = Enterobacter agglomerans
SEQUENCE: 82
MKKRRDLVEV FGYNPMDLSP EVRALWNLGA CPFLNKECIK INHDQTIIYG TCSVTSPYGD  60
VIICPNRLYA NDYETLHKVS RDAFGDDVPF LTYSNFIKYR ATYKDCIVAL GKNSGKEVQV  120
GRALSMDWVL VRITDGELKE YVGVEIQSID ITGNYRDAWH AYKNLKPIDI IDNLPTSQHG  180
LNWANVHKRL IPQIIRKGVV YSRSNYVKKG LYFILPEIVY NKFEDVIGAD IPLLKTQTNK  240
SITVHTYSLG EPAANGEQRK LISEREIIFD LDEFSKRFTT GPNLPKGDDL DAVIKKALGM  300
M                                                                  301

SEQ ID NO: 83             moltype = AA  length = 277
FEATURE                   Location/Qualifiers
source                    1..277
                          mol_type = protein
                          organism = Escherichia coli
SEQUENCE: 83
MSNKKQSNRL TEQHKLSQGV IGIFGDYAKA HDLAVGEVSK LVKKALSNEY PQLSFRYRDS  60
IKKTEINEAL KKIDPDLGGT LFVSNSSIKP DGGIVEVKDD YGEWRVVLVA EAKHQGKDII  120
NIRNGLLVGK RGDQDLMAAG NAIERSHKNI SEIANFMLSE SHFPYVLFLE GSNFLTENIS  180
ITRPDGRVVN LEYNSGILNR LDRLTAANYG MPINSNLCIN KFVNHKDKSI MLQAASIYTQ  240
GDGREWDSKI MFEIMFDIST TSLRVLGRDL FEQLTSK                            277

SEQ ID NO: 84             moltype = AA  length = 245
FEATURE                   Location/Qualifiers
source                    1..245
                          mol_type = protein
                          organism = Escherichia coli
SEQUENCE: 84
MSLRSDLINA LYDENQKYDV CGIISAEGKI YPLGSDTKVL STIFELFSRP IINKIAEKHG  60
YIVEEPKQQN HYPDFTLYKP SEPNKKIAID IKTTYTNKEN EKIKFTLGGY TSFIRNNTKN  120
```

```
IVYPFDQYIA HWIIGYVYTR VATRKSSLKT YNINELNEIP KPYKGVKVFL QDKWVIAGDL  180
AGSGNTTNIG SIHAHYKDFV EGKGIFDSED EFLDYWRNYE RTSQLRNDKY NNISEYRNWI  240
YRGRK                                                              245

SEQ ID NO: 85          moltype = AA  length = 300
FEATURE                Location/Qualifiers
source                 1..300
                       mol_type = protein
                       organism = Haemophilus influenzae
SEQUENCE: 85
MKKSALEKLL SLIENLTNQE FKQATNSLIS FIYKLNRNEV IELVRSIGIL PEAIKPSSTQ  60
EKLFSKAGDI VLAKAFQLLN LNSKPLEQRG NAGDVIALSK EFNYGLVADA KSFRLSRTAK  120
NQKDFKVKAL SEWREDKDYA VLTAPFFQYP TTKSQIFKQS LDENVLLFSW EHLAILLQLD  180
LEETNIFPFE QLWNFPKKQS KKTSVSDAEN NFMRDFNKYF MDLFKIDKDT LNQLLQKEIN  240
FIEERSLIEK EYWKKQINII KNFTREEAIE ALLKDINMSS KIETIDSFIK GIKSNDRLYL  300

SEQ ID NO: 86          moltype = AA  length = 254
FEATURE                Location/Qualifiers
source                 1..254
                       mol_type = protein
                       organism = Haemophilus parainfluenzae
SEQUENCE: 86
MKYEEINFKV PVESPYYPNY SQCVIERIYS ILRNQKDMGD DRIIINTNLK KGLPLENINK  60
IAGPMIEAWA EEVFSGIRDN RDNQYNLINV EAQERLGISD IILQFQVNNN VITGNVDVKA  120
TSNDIPDSGK SPNITSFSRI RTAYVKDPNF IFIILSIKHS VYVKRNEYTN LMDGIMQIID  180
FNVYDLKYIS DSDISYNPAL GTGQIQIKDI HYVSSQKRTT WQMCQLLDLK YLRSKKRTIE  240
QFYNEAKRNK WIKD                                                    254

SEQ ID NO: 87          moltype = AA  length = 218
FEATURE                Location/Qualifiers
source                 1..218
                       mol_type = protein
                       organism = Klebsiella pnermoniae
SEQUENCE: 87
MDVFDKVYSD DNNSYDQKTV SQRIEALFLN NLGKVVTRQQ IIRAATDPKT GKQPENWHQR  60
LSELRTDKGY TILSWRDMKV LAPQEYIMPH ATRRPKAAKR VLPTKETWEQ VLDRANYSCE  120
WQEDGQHCGL VEGDIDPIGG GTVKLTPDHM TPHSIDPATD VNDPKMWQAL CGRHQVMKKN  180
YWDSNNGKIN VIGILQSVNE KQKNDALEFL LNYYGLKR                          218

SEQ ID NO: 88          moltype = AA  length = 288
FEATURE                Location/Qualifiers
source                 1..288
                       mol_type = protein
                       organism = Nocardia corallina
SEQUENCE: 88
MATAPGHLLG QIIGNVMEEA LKPVLQEMAD RHDLYLDSKG LRPGVRSGAL VTWTDDLGNN  60
HDLDFVLERG GSATKAGNPA AFIEAAWRRY TKHSKAKAQE IQGAVLPVLA AWNNVKPTPA  120
AVVAGQWTAP SLQQMRSNGF VVLHLHFPTT AQVFGGNGIN IEGTGEGTPD AFWQQQCDAY  180
TSKSEADKDS LATALRTAHA QEFRTFVAEL ERRVVRAIDY VVVTPLHGHG SQYTSIENAI  240
EAVRTYSCGE ESAPFLRFEI RISYTNGDVI QATFGSSSDA IEFLDTFN               288

SEQ ID NO: 89          moltype = AA  length = 328
FEATURE                Location/Qualifiers
source                 1..328
                       mol_type = protein
                       organism = Neisseria mucosa
SEQUENCE: 89
MSSYHDDLNI LNVDFNHLRL TELIKLADQA EPFYLWVEKI FRQVSGRADS LETIIEVEER  60
VVLKMAILTC FTSDEKELPK LFNGVGVPYP HIKACYFFFA WLVRDAATQR LDPLIREAFT  120
QLKSIHPQMK KTELESEIFS QLLVNYRNEL IHFSWPVIRE VLISRLEGSR RAARGSYLEL  180
FVRTALAQSI TYFYKIYGNY GKFLDVKIHD KPLKVKNRTY DVVAELIGNN HNTQYLILPV  240
KTRETQGGGH AHLFTRDIEQ SNNDIRELYP NAVIAPVIIA ENWSDTEKDL ENVGYNDIFH  300
FSVNPNRFAG FSDVEQIRLN RLVERILL                                     328

SEQ ID NO: 90          moltype = AA  length = 383
FEATURE                Location/Qualifiers
source                 1..383
                       mol_type = protein
                       organism = Nocardia otitidiscaviarum
SEQUENCE: 90
MRSDTSVEPE GANFIAEFFG HRVYPEVVST EAARNDQATG TCPFLTAAKL VETSCVKAET  60
SRGVCVVNTA VDNERYDWLV CPNRALDPLF MSAASRKLFG YGPTEPLQFI AAPTLADQAV  120
RDGIREWLDR GVHVVAYFQE KLGGELSISK TDSSPEFSFD WTLAEVESIY PVPKIKRYGV  180
LEIQTMDFHG SYKHAVGAID IALVEGIDFH GWLPTPAGRA ALSKKMEGPN LSNVFKRTFY  240
QMAYKFALSG HQRCAGTGFA IPQSVWKSWL RHLANPTLID NGDGTFSLGD TRNDSENAWI  300
FVFELDPDTD ASPRPLAPHL EIRVNVDTLI DLALRESPRA ALGPSGPVAT FTDKVEARML  360
RFWPKTRRRR STTPGGQRGL FDA                                          383

SEQ ID NO: 91          moltype = AA  length = 326
```

```
FEATURE                 Location/Qualifiers
source                  1..326
                        mol_type = protein
                        organism = Providencia stuartii
SEQUENCE: 91
MKELKLKEAK EILKALGLPP QQYNDRSGWV LLALANIKPE DSWKEAKAPL LPTVSIMEFI  60
RTEYGKDYKP NSRETIRRQT LHQFEQARIV DRNRDLPSRA TNSKDNNYSL NQVIIDILHN  120
YPNGNWKELI QQFLTHVPSL QELYERALAR DRIPIKLLDG TQISLSPGEH NQLHADIVHE  180
FCPRFVGDMG KILYIGDTAS SRNEGGKLMV LDSEYLKKLG VPPMSHDKLP DVVVYDEKRK  240
WLFLIEAVTS HGPISPKRWL ELEAALSSCT VGKVYVTAFP TRTEFRKNAA NIAWETEVWI  300
ADNPDHMVHF NGDRFLGPHD KKPELS                                        326

SEQ ID NO: 92           moltype = AA  length = 157
FEATURE                 Location/Qualifiers
source                  1..157
                        mol_type = protein
                        organism = Proteus vulgaris
SEQUENCE: 92
MSHPDLNKLL ELWPHIQEYQ DLALKHGIND IFQDNGGKLL QVLLITGLTV LPGREGNDAV  60
DNAGQEYELK SINIDLTKGF STHHHMNPVI IAKYRQVPWI FAIYRGIAIE AIYRLEPKDL  120
EFYYDKWERK WYSDGHKDIN NPKIPVKYVM EHGTKIY                            157

SEQ ID NO: 93           moltype = AA  length = 358
FEATURE                 Location/Qualifiers
source                  1..358
                        mol_type = protein
                        organism = Streptomyces achromogenes
SEQUENCE: 93
MGITIKKSTA EQVLRKAYEA AASDDVFLED WIFLATSLRE VDAPRTYTAA LVTALLARAC  60
DDRVDPRSIK EKYDDRAFSL RTLCHGVVVP MSVELGFDLG ATGREPINNQ PFFRYDQYSE  120
IVRVQTKARP YLDRVSSALA RVDEEDYSTE ESFRALVAVL AVCISVANKK QRVAVGSAIV  180
EASLIAETQS FVVSGHDVPR KLQACVAAGL DMVYSEVVSR RINDPSRDFP GDVQVILDGD  240
PLLTVEVRGK SVSWEGLEQF VSSATYAGFR RVALMVDAAS HVSLMSADDL TSALERKYEC  300
IVKVNESVSS FLRDVFVWSP RDVHSILSAF PEAMYRRMIE IEVREPELDR WAEIFPET    358

SEQ ID NO: 94           moltype = AA  length = 315
FEATURE                 Location/Qualifiers
source                  1..315
                        mol_type = protein
                        organism = Streptomyces albus
SEQUENCE: 94
MINADKPHRW NDDVQASVRL YNQWFLDAAP KAYRDTRQLT IDEVEQAFQR TANMTSITPE  60
VLKAHPKTLA TLRMSTAPPI ARDRLVGLSH GSKSLLDTME KGKLPPRMKG DVLDTHLAKM  120
CAVLTDLLDL DLFHWYPTGE PAEPRQRELA ATVVADRLCG AIADPIVRNA QERRQLALIE  180
EWLLARGYTK KTHSASLPLN TMQPGTFSFR QNVVVGSDLP VNIPVDAVIQ PHTPHSHKLP  240
ILIEAKSAGD FTNTNKRRKE EATKIHQLQL KYGNEISLTL FLCGYFNTGY LGYSAAEGLD  300
WVWEHRIDDL EAAGA                                                    315

SEQ ID NO: 95           moltype = AA  length = 432
FEATURE                 Location/Qualifiers
source                  1..432
                        mol_type = protein
                        organism = Saccharopolyspora sp.
SEQUENCE: 95
MRRLATQRRE DAYKSNRDYQ TVHEAQSLRV NSTDDDNLSL FLLKDISPRE DSKNIVGFGG  60
FVKPEIATTM ALTLTTDIDK QIKSVPLSSN WNRISIVAKF ASNPSVSITL GFDQTPWVDF  120
WGINSDDIGL SFVSDAVPLE MSMIDSIHIA PETLYLDHSS ACLLDIDPVE STRFKTGHGD  180
PLSLKKCSYC GRLLPIDLER PGKLSFHKHR AKITNHQNEC RSCKKWRINN SFNPMRTIDQ  240
LNESALITRE RKIFLQEPEI LQEIKDRTGA GLKSQVWERF HRKCFNCRKD LKLSEVQLDH  300
TRPLAYLWPI DEHATCLCAQ CNNTKKDRFP VDFYSEQQIR ELSDICGLPY QDLCARSLNL  360
DQLDRIERNI AEFSKEWDVR TFASTARRIS EVYPARDLFE TLKKESESAY NKIIEKLKER  420
PDALLDEALP LD                                                       432

SEQ ID NO: 96           moltype = AA  length = 323
FEATURE                 Location/Qualifiers
source                  1..323
                        mol_type = protein
                        organism = Streptomyces sp.
SEQUENCE: 96
MNSSDGIDGT VASIDTARAL LKRFGFDAQR YNVRSAVTLL ALAGLKPGDR WVDSTTPRLG  60
VQKIMDWSGE HWAKPYATGS REDFRKKTLR QWVDNGFAVL NADNLNIATN SQLNEYCLSD  120
EALQALRAYG TEGFEESLVV FLDEASKAVK ARAEALQAAM ISVDLPGGEE FLLSPAGQNP  180
LLKKMVEEFV PRFAPRSTVL YLGDTRGKHS LFEREIFEEV LGLTFDPHGR MPDLILHDEV  240
RGWLFLMEAV KSKGPFDEER HRSLQELFVT PSAGLIFVNC FENRESMRQW LPELAWETEA  300
WVAEDPDHLI HLNGSRFLGP YER                                           323

SEQ ID NO: 97           moltype = AA  length = 227
FEATURE                 Location/Qualifiers
source                  1..227
```

```
                         mol_type = protein
                         organism = Streptomyces caespitosus
SEQUENCE: 97
MINDQLPRWV REARVGTRTG GPAMRPKTSD SPYFGWDSED WPEVTRQLLS EQPLSGDTLV  60
DAVLASWESI FESRLGSGFH IGTQIRPTPQ IMGFLLHALI PLELANGDPS WRADLNSSEK  120
DLVYQPDHKY SIEMKTSSHK DQIFGNRSFG VENPGKGKKA KDGYYVAVNF EKWSDAPGRL  180
PRIRTIRYGW LDHTDWVAQK SQTGQQSSLP AVVSNTQLLA IHTGGQR                227

SEQ ID NO: 98            moltype = AA  length = 235
FEATURE                  Location/Qualifiers
source                   1..235
                         mol_type = protein
                         organism = Streptomyces phaeochromogenes
SEQUENCE: 98
MTSKDPIVLS ADQIAWLRQL KMSKRAALVR DYILEYGAVT TGKLAELGYS HPPRAARDLK  60
DAGAGVVTIM VKGPDGRRMA SYAFNGKANE DGAGRVVIPK AFGEALKRAH GGKCAVCYGD  120
FSERELQCDH RVPFAIAGDK PKLVQEDFMP LCASDNRAKS WSCENCPNWE LKDEDTCRSC  180
FWASPENYTH VSTRPERRIN LLFQGDEVEI FDALKNAAAN EGVSLTEATK RKLAD       235

SEQ ID NO: 99            moltype = AA  length = 281
FEATURE                  Location/Qualifiers
source                   1..281
                         mol_type = protein
                         organism = Sphaerotilus sp.
SEQUENCE: 99
MSKAAYQDFT KRFSLLIKKH PNLITMTLSN IFTMRLIGNK THGDLAEIAI SEFINQYMYD  60
FKSIHVGKDL YRAKSKEEDI TVENEITKEK FPISLKAYGD GPLQLSTDKN FLMYPLLEEI  120
GAFINAKEKI EEIFANEAFS CFSEINVLPL IYDEKRQRCN ILVFDAARAR AETAYIRKET  180
EGSGRKHPAY RFFDKNKNYI CEVRYGNAAA NALQRGLWTN TKNATSFFDS VTNGWVDYSH  240
NLVLVKLLSH ALVSSRKGHE AALEEIKKDI LQLKQTNGIN V                      281

SEQ ID NO: 100           moltype = DNA  length = 1077
FEATURE                  Location/Qualifiers
source                   1..1077
                         mol_type = other DNA
                         organism = Anabaena variabilis
SEQUENCE: 100
atggaagaag accttgattt atctgaaaat atcgaagctg catctgcgga gcttacgact  60
ctttatcagg tagctgctga tgctatgaaa gattatattg aaatctatct tgcgctgagt  120
aaacagtctg atgggtttc aaatattaac aatcttgact taacttctcg taacaggcgt  180
ttggtagtta tacatggact ttcgttagag ttagatccag atacttcgac tccagaggaa  240
attaaacgtg aagctgaacg aatgctagcg atagctcttg atacagagtc agcaattacg  300
gcaggagtat atgaaaaaat gcgtctcttc gcaagctctt tagtagatca gctatttgaa  360
caaacggatg aacttaattc attatcatcg gaatatttgt cagcaaatcc aggatttttg  420
ccgtttttcc agcagttggc ggggcttaga agtaaatcag agttaaagag agaagtagga  480
aatgcctctg acaatagtat ttctaaagcg gttgcagaga gaatattaga gcgcattata  540
cgtaacttga gaattcgcac tttttccaaa gagaaactat tacaagctgt tgagcctact  600
ttagaaggaa tagtcaggga tctcgtagga aaagtgttat tggaaaatat agttgctgat  660
gctttatctg atttacaagt tcctttcatg cgtgaatcag agtatcaaag ccttaaagga  720
gtgatttatg atttccgcgc tgattttgtg ataccagacg cacaaaatcc aattgctttt  780
atcgaggtgc gaaaaagctc tacacgacat gcgtcactct atgccaagga taagatgttt  840
tcagcgatta attggaaagg aaaaaataaa aggcttttgg gtattttggt tgtggaagga  900
ccttggacaa gagaaactct tcgcgtcatg gcaaatgtgt ttgattacgt tacaccttta  960
actcgtgttt cccaagttgc agaagctatc agagcatatc tagatgggga taaaacgaga  1020
ctgaagtggt tagttaattt cagtattgaa gaagcagacc acgacaacat aacctaa     1077

SEQ ID NO: 101           moltype = DNA  length = 1293
FEATURE                  Location/Qualifiers
source                   1..1293
                         mol_type = other DNA
                         organism = Bacillus sphaericus
SEQUENCE: 101
atgagacgat tagcaaaaaa ttcacggaac gacagttatt taagtaatag ggattaccag  60
gaaatcgtga gggaaaatac cactacaata tcgtttccct taaaagaaaa acatactctg  120
actttaacga aaaaaatagg gctaaatcag actgctggat tcggaggatg gtttttccct  180
gattcaccat gtttattaac agtaactgta ctatcctctt tcggtacaaa ggtaacttct  240
aaaaccttta gcctttctaa agattggaat cgtgttgggc ttgcttggat taacgagcat  300
tcgagtgaca ccataagcat tgtcctagag tttagtgatg tggaaatagt tcatacatgg  360
ggacttacat gtgatgtttt taatgtccat gaattaatta ttgatgctat agaagatcaa  420
aataaactaa tagacgtgct aaatcaagaa catttatctc ctgaaacata ttatttaaac  480
catgactctg atactgattt aattgagaat ttggaatcta cagaagagat aaagatagtt  540
aaccaaagcc aaaagcaaat ctctttaaaa aaatgctgtt attgtcaacg ttatatgcct  600
gtgaacatat tagttcgttc aaattcatca tttcataaac acaagagtaa gaaaactggt  660
tttcaaaatg aatgtcgggc ttgtaagaag tggagaataa ataattcatt caatccagtc  720
agaacaaaag accaactaca tgaatcagca gttattacac gtgaaaaaaa aatattactt  780
aaagaacctg aaatattaca gaaaatcaaa aatagaaata acggtgaggg cttaaaaagt  840
attatatgga aaaaatttga taaaaaatgc tttaattgtg aaaaagaatt aaccattgaa  900
gaggtacgcc tagaccatac aagaccactt gcttatctgt ggcctatcga tgaacacgca  960
acttgtttat gtgaaaaatg caacaataca aaacatgata tgtttcctat cgatttttat  1020
```

```
caaggggacg aagacaaatt aagacgttta gctagaatta cggggttaga ttatgaatct  1080
ctagttaaga gggacgtaaa tgaagttgaa cttgcaagaa taatcaataa cattgaagac  1140
tttgcaacta atgtagaggc acgtactttt cgctcaataa gaaataaagt aaaagaagta  1200
cgtcccgata ctgacctatt tgaaattctt aaatctaaaa atattaattt atataatgaa  1260
cttcaatatg aacttcttac ccgtaaggat taa                                1293

SEQ ID NO: 102          moltype = DNA  length = 2189
FEATURE                 Location/Qualifiers
misc_feature            1..2189
                        note = plasmid placzz2
source                  1..2189
                        mol_type = other DNA
                        organism = synthetic construct
SEQUENCE: 102
ctggcgaaag ggggatgtgc tgcaaggcga ttaagttggg taacgccagg gttttcccag  60
tcacgacgtt gtaaaacgac ggccagtgaa ttcgagctcg gtacccgggg gcgcgccgga  120
tccttaatta agtctagagt cgactgttta aacctgcagg catgcaagct tggcgtaatc  180
atggtcatat gttaacctcc ggcgtaatca tggtcatagc tgtttcctgt gtgaaattgt  240
tatccgctca caattccaca caacatacga gccggaagca taaagtgtaa agcctggggt  300
gcctaatgag tgagctaact cacattaatt gcgttgcgct cactgcccgc tttccagtcg  360
ggaaacctgt cgtgccagca tgtgagcaaa aggccagcaa aaggccagga accgtaaaaa  420
ggccgcgttg ctggcgtttt tccataggct ccgcccccct gacgagcatc acaaaaatcg  480
acgctcaagt cagaggtggc gaaacccgac aggactataa agataccagg cgtttccccc  540
tggaagctcc ctcgtgcgct ctcctgttcc gaccctgccg cttaccggat acctgtccgc  600
ctttctccct tcgggaagcg tggcgctttc tcatagctca cgctgtaggt atctcagttc  660
ggtgtaggtc gttcgctcca agctgggctg tgtgcacgaa ccccccgttc agcccgaccg  720
ctgcgcctta tccggtaact atcgtcttga gtccaacccg gtaagacacg acttatcgcc  780
actggcagca gccactggta acaggattag cagagcgagg tatgtaggcg gtgctacaga  840
gttcttgaag tggtggccta actacggcta cactagaagg acagtatttg gtatctgcgc  900
tctgctgaag ccagttacct tcggaaaaag agttggtagc tcttgatccg gcaaacaaac  960
caccgctggt agcggtggtt tttttgtttg caagcagcag attacgcgca gaaaaaaagg  1020
atctcaagaa gatcctttga tcttttctac ggggtctgac gctcagtgga acgaaaactc  1080
acgttaaggg attttggtca tgagattatc aaaaaggatc ttcacctaga tccttttaaa  1140
ttaaaaatga agttttaaat caatctaaag tatatatgag taaacttggt ctgacagtta  1200
ccaatgctta atcagtgagg cacctatctc agcgatctgt ctatttcgtt catccatagt  1260
tgcctgactc cccgtcgtgt agataactac gatacgggag ggcttaccat ctggccccag  1320
tgctgcaatg ataccgcgag acccacgctc accggctcca gatttatcag caataaacca  1380
gccagccgga agggccgagc gcagaagtgg tcctgcaact ttatccgcct ccatccagtc  1440
tattaattgt tgccgggaag ctagagtaag tagttcgcca gttaatagtt tgcgcaacgt  1500
tgttgccatt gctacaggca tcgtggtgtc acgctcgtcg tttggtatgg cttcattcag  1560
ctccggttcc caacgatcaa ggcgagttac atgatccccc atgttgtgca aaaaagcggt  1620
tagctccttc ggtcctccga tcgttgtcag aagtaagttg gccgcagtgt tatcactcat  1680
ggttatggca gcactgcata attctcttac tgtcatgcca tccgtaagat gcttttctgt  1740
gactggtgag tactcaacca agtcattctg agaatagtgt atgcggcgac cgagttgctc  1800
ttgcccggcg tcaatacggg ataataccgc gccacatagc agaactttaa aagtgctcat  1860
cattggaaaa cgttcttcgg ggcgaaaact ctcaaggatc ttaccgctgt tgagatccag  1920
ttcgatgtaa cccactcgtg cacccaactg atcttcagca tcttttactt tcaccagcgt  1980
ttctgggtga gcaaaaacag gaaggcaaaa tgccgcaaaa aagggaataa gggcgacacg  2040
gaaatgttga atactcatac tcttcctttt tcaatattat tgaagcattt atcagggtta  2100
ttgtctcatg agcggataca tatttgaatg tatttagaaa aataaacaaa taggggttcc  2160
gcgcacattt ccccgaaaag tgccacctg                                     2189

SEQ ID NO: 103          moltype = DNA  length = 10673
FEATURE                 Location/Qualifiers
misc_feature            1..10673
                        note = plasmid pBC4
source                  1..10673
                        mol_type = other DNA
                        organism = synthetic construct
SEQUENCE: 103
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgagctcggt acccggggat  420
cctctagagt cgaaccccgg atccggccgt ccgccgtgat ccatgcggtt accgcccgcg  480
tgtcgaaccc aggtgtgcga cgtcagacaa cgggggagcg ctccttttgg cttccttcca  540
ggcgcggcgg ctgctgcgct agcttttttg gccactggcc gcgcgcggcg taagcggtta  600
ggctggaaag cgaaagcatt aagtggctcg ctccctgtag ccggagggtt attttccaag  660
ggttgagtcg caggaccccc ggttcgagtc tcgggccggc cggactgcgg cgaacggggg  720
tttgcctccc cgtcatgcaa gaccccgctt gcaaattcct ccggaaacag ggacgagccc  780
ctttttttgct tttcccagat gcatccggtg ctgcggcaga tgcgcccccc tcctcagcag  840
cggcaagagc aagagcagcg gcagacatgc agggcaccct ccccttctcc taccgcgtca  900
ggaggggcaa catccgcggc tgacgcggcg gcagatggtg attacgaacc cccgcggcgc  960
cgggcccggc actacctgga cttggaggag ggcgagggcc tggcgcggct aggagcgccc  1020
tctcctgagc gacacccaag ggtgcagctg aagcgtgaca cgcgcgaggc gtacgtgccg  1080
cggcagaacc tgtttcgcga ccgcgaggga gaggagcccg aggagatgcg ggatcgaaag  1140
```

```
ttccacgcag ggcgcgagtt gcggcatggc ctgaaccgcg agcggttgct gcgcgaggag  1200
gactttgagc ccgacgcgcg gaccgggatt agtcccgcgc gcgcacacgt ggcggccgcc  1260
gacctggtaa ccgcgtacga gcagacggtg aaccaggaga ttaactttca aaaaagcttt  1320
aacaaccacg tgcgcacgct tgtggcgcgc gaggaggtgg ctataggact gatgcatctg  1380
tgggactttg taagcgcgct ggagcaaaac ccaaatagca agccgctcat ggcgcagctg  1440
ttccttatag tgcagcacag cagggacaac gaggcattca gggatgcgct gctaaacata  1500
gtagagcccg agggccgctg gctgctcgat ttgataaaca ttctgcagag catagtggtg  1560
caggagcgca gcttgagcct ggctgacaag gtggccgcca ttaactattc catgctcagt  1620
ctgggcaagt tttacgcccg caagatatac catacccctt acgttcccat agacaaggag  1680
gtaaagatcg aggggttcta catgcgcatg gcgttgaagg tgcttacctt gagcgacgac  1740
ctgggcgttt atcgcaacga gcgcatccac aaggccgtga gcgtgagccg gcggcgcgag  1800
ctcagcgacc gcgagctgat gcacagcctg caaagggccc tggctggcac gggcagcggc  1860
gatagagagg ccgagtccta ctttgacgcg ggcgctgacc tgcgctgggc cccaagccga  1920
cgcgccctgg aggcagctgg ggccggacct gggctggcgg tggcacccgc gcgcgctggc  1980
aacgtcggcg gcgtggagga atatgacgag gacgatgagt acgagccaga ggacggcgag  2040
tactaagcgg tgatgtttct gatcagatga tgcaagacgc aacggacccg gcggtgcggg  2100
cggcgctgca gagccagccg tccggcctta actccacgga cgactggcgc caggtcatgg  2160
accgcatcat gtcgctgact gcgcgtaacc ctgacgcgtt ccggcagcag ccgcaggcca  2220
accggctctc cgcaattctg gaagcggtgg tcccggcgcg cgcaaacccc acgcacgaga  2280
aggtgctggc gatcgtaaac gcgctggccg aaaacagggc catccggccc gatgaggccg  2340
gcctggtcta cgacgcgctg cttcagcgcg tggctcgtta caacagcggc aacgtgcaga  2400
ccaacctgga ccggctggtg ggggatgtgc gcgaggccgt ggcgcagcgt gagcgcgcgc  2460
agcagcaggg caacctgggc tccatggttg cactaaacgc cttcctgagt acacagcccg  2520
ccaacgtgcc gcggggacag gaggactaca ccaactttgt gagcgcactg cggctaatgg  2580
tgactgagac accgcaaagt gaggtgtacc agtccgggcc agactatttt ttccagacca  2640
gtagacaagg cctgcagacc gtaaacctga gccaggcttt caagaacttg caggggctgt  2700
ggggggtgcg ggctcccaca ggcgaccgcg cgaccgtgtc tagcttgctg acgcccaact  2760
cgcgcctgtt gctgctgcta atagcgccct tcacggacag tggcagcgtg tcccgggaca  2820
catacctagg tcacttgctg acactgtacc gcgaggccat aggtcaggcg catgtggacg  2880
agcatacttt ccaggagatt acaagtgtca gccgcgcgct ggggcaggag gacacgggca  2940
gcctggaggc aaccctgaac tacctgctga ccaaccggcg gcagaagatc ccctcgttgc  3000
acagtttaaa cagcgaggag gagcgcatct tgcgctatgt gcagcagagc gtgagcctta  3060
acctgatgcg cgacggggta acgcccagcg tggcgctgga catgaccgcg cgcaacatgg  3120
aaccgggcat gtatgcctca aaccggccgt ttatcaatcg cctaatggac tacttgcatc  3180
gcgcggccgc cgtgaacccc gagtatttca ccaatgccat cttgaacccg cactggctac  3240
cgccccctgg tttctacacc gggggatttg aggtgcccga gggtaacgat ggattcctct  3300
gggacgacat agacgacagc gtgttttccc cgcaaccgca gaccctgcta gagttgcaac  3360
agcgcgagca ggcagaggcg gcgctgcgaa aggaaagctt ccgcaggcca agcagcttgt  3420
ccgatctagg cgctgcggcc ccgcggtcag atgcgagtag cccatttcca agcttgatag  3480
ggtcttttac cagcactcgc accacccgcc cgcgcctgct gggcgaggag gagtacctaa  3540
acaactcgct gctgcagccg cagcgcgaaa agaacctgcc tccggcattt cccaacaacg  3600
ggatagagag cctagtggac aagatgagta gatggaagac gtatgcgcag gagcacaggg  3660
atgtgcccgg cccgcgcccg cccacccgtc gtcaaaggca cgaccgtcag cggggtctgg  3720
tgtgggagga cgatgactcg gcagacgaca gcagcgtcct ggatttggga gggagtggca  3780
acccgtttgc gcaccttcgc cccaggctgg ggagaatgtt ttaaaaaaaa aaaaaaaaag  3840
catgatgcaa aataaaaaac tcaccaaggc catggcaccg agcgttggtt ttcttgtatt  3900
ccccttagta tgcagcgcgc ggcgatgtat gaggaaggtc ctcctccctc ctacgagagc  3960
gtggtgagcg cggcgccagt ggcggcggcg ctgggttccc ccttcgatgc tcccctggac  4020
ccgccgtttg tgcctccgcg gtacctgcgg cctaccgggg ggagaaacag catccgttac  4080
tctgagttgg caccccctatt cgacaccacc cgtgtgtacc ttgtggacaa caagtcaacg  4140
gatgtggcat ccctgaacta ccagaacgac cacagcaact ttctaaccac ggtcattcaa  4200
aacaatgact acagcccggg ggaggcaagc acacagacca tcaatcttga cgaccgttcg  4260
cactggggcg gcgacctgaa aaccatcctg cataccaaca tgccaaatgt gaacgagttc  4320
atgtttacca ataagtttaa ggcgcgggtg atggtgtcgc gctcgcttac taaggacaaa  4380
caggtggagc tgaaatatga gtgggtggag ttcacgctgc ccgagggcaa ctactccgag  4440
accatgacca tagaccttat gaacaacgcg atcgtggagc actacttgaa agtgggcagg  4500
cagaacgggg ttctggaaag cgacatcggg gtaaagtttg acacccgcaa cttcagactg  4560
gggtttgacc cagtcactgg tcttgtcatg cctggggtat atacaaacga agccttccat  4620
ccagacatca ttttgctgcc aggatgcggg gtggacttca cccacagccg cctgagcaac  4680
ttgttgggca tccgcaagcg gcaacccttc caggagggct ttaggatcac ctacgatgac  4740
ctggagggtg gtaacattcc cgcactgttg gatgtggacg cctaccaggc aagcttaaaa  4800
gatgacaccg aacagggcgg ggatggcgca ggcggcggca acaacagtgg cagcggcgcg  4860
gaagagaact ccaacgcggc agccgcggca atgcagccgg tggaggacat gaacgatcat  4920
gccattcgcg gcgacacctt tgccacacgg gcggaggaga agcgcgctga ggccgaggca  4980
gcggcagaag ctgccgcccc cgctgcgcaa cccgaggtcg agaagcctca gaagaaaccg  5040
gtgatcaaac ccctgacaga ggacagcaag aaacgcagtt acaacctaat aagcaatgac  5100
agcaccttca cccagtaccg cagctggtac cttgcataca actacggcga ccctcagacc  5160
gggatccgct catggaccct cctttgcact cctgacgtaa cctgcggctc ggagcaggtc  5220
tactggtcgt tgccagacat gatgcaagac cccgtgacct tccgctccac gagccagatc  5280
agcaactttc cggtggtggg cgccgagctg ttgcccgtgc actccaagag cttctacaac  5340
gaccaggccg tctactccca gctcatccgc cagtttacct ctctgaccca cgtgttcaat  5400
cgctttcccg agaaccagat tttggcgcgc ccgccagccc ccaccatcac caccgtcagt  5460
gaaaacgttc ctgctctcac agatcacggg acgctaccgc tgcgcaacag catcggagga  5520
gtccagcgag tgaccattac tgacgccaga cgccgcacct gccccctacgt ttacaaggcc  5580
ctgggcatag tctcgccgcg cgtcctatcg agccgcactt tttgagcaaa catgtccatc  5640
cttatatcgc ccagcaataa cacaggctgg ggcctgcgct tcccaagcaa gatgtttggc  5700
ggggcaaaga agcgctccga ccaacaccca gtgcgcgtgc gcgggcacta ccgcgcgccc  5760
tggggcgcgc acaaacgcgg ccgcactggg cgcaccaccg tcgatgacgc cattgacgcg  5820
gtggtggagg aggcgcgcaa ctacacgccc acgccgccac cagtgtccac agtggacgcg  5880
```

-continued

```
gccattcaga ccgtggtgcg cggagcccgg cgttatgcta aaatgaagag acggcggagg  5940
cgcgtagcac gtcgccaccg ccgccgaccc ggcactgccg cccaacgcgc ggcggcggcc  6000
ctgcttaacc gcgcacgtcg caccggccga cgggcggcca tgcgggccgc tcgaaggctg  6060
gccgcgggta ttgtcactgt gcccccccagg tccaggcgac gagcggccgc cgcagcagcc  6120
gcggccatta gtgctatgac tcagggtcgc aggggcaacg tgtactgggt gcgcgactcg  6180
gttagcggcc tgcgcgtgcc cgtgcgcacc cgcccccccgc gcaactagat tgcaagaaaa  6240
aactacttag actcgtactg ttgtatgtat ccagcggcgg cggcgcgcaa cgaagctatg  6300
tccaagcgca aaatcaaaga agagatgctc caggtcatcg cgccggagat ctatggcccc  6360
ccgaagaagg aagagcagga ttacaagccc cgaaagctaa agcgggtcaa aaagaaaaag  6420
aaagatgatg atgatgatga acttgacgac gaggtggaac tgctgcacgc aaccgcgccc  6480
aggcggcggg tacagtggaa aggtcgacgc gtaagacgtg ttttgcgacc cggcaccacc  6540
gtagttttta cgcccggtga gcgctccacc cgcacctaca agcgcgtgta tgatgaggtg  6600
tacggcgacg aggacctgct tgagcaggcc aacgagcgcc tcggggagtt tgcctacgga  6660
aagcggcata aggacatgtt ggcgttgccg ctggacgagg gcaacccaac acctagccta  6720
aagcccgtga cactgcagca ggtgctgccc acgcttgcac cgtccgaaga aaagcgcggc  6780
ctaaagcgcg agtctggtga cttggcaccc accgtgcagc tgatggtacc caagcgccag  6840
cgactggaag atgtcttgga aaaaatgacc gtggagcctg ggctggagcc cgaggtccgc  6900
gtgcggccaa tcaagcaggt ggcaccggga ctgggcgtgc agaccgtgga cgttcagata  6960
cccaccacca gtagcactag tattgccact gccacagagg gcatggagac acaaacgtcc  7020
ccggttgcct cggcggtggc agatgccgcg gtgcaggcgg ccgctgcggc cgcgtccaaa  7080
acctctacgg aggtgcaaac ggacccgtgg atgtttcgcg tttcagcccc ccggcgcccg  7140
cgccgttcca ggaagtacgg caccgccagc gcactactgc ccgaatatgc cctacatcct  7200
tccatcgcgc ctacccccgg ctatcgtggc tacacctacc gccccagaag acgagcgact  7260
acccgacgcc gaaccaccac tggaacccgc cgccgccgtc gccgtcgcca gcccgtgctg  7320
gccccgattt ccgtgcgcag ggtggctcgc gaaggaggca ggaccctggt gctgccaaca  7380
gcgcgctacc accccagcat cgtttaaaag ccggtctttg tggttcttgc agatatggcc  7440
ctcacctgcc gcctccgttt cccggtgccg ggattccgag gaagaatgca ccgtaggagg  7500
ggcatggccg gccacggcct gacgggcggc atgcgtcgtg cgcaccaccg gcggcggcgc  7560
gcgtcgcacc gtcgcatgcg cggcggtatc ctgcccctcc ttattccact gatcgccgcg  7620
gcgattggcg ccgtgcccgg aattgcatcc gtggccttgc aggcgcagag acactgatta  7680
aaaacaagtt gcatgtggaa aaatcaaaat aaaaagtctg gagtctcacg ctcgcttggt  7740
cctgtaacta ttttgtagaa tggaagacat caactttgcg tctctggccc cgcgacacgg  7800
ctcgcgcccg ttcatgggaa actggcaaga tatcggcacc agcaatatga gcggtggcgc  7860
cttcagctgg ggctcgctgt ggagcggcat taaaaatttc ggttccacca ttaagaacta  7920
tggcagcaag gcctggaaca gcagcacagg ccagatgctg agggacaagt tgaaagagca  7980
aaatttccaa caaaaggtgg tagatggcct ggcctctggc attagcgggg tggtggacct  8040
ggccaaccag gcagtgcaaa ataagattaa cagtaagctt gatccccgcc ctcccgtaga  8100
ggagcctcca ccggccgtgg agacagtgtc tccagagggg cgtggcgaaa agcgtccgcg  8160
gcccgacagg gaagaaactc tggtgacgca aatagatgag cctccctcgt acgaggaggc  8220
actaaagcaa ggcctgccca ccacccgtcc catcgcgccc atggctaccg gagtgctggg  8280
ccagcacaca cctgtaacgc tggacctgcc tccccccgct gacacccagc agaaacctgt  8340
gctgccaggg ccgtccgccg ttgttgtaac ccgccctagc cgcgcgtccc tgcgccgtgc  8400
cgccagcggt ccgcgatcga cctgcaggca tgcaagcttg gcgtaatcat ggtcatagct  8460
gtttcctgtg tgaaattgtt atccgctcac aattccacac aacatacgag ccggaagcat  8520
aaagtgtaaa gcctggggtg cctaatgagt gagctaactc acattaattg cgttgcgctc  8580
actgcccgct ttccagtcgg gaaacctgtc gtgccagctg cattaatgaa tcggccaacg  8640
cgcggggaga ggcggtttgc gtattgggcg ctcttccgct tcctcgctca ctgactcgct  8700
gcgctcggtc gttcggctgc ggcgagcggt atcagctcac tcaaaggcgg taatacggtt  8760
atccacagaa tcaggggata acgcaggaaa gaacatgtga gcaaaaggcc agcaaaaggc  8820
caggaaccgt aaaaaggccg cgttgctggc gtttttccat aggctccgcc cccctgacga  8880
gcatcacaaa aatcgacgct caagtcagag gtggcgaaac ccgacaggac tataaagata  8940
ccaggcgttt ccccctggaa gctccctcgt gcgctctcct gttccgaccc tgccgcttac  9000
cggatacctg tccgcctttc tcccttcggg aagcgtggcg ctttctcaat gctcacgctg  9060
taggtatctc agttcggtgt aggtcgttcg ctccaagctg ggctgtgtgc acgaaccccc  9120
cgttcagccc gaccgctgcg ccttatccgg taactatcgt cttgagtcca acccggtaag  9180
acacgactta tcgccactgg cagcagccac tggtaacagg attagcagag cgaggtatgt  9240
aggcggtgct acagagttct tgaagtggtg gcctaactac ggctacacta gaaggacagt  9300
atttggtatc tgcgctctgc tgaagccagt taccttcgga aaaagagttg gtagctcttg  9360
atccggcaaa caaaccaccg ctggtagcgg tggttttttt gtttgcaagc agcagattac  9420
gcgcagaaaa aaaggatctc aagaagatcc tttgatcttt tctacggggt ctgacgctca  9480
gtggaacgaa aactcacgtt aagggatttt ggtcatgaga ttatcaaaaa ggatcttcac  9540
ctagatcctt ttaaattaaa aatgaagttt taaatcaatc taaagtatat atgagtaaac  9600
ttggtctgac agttaccaat gcttaatcag tgaggcacct atctcagcga tctgtctatt  9660
tcgttcatcc atagttgcct gactccccgt cgtgtagata actacgatac gggagggctt  9720
accatctggc cccagtgctg caatgatacc gcgagaccca cgctcaccgg ctccagattt  9780
atcagcaata aaccagccag ccggaagggc cgagcgcaga agtggtcctg caactttatc  9840
cgcctccatc cagtctatta attgttgccg ggaagctaga gtaagtagtt cgccagttaa  9900
tagtttgcgc aacgttgttg ccattgctac aggcatcgtg gtgtcacgct cgtcgtttgg  9960
tatggcttca ttcagctccg gttcccaacg atcaaggcga gttacatgat cccccatgtt  10020
gtgcaaaaaa gcggttagct ccttcggtcc tccgatcgtt gtcagaagta agttggccgc  10080
agtgttatca ctcatggtta tggcagcact gcataattct cttactgtca tgccatccgt  10140
aagatgcttt tctgtgactg gtgagtactc aaccaagtca ttctgagaat agtgtatgcg  10200
gcgaccgagt tgctcttgcc cggcgtcaat acgggataat accgcgccac atagcagaac  10260
tttaaaagtg ctcatcattg gaaaacgttc ttcggggcga aaactctcaa ggatcttacc  10320
gctgttgaga tccagttcga tgtaacccac tcgtgcaccc aactgatctt cagcatcttt  10380
tactttcacc agcgtttctg ggtgagcaaa aacaggaagg caaaatgccg caaaaaaggg  10440
aataagggcg acacggaaat gttgaatact catactcttc ctttttcaat attattgaag  10500
catttatcag ggttattgtc tcatgagcgg atacatattt gaatgtattt agaaaaataa  10560
acaaataggg gttccgcgca catttccccg aaaagtgcca cctgacgtct aagaaaccat  10620
```

```
tattatcatg acattaacct ataaaaatag gcgtatcacg aggccctttc gtc        10673

SEQ ID NO: 104         moltype = DNA  length = 22563
FEATURE                Location/Qualifiers
misc_feature           1..22563
                       note = plasmid pXba
source                 1..22563
                       mol_type = other DNA
                       organism = synthetic construct
SEQUENCE: 104
tcgcgcgttt cggtgatgac ggtgaaaacc tctgacacat gcagctcccg gagacggtca  60
cagcttgtct gtaagcggat gccgggagca gacaagcccg tcagggcgcg tcagcgggtg  120
ttggcgggtg tcggggctgg cttaactatg cggcatcaga gcagattgta ctgagagtgc  180
accatatgcg gtgtgaaata ccgcacagat gcgtaaggag aaaataccgc atcaggcgcc  240
attcgccatt caggctgcgc aactgttggg aagggcgatc ggtgcgggcc tcttcgctat  300
tacgccagct ggcgaaaggg ggatgtgctg caaggcgatt aagttgggta acgccagggt  360
tttcccagtc acgacgttgt aaaacgacgg ccagtgaatt cgagctcggt acccggggat  420
ccttctagac cgtgcaaaag gagagcctgt aagcgggcac tcttccgtgg tctggtggat  480
aaattcgcaa gggtatcatg gcggacgacc ggggttcgaa ccccggatcc ggccgtccgc  540
cgtgatccat gcggttaccg cccgcgtgtc gaacccaggt gtgcgacgtc agacaacggg  600
ggagcgctcc ttttggcttc cttccaggcg cggcggctgc tgcgctagct tttttggcca  660
ctggccgcgc gcggcgtaag cggttaggct ggaaagcgaa agcattaagt ggctcgctcc  720
ctgtagccgg agggttattt tccaagggtt gagtcgcagg acccccggtt cgagtctcgg  780
gccggccgga ctgcggcgaa cgggggtttg cctccccgtc atgcaagacc ccgcttgcaa  840
attcctccgg aaacagggac gagccccttt tttgcttttc ccagatgcat ccggtgctgc  900
ggcagatgcg ccccccctcct cagcagcggc aagagcaaga gcagcggcag acatgcaggg  960
caccctcccc ttctcctacc gcgtcaggag gggcaacatc cgcggctgac gcggcggcag  1020
atggtgatta cgaacccccg cggcgccggg cccggcacta cctggacttg gaggagggcg  1080
agggcctggc gcggctagga gcgccctctc ctgagcgaca cccaagggtg cagctgaagc  1140
gtgacacgcg cgaggcgtac gtgccgcggc agaacctgtt tcgcgaccgc gagggagagg  1200
agcccgagga gatgcgggat cgaaagttcc acgcagggcg cgagttgcgg catggcctga  1260
accgcgagcg gttgctgcgc gaggaggact ttgagcccga cgcgcggacc gggattagtc  1320
ccgcgcgcgc acacgtggcg gccgccgacc tggtaaccgc gtacgagcag acggtgaacc  1380
aggagattaa ctttcaaaaa agctttaaca accacgtgcg cacgcttgtg gcgcgcgagg  1440
aggtggctat aggactgatg catctgtggg actttgtaag cgcgctggag caaaacccaa  1500
atagcaagcc gctcatggcg cagctgttcc ttatagtgca gcacagcagg gacaacgagg  1560
cattcaggga tgcgctgcta aacatagtag agcccgaggg ccgctggctg ctcgatttga  1620
taaacattct gcagagcata gtggtgcagg agcgcagctt gagcctggct gacaaggtgg  1680
ccgccattaa ctattccatg ctcagtctgg gcaagtttta cgcccgcaag atataccata  1740
ccccttacgt tcccatagac aaggaggtaa agatcgaggg gttctacatg cgcatggcgt  1800
tgaaggtgct taccttgagc gacgacctgg gcgtttatcg caacgagcgc atccacaagg  1860
ccgtgagcgt gagccggcgg cgcgagctca gcgaccgcga gctgatgcac agcctgcaaa  1920
gggccctggc tggcacgggc agcggcgata gagaggccga gtcctacttt gacgcgggcg  1980
ctgacctgcg ctgggcccca agccgacgcg ccctggaggc agctggggcc ggacctgggc  2040
tggcggtggc acccgcgcgc gctggcaacg tcggcggcgt ggaggaatat gacgaggacg  2100
atgagtacga gccagaggac ggcgagtact aagcggtgat gtttctgatc agatgatgca  2160
agacgcaacg gacccggcgg tgcgggcggc gctgcagagc cagccgtccg gccttaactc  2220
cacggacgac tggcgccagg tcatggaccg catcatgtcg ctgactgcgc gtaaccctga  2280
cgcgttccgg cagcagccgc aggccaaccg gctctccgca attctggaag cggtggtccc  2340
ggcgcgcgca aaccccacgc acgagaaggt gctggcgatc gtaaacgcgc tggccgaaaa  2400
cagggccatc cggcccgatg aggccggcct ggtctacgac gcgctgcttc agcgcgtggc  2460
tcgttacaac agcggcaacg tgcagaccaa cctggaccgg ctggtggggg atgtgcgcga  2520
ggccgtggcg cagcgtgagc gcgcgcagca gcagggcaac ctgggctcca tggttgcact  2580
aaacgccttc ctgagtacac agcccgccaa cgtgccgcgg ggacaggagg actacaccaa  2640
ctttgtgagc gcactgcggc taatggtgac tgagacaccg caaagtgagg tgtaccagtc  2700
cgggccagac tattttttcc agaccagtag acaaggcctg cagaccgtaa acctgagcca  2760
ggctttcaag aacttgcagg ggctgtgggg ggtgcgggct cccacaggcg accgcgcgac  2820
cgtgtctagc ttgctgacgc ccaactcgcg cctgttgctg ctgctaatag cgcccttcac  2880
ggacagtggc agcgtgtccc gggacacata cctaggtcac ttgctgacac tgtaccgcga  2940
ggccataggt caggcgcatg tggacgagca tactttccag gagattacaa gtgtcagccg  3000
cgcgctgggg caggaggaca cggcagcct ggaggcaacc ctgaactacc tgctgaccaa  3060
ccggcggcag aagatcccct cgttgcacag tttaaacagc gaggaggagc gcatcttgcg  3120
ctatgtgcag cagagcgtga gccttaacct gatgcgcgac ggggtaacgc ccagcgtggc  3180
gctggacatg accgcgcgca acatggaacc gggcatgtat gcctcaaacc ggccgtttat  3240
caatcgccta atggactact tgcatcgcgc ggccgccgtg aaccccgagt atttcaccaa  3300
tgccatcttg aacccgcact ggctaccgcc ccctggtttc tacaccgggg gatttgaggt  3360
gcccgagggt aacgatggat tcctctggga cgacatagac gacagcgtgt tttccccgca  3420
accgcagacc ctgctagagt tgcaacagcg cgagcaggca gaggcggcgc tgcgaaagga  3480
aagcttccgc aggccaagca gcttgtccga tctaggcgct gcggccccgc ggtcagatgc  3540
gagtagccca tttccaagct tgatagggtc ttttaccagc actcgcacca cccgcccgcg  3600
cctgctgggc gaggaggagt acctaaacaa ctcgctgctg cagccgcagc gcgaaaagaa  3660
cctgcctccg gcatttccca acaacgggat agagagccta gtggacaaga tgagtagatg  3720
gaagacgtat gcgcaggagc acagggatgt gcccggcccg cgcccgccca cccgtcgtca  3780
aaggcacgac cgtcagcggg gtctggtgtg ggaggacgat gactcggcag acgacagcag  3840
cgtcctggat ttgggaggga gtggcaaccc gtttgcgcac cttcgcccca ggctggggag  3900
aatgttttaa aaaaaaaaaa aaaaagcatg atgcaaaata aaaaactcac caaggccatg  3960
gcaccgagcg ttggttttct tgtattcccc ttagtatgca gcgcgcggcg atgtatgagg  4020
aaggtcctcc tccctcctac gagagcgtgg tgagcgcggc gccagtggcg gcggcgctgg  4080
gttccccctt cgatgctccc ctggacccgc cgtttgtgcc tccgcggtac ctgcggccta  4140
```

-continued

```
ccgggggag aaacagcatc cgttactctg agttggcacc cctattcgac accacccgtg 4200
tgtaccttgt ggacaacaag tcaacggatg tggcatccct gaactaccag aacgaccaca 4260
gcaactttct aaccacggtc attcaaaaca atgactacag cccgggggag gcaagcacac 4320
agaccatcaa tcttgacgac cgttcgcact ggggcggcga cctgaaaacc atcctgcata 4380
ccaacatgcc aaatgtgaac gagttcatgt ttaccaataa gtttaaggcg cgggtgatgg 4440
tgtcgcgctc gcttactaag gacaaacagg tggagctgaa atatgagtgg gtggagttca 4500
cgctgcccga gggcaactac tccgagacca tgaccataga ccttatgaac aacgcgatcg 4560
tggagcacta cttgaaagtg ggcaggcaga acggggttct ggaaagcgac atcggggtaa 4620
agtttgacac ccgcaacttc agactggggt ttgacccagt cactggtctt gtcatgcctg 4680
gggtatatac aaacgaagcc ttccatccag acatcatttt gctgccagga tgcggggtgg 4740
acttcaccca cagccgcctg agcaacttgt tgggcatccg caagcggcaa cccttccagg 4800
agggctttag gatcacctac gatgacctgg agggtggtaa cattcccgca ctgttggatg 4860
tggacgccta ccaggcaagc ttaaaagatg acaccgaaca gggcggggat ggcgcaggcg 4920
gcggcaacaa cagtggcagc ggcgcggaag agaactccaa cgcggcagcc gcggcaatgc 4980
agccggtgga ggacatgaac gatcatgcca ttcgcggcga cacctttgcc acacgggcgg 5040
aggagaagcg cgctgaggcc gaggcagcgg cagaagctgc cgcccccgct gcgcaacccg 5100
aggtcgagaa gcctcagaag aaaccggtga tcaaacccct gacagaggac agcaagaaac 5160
gcagttacaa cctaataagc aatgacagca ccttcaccca gtaccgcagc tggtaccttg 5220
catacaacta cggcgaccct cagaccggga tccgctcatg gaccctcctt tgcactcctg 5280
acgtaacctg cggctcggag caggtctact ggtcgttgcc agacatgatg caagaccccg 5340
tgaccttccg ctccacgagc cagatcagca actttccggt ggtgggcgcc gagctgttgc 5400
ccgtgcactc caagagcttc tacaacgacc aggccgtcta ctcccagctc atccgccagt 5460
ttacctctct gacccacgtg ttcaatcgct ttcccgagaa ccagattttg gcgcgcccgc 5520
cagcccccac catcaccacc gtcagtgaaa acgttcctgc tctcacagat cacgggacgc 5580
taccgctgcg caacagcatc ggaggagtcc agcgagtgac cattactgac gccagacgcc 5640
gcacctgccc ctacgtttac aaggccctgg gcatagtctc gccgcgcgtc ctatcgagcc 5700
gcacttttttg agcaaacatg tccatcctta tatcgcccag caataacaca ggctggggcc 5760
tgcgcttccc aagcaagatg tttggcgggg caaagaagcg ctccgaccaa cacccagtgc 5820
gcgtgcgcgg gcactaccgc gcgccctggg gcgcgcacaa acgcggccgc actgggcgca 5880
ccaccgtcga tgacgccatt gacgcggtgg tggaggaggc gcgcaactac acgcccacgc 5940
cgccaccagt gtccacagtg gacgcggcca ttcagaccgt ggtgcgcgga gcccggcgtt 6000
atgctaaaat gaagagacgg cggaggcgcg tagcacgtcg ccaccgccgc cgacccggca 6060
ctgccgccca acgcgcggcg gcggccctgc ttaaccgcgc acgtcgcacc ggccgacggg 6120
cggccatgcg ggccgctcga aggctggccg cgggtattgt cactgtgccc cccaggtcca 6180
ggcgacgagc ggccgccgca gcagccgcgg ccattagtgc tatgactcag ggtcgcaggg 6240
gcaacgtgta ctgggtgcgc gactcggtta gcggcctgcg cgtgcccgtg cgcacccgcc 6300
ccccgcgcaa ctagattgca agaaaaaact acttagactc gtactgttgt atgtatccag 6360
cggcggcggc gcgcaacgaa gctatgtcca agcgcaaaat caaagaagag atgctccagg 6420
tcatcgcgcc ggagatctat ggccccccga agaaggaaga gcaggattac aagccccgaa 6480
agctaaagcg ggtcaaaaag aaaaagaaag atgatgatga tgatgaactt gacgacgagg 6540
tggaactgct gcacgcaacc gcgcccaggc ggcgggtaca gtggaaaggt cgacgcgtaa 6600
gacgtgtttt gcgacccggc accaccgtag tttttacgcc cggtgagcgc tccacccgca 6660
cctacaagcg cgtgtatgat gaggtgtacg gcgacgagga cctgcttgag caggccaacg 6720
agcgcctcgg ggagtttgcc tacggaaagc ggcataagga catgttggcg ttgccgctgg 6780
acgagggcaa cccaacacct agcctaaagc ccgtgacact gcagcaggtg ctgcccacgc 6840
ttgcaccgtc cgaagaaaag cgcggcctaa agcgcgagtc tggtgacttg gcacccaccg 6900
tgcagctgat ggtacccaag cgccagcgac tggaagatgt cttggaaaaa atgaccgtgg 6960
agcctgggct ggagcccgag gtccgcgtgc ggccaatcaa gcaggtggca ccgggactgg 7020
gcgtgcagac cgtggacgtt cagataccca ccaccagtag cactagtatt gccactgcca 7080
cagagggcat ggagacacaa acgtccccgg ttgcctcggc ggtggcagat gccgcggtgc 7140
aggcggccgc tgcggccgcg tccaaaacct ctacggaggt gcaaacggac ccgtggatgt 7200
ttcgcgtttc agcccccccgg cgcccgcgcc gttccaggaa gtacggcacc gccagcgcac 7260
tactgcccga atatgcccta catccttcca tcgcgcctac ccccggctat cgtggctaca 7320
cctaccgccc cagaagacga gcgactaccc gacgccgaac caccactgga acccgccgcc 7380
gccgtcgccg tcgccagccc gtgctggccc cgatttccgt gcgcagggtg gctcgcgaag 7440
gaggcaggac cctggtgctg ccaacagcgc gctaccaccc cagcatcgtt taaaagccgg 7500
tctttgtggt tcttgcagat atggccctca cctgccgcct ccgtttcccg gtgccgggat 7560
tccgaggaag aatgcaccgt aggaggggca tggccggcca cggcctgacg ggcggcatgc 7620
gtcgtgcgca ccaccggcgg cggcgcgcgt cgcaccgtcg catgcgcggc ggtatcctgc 7680
ccctccttat tccactgatc gccgcggcga ttggcgccgt gcccggaatt gcatccgtgg 7740
ccttgcaggc gcagagacac tgattaaaaa caagttgcat gtggaaaaat caaaataaaa 7800
agtctggagt ctcacgctcg cttggtcctg taactatttt gtagaatgga agacatcaac 7860
tttgcgtctc tggccccgcg acacggctcg cgcccgttca tgggaaactg gcaagatatc 7920
ggcaccagca atatgagcgg tggcgccttc agctggggct cgctgtggag cggcattaaa 7980
aatttcggtt ccaccattaa gaactatggc agcaaggcct ggaacagcag cacaggccag 8040
atgctgaggg acaagttgaa agagcaaaat ttccaacaaa aggtggtaga tggcctggcc 8100
tctggcatta gcggggtggt ggacctggcc aaccaggcag tgcaaaataa gattaacagt 8160
aagcttgatc cccgccctcc cgtagaggag cctccaccgg ccgtggagac agtgtctcca 8220
gaggggcgtg gcgaaaagcg tccgcggccc gacagggaag aaactctggt gacgcaaata 8280
gatgagcctc cctcgtacga ggaggcacta aagcaaggcc tgcccaccac ccgtcccatc 8340
gcgcccatgg ctaccggagt gctgggccag cacacacctg taacgctgga cctgcctccc 8400
cccgctgaca cccagcagaa acctgtgctg ccagggccgt ccgccgttgt tgtaacccgc 8460
cctagccgcg cgtccctgcg ccgtgccgcc agcggtccgc gatcgatgcg gcccgtagcc 8520
agtggcaact ggcaaagcac actgaacagc atcgtgggtc tgggggtgca atccctgaag 8580
cgccgacgat gcttctaaat agctaacgtg tcgtatgtgt catgtatgcg tccatgtcgc 8640
cgccagagga gctgctgagc cgccgtgcgc ccgctttcca agatggctac cccttcgatg 8700
atgccgcagt ggtcttacat gcacatctcg ggccaggacg cctcggagta cctgagcccc 8760
gggctggtgc agtttgcccg cgccaccgag acgtacttca gcctgaataa caagtttaga 8820
aaccccacgg tggcacctac gcacgacgta accacagacc ggtcccagcg tttgacgctg 8880
```

-continued

```
cggttcatcc ctgtggaccg cgaggatacc gcgtactcgt acaaagcgcg gttcaccctg  8940
gctgtgggtg acaaccgtgt gcttgatatg gcttccacgt actttgacat ccgcggcgtg  9000
ctggacaggg ggcctacttt taagccctac tccggcactg cctacaacgc tctagctccc  9060
aagggcgctc ctaactcctg tgagtgggaa caaaccgaag atagcggccg ggcagttgcc  9120
gaggatgaag aagaggaaga tgaagatgaa gaagaggaag aagaagagca aaacgctcga  9180
gatcaggcta ctaagaaaac acatgtctat gcccaggctc ctttgtctgg agaaacaatt  9240
acaaaaagcg ggctacaaat aggatcagac aatgcagaaa cacaagctaa acctgtatac  9300
gcagatcctt cctatcaacc agaacctcaa attggcgaat ctcagtggaa cgaagctgat  9360
gctaatgcgg caggagggag agtgcttaaa aaaacaactc ccatgaaacc atgctatgga  9420
tcttatgcca ggcctacaaa tccttttggt ggtcaatccg ttctggttcc ggatgaaaaa  9480
ggggtgcctc ttccaaaggt tgacttgcaa ttcttctcaa atactacctc tttgaacgac  9540
cggcaaggca atgctactaa accaaaagtg gttttgtaca gtgaagatgt aaatatggaa  9600
accccagaca cacatctgtc ttacaaacct ggaaaaggtg atgaaaattc taaagctatg  9660
ttgggtcaac aatctatgcc aaacagaccc aattacattg ctttcaggga caattttatt  9720
ggcctaatgt attataacag cactggcaac atgggtgttc ttgctggtca ggcatcgcag  9780
ctaaatgccg tggtagattt gcaagacaga aacacagagc tgtcctatca actcttgctt  9840
gattccatag gtgatagaac cagatatttt tctatgtgga atcaggctgt agacagctat  9900
gatccagatg ttagaatcat tgaaaaccat ggaactgagg atgaattgcc aaattattgt  9960
tttcctcttg gggtattggg ggtaactgac acctatcaag ctattaaggc taatggcaat  10020
ggctcaggcg ataatggaga tactacatgg acaaaagatg aaacttttgc aacacgtaat  10080
gaaataggag tgggtaacaa ctttgccatg gaaattaacc taaatgccaa cctatggaga  10140
aatttccttt actccaatat tgcgctgtac ctgccagaca agctaaaata caaccccacc  10200
aatgtggaaa tatctgacaa ccccaacacc tacgactaca tgaacaagcg agtggtggct  10260
cccgggcttg tagactgcta cattaacctt ggggcgcgct ggtctctgga ctacatggac  10320
aacgttaatc cctttaacca ccaccgcaat gcgggcctcc gttatcgctc catgttgttg  10380
ggaaacggcc gctacgtgcc ctttcacatt caggtgcccc aaaagttttt tgccattaaa  10440
aacctcctcc tcctgccagg ctcatataca tatgaatgga acttcaggaa ggatgttaac  10500
atggttctgc agagctctct gggaaacgat cttagagttg acggggctag cattaagttt  10560
gacagcattt gtctttacgc caccttcttc cccatggccc acaacacggc ctccacgctg  10620
gaagccatgc tcagaaatga caccaacgac cagtccttta atgactacct ttccgccgcc  10680
aacatgctat accccatacc cgccaacgcc accaacgtgc ccatctccat cccatcgcgc  10740
aactgggcag catttcgcgg ttgggccttc acacgcttga agacaaagga aaccccttcc  10800
ctgggatcag gctacgaccc ttactacacc tactctggct ccataccata ccttgacgga  10860
accttctatc ttaatcacac ctttaagaag gtggccatta cctttgactc ttctgttagc  10920
tggccgggca acgaccgcct gcttactccc aatgagtttg agattaaacg ctcagttgac  10980
ggggagggct acaacgtagc tcagtgcaac atgaccaagg actggttcct ggtgcagatg  11040
ttggccaact acaatattgg ctaccagggc ttctacattc cagaaagcta caaggaccgc  11100
atgtactcgt tcttcagaaa cttccagccc atgagccggc aagtggttga cgatactaaa  11160
tacaaggagt atcagcaggt tggaattctt caccagcata acaactcagg attcgtaggc  11220
tacctcgctc ccaccatgcg cgagggacag gcttaccccg ccaacgtgcc ctacccacta  11280
ataggcaaaa ccgcggttga cagtattacc cagaaaaagt ttctttgcga tcgcaccctt  11340
tggcgcatcc cattctccag taactttatg tccatgggcg cactcacaga cctgggccaa  11400
aaccttctct acgccaactc cgcccacgcg ctagacatga cttttgaggt ggatcccatg  11460
gacgagccca cccttcttta tgttttgttt gaagtctttg acgtggtccg tgtgcaccag  11520
ccgcaccgcg gcgtcatcga gaccgtgtac ctgcgcacgc ccttctcggc cggcaacgcc  11580
acaacataaa agaagcaagc aacatcaaca acagctgccg ccatgggctc cagtgagcag  11640
gaactgaaag ccattgtcaa agatcttggt tgtgggccat attttttggg cacctatgac  11700
aagcgctttc caggctttgt ttctccacac aagctcgcct gcgccatagt caatacggcc  11760
ggtcgcgaga ctgggggcgt acactggatg gcctttgcct ggaacccgcg ctcaaaaaca  11820
tgctacctct ttgagccctt tggcttttct gaccaacgac tcaagcaggt ttaccagttt  11880
gagtacgagt cactcctgcg ccgtagcgcc attgcttctt cccccgaccg ctgtataacg  11940
ctggaaaagt ccacccaaag cgtgcagggg cccaactcgg ccgcctgtgg actattctgc  12000
tgcatgtttc tccacgcctt tgccaactgg ccccaaactc ccatggatca caaccccacc  12060
atgaacctta ttaccggggt acccaactcc atgcttaaca gtccccaggt acagcccacc  12120
ctgcgtcgca accaggaaca gctctacagc ttcctggagc gccactcgcc ctacttccgc  12180
agccacagtg cgcagattag gagcgccact tctttttgtc acttgaaaaa catgtaaaaa  12240
taatgtacta ggagacactt tcaataaagg caaatgtttt tatttgtaca ctctcgggtg  12300
attatttacc ccccaccctt gccgtctgcg ccgtttaaaa atcaaagggg ttctgccgcg  12360
catcgctatg cgccactggc agggacacgt tgcgatactg gtgtttagtg ctccacttaa  12420
actcaggcac aaccatccgc ggcagctcgg tgaagttttc actccacagg ctgcgcacca  12480
tcaccaacgc gtttagcagg tcgggcgccg atatcttgaa gtcgcagttg gggcctccgc  12540
cctgcgcgcg cgagttgcga tacacagggt tgcagcactg gaacactatc agcgccgggt  12600
ggtgcacgct ggccagcacg ctcttgtcgg agatcagatc cgcgtccagg tcctccgcgt  12660
tgctcagggc gaacggagtc aactttggta gctgccttcc caaaaagggt gcatgcccag  12720
gctttgagtt gcactcgcac cgtagtggca tcagaaggtg accgtgcccg gtctgggcgt  12780
taggatacag cgcctgcatg aaagccttga tctgcttaaa agccacctga gcctttgcgc  12840
cttcagagaa gaacatgccg caagacttgc cggaaaactg attggccgga caggccgcgt  12900
catgcacgca gcaccttgcg tcggtgttgg agatctgcac cacatttcgg ccccaccggt  12960
tcttcacgat cttggccttg ctagactgct ccttcagcgc gcgctgcccg ttttcgctcg  13020
tcacatccat ttcaatcacg tgctccttat ttatcataat gctcccgtgt agacacttaa  13080
gctcgccttc gatctcagcg cagcggtgca gccacaacgc gcagcccgtg ggctcgtggt  13140
gcttgtaggt tacctctgca aacgactgca ggtacgcctg caggaatcgc cccatcatcg  13200
tcacaaaggt cttgttgctg gtgaaggtca gctgcaaccc gcggtgctcc tcgtttagcc  13260
aggtcttgca tacggccgcc agagcttcca cttggtcagg cagtagcttg aagtttgcct  13320
ttagatcgtt atccacgtgg tacttgtcca tcaacgcgcg cgcagcctcc atgcccttct  13380
cccacgcaga cacgatcggc aggctcagcg ggtttatcac cgtgctttca ctttccgctt  13440
cactggactc ttccttttcc tcttgcgtcc gcataccccg cgccactggg tcgtcttcat  13500
tcagccgccg caccgtgcgc ttacctccct tgccgtgctt gattagcacc ggtgggttgc  13560
tgaaacccac catttgtagc gccacatctt ctctttcttc ctcgctgtcc acgatcacct  13620
```

```
ctggggatgg cgggcgctcg ggcttgggag aggggcgctt ctttttcttt ttggacgcaa  13680
tggccaaatc cgccgtcgag gtcgatggcc gcgggctggg tgtgcgcggc accagcgcat  13740
cttgtgacga gtcttcttcg tcctcggact cgagacgccg cctcagccgc ttttttgggg  13800
gcgcgcgggg aggcggcggc gacggcgacg gggacgacac gtcctccatg gttggtggac  13860
gtcgcgccgc accgcgtccg cgctcggggg tggtttcgcg ctgctcctct tcccgactgg  13920
ccatttcctt ctcctatagg cagaaaaaga tcatggagtc agtcgagaag gaggacagcc  13980
taaccgcccc ctttgagttc gccaccaccg cctccaccga tgccgccaac gcgcctacca  14040
ccttccccgt cgaggcaccc ccgcttgagg aggaggaagt gattatcgag caggacccag  14100
gttttgtaag cgaagacgac gaggatcgct cagtaccaac agaggataaa aagcaagacc  14160
aggacgacgc agaggcaaac gaggaacaag tcgggcgggg ggaccaaagg catggcgact  14220
acctagatgt gggagacgac gtgctgttga agcatctgca gcgccagtgc gccattatct  14280
gcgacgcgtt gcaagagcgc agcgatgtgc ccctcgccat agcggatgtc agccttgcct  14340
acgaacgcca cctgttctca ccgcgcgtac cccccaaacg ccaagaaaac ggcacatgcg  14400
agcccaaccc gcgcctcaac ttctaccccg tatttgccgt gccagaggtg cttgccacct  14460
atcacatctt tttccaaaac tgcaagatac ccctatcctg ccgtgccaac cgcagccgag  14520
cggacaagca gctggccttg cggcagggcg ctgtcatacc tgatatcgcc tcgctcgacg  14580
aagtgccaaa aatctttgag ggtcttggac gcgacgagaa acgcgcggca aacgctctgc  14640
aacaagaaaa cagcgaaaat gaaagtcact gtggagtgct ggtggaactt gagggtgaca  14700
acgcgcgcct agccgtgctg aaacgcagca tcgaggtcac ccactttgcc tacccggcac  14760
ttaacctacc ccccaaggtt atgagcacag tcatgagcga gctgatcgtg cgccgtgcac  14820
gacccctgga gagggatgca aacttgcaag aacaaaccga ggagggccta cccgcagttg  14880
gcgatgagca gctggcgcgc tggcttgaga cgcgcgagcc tgccgacttg gaggagcgac  14940
gcaagctaat gatggccgca gtgcttgtta ccgtggagct tgagtgcatg cagcggttct  15000
ttgctgaccc ggagatgcag cgcaagctag aggaaacgtt gcactacacc tttcgccagg  15060
gctacgtgcg ccaggcctgc aaaatttcca acgtggagct ctgcaacctg gtctcctacc  15120
ttggaatttt gcacgaaaac cgcctcgggc aaaacgtgct tcattccacg ctcaagggcg  15180
aggcgcgccg cgactacgtc cgcgactgcg tttacttatt tctgtgctac acctggcaaa  15240
cggccatggg cgtgtggcag caatgcctgg aggagcgcaa cctaaaggag ctgcagaagc  15300
tgctaaagca aaacttgaag gacctatgga cggccttcaa cgagcgctcc gtggccgcgc  15360
acctggcgga cattatcttc cccgaacgcc tgcttaaaac cctgcaacag ggtctgccag  15420
acttcaccag tcaaagcatg ttgcaaaact ttaggaactt tatcctagag cgttcaggaa  15480
ttctgcccgc cacctgctgt gcgcttccta gcgactttgt gcccattaag taccgtgaat  15540
gccctccgcc gctttggggt cactgctacc ttctgcagct agccaactac cttgcctacc  15600
actccgacat catggaagac gtgagcggtg acggcctact ggagtgtcac tgtcgctgca  15660
acctatgcac cccgcaccgc tccctggtct gcaattcgca actgcttagc gaaagtcaaa  15720
ttatcggtac ctttgagctg cagggtccct cgcctgacga aaagtccgcg gctccggggt  15780
tgaaactcac tccggggctg tggacgtcgg cttaccttcg caaatttgta cctgaggact  15840
accacgccca cgagattagg ttctacgaag accaatcccg cccgccaaat gcggagctta  15900
ccgcctgcgt cattacccag ggccacatcc ttggccaatt gcaagccatc aacaaagccc  15960
gccaagagtt tctgctacga aagggacggg gggtttacct ggacccccag tccggcgagg  16020
agctcaaccc aatccccccg ccgccgcagc cctatcagca gccgcgggcc cttgcttccc  16080
aggatggcac ccaaaaagaa gctgcagctg ccgccgccgc cacccacgga cgaggaggaa  16140
tactgggaca gtcaggcaga ggaggttttg gacgaggagg aggagatgat ggaagactgg  16200
gacagcctag acgaagcttc cgaggccgaa gaggtgtcag acgaaacacc gtcaccctcg  16260
gtcgcattcc cctcgccggc gccccagaaa ttggcaaccg ttcccagcat cgctacaacc  16320
tccgctcctc aggcgccgcc ggcactgcct gttcgccgac ccaaccgtag atgggacacc  16380
actggaacca gggccggtaa gtctaagcag ccgccgccgt tagcccaaga gcaacaacag  16440
cgccaaggct accgctcgtg gcgcgggcac aagaacgcca tagttgcttg cttgcaagac  16500
tgtgggggca acatctcctt cgcccgccgc tttcttctct accatcacgg cgtggccttc  16560
ccccgtaaca tcctgcatta ctaccgtcat ctctacagcc cctactgcac cggcggcagc  16620
ggcagcggca gcaacagcag cggtcacaca gaagcaaagg cgaccggata gcaagactct  16680
gacaaagccc aagaaatcca cagcggcggc agcagcagga ggaggagcgc tgcgtctggc  16740
gcccaacgaa cccgtatcga cccgcgagct tagaaatagg atttttccca ctctgtatgc  16800
tatatttcaa caaagcaggg gccaagaaca agagctgaaa ataaaaaaca ggtctctgcg  16860
ctccctcacc cgcagctgcc tgtatcacaa aagcgaagat cagcttcggc gcacgctgga  16920
agacgcggag gctctcttca gcaaatactg cgcgctgact cttaaggact agtttcgcgc  16980
cctttctcaa atttaagcgc gaaaactacg tcatctccag cggccacacc cggcgccagc  17040
acctgtcgtc agcgccatta tgagcaagga aattcccacg ccctacatgt ggagttacca  17100
gccacaaatg ggacttgcgg ctggagctgc ccaagactac tcaacccgaa taaactacat  17160
gagcgcggga ccccacatga tatcccgggt caacggaatc cgcgcccacc gaaaccgaat  17220
tctcctcgaa caggcggcta ttaccaccac acctcgtaat aaccttaatc cccgtagttg  17280
gcccgctgcc ctggtgtacc aggaaagtcc cgctcccacc actgtggtac ttcccagaga  17340
cgcccaggcc gaagttcaga tgactaactc aggggcgcag cttgcgggcg gctttcgtca  17400
cagggtgcgg tcgcccgggc agggtataac tcacctgaaa atcagagggc gaggtattca  17460
gctcaacgac gagtcggtga gctcctctct tggtctccgt ccggacggga catttcagat  17520
cggcggcgct ggccgctctt catttacgcc ccgtcaggcg atcctaactc tgcagacctc  17580
gtcctcggag ccgcgctccg gaggcattgg aactctacaa tttattgagg agttcgtgcc  17640
ttcggtttac ttcaacccct tttctggacc tcccggccac tacccggacc agtttattcc  17700
caactttgac gcggtgaaag actcggcgga cggctacgac tgaatgacca gtggagaggc  17760
agagcgactg cgcctgacac acctcgacca ctgccgccgc cacaagtgct ttgcccgcgg  17820
ctccggtgag ttttgttact ttgaattgcc cgaagagcat atcgagggcc cggcgcacgg  17880
cgtccggctc accacccagg tagagcttac acgtagcctg attcgggagt ttaccaagcg  17940
ccccctgcta gtggagcggg agcggggtcc ctgtgttctg accgtggttt gcaactgtcc  18000
taaccctgga ttacatcaag atctttgttg tcatctctgt gctgagtata ataaatacag  18060
aaattagaat ctactggggc tcctgtcgcc atcctgtgaa cgccaccgtt tttacccacc  18120
caaagcagac caaagcaaac ctcacctccg gtttgcacaa gcgggccaat aagtacctta  18180
cctggtactt taacggctct tcatttgtaa tttacaacag tttccagcga gacgaagtaa  18240
gtttgccaca caaccttctc ggcttcaact acaccgtcaa gaaaaacacc accaccacca  18300
ccctcctcac ctgccgggaa cgtacgagtg cgtcaccggt tgctgcgccc acacctacag  18360
```

```
cctgagcgta accagacatt actcccattt ttccaaaaca ggaggtgagc tcaactcccg  18420
gaactcaggt caaaaaagca ttttgcgggg tgctgggatt ttttaattaa gtatatgagc  18480
aattcaagta actctacaag cttgtctaat ttttctggaa ttggggtcgg ggttatcctt  18540
actcttgtaa ttctgtttat tcttatacta gcacttctgt gccttagggt tgccgcctgc  18600
tgcacgcacg tttgtaccta ttgtcagctt tttaaacgct gggggcaaca tccaagatga  18660
ggtacatgat tttaggcttg ctcgcccttg cggcagtctg cagcgctgcc aaaaaggttg  18720
agtttaagga accagcttgc aatgttacat ttaaatcaga agctaatgaa tgcactactc  18780
ttataaaatg caccacagaa catgaaaagc ttattattcg ccacaaagac aaaattggca  18840
agtatgctgt atatgctatt tggcagccag gtgacactaa cgactataat gtcacagtct  18900
tccaaggtga aaatcgtaaa acttttatgt ataaatttcc attttatgaa atgtgcgata  18960
ttaccatgta catgagcaaa cagtacaagt tgtggccccc acaaaagtgt ttagagaaca  19020
ctggcacctt ttgttccacc gctctgctta ttacagcgct tgctttggta tgtaccttac  19080
tttatctcaa atacaaaagc agacgcagtt ttattgatga aaagaaaatg ccttgatttt  19140
ccgcttgctt gtattcccct ggacaattta ctctatgtgg gatatgctcc aggcgggcaa  19200
gattataccc acaaccttca aatcaaactt tcctggacgt tagcgcctga tttctgccag  19260
cgcctgcact gcaaatttga tcaaacccag cttcagcttg cctgctccag agatgaccgg  19320
ctcaaccatc gcgcccacaa cggactatcg caacaccact gctaccggac taacatctgc  19380
cctaaattta ccccaagttc atgcctttgt caatgactgg gcgagcttgg acatgtggtg  19440
gttttccata gcgcttatgt ttgtttgcct tattattatg tggcttattt gttgcctaaa  19500
gcgcagacgc gccagacccc ccatctatag gcctatcatt gtgctcaacc cacacaatga  19560
aaaaattcat agattggacg gtctgaaacc atgttctctt cttttacagt atgattaaat  19620
gagacatgat tcctcgagtt cttatattat tgacccttgt tgcgcttttc tgtgcgtgct  19680
ctacattggc cgcggtcgct cacatcgaag tagattgcat cccacctttc acagtttacc  19740
tgctttacgg atttgtcacc cttatcctca tctgcagcct cgtcactgta gtcatcgcct  19800
tcattcagtt cattgactgg gtttgtgtgc gcattgcgta cctcaggcac catccgcaat  19860
acagagacag gactatagct gatcttctca gaattcttta attatgaaac ggagtgtcat  19920
ttttgttttg ctgatttttt gcgccctacc tgtgctttgc tcccaaacct cagcgcctcc  19980
caaaagacat atttcctgca gattcactca aatatggaac attcccagct gctacaacaa  20040
acagagcgat ttgtcagaag cctggttata cgccatcatc tctgtcatgg tttttttgcag  20100
taccattttt gccctagcca tatatccata ccttgacatt ggctggaatg ccatagatgc  20160
catgaaccac cctactttcc cagtgcccgc tgtcatacca ctgcaacagg ttattgcccc  20220
aatcaatcag cctcgccccc cttctcccac ccccactgag attagctact ttaatttgac  20280
aggtggagat gactgaatct ctagagtcga cctgcaggca tgcaagcttg gcgtaatcat  20340
ggtcatagct gtttcctgtg tgaaattgtt atccgctcac aattccacac aacatacgag  20400
ccggaagcat aaagtgtaaa gcctggggtg cctaatgagt gagctaactc acattaattg  20460
cgttgcgctc actgcccgct ttccagtcgg gaaacctgtc gtgccagctg cattaatgaa  20520
tcggccaacg cgcggggaga ggcggtttgc gtattgggcg ctcttccgct tcctcgctca  20580
ctgactcgct gcgctcggtc gttcggctgc ggcgagcggt atcagctcac tcaaaggcgg  20640
taatacggtt atccacagaa tcaggggata acgcaggaaa gaacatgtga gcaaaaggcc  20700
agcaaaaggc caggaaccgt aaaaaggccg cgttgctggc gtttttccat aggctccgcc  20760
cccctgacga gcatcacaaa aatcgacgct caagtcagag gtggcgaaac ccgacaggac  20820
tataaagata ccaggcgttt ccccctggaa gctccctcgt gcgctctcct gttccgaccc  20880
tgccgcttac cggatacctg tccgcctttc tcccttcggg aagcgtggcg ctttctcaat  20940
gctcacgctg taggtatctc agttcggtgt aggtcgttcg ctccaagctg ggctgtgtgc  21000
acgaaccccc cgttcagccc gaccgctgcg ccttatccgg taactatcgt cttgagtcca  21060
acccggtaag acacgactta tcgccactgg cagcagccac tggtaacagg attagcagag  21120
cgaggtatgt aggcggtgct acagagttct tgaagtggtg gcctaactac ggctacacta  21180
gaaggacagt atttggtatc tgcgctctgc tgaagccagt taccttcgga aaaagagttg  21240
gtagctcttg atccggcaaa caaaccaccg ctggtagcgg tggttttttt gtttgcaagc  21300
agcagattac gcgcagaaaa aaaggatctc aagaagatcc tttgatcttt tctacggggt  21360
ctgacgctca gtggaacgaa aactcacgtt aagggatttt ggtcatgaga ttatcaaaaa  21420
ggatcttcac ctagatcctt ttaaattaaa aatgaagttt taaatcaatc taaagtatat  21480
atgagtaaac ttggtctgac agttaccaat gcttaatcag tgaggcacct atctcagcga  21540
tctgtctatt tcgttcatcc atagttgcct gactccccgt cgtgtagata actacgatac  21600
gggagggctt accatctggc cccagtgctg caatgatacc gcgagaccca cgctcaccgg  21660
ctccagattt atcagcaata aaccagccag ccggaagggc cgagcgcaga agtggtcctg  21720
caactttatc cgcctccatc cagtctatta attgttgccg ggaagctaga gtaagtagtt  21780
cgccagttaa tagtttgcgc aacgttgttg ccattgctac aggcatcgtg gtgtcacgct  21840
cgtcgtttgg tatggcttca ttcagctccg gttcccaacg atcaaggcga gttacatgat  21900
cccccatgtt gtgcaaaaaa gcggttagct ccttcggtcc tccgatcgtt gtcagaagta  21960
agttggccgc agtgttatca ctcatggtta tggcagcact gcataattct cttactgtca  22020
tgccatccgt aagatgcttt tctgtgactg gtgagtactc aaccaagtca ttctgagaat  22080
agtgtatgcg gcgaccgagt tgctcttgcc cggcgtcaat acgggataat accgcgccac  22140
atagcagaac tttaaaagtg ctcatcattg gaaaacgttc ttcggggcga aaactctcaa  22200
ggatcttacc gctgttgaga tccagttcga tgtaacccac tcgtgcaccc aactgatctt  22260
cagcatcttt tactttcacc agcgtttctg ggtgagcaaa aacaggaagg caaaatgccg  22320
caaaaaaggg aataagggcg acacggaaat gttgaatact catactcttc ctttttcaat  22380
attattgaag catttatcag ggttattgtc tcatgagcgg atacatattt gaatgtattt  22440
agaaaaataa acaaataggg gttccgcgca catttccccg aaaagtgcca cctgacgtct  22500
aagaaaccat tattatcatg acattaacct ataaaaatag gcgtatcacg aggccctttc  22560
gtc                                                                 22563
```

```
SEQ ID NO: 105          moltype = DNA  length = 8350
FEATURE                 Location/Qualifiers
misc_feature            1..8350
                        note = plasmid psyx20-lacIq
source                  1..8350
                        mol_type = other DNA
                        organism = synthetic construct
```

SEQUENCE: 105
cagctggcgt aatagcgaag aggcccgcac cgatcgccct tcccaacagt tgcgcagcct 60
gaatggcgaa tgggacgcgc cctgtagcgg cgcattaagc gcggcgggtg tggtggttac 120
gcgcagcgtg accgctacac ttgccagcgc cctagcgccc gctcctttcg ctttcttccc 180
ttcctttctc gccacgttcg ccggctttcc ccgtcaagct ctaaatcggg ggctcccttt 240
agggttccga tttagtgctt tacggcacct cgaccccaaa aaacttgatt agggtgatgg 300
ttcacgtagt gggccatcgc cctgatagac ggtttttcgc cctttgacgt tggagtccac 360
gttctttaat agtggactct tgttccaaac tggaacaaca ctcaacccta tctcggtcta 420
ttcttttgat ttataaggga ttttgccgat ttcggcctat tggttaaaaa atgagctgat 480
ttaacaaaaa tttaacgcga attttaacaa aattcgaccg atgcccttga gagccttcaa 540
cccagtcagc tccttccggt gggcgcgggg catgactatc gtcgccgcac ttatgactgt 600
cttctttatc atgcaactcg taggacaggt gccggcagcg ctctgggtca ttttcggcga 660
ggaccgcttt cgctggagcg cgacgatgat cggcctgtcg cttgcggtat tcggaatctt 720
gcacgccctc gctcaagcct tcgtcactgg tcccgccacc aaacgtttcg gcgagaagca 780
ggccattatc gccggcatgg cggccgacgc gctgggctac gtcttgctgg cgttcgcgac 840
gcgaggctgg atggccttcc ccattatgat tcttctcgct tccggcggca tcgggatgcc 900
cgcgttgcag gccatgctgt ccaggcaggt agatgacgac catcagggac agcttcaagg 960
atcgctcgcg gctcttacca gcctaacttc gatcattgga ccgctgatcg tcacggcgat 1020
ttatgccgcc tcggcgagca catggaacgg gttggcatgg attgtaggcg ccgccctata 1080
ccttgtctgc ctccccgcgt tgcgtcgcgg tgcatggagc cgggccacct cgacctgaat 1140
ggaagccggc ggcacctcgc taacggattc accactccgc agacccgcca taaaacgccc 1200
tgagaagccc gtgacgggct tttcttgtat tatgggtagt ttccttgcat gaatccataa 1260
aaggcgcctg tagtgccatt tacccccatt cactgccaga gccgtgagcg cagcgaactg 1320
aatgtcacga aaaagacagc gactcaggtg cctgatggtc ggagacaaaa ggaatattca 1380
gcgatttgcc cgagcttgcg agggtgctac ttaagccttt agggttttaa ggtctgtttt 1440
gtagaggagc aaacagcgtt tgcgacatcc ttttgtaata ctgcggaact gactaaagta 1500
gtgagttata cacagggctg ggatctattc tttttatctt tttttattct ttctttattc 1560
tataaattat aaccacttga atataaacaa aaaaaacaca caaaggtcta gcggaattta 1620
cagagggtct agcagaattt acaagttttc cagcaaaggt ctagcagaat ttacagatac 1680
ccacaactca aaggaaaagg actagtaatt atcattgact agcccatctc aattggtata 1740
gtgattaaaa tcacctagac caattgagat gtatgtctga attagttgtt ttcaaagcaa 1800
atgaactagc gattagtcgc tatgacttaa cggagcatga aaccaagcta attttatgct 1860
gtgtggcact actcaacccc acgattgaaa accctacaag gaaagaacgg acggtatcgt 1920
tcacttataa ccaatacgct cagatgatga acatcagtag ggaaaatgct tatggtgtat 1980
tagctaaagc aaccagagag ctgatgacga gaactgtgga aatcaggaat cctttggtta 2040
aaggctttga gattttccag tggacaaact atgccaagtt ctcaagcgaa aaattagaat 2100
tagtttttag tgaagagata ttgccttatc ttttccagtt aaaaaaattc ataaaatata 2160
atctggaaca tgttaagtct tttgaaaaca aatactctat gaggatttat gagtggttat 2220
taaaagaact aacacaaaag aaaactcaca aggcaaatat agagattagc cttgatgaat 2280
ttaagttcat gttaatgctt gaaaataact accatgagtt taaaaggctt aaccaatggg 2340
ttttgaaacc aataagtaaa gatttaaaca cttacagcaa tatgaaattg gtggttgata 2400
agcgaggccg cccgactgat acgttgattt tccaagttga actagataga caaatggatc 2460
tcgtaaccga acttgagaac aaccagataa aaatgaatgg tgacaaaata ccaacaacca 2520
ttacatcaga ttcctaccta cataacggac taagaaaaac actacacgat gctttaactg 2580
caaaaattca gctcaccagt tttgaggcaa aatttttgag tgacatgcaa agtaagtatg 2640
atctcaatgg ttcgttctca tggctcacgc aaaaacaacg aaccacacta gagaacatac 2700
tggctaaata cggaaggatc tgaggttctt atggctcttg tatctatcag tgaagcatca 2760
agactaacaa acaaaagtag aacaactgtt caccgttaca tatcaaaggg aaaactgtcc 2820
atatgcacag atgaaaacgg tgtaaaaaag atagatacat cagagctttt acgagttttt 2880
ggtgcattca aagctgttca ccatgaacag atcgacaatg taacagatga acagcatgta 2940
acacctaata gaacaggtga aaccagtaaa acaaagcaac tagaacatga aattgaacac 3000
ctgagacaac ttgttacagc tcaacagtca cacatagaca gcctgaaaca ggcgatgctg 3060
cttatcgaat caaagctgcc gacaacacgg gagccagtga cgcctcccgt ggggaaaaaa 3120
tcatggcaat tctggaagaa atagcgcttt cagccggcaa accggctgaa gccggatctg 3180
cgattctgat aacaaactag caacaccaga acagcccgtt tgcgggcagc aaaacccgta 3240
cttttggacg ttccggcggt tttttgtggc gagtggtgtt cgggcggtgc gcgattattg 3300
aagcatttat cagggttatt gtctcatgag cggatacata tttgaatgta tttagaaaaa 3360
taaacaaata ggggttccgc gcacatttcc ccgaaaagtg ccacctgacg tctaagaaac 3420
cattattatc atgacattaa cctataaaaa taggcgtatc acgaggccct ttcgtcttca 3480
agaattcgcg cgcgaaggcc aagcggcatg catttacgtt gacaccatcg aatggcgcaa 3540
aacctttcgc ggtatggcat gatagcgccc ggaagagagt caattcaggg tggtgaatgt 3600
gaaaccagta acgttatacg atgtcgcaga gtatgccggt gtctcttatc agaccgtttc 3660
ccgcgtggtg aaccaggcca gccacgtttc tgcgaaaacg cgggaaaaag tggaagcggc 3720
gatggcggag ctgaattaca ttcccaaccg cgtggcacaa caactggcgg gcaaacagtc 3780
gttgctgatt ggcgttgcca cctccagtct ggccctgcac gcgccgtcgc aaattgtcgc 3840
ggcgattaaa tctcgcgccg atcaactggg tgccagcgtg gtggtgtcga tggtagaacg 3900
aagcggcgtc gaagcctgta aagcggcggt gcacaatctt ctcgcgcaac gcgtcagtgg 3960
gctgatcatt aactatccgc tggatgacca ggatgccatt gctgtggaag ctgcctgcac 4020
taatgttccg gcgttatttc ttgatgtctc tgaccagaca cccatcaaca gtattatttt 4080
ctcccatgaa gacggtacgc gactgggcgt ggagcatctg gtcgcattgg gtcaccagca 4140
aatcgcgctg ttagcgggcc cattaagttc tgtctcggcg cgtctgcgtc tggctggctg 4200
gcataaatat ctcactcgca atcaaattca gccgatagcg gaacgggaag gcgactggag 4260
tgccatgtcc ggttttcaac aaaccatgca aatgctgaat gagggcatcg ttcccactgc 4320
gatgctggtt gccaacgatc agatggcgct gggcgcaatg cgcgccatta ccgagtccgg 4380
gctgcgcgtt ggtgcggata tctcggtagt gggatacgac gataccgaag acagctcatg 4440
ttatatcccg ccgtcaacca ccatcaaaca ggattttcgc ctgctggggc aaaccagcgt 4500
ggaccgcttg ctgcaactct ctcagggcca ggcggtgaag ggcaatcagc tgttgcccgt 4560
ctcactggtg aaaagaaaaa ccaccctggc gcccaatacg caaaccgcct ctccccgcgc 4620
gttggccgat tcattaatgc agctggcacg acaggtttcc cgactggaaa gcgggcagtg 4680

-continued

```
agcgcaacgc aattaatgtg agttagctca ctcattaggc gaattctcat gtttgacagc  4740
ttatcatcga taagctttaa tgcggtagtt tatcacagtt aaattgctaa cgcagtcagg  4800
caccgtgtat gaaatctaac aatgcgctca tcgtcatcct cggcaccgtc accctggatg  4860
ctgtaggcat aggcttggtt atgccggtac tgccgggcct cttgcgggat atcgtccatt  4920
ccgacagcat cgccagtcac tatggcgtgc tgctagcgct atatgcgttg atgcaatttc  4980
tatgcgcacc cgttctcgga gcactgtccg accgctttgg ccgccgccca gtcctgctcg  5040
cttcgctact tggagccact atcgactacg cgatcatggc gaccacaccc gtcctgtgga  5100
tcctctacgc cggacgcatc gtggccggca tcaccggcgc cacaggtgcg gttgctggcg  5160
cctatatcgc cgacatcacc gatggggaag atcgggctcg ccacttcggg ctcatgagcg  5220
cttgtttcgg cgtgggtatg gtggcaggcc ccgtggccgg gggactgttg ggcgccatct  5280
ccttgcatgc accattcctt gcggcggcgg tgctcaacgg cctcaaccta ctactgggct  5340
gcttcctaat gcaggaatcg cataagggag agcgtcgacc gatgcccttg agagccttca  5400
acccagtcag ctccttccgg tgggcgcggg gcatgactat cgtcgccgca cttatgactg  5460
tcttctttat catgcaactc gtaggacagg tgccggcagc gctctgggtc attttcggcg  5520
aggaccgctt tcgctggagc gcgacgatga tcggcctgtc gcttgcggta ttcggaatct  5580
tgcacgccct cgctcaagcc ttcgtcactg gtcccgccac caaacgtttc ggcgagaagc  5640
aggccattat cgccggcatg gcggccgacg cgctgggcta cgtcttgctg gcgttcgcga  5700
cgcgaggctg gatggccttc cccattatga ttcttctcgc ttccggcggc atcgggatgc  5760
ccgcgttgca ggccatgctg tccaggcagg tagatgacga ccatcaggga cagcttcaag  5820
gatcgctcgc ggctcttacc agcctaactt cgatcattgg accgctgatc gtcacggcga  5880
tttatgccgc ctcggcgagc acatggaacg ggttggcatg gattgtaggc gccgccctat  5940
accttgtctg cctccccgcg ttgcgtcgcg gtgcatggag ccgggccacc tcgacctgaa  6000
tggaagccgg cggcacctcg ctaacggatt caccactcca agaattggag ccaatcaatt  6060
cttgcggaga actgtgaatg cgcaaaccaa cccttggcag aacatatcca tcgcgtccgc  6120
catctccagc agccgcacgc ggcgcatctc gggcagcgtt gggtcctggc cacgggtgcg  6180
catgatcgtg ctcctgtcgt tgaggacccg gctaggctgg cggggttgcc ttactggtta  6240
gcagaatgaa tcaccgatac gcgagcgaac gtgaagcgac tgctgctgca aaacgtctgc  6300
gacctgagca acaacatgaa tggtcttcgg tttccgtgtt tcgtaaagtc tggaaacgcg  6360
gaagtcagcg ccctgcacca ttatgttccg gatctgcatc gcaggatgct gctggctacc  6420
ctgtggaaca cctacatctg tattaacgaa gcgctggcat tgaccctgag tgatttttct  6480
ctggtcccgc cgcatccata ccgccagttg tttaccctca caacgttcca gtaaccgggc  6540
atgttcatca tcagtaaccc gtatcgtgag catcctctct cgtttcatcg gtatcattac  6600
ccccatgaac agaaatcccc cttacacgga ggcatcagtg accaaacagg aaaaaaccgc  6660
ccttaacatg gcccgcttta tcagaagcca gacattaacg cttctggaga aactcaacga  6720
gctggacgcg gatgaacagg cagacatctg tgaatcgctt cacgaccacg ctgatgagct  6780
ttaccgcagc gcgcagggtc agcctgaata cgcgtttaat gaccagcaca gtcgtgatgg  6840
caaggtcaga atagcgctga ggtctgcctc gtgaagaagg tgttgctgac tcataccagg  6900
cctgaatcgc cccatcatcc agccagaaag tgagggagcc acggttgatg agagctttgt  6960
tgtaggtgga ccagttggtg attttgaact tttgctttgc cacggaacgg tctgcgttgt  7020
cgggaagatg cgtgatctga tccttcaact cagcaaaagt tcgatttatt caacaaagcc  7080
acgttgtgtc tcaaaatctc tgatgttaca ttgcacaaga taaaaatata tcatcatgaa  7140
caataaaact gtctgcttac ataaacagta atacaagggg tgttatgagc catattcaac  7200
gggaaacgtc ttgctcgagg ccgcgattaa attccaacat ggatgctgat ttatatgggt  7260
ataaatgggc tcgcgataat gtcgggcaat caggtgcgac aatctatcga ttgtatggga  7320
agcccgatgc gccagagttg tttctgaaac atggcaaagg tagcgttgcc aatgatgtta  7380
cagatgagat ggtcagacta aactggctga cggaatttat gcctcttccg accatcaagc  7440
attttatccg tactcctgat gatgcatggt tactcaccac tgcgatcccc gggaaaacag  7500
cattccaggt attagaagaa tatcctgatt caggtgaaaa tattgttgat gcgctggcag  7560
tgttcctgcg ccggttgcat tcgattcctg tttgtaattg tccttttaac agcgatcgcg  7620
tatttcgtct cgctcaggcg caatcacgaa tgaataacgg tttggttgat gcgagtgatt  7680
ttgatgacga gcgtaatggc tggcctgttg aacaagtctg gaaagaaatg cataagcttt  7740
tgccattctc accggattca gtcgtcactc atggtgattt ctcacttgat aaccttattt  7800
ttgacgaggg gaaattaata ggttgtattg atgttggacg agtcggaatc gcagaccgat  7860
accaggatct tgccatccta tggaactgcc tcggtgagtt ttctccttca ttacagaaac  7920
ggctttttca aaaatatggt attgataatc ctgatatgaa taaattgcag tttcatttga  7980
tgctcgatga gtttttctaa tcagaattgg ttaattggtt gtaacactgg cagagcatta  8040
cgctgacttg acgggacggc ggctttgttg aataaatcga acttttgctg agttgaagga  8100
tcagatcacg catcttcccg acaacgcaga ccgttccgtg gcaaagcaaa agttcaaaat  8160
caccaactgg tccacctaca acaaagctct catcaaccgt ggctccctca ctttctggct  8220
ggatgatggg gcgattcagg cctggtatga gtcagcaaca ccttcttcac gaggcagacc  8280
tcagcgctat tctgaccttg ccatcacgac tgtgctggtc attaaacgcg tattcaggct  8340
gaccctgcgc                                                         8350
```

```
SEQ ID NO: 106          moltype = DNA  length = 3190
FEATURE                 Location/Qualifiers
misc_feature            1..3190
                        note = plasmid pAGR3
source                  1..3190
                        mol_type = other DNA
                        organism = synthetic construct
SEQUENCE: 106
aagtgaccaa acaggaaaaa accgccctta acatggcccg ctttatcaga agccagacat  60
taacgcttct ggagaaactc aacgagctgg acgcggatga acaggcagac atctgtgaat  120
cgcttcacga ccacgctgat gagctttacc gcagctgcct cgcgcgtttc ggtgatgacg  180
gtgaaaacct ctgacacatg cagctcccgg agacggtcac agcttgtctg taagcggatg  240
ccgggagcag acaagcccgt cagggcgcgt cagcgggtgt tggcgggtgt cggggcgcag  300
ccatgaccca gtcacgtagc gatagcggag tgtatactgg cttaactatg cggcatcaga  360
gcagattgta ctgagagtgc accatatgcg gtgtgaaata ccgcacagat gcgtaaggag  420
aaaataccgc atcaggcgct cttccgcttc ctcgctcact gactcgctgc gctcggtcgt  480
```

-continued

```
tcggctgcgg cgagcggtat cagctcactc aaaggcggta atacggttat ccacagaatc  540
aggggataac gcaggaaaga acatgtgagc aaaaggccag caaaaggcca ggaaccgtaa  600
aaaggccgcg ttgctggcgt ttttccatag gctccgcccc cctgacgagc atcacaaaaa  660
tcgacgctca agtcagaggt ggcgaaaccc gacaggacta taaagatacc aggcgtttcc  720
ccctggaagc tccctcgtgc gctctcctgt tccgaccctg ccgcttaccg gatacctgtc  780
cgcctttctc ccttcgggaa gcgtggcgct ttctcatagc tcacgctgta ggtatctcag  840
ttcggtgtag gtcgttcgct ccaagctggg ctgtgtgcac gaaccccccg ttcagcccga  900
ccgctgcgcc ttatccggta actatcgtct tgagtccaac ccggtaagac acgacttatc  960
gccactggca gcagccactg gtaacaggat tagcagagcg aggtatgtag gcggtgctac  1020
agagttcttg aagtggtggc ctaactacgg ctacactaga aggacagtat ttggtatctg  1080
cgctctgctg aagccagtta ccttcggaaa aagagttggt agctcttgat ccggcaaaca  1140
aaccaccgct ggtagcggtg gtttttttgt ttgcaagcag cagattacgc gcagaaaaaa  1200
aggatctcaa gaagatcctt tgatcttttc tacggggtct gacgctcagt ggaacgaaaa  1260
ctcacgttaa gggattttgg tcatgagatt atcaaaaagg atcttcacct agatcctttt  1320
aaattaaaaa tgaagtttta aatcaatcta aagtatatat gagtaaactt ggtctgacag  1380
ttaccaatgc ttaatcagtg aggcacctat ctcagcgatc tgtctatttc gttcatccat  1440
agttgcctga ctccccgtcg tgtagataac tacgatacgg gagggcttac catctggccc  1500
cagtgctgca atgataccgc gagacccacg ctcaccggct ccagatttat cagcaataaa  1560
ccagccagcc ggaagggccg agcgcagaag tggtcctgca actttatccg cctccatcca  1620
gtctattaat tgttgccggg aagctagagt aagtagttcg ccagttaata gtttgcgcaa  1680
cgttgttgcc attgctgcag gcatcgtggt gtcacgctcg tcgtttggta tggcttcatt  1740
cagctccggt tcccaacgat caaggcgagt tacatgatcc cccatgttgt gcaaaaaagc  1800
ggttagctcc ttcggtcctc cgatcgttgt cagaagtaag ttggccgcag tgttatcact  1860
catggttatg gcagcactgc ataattctct tactgtcatg ccatccgtaa gatgcttttc  1920
tgtgactggt gagtactcaa ccaagtcatt ctgagaatag tgtatgcggc gaccgagttg  1980
ctcttgcccg gcgtcaacac gggataatac cgcgccacat agcagaactt taaaagtgct  2040
catcattgga aaacgttctt cggggcgaaa actctcaagg atcttaccgc tgttgagatc  2100
cagttcgatg taacccactc gtgcacccaa ctgatcttca gcatctttta ctttcaccag  2160
cgtttctggg tgagcaaaaa caggaaggca aaatgccgca aaaaagggaa taagggcgac  2220
acggaaatgt tgaatactca tactcttcct ttttcaatat tattgaagca tttatcaggg  2280
ttattgtctc atgagcggat acatatttga atgtatttag aaaaataaac aaataggggt  2340
tccgcgcaca tttccccgaa aagtgccacc tgacgtctaa gaaaccatta ttatcatgac  2400
attaacctat aaaaataggc gtatcacgag gccctttcgt cttcaagaat taattcccaa  2460
ttccaggcat caaataaaac gaaaggctca gtcgaaagac tgggcctttc gttttatctg  2520
ttgtttgtcg gtgaacgctc tcctgagtag gacaaatccg ccgggagcgg atttgaacgt  2580
tgcgaagcaa cggcccggag ggtggcgggc aggacgcccg ccataaactg ccaggaatta  2640
attccaggca tcaaataaaa cgaaaggctc agtcgaaaga ctgggccttt cgttttatct  2700
gttgtttgtc ggtgaacgct ctcctgagta ggacaaatcc gccgggagcg gatttgaacg  2760
ttgcgaagca acggcccgga gggtggcggg caggacgccc gccataaact gccaggaatt  2820
aattccaggc atcaaataaa acgaaaggct cagtcgaaag actgggcctt tcgttttatc  2880
tgttgtttgt cggtgaacgc tctcctgagt aggacaaatc cgccgggagc ggatttgaac  2940
gttgcgaagc aacggcccgg agggtggcgg gcaggacgcc cgccataaac tgccaggaat  3000
taattccagg catcaaataa aacgaaaggc tcagtcgaaa gactgggcct ttcgttttat  3060
ctgttgtttg tcggtgaacg ctctcctgag taggacaaat ccgccgggag cggatttgaa  3120
cgttgcgaag caacggcccg gagggtggcg ggcaggacgc ccgccataaa ctgccaggaa  3180
ttggggatcg                                                         3190
```

HIGH FIDELITY RESTRICTION ENDONUCLEASES

BACKGROUND

Restriction endonucleases are enzymes that cleave double-stranded DNAs in a sequence-specific manner (Roberts, R. J., *Proc Natl Acad Sci USA,* 102:5905-5908 (2005); Roberts, et al., *Nucleic Acids Res,* 31:1805-1812 (2003); Roberts, et al., *Nucleic Acids Res,* 33:D230-232 (2005); Alves, et al., *Restriction Endonucleases*, "Protein Engineering of Restriction Enzymes," ed. Pingoud, Springer-Verlag Berlin Heidelberg, New York, 393-407 (2004)). They are ubiquitously present among prokaryotic organisms (Raleigh, et al., *Bacterial Genomes Physical Structure and Analysis*, Ch.8, eds. De Bruijin, et al., Chapman & Hall, New York, 78-92 (1998)), in which they form part of restriction-modification systems, which mainly consist of an endonuclease and a methyltransferase. The cognate methyltransferase methylates the same specific sequence that its paired endonuclease recognizes and renders the modified DNA resistant to cleavage by the endonuclease so that the host DNA can be properly protected. However, when there is an invasion of foreign DNA, in particular bacteriophage DNA, the foreign DNA will be degraded before it can be completely methylated. The major biological function of the restriction-modification system is to protect the host from bacteriophage infection (Arber, *Science,* 205:361-365 (1979)). Other functions have also been suggested, such as involvement in recombination and transposition (Carlson, et al., *Mol Microbiol,* 27:671-676 (1998); *Heitman, Genet Eng* (NY), 15:57-108 (1993); McKane, et al., *Genetics,* 139:35-43 (1995)).

The specificity of the approximately 3,000 known restriction endonucleases for their greater than 250 different target sequences could be considered their most interesting characteristic. After the discovery of the sequence-specific nature of the first restriction endonuclease (Danna, et al., *Proc Natl Acad Sci USA,* 68:2913-2917 (1971); Kelly, et al., *J Mol Biol,* 51:393-409 (1970)), it did not take long for scientists to find that certain restriction endonucleases cleave sequences which are similar but not identical to their defined recognition sequences under non-optimal conditions (Polisky, et al., *Proc Natl Acad Sci USA,* 72:3310-3314 (1975); Nasri, et al., *Nucleic Acids Res,* 14:811-821 (1986)). This relaxed specificity is referred to as star activity of the restriction endonuclease. It has been suggested that water-mediated interactions between the restriction endonuclease and DNA are the key differences between specific complexes and star complexes (Robinson, et al., *J Mol Biol,* 234:302-306 (1993); Robinson, et al., *Proc Natl Acad Sci USA,* 92:3444-3448 (1995), Sidorova, et al., *Biophys J,* 87:2564-2576 (2004)).

Star activity is a problem in molecular biology reactions. Star activity introduces undesirable cuts in a cloning vector or other DNA. In cases such as forensic applications, where a certain DNA substrate needs to be cleaved by a restriction endonuclease to generate a unique fingerprint, star activity will alter a cleavage pattern profile, thereby complicating analysis. Avoiding star activity is also critical in applications such as strand displacement amplification (Walker, et al., *Proc Natl Acad Sci USA,* 89:392-396 (1992)) and serial analysis of gene expression (Velculescu, et al., *Science,* 270:484-487 (1995)).

SUMMARY

In an embodiment of the invention, a composition is provided that includes a restriction endonuclease having at least one artificially introduced mutation and an overall fidelity index (FI) improvement factor of at least two, the restriction endonuclease being capable of cleaving a substrate with at least a similar cleavage activity to that of the restriction endonuclease absent the artificially introduced mutation in a predetermined buffer, the artificially introduced mutation being the product of at least one of a targeted mutation, saturation mutagenesis, or a mutation introduced through a PCR amplification procedure.

In a further embodiment of the invention, at least one of the artificially introduced mutations is a targeted mutation resulting from replacement of a naturally occurring residue with an oppositely charged residue. An Alanine or a Phenylalanine may replace the naturally occurring residue at the target site.

In a further embodiment of the invention, a composition of the type described above includes a restriction enzyme absent the artificially introduced mutation selected from the group consisting of: BamHI, EcoRI, ScaI, SalI, SphI, PstI, NcoI, NheI, SspI, NotI, SacI, PvuII, MfeI, HindIII, SbfI, EagI, EcoRV, AvrII, BstXI, PciI, HpaI, AgeI, BsmBI, BspQI, SapI, KpnI and BsaI.

Further embodiments of the invention include compositions listed in Table 4.

In a further embodiment of the invention, a DNA encoding any of the enzymes listed in Table 4 is provided, a vector comprising the DNA and a host cell for expressing the protein from the vector.

In an embodiment of the invention, a method is provided having the steps of (a) identifying which amino acid residues in an amino acid sequence of a restriction endonuclease having star activity are charged amino acids; (b) mutating one or more codons encoding one or more of the charged residues in a gene sequence encoding the restriction endonuclease; (c) generating a library of gene sequences having one or more different codon mutations in different charged residues; (d) obtaining a set of proteins expressed by the mutated gene sequences; and (e) determining an FI in a predetermined buffer and a cleavage activity for each expressed protein.

An embodiment of the method includes the step of determining an overall FI improvement factor for proteins belonging to the set of proteins in a defined set of buffers where for example, the set of buffers contains NEB1, NEB2, NEB3 and NEB4 buffers.

An embodiment of the method includes the steps described above and additionally mutating codons encoding hydroxylated amino acids or amide amino acids in a same or subsequent step to that of mutating codons for the charged amino acids.

In an embodiment of the invention described above, the codons are mutated to an Alanine except for Tyrosine which is mutated to a Phenylalanine.

In a further embodiment, the overall FI improvement factor is improved using saturation mutagenesis of one or more of the mutated codon.

BRIEF DESCRIPTION OF THE DRAWINGS

For FIGS. 1-32:

The * symbol indicates the lane to its left that contains the lowest concentration of enzyme for which star activity is observed.

The #symbol refers to the lane showing incomplete cleavage, which is adjacent to and to the right side of the lane containing a concentration of enzyme sufficient for complete cleavage of the substrate.

The gray triangle denotes the serial decrease of restriction endonuclease concentration.

"U" denotes units of enzyme.

In each of the reactions described in FIGS. 1-32, the reaction mixture contains a volume of 3 μl unless otherwise specified of a buffer from New England Biolabs, Inc. (NEB), Ipswich, MA, (see Table 1 and NEB catalog), 3 μl unless otherwise specified of a specified restriction endonuclease in a diluent from NEB, Ipswich, MA (See Table 1 and NEB catalog) as well as variable volumes of specified substrate (containing 0.6 g) substrate and a volume of water to bring the reaction mixture to a total of 30 μl. Reactions were conducted at 37° C. for an incubation time of 1 hour. The results are analyzed on a 0.8% agarose gel. Where the overall volume of the reaction mix, amount of substrate, temperature of the reaction or incubation time varies from above, values are provided in the description of the figures.

The theoretical digestion pattern is provided on the right side of the gel for FIGS. 1, 5, 8, 11-18 and 20-32. Those substrates with only one restriction endonuclease site should be digested into one linear band from supercoiled form.

Figure 1:
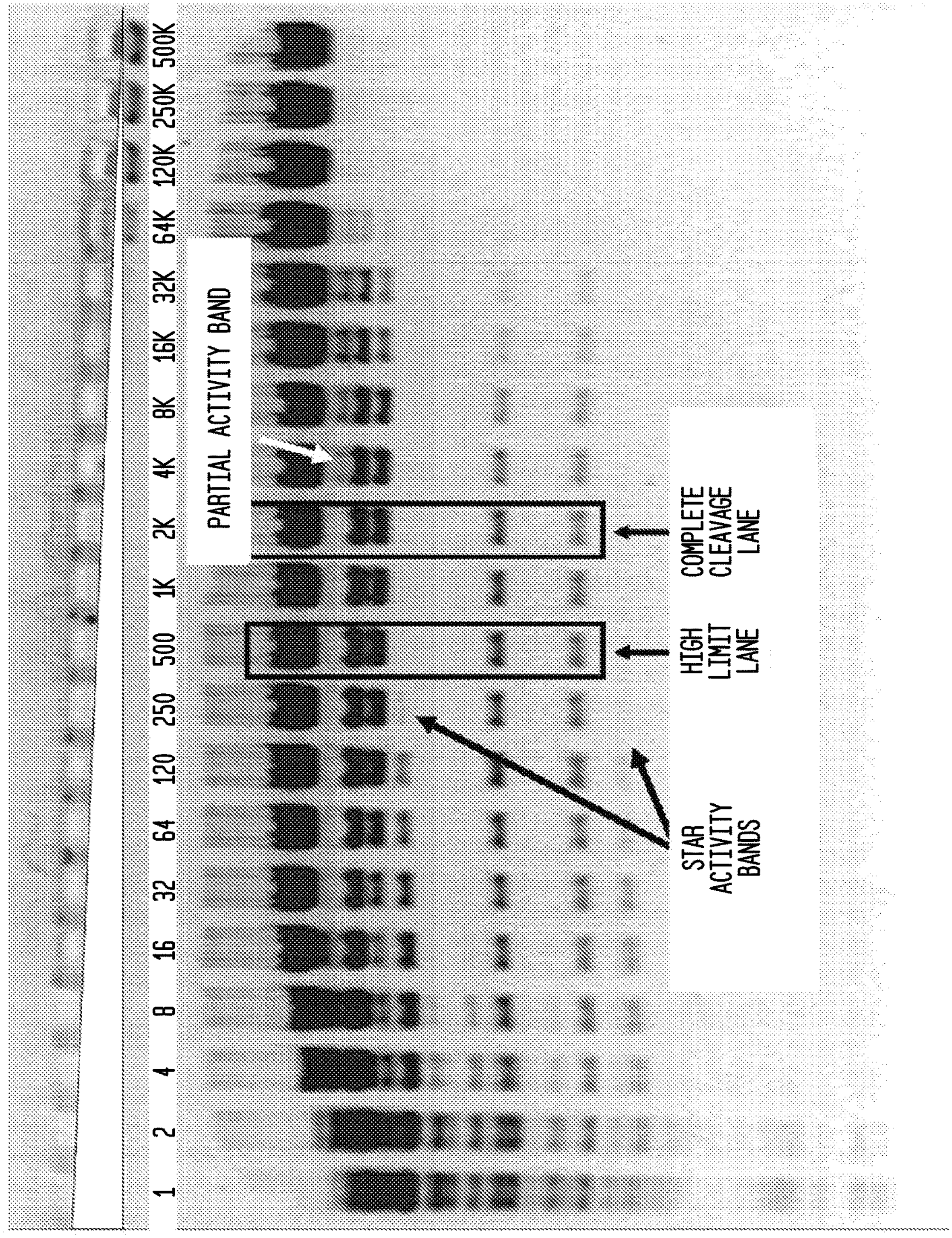

FIG. 1 shows the determination of the FI for wild type (WT) ScaI by digesting 1.2 μl lambda DNA substrate (0.6 μg) with a two-fold serial dilution using diluent A of a preparation of WT ScaI (1,200 U) in NEB3 buffer and examining the digestion products on an agarose gel. The highest concentration of a restriction endonuclease with no star activity is shown with a solid arrow; and the minimum concentration giving rise to complete digestion of substrate is shown with a hollow arrow.

FIGS. 2A-D show the results of digesting 0.5 μl pUC19 substrate (0.5 μg) with WT BamHI or BamHI(E86P) enzyme in a three-fold serial dilution using diluent A for 1 hour at a starting concentration of 172 U or 512 U. The middle lane is the NEB 1 kb marker (New England Biolabs, Inc. (NEB), Ipswich, MA).

Figure 2A:
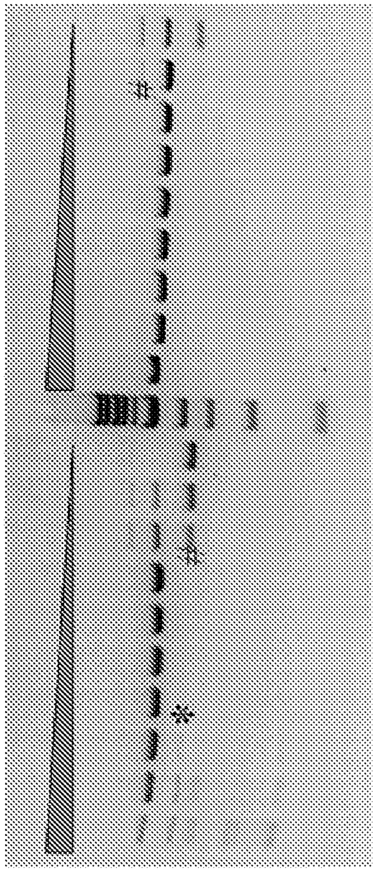

FIG. 2A shows results using NEB1 buffer.

Figure 2B:
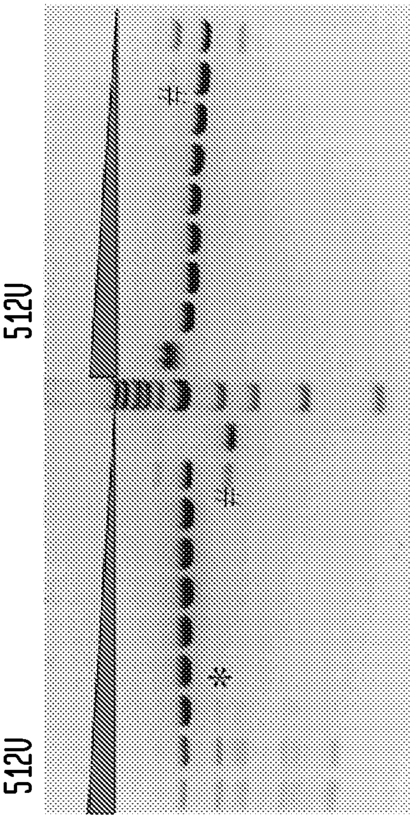

FIG. 2B shows results using NEB2 buffer.

Figure 2C:
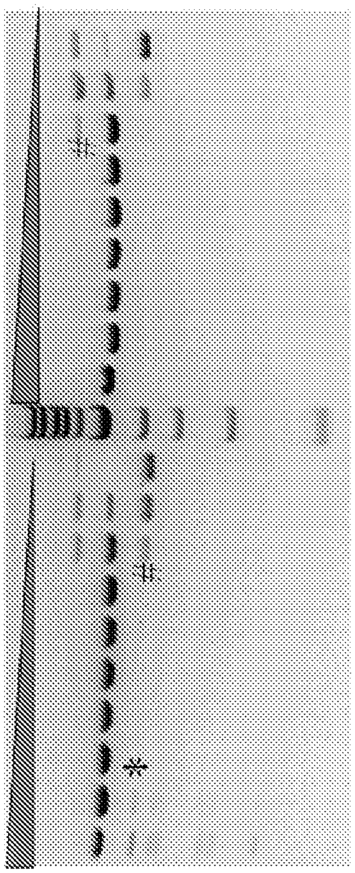

FIG. 2C shows results using NEB3 buffer.

Figure 2D:
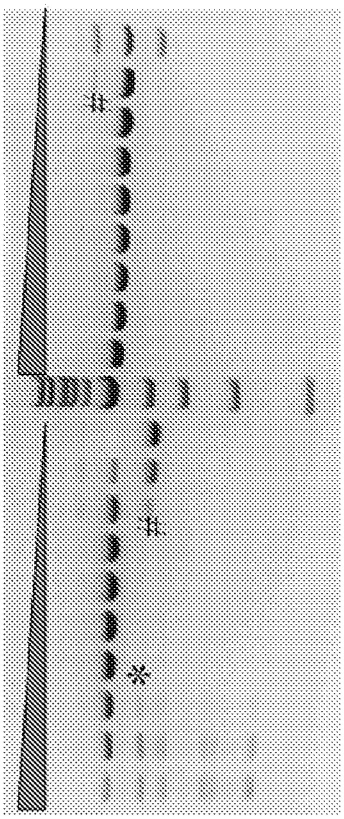

FIG. 2D shows results using NEB4 buffer.

Figure 3A:
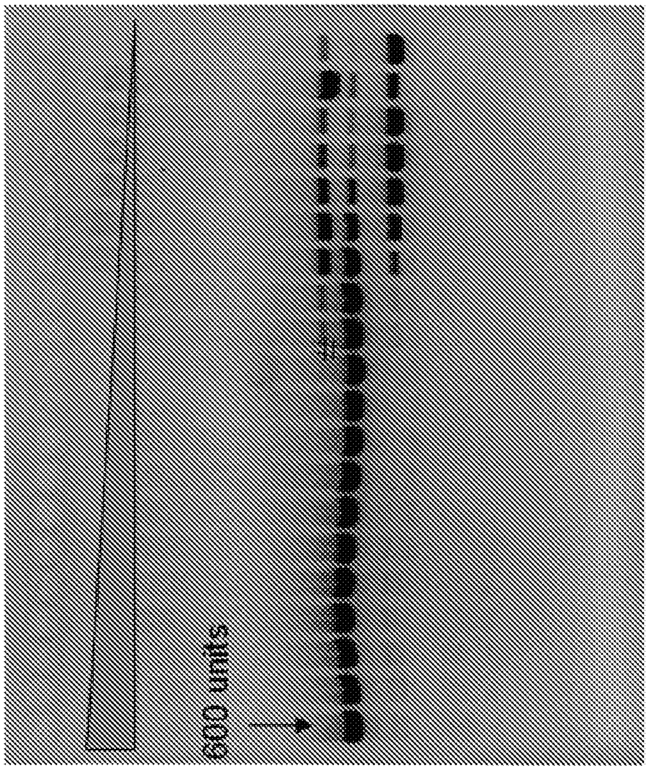
Figure 3B:
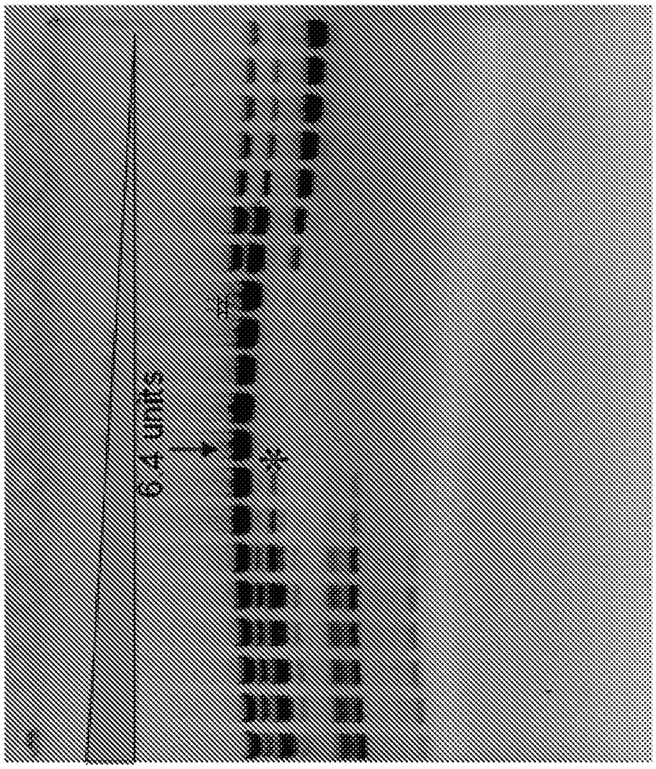

FIGS. 3A-B show a comparison of BamHI(E86P) activity over two time periods using 0.6 μl pBR322 substrate (which contains only 1 BamHI cleavage site) in NEB2 buffer using an initial concentration of 600 U of enzyme in a 2-fold serial dilution using diluent A.

FIG. 3A shows results in 1 hour.

FIG. 3B shows results in 14 hours.

Figure 4A:
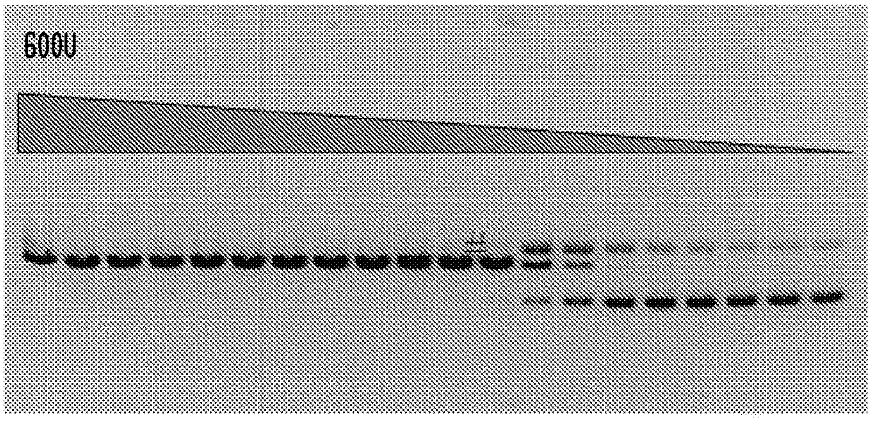
Figure 4B:
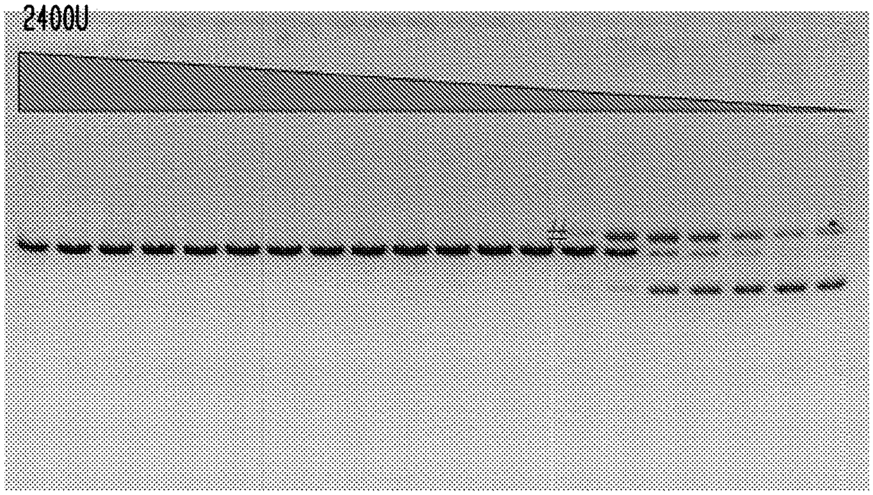

FIGS. 4A-B show the cleavage of 0.6 μl pBR322 substrate in a 2-fold serial dilution of BamHI-HF (E163A/E167T) using diluent A after 14 hours incubation in two different buffers on an agarose gel.

FIG. 4A shows the results with NEB2 buffer with an initial concentration of 600 U of enzyme.

FIG. 4B shows the results with NEB1 buffer with an initial concentration of 2,400 U of enzyme.

Figures 5A, 5B:
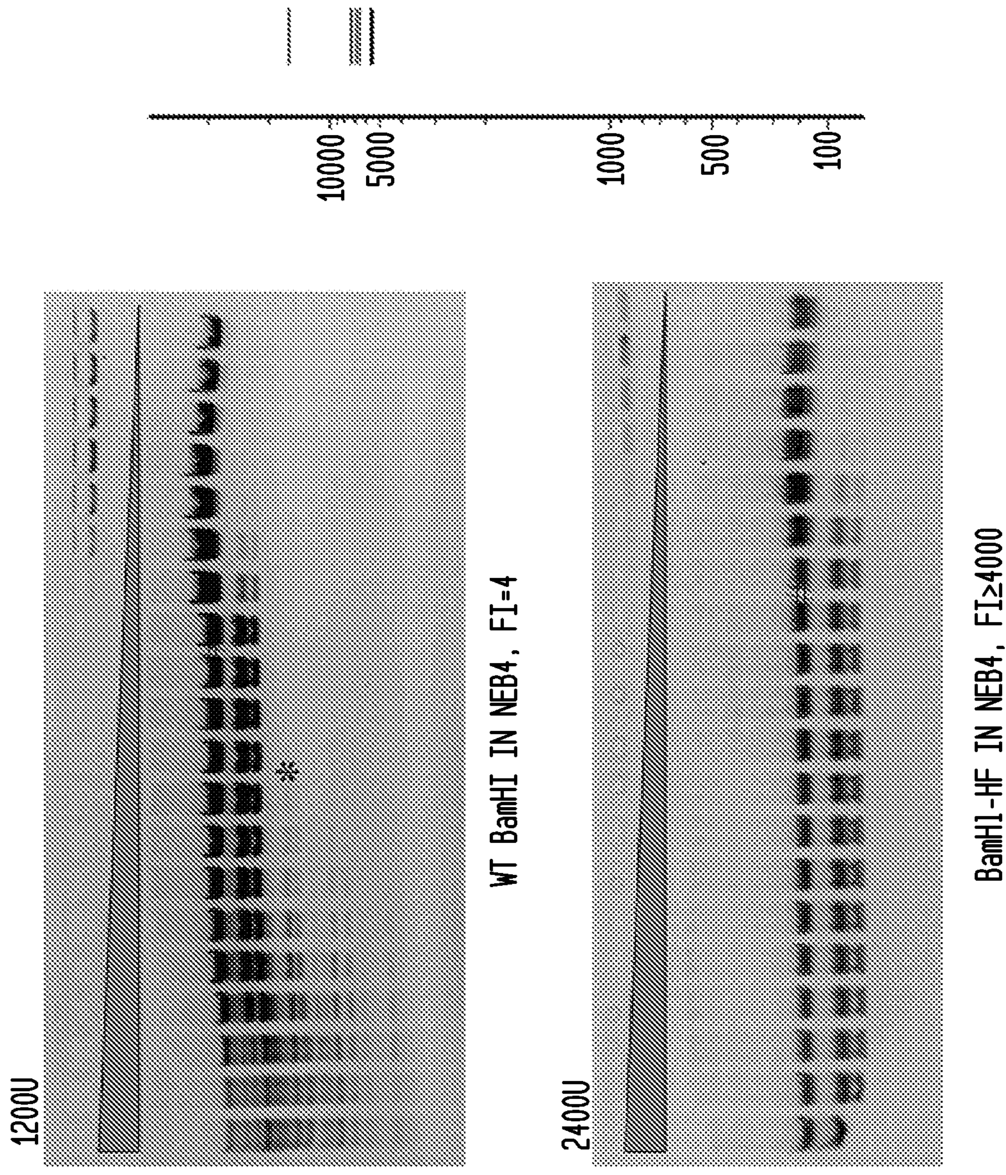

FIGS. 5A-B show a comparison of cleavage reactions using BamHI-HF and WT BamHI in NEB4 buffer. The reaction was carried out in NEB4 buffer using 1.2 μl lambda DNA substrate in a 2-fold serial dilution using diluent A.

FIG. 5A shows WT BamHI with a starting concentration of 1,200 U where the FI equals 4.

FIG. 5B shows BamHI-HF with a starting concentration of 2,400 U where the FI≥4000.

FIGS. 6A-D show a comparison of WT EcoRI and EcoRI(K62A) in NEB1-4 buffers in a 3-fold serial dilution using NEB diluent C. The reaction mixture contained 2 μl lambda DNA substrate (1 g) in NEB1-4 buffers.

Figure 6A:
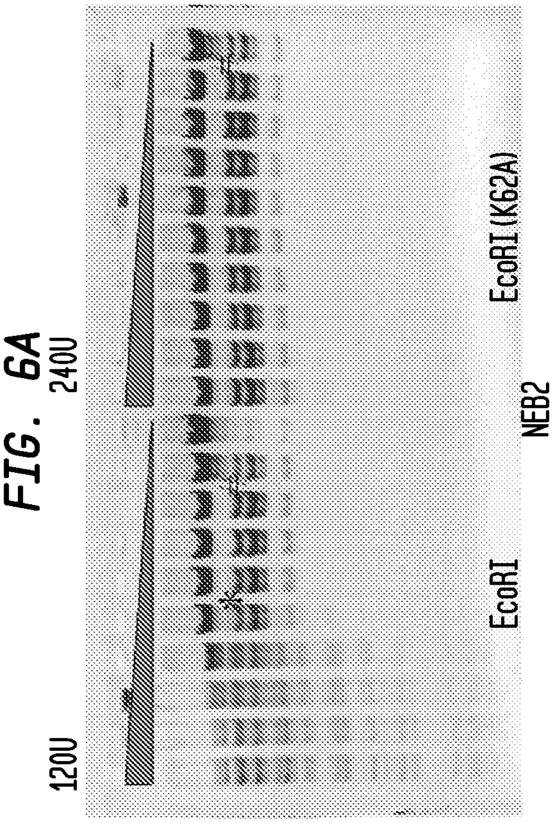

FIG. 6A shows the cleavage results following 2-fold serial dilution, 120 U WT EcoRI and 240 U of EcoRI (K62A) in NEB2 buffer.

Figure 6B:
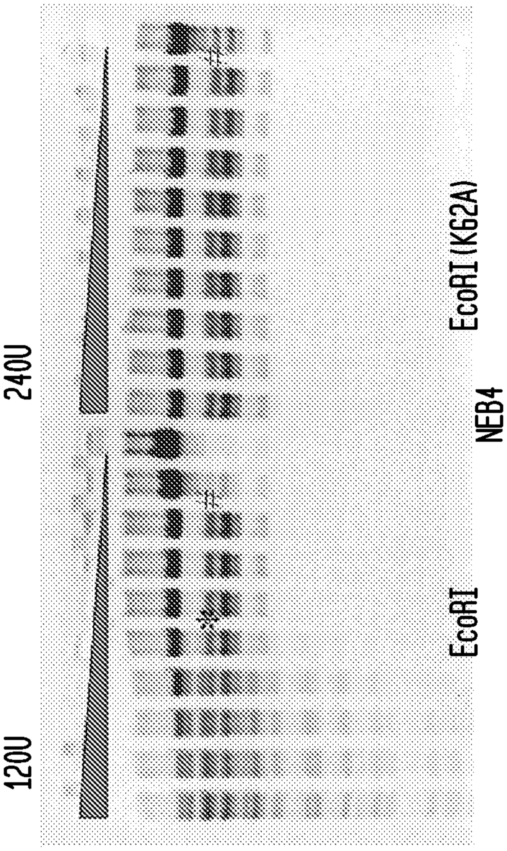

FIG. 6B shows the cleavage results following 2-fold serial dilution, 120 U WT EcoRI and 240 U of EcoRI (K62A) in NEB4 buffer.

Figure 6C:
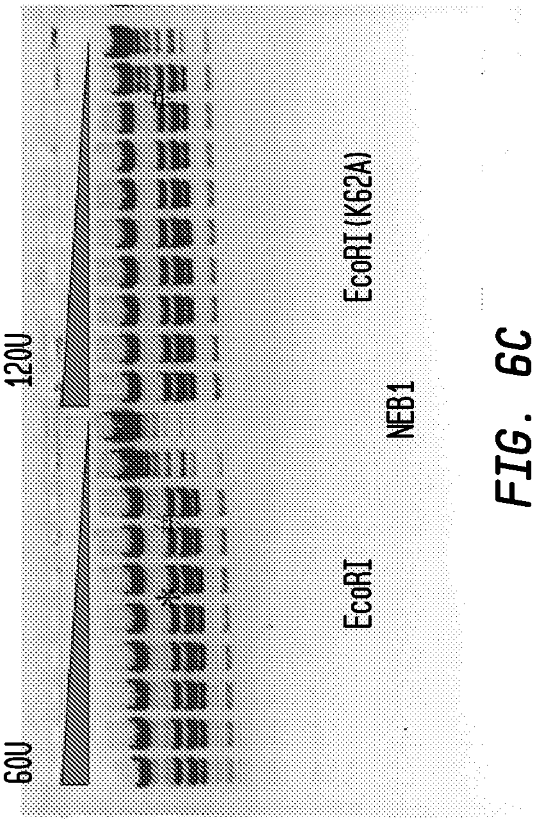

FIG. 6C shows the cleavage results following 2-fold serial dilution, 60 U WT EcoRI and 120 U of EcoRI (K62A) in NEB1 buffer.

Figure 6D:
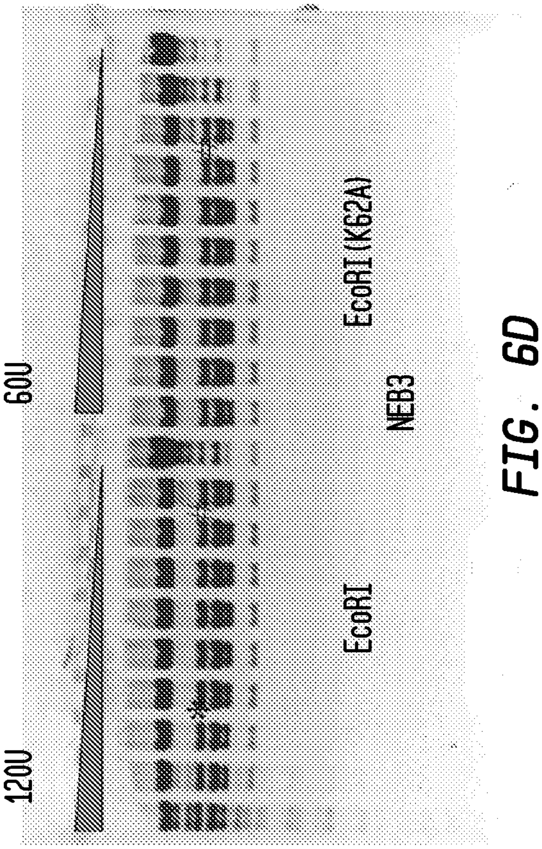

FIG. 6D shows the cleavage results following 2-fold serial dilution, 120 U WT EcoRI and 60 U of EcoRI (K62A) in NEB3 buffer.

Figure 7A:
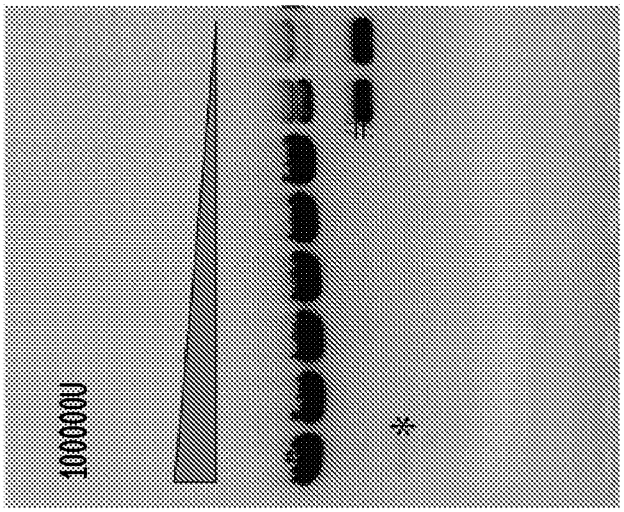
Figure 7B:
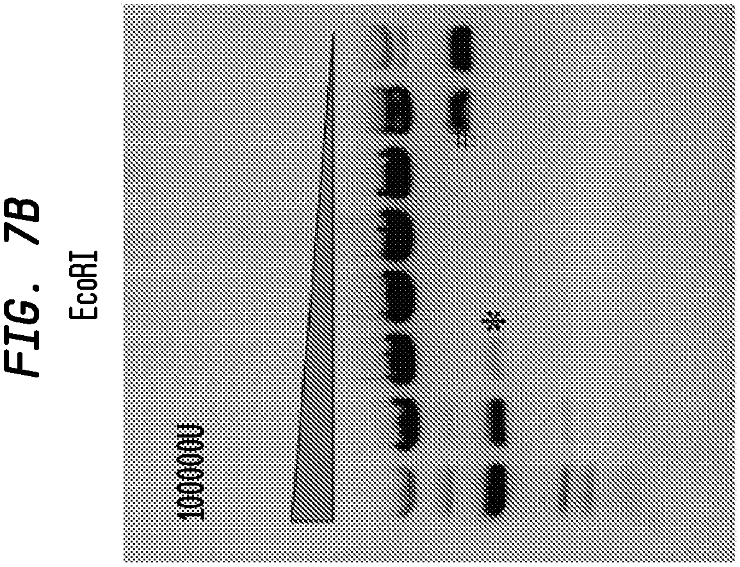
Figure 7C:
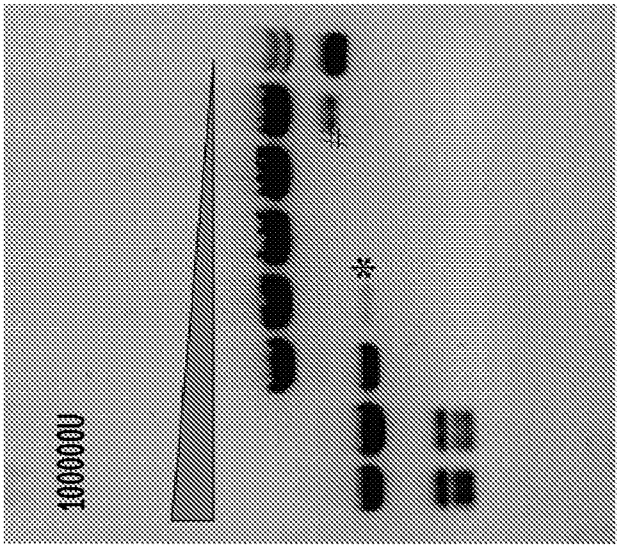

FIGS. 7A-C show the cleavage results with 2 different EcoRI mutants and WT EcoRI. The digestion of 100,000 U of enzyme and a 10-fold serial dilution thereof in diluent C over 10 hours using 0.6 μl of Litmus28 substrate in various buffers is shown. There is only one EcoRI cleavage site in Litmus28 substrate.

FIG. 7A: EcoRI mutant K62E in NEB4 buffer.

FIG. 7B: EcoRI mutant K62A in NEB4 buffer.

FIG. 7C: WT EcoRI in EcoRI buffer (see NEB catalog 2007-8).

FIGS. 8A-B shows a comparison of EcoRI-HF and WT EcoRI in NEB4 buffer. The reaction utilized 1.2 μl lambda DNA substrate in a 2-fold serial dilution using diluent C.

FIG. 8A: WT EcoRI with a starting concentration of 19,200 U reveals a FI=4 in NEB4 buffer.

FIG. 8B: EcoRI-HF with a starting concentration of 38,400 U reveals a FI=16,000 in NEB4 buffer.

Figure 9A:
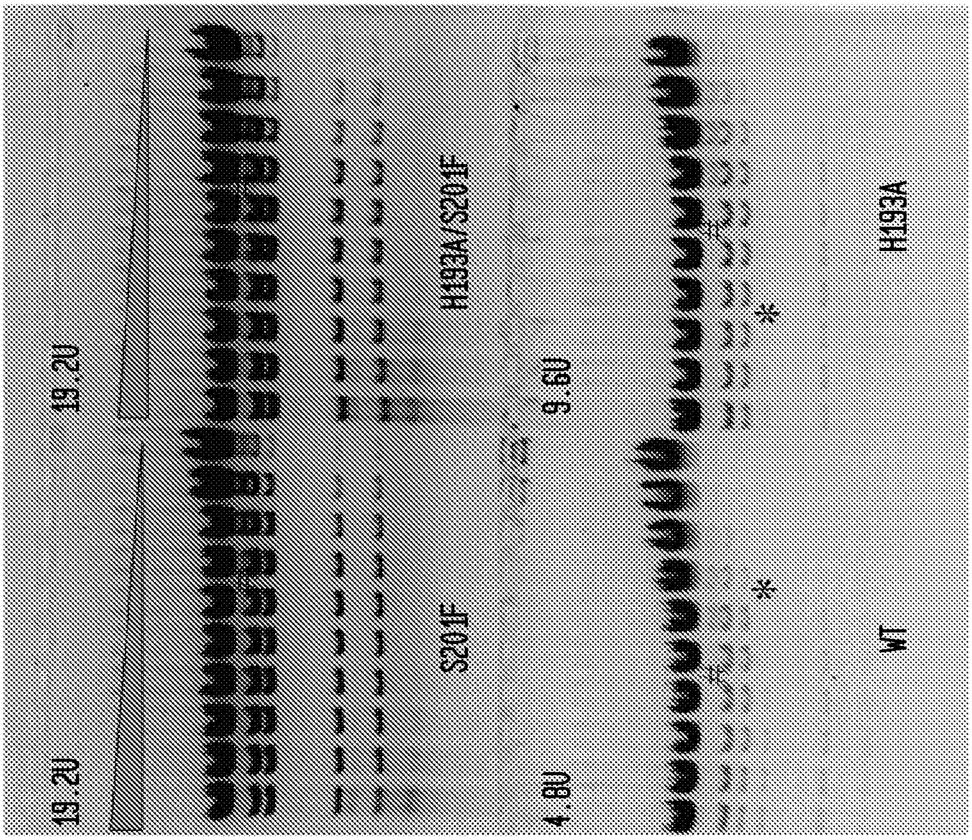
Figure 9B:
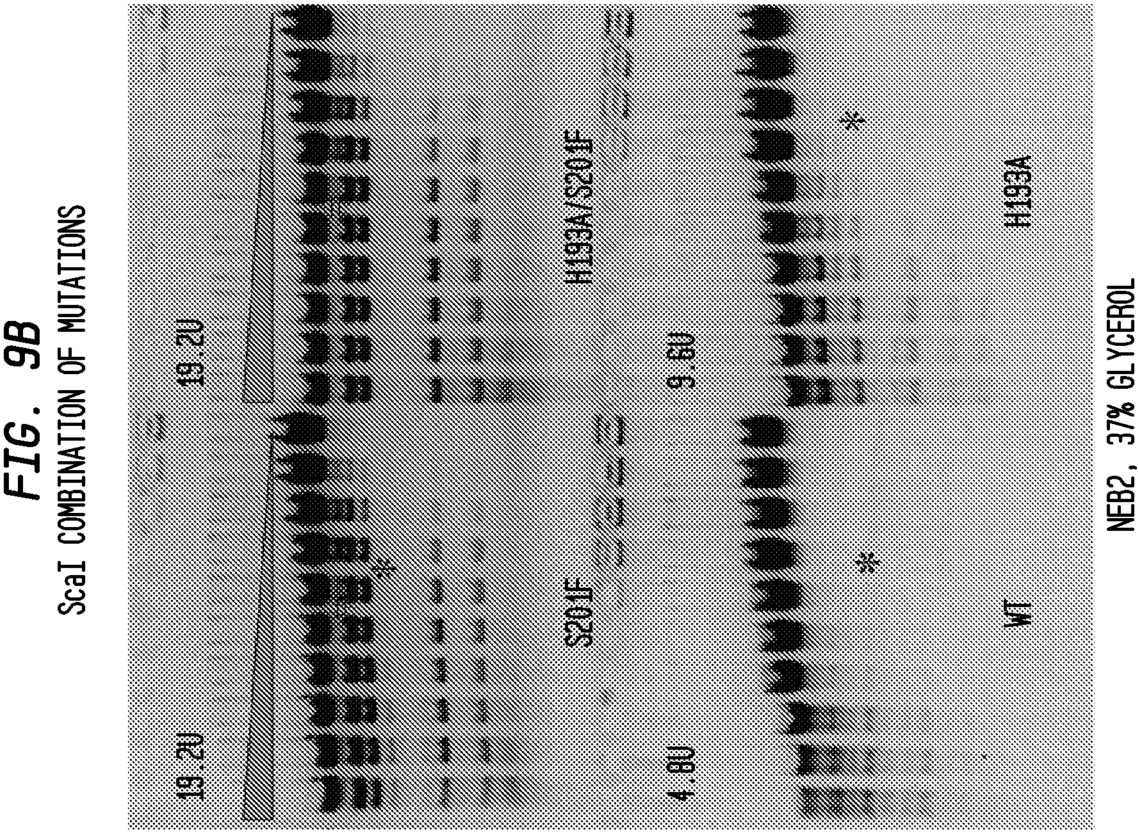

FIGS. 9A-B shows a comparison of serial dilutions of WT ScaI (4.8 U), ScaI(H193A) (9.6 U), ScaI(S201F) (19.2 U), and ScaI(H193A/S201F) (19.2 U). Each sample was initially diluted by 1/10, followed by a 2-fold serial dilution in NEB2 buffer with the specified percentage of glycerol. Each reaction mixture contains 2 μl of lambda DNA substrate (1 g).

FIG. 9A: 5% glycerol.

FIG. 9B: 37% glycerol.

FIGS. 10A-D shows a comparison of WT ScaI and ScaI-HF (H193A/S201F). The enzymes (unit concentration as specified) were each diluted in a 2.5-fold serial dilution with diluent A. The reaction mixture contains 2 μl lambda DNA substrate and NEB1-4 buffers.

Figure 10A:
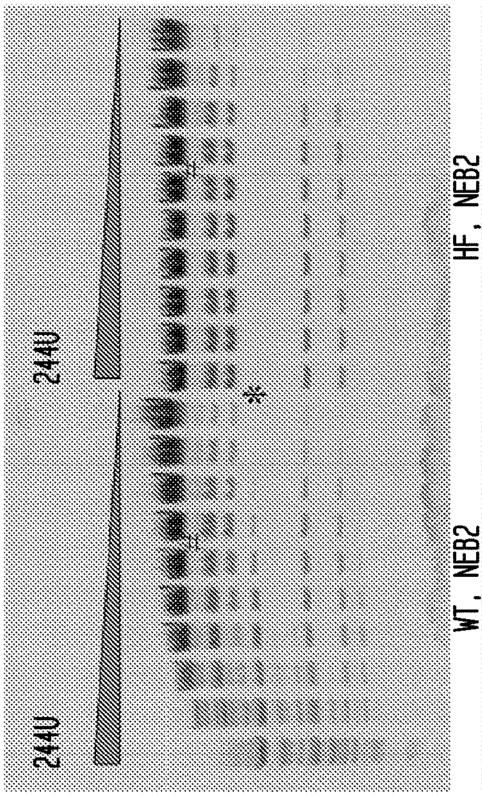

FIG. 10A: cleavage in NEB2 buffer.

Figure 10B:
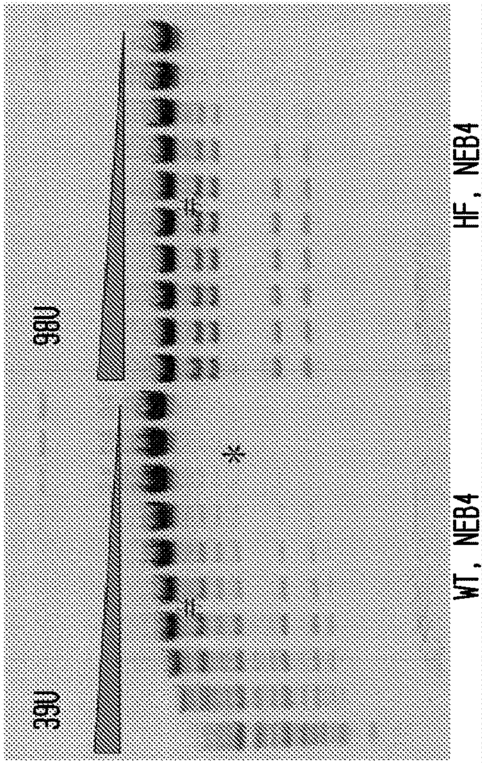

FIG. 10B: cleavage in NEB4 buffer.

Figure 10C:
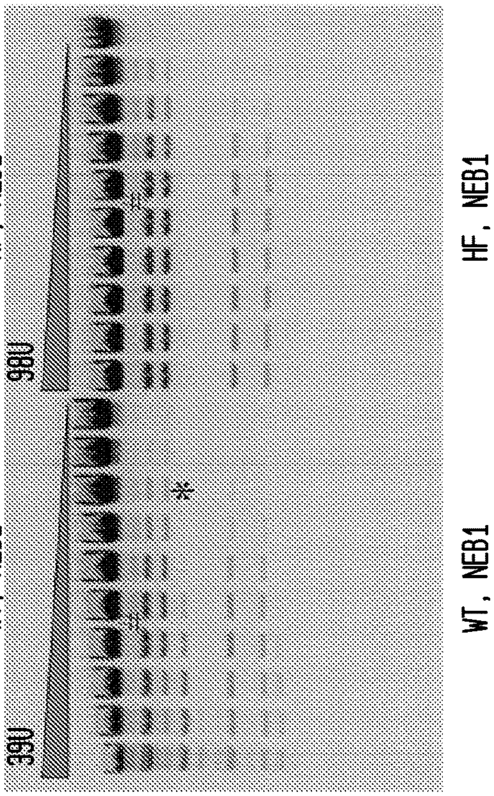

FIG. 10C: cleavage in NEB1 buffer.

Figure 10D:
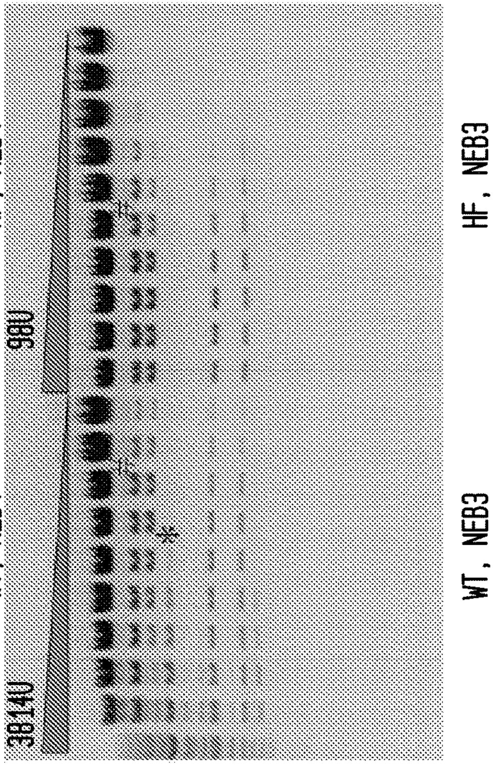

FIG. 10D: cleavage in NEB3 buffer.

FIGS. 11A-H show the FI determination for SalI-HF and WT SalI. Both enzymes were diluted in 2-fold serial dilutions using diluent A. The reaction mixture contains 2 μl HindIII-digested lambda DNA substrate.

FIGS. 11A, B, C and D show a serial dilution of 1,200 U, 1,200 U, 300 U and 1,200 U of SalI-HF demonstrating a FI≥1,000, FI ≥2,000, FI ≥500 and FI ≥2,000 in NEB1, 2, 3 and 4 buffers, respectively.

FIGS. 11E, F, G, and H show a serial dilution of 19.2 U, 150 U, 9,600 U and 38.4 U of WT SalI demonstrating a FI=8, FI=1, FI=32 and FI=1 in NEB1, 2, 3 and 4 buffers, respectively.

FIGS. 12A-B show the results of a 2-fold serial dilution of SphI-HF (19,200 U) in diluent A and WT SphI (143,600 U) in diluent B reacted in NEB 4 buffer with 1.2 μl lambda DNA substrate.

FIG. 12A shows cleavage by WT SphI.

FIG. 12B shows cleavage by SphI-HF.

Figures 13A, 13B:
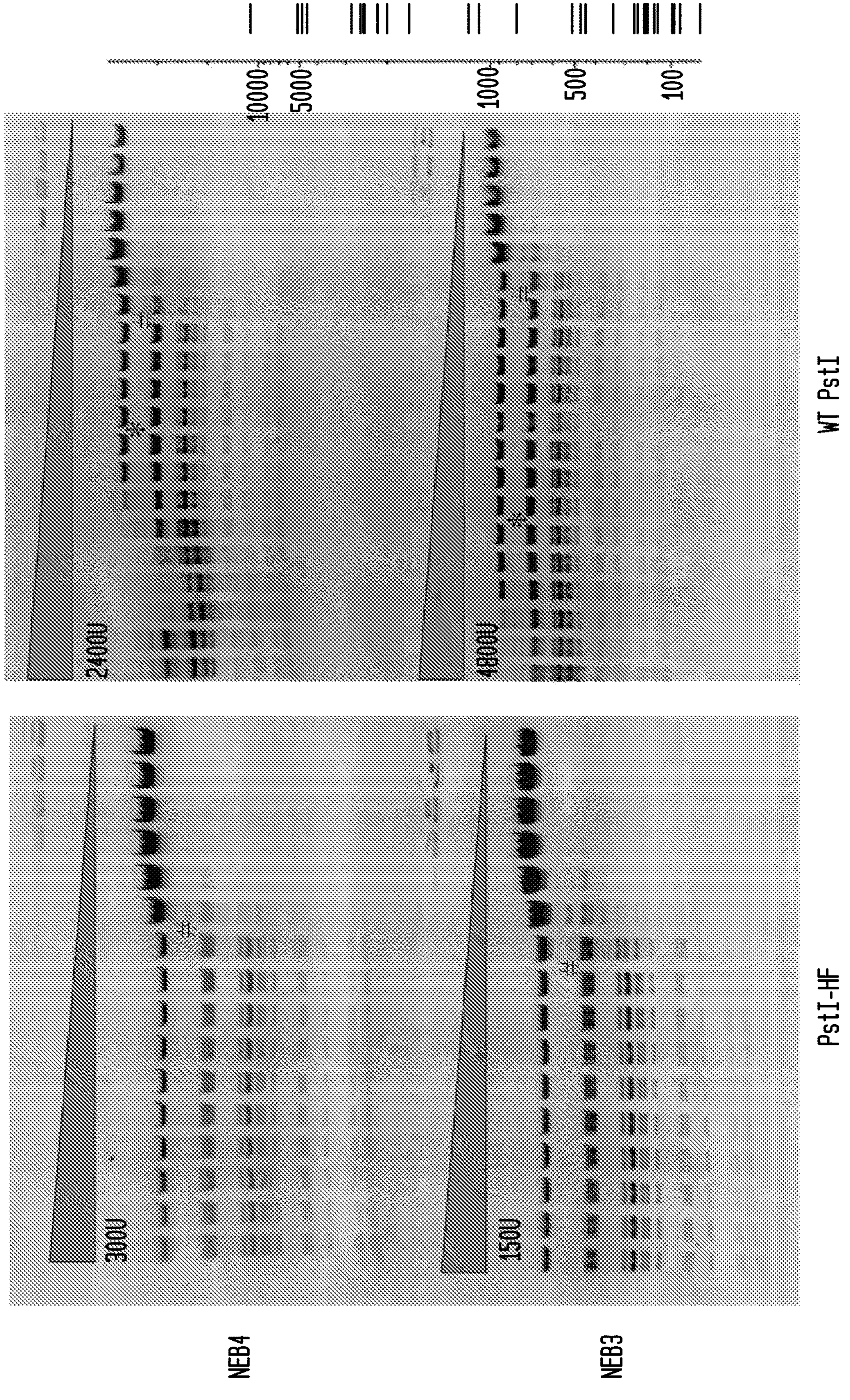

FIGS. 13A-B show cleavage of 1.2 μl lambda DNA substrate using 2-fold serial dilutions of PstI-HF (300 U and 150 U) and 2-fold serial dilutions of WT PstI (2,400 U and 4,800 U) in NEB3 and, NEB4 buffers, respectively. Serial dilutions were performed in diluent C.

FIG. 13A shows cleavage by PstI-HF in NEB4 buffer (upper panel) and NEB3 buffer (lower panel).

FIG. 13B shows cleavage by WT PstI in NEB4 buffer (upper panel) and NEB3 buffer (lower panel).

Figure 14B:
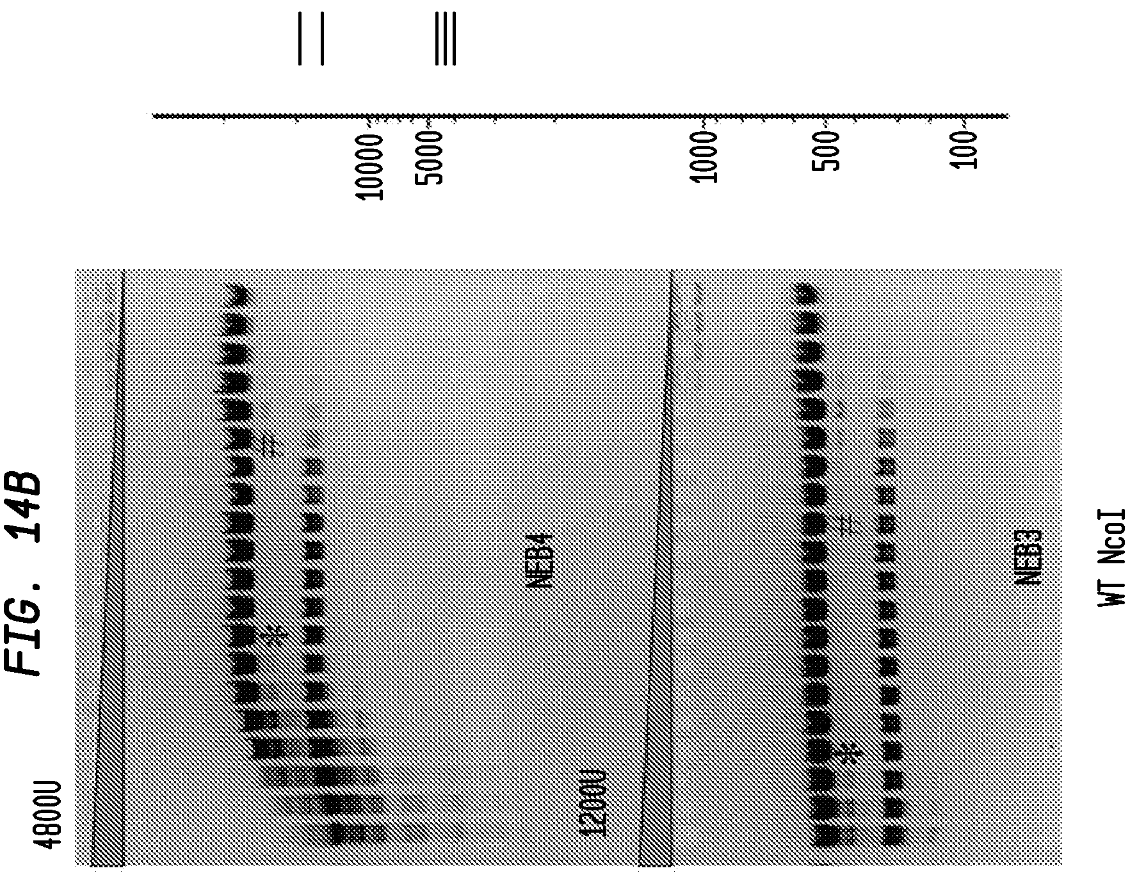
Figure 14A:
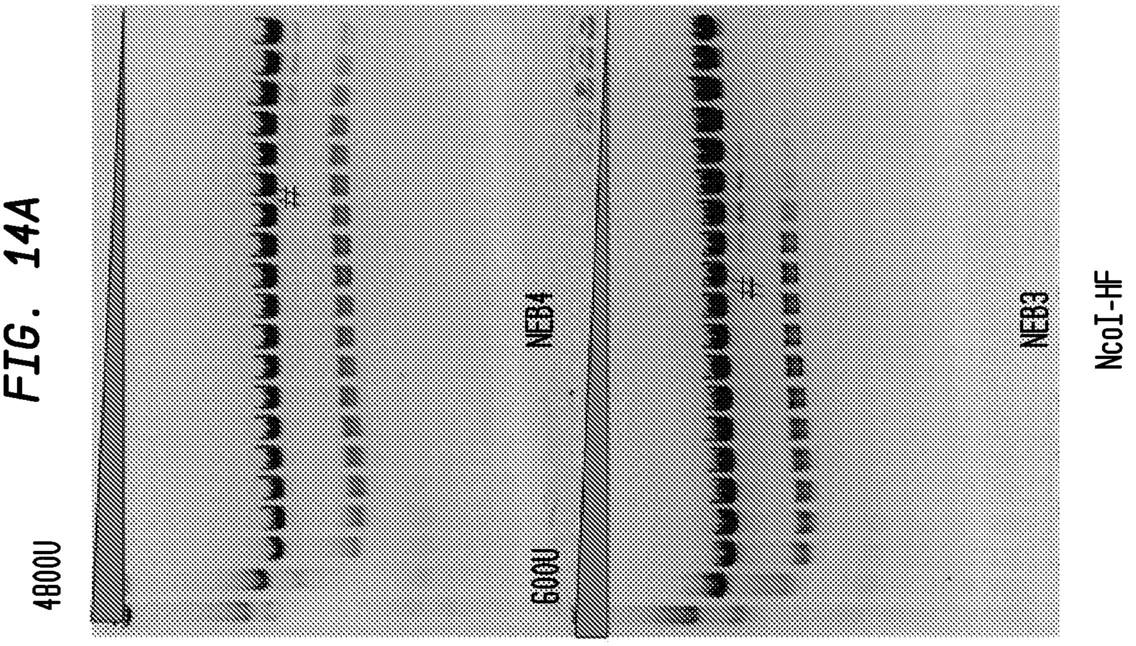

FIGS. 14A-B show cleavage of 1.2 μl lambda DNA substrate using 2-fold serial dilutions of NcoI-HF (4,800 U and 600 U) and 2-fold serial dilutions of WT NcoI (4,800 U and 1,200 U) in NEB3 and NEB4 buffers, respectively. Serial dilutions were performed in diluent A.

FIG. 14A shows cleavage by NcoI-HF in NEB4 buffer (upper panel) and NEB3 buffer (lower panel).

FIG. 14B shows cleavage by WT NcoI in NEB4 buffer (upper panel) and NEB3 buffer (lower panel).

Figures 15A, 15B:
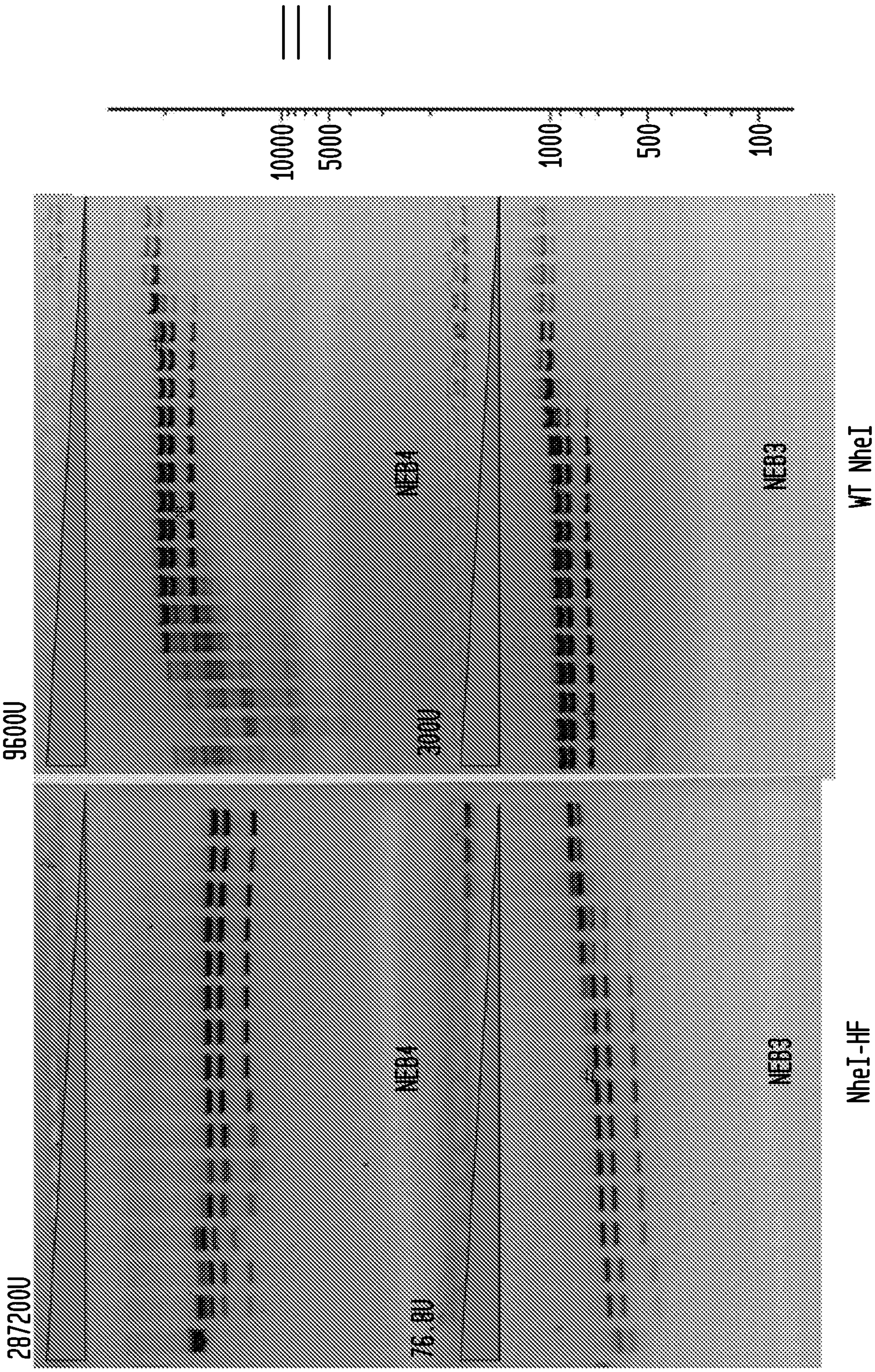

FIGS. 15A-B show cleavage of 1.2 μl pXba DNA substrate using 2-fold serial dilutions of NheI-HF (287,200 U and 76.8 U) and 2-fold serial dilutions of WT NheI (9,600 U and 300 U) in NEB3 and NEB4 buffers, respectively. Serial dilutions were performed in diluent A.

FIG. 15A shows cleavage by NheI-HF in NEB4 buffer (upper panel) and NEB3 buffer (lower panel).

FIG. 15B shows cleavage by WT NheI in NEB4 buffer (upper panel) and NEB3 buffer (lower panel.)

Figures 16A, 16B:
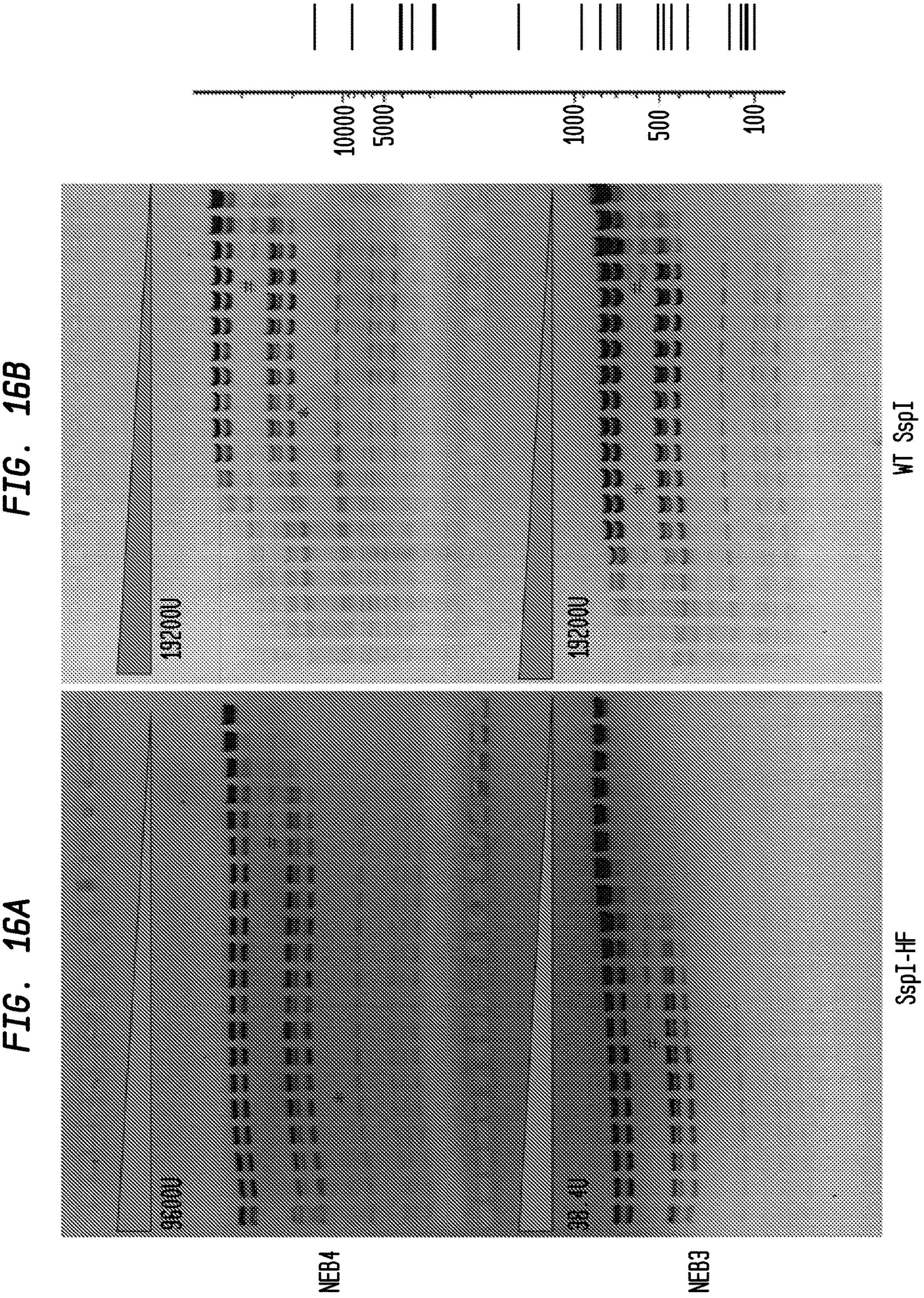

FIGS. 16A-B show cleavage of 1.2 μl lambda DNA substrate using 2-fold serial dilutions of SspI-HF (9,600 U and 38.4 U) and 2-fold serial dilutions of WT SspI (19,200 U and 19,200 U) in NEB3 and NEB4 buffers, respectively. Serial dilutions were performed in diluent C.

FIG. 16A shows cleavage by SspI-HF in NEB4 buffer (upper panel) and NEB3 buffer (lower panel).

FIG. 16B shows cleavage by WT SspI in NEB4 buffer (upper panel) and NEB3 buffer (lower panel).

Figures 17A, 17B:
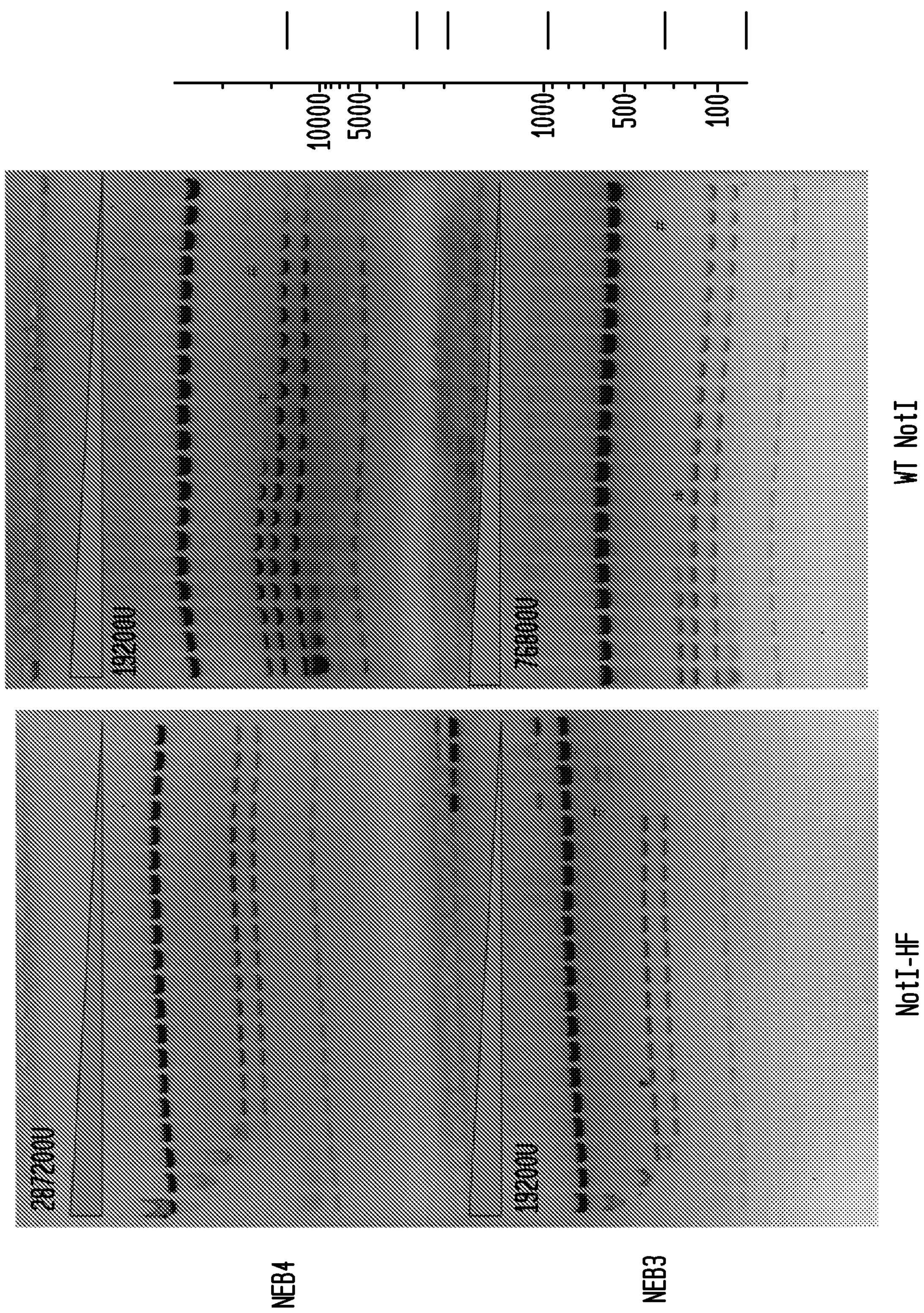

FIGS. 17A-B show cleavage of 1.2 μl pXba DNA substrate using 2-fold serial dilutions of NotI-HF (287,200 U and 19,200 U) and 2-fold serial dilutions of WT NotI (19,200 U and 76,800 U) in NEB3 and NEB4 buffers, respectively. Serial dilutions were performed in diluent C.

FIG. 17A shows cleavage by NotI-HF in NEB4 buffer (upper panel) and NEB3 buffer (lower panel).

FIG. 17B shows cleavage by WT NotI I in NEB4 buffer (upper panel) and NEB3 buffer (lower panel).

Figures 18A, 18B:
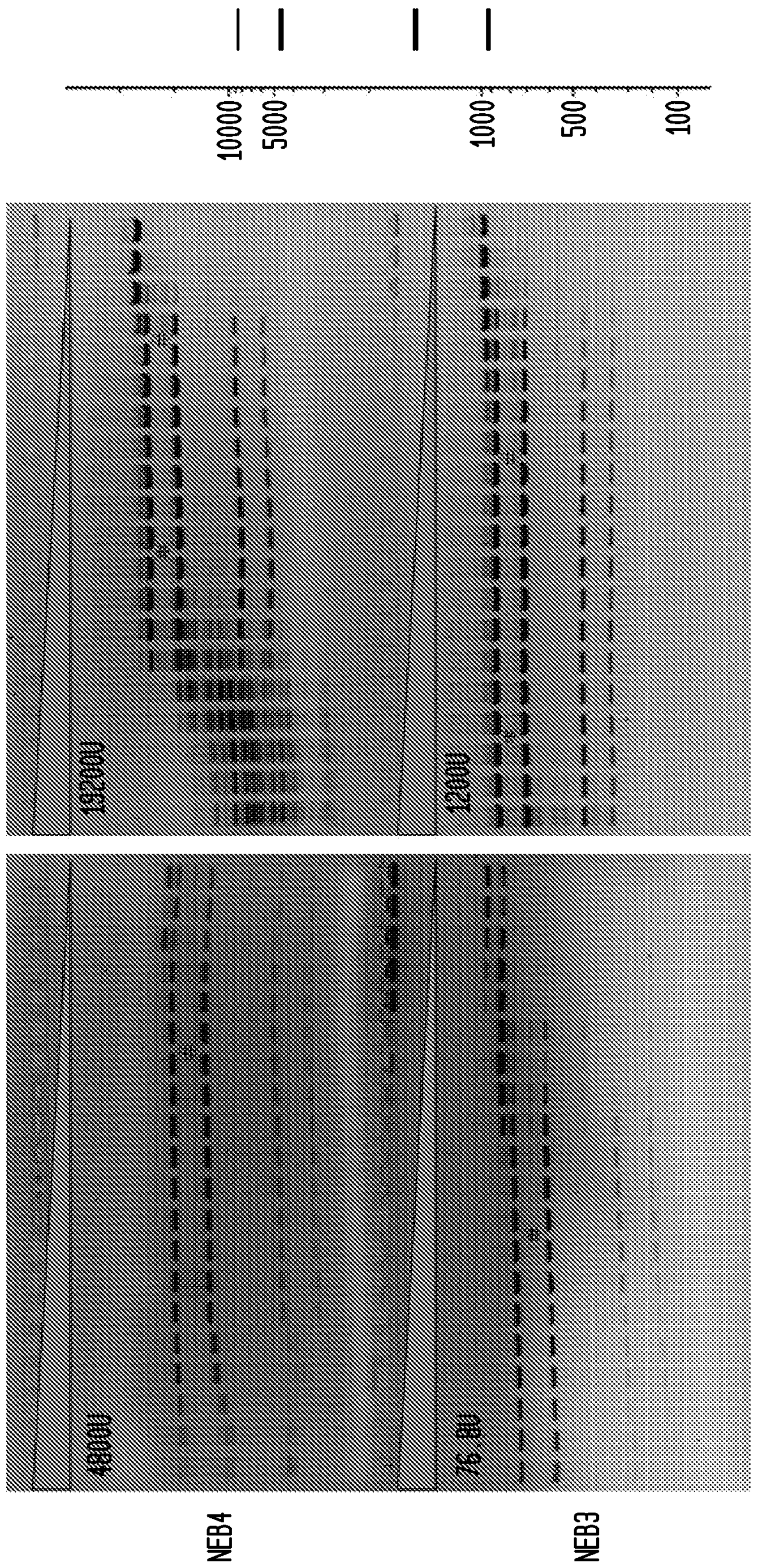

FIGS. 18A-B show cleavage of 1.2 μl pXba DNA substrate using 2-fold serial dilutions of SacI-HF (4,800 U and 76.8 U) and 2-fold serial dilutions of WT SacI (19,200 U and 1200 U) in NEB3 and NEB4 buffers, respectively. Serial dilutions were performed in diluent A.

FIG. 18A shows cleavage by SacI-HF in NEB4 buffer (upper panel) and NEB3 buffer (lower panel).

FIG. 18B shows cleavage by WT Sac in NEB4 buffer (upper panel) and NEB3 buffer (lower panel).

Figure 19B:
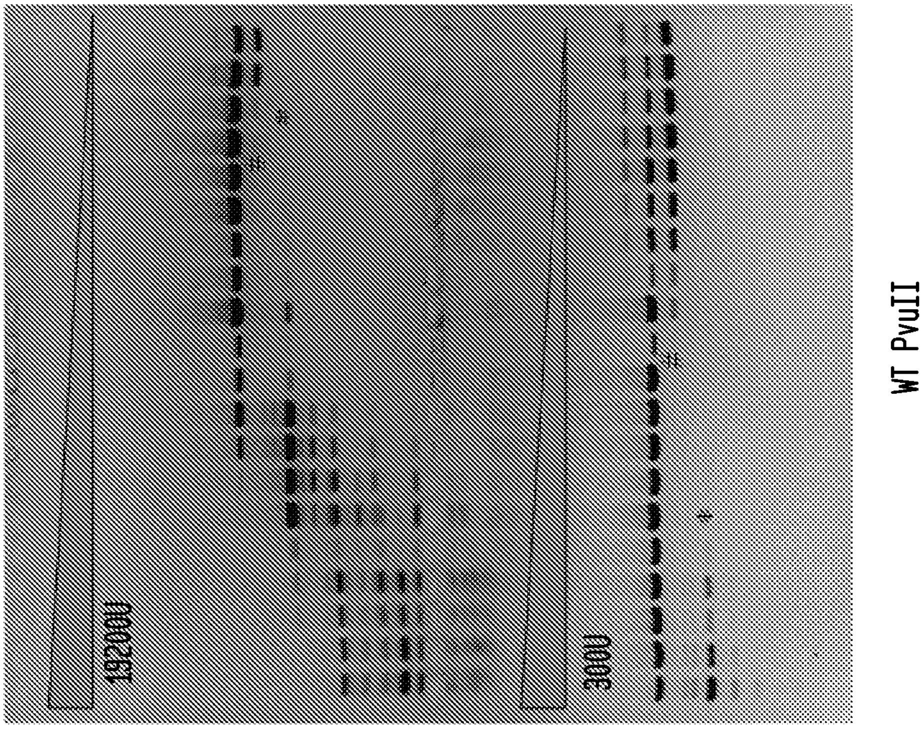
Figure 19A:
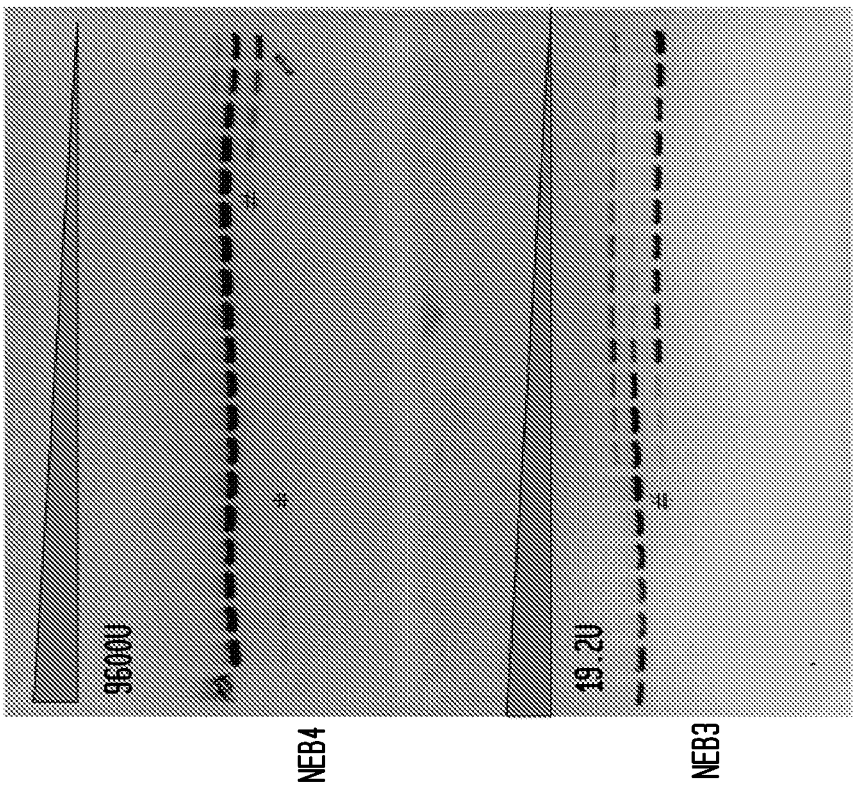

FIGS. 19A-B show cleavage of 0.6 μl pBR322 DNA substrate using 2-fold serial dilutions of PvuII-HF (9,600 U and 19.2 U) and 2-fold serial dilutions of WT PvuII (19,200 U and 300 U) in NEB3 and NEB4 buffers, respectively. Serial dilutions were performed in diluent A.

FIG. 19A shows cleavage by PvuII-HF in NEB4 buffer (upper panel) and NEB3 buffer (lower panel)

FIG. 19B shows cleavage by WT PvuII in NEB4 buffer (upper panel) and NEB3 buffer (lower panel).

Figure 20B:
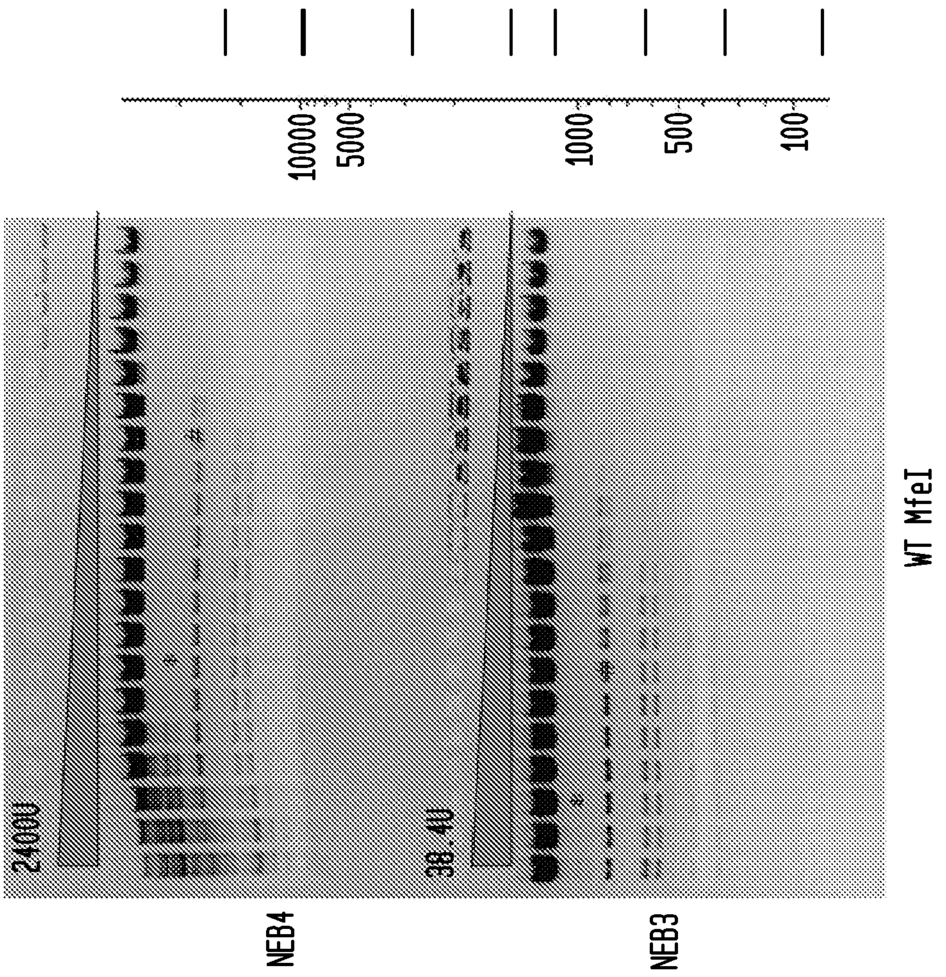
Figure 20A:
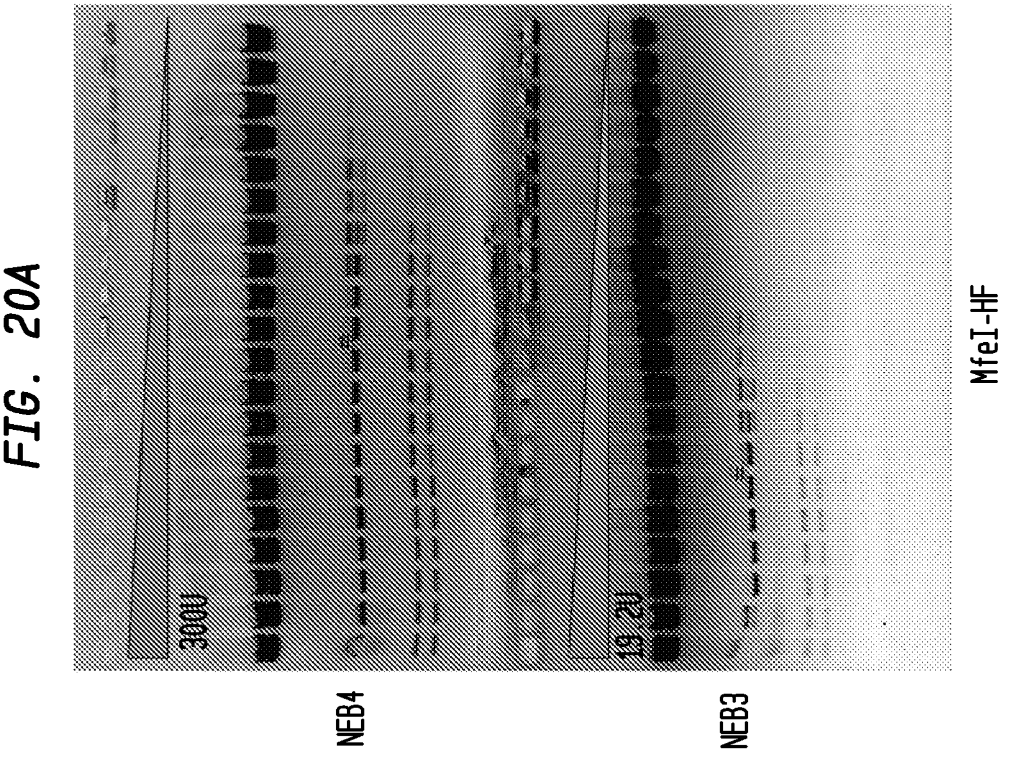

FIGS. 20A-B show cleavage of 1.2 μl lambda DNA substrate using 2-fold serial dilutions of MfeI-HF (300 U and 19.2 U) and 2-fold serial dilutions of WT MfeI (2,400 U and 38.4 U) in NEB3 and NEB4 buffers, respectively. Serial dilutions were performed in diluent A.

FIG. 20A shows cleavage by MfeI-HF in NEB4 buffer (upper panel) and NEB3 buffer (lower panel).

FIG. 20B shows cleavage by WT MfeI in NEB4 buffer (upper panel) and NEB3 buffer (lower panel).

Figure 21B:
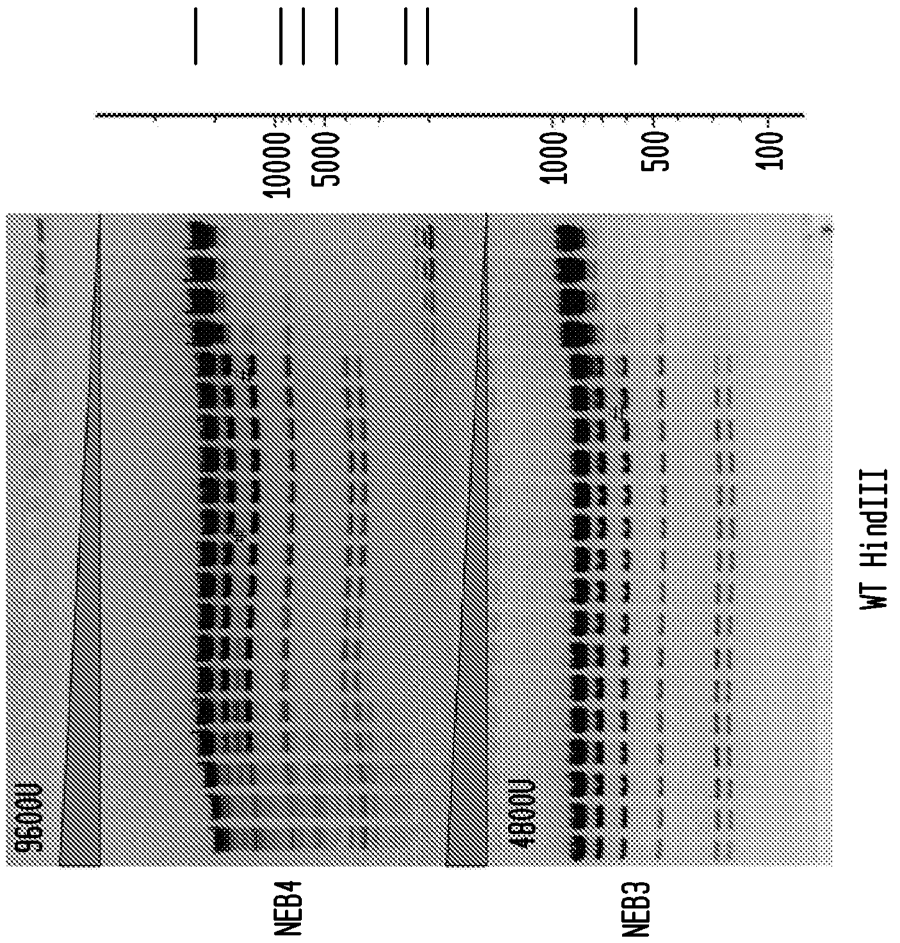
Figure 21A:
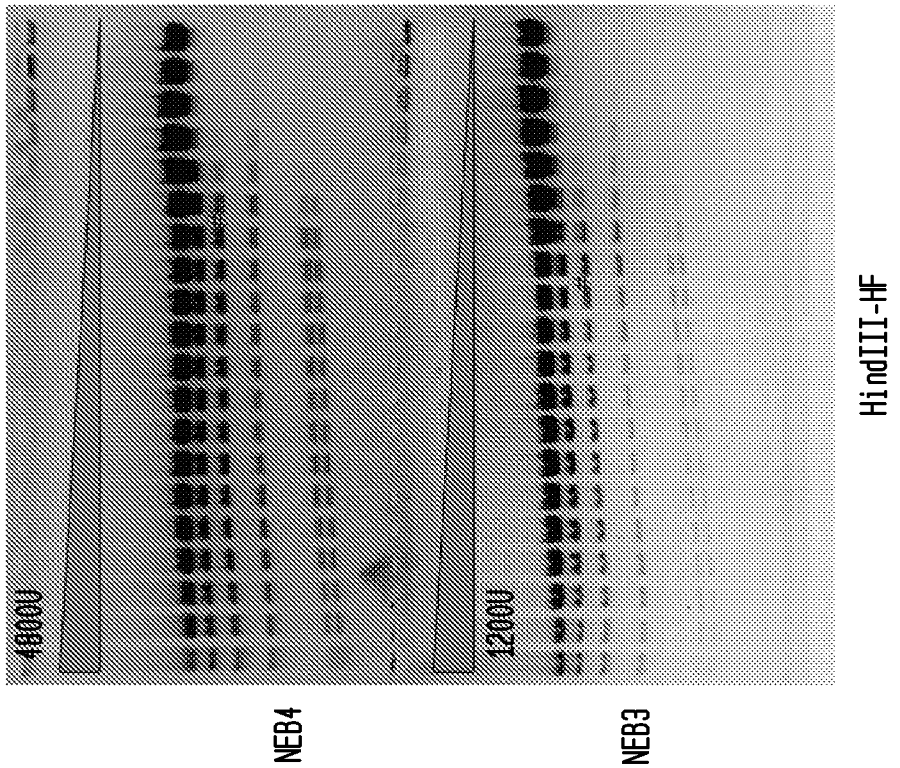

FIGS. 21A-B show cleavage of 1.2 μl lambda DNA substrate using a 2-fold serial dilution of HindIII-HF (4,800 U and 1,200 U) and a 2-fold serial dilution of WT HindIII (9,600 U and 4,800 U) in NEB3 and NEB4 buffers, respectively. Serial dilutions were performed in diluent A.

FIG. 21A shows cleavage by HindIII-HF in NEB4 buffer (upper panel) and NEB3 buffer (lower panel).

FIG. 21B shows cleavage by WT HindIII in NEB4 buffer (upper panel) and NEB3 buffer (lower panel)

FIGS. 22A-B show cleavage of 1.2 μl lambda DNA substrate in a 2-fold serial dilution using diluent C of SbfI-HF (starting concentration: 76,800 U) and WT SbfI (starting concentration: 76,800 U) in NEB4 buffer.

FIG. 22A shows cleavage by WT SbfI.

FIG. 22B shows cleavage by SbfI-HF.

Figure 23A:
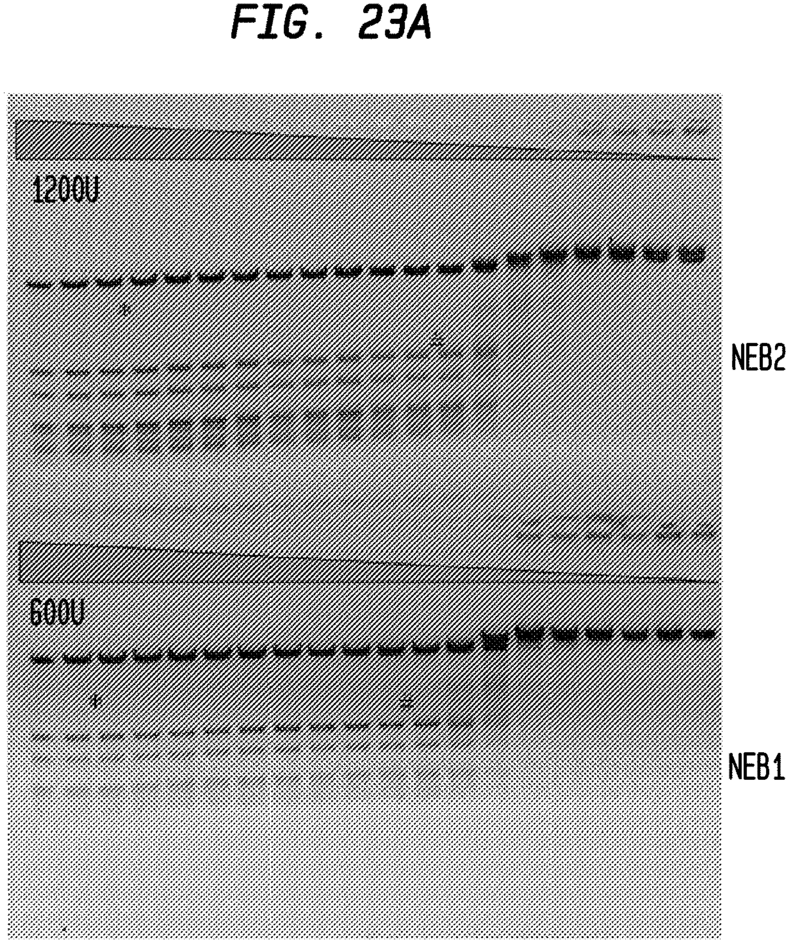
Figure 23B:
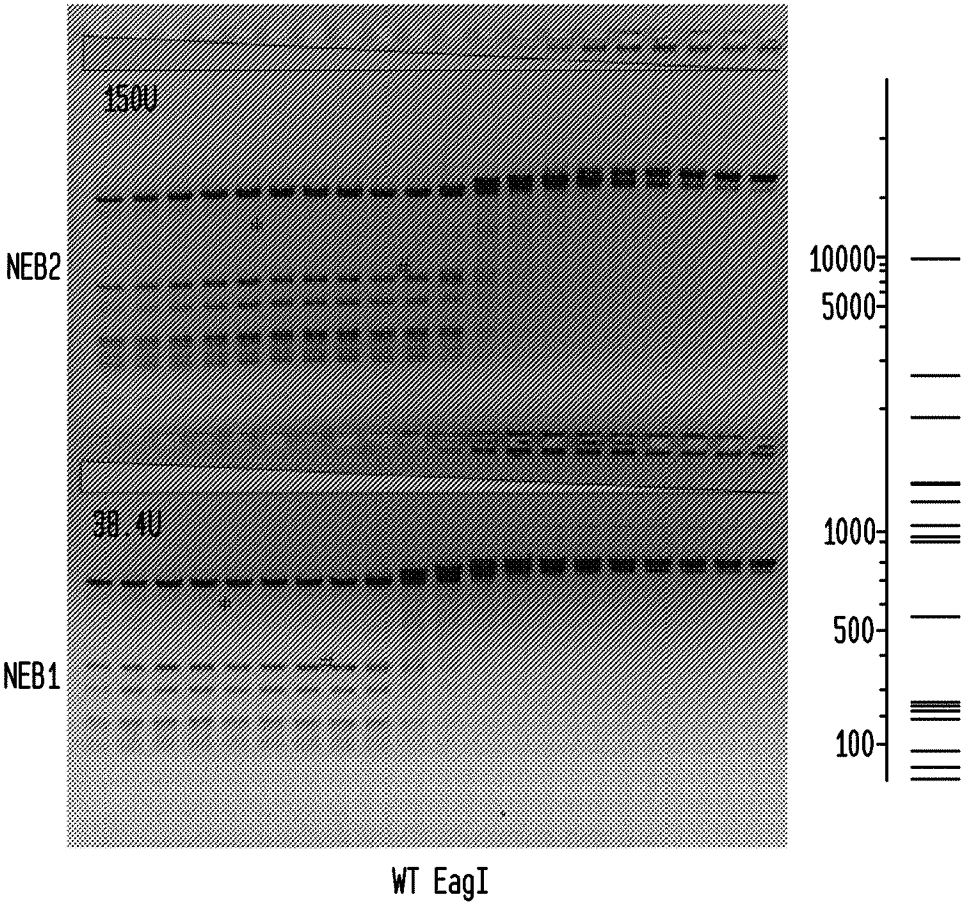

FIGS. 23A-B shows cleavage of 1.2 μl pXba DNA substrate in a 2-fold serial dilution of EagI-HF (1,200 U and 600 U) and a 2-fold serial dilution of WT EagI (150 U and 38.4 U) in NEB2 and NEB1 buffers, respectively, using diluent C.

FIG. 23A shows cleavage by EagI-HF in NEB2 buffer (upper panel) and NEB1 buffer (lower panel).

FIG. 23B shows cleavage by WT EagI in NEB2 buffer (upper panel) and NEB1 buffer (lower panel).

Figures 24A, 24B:
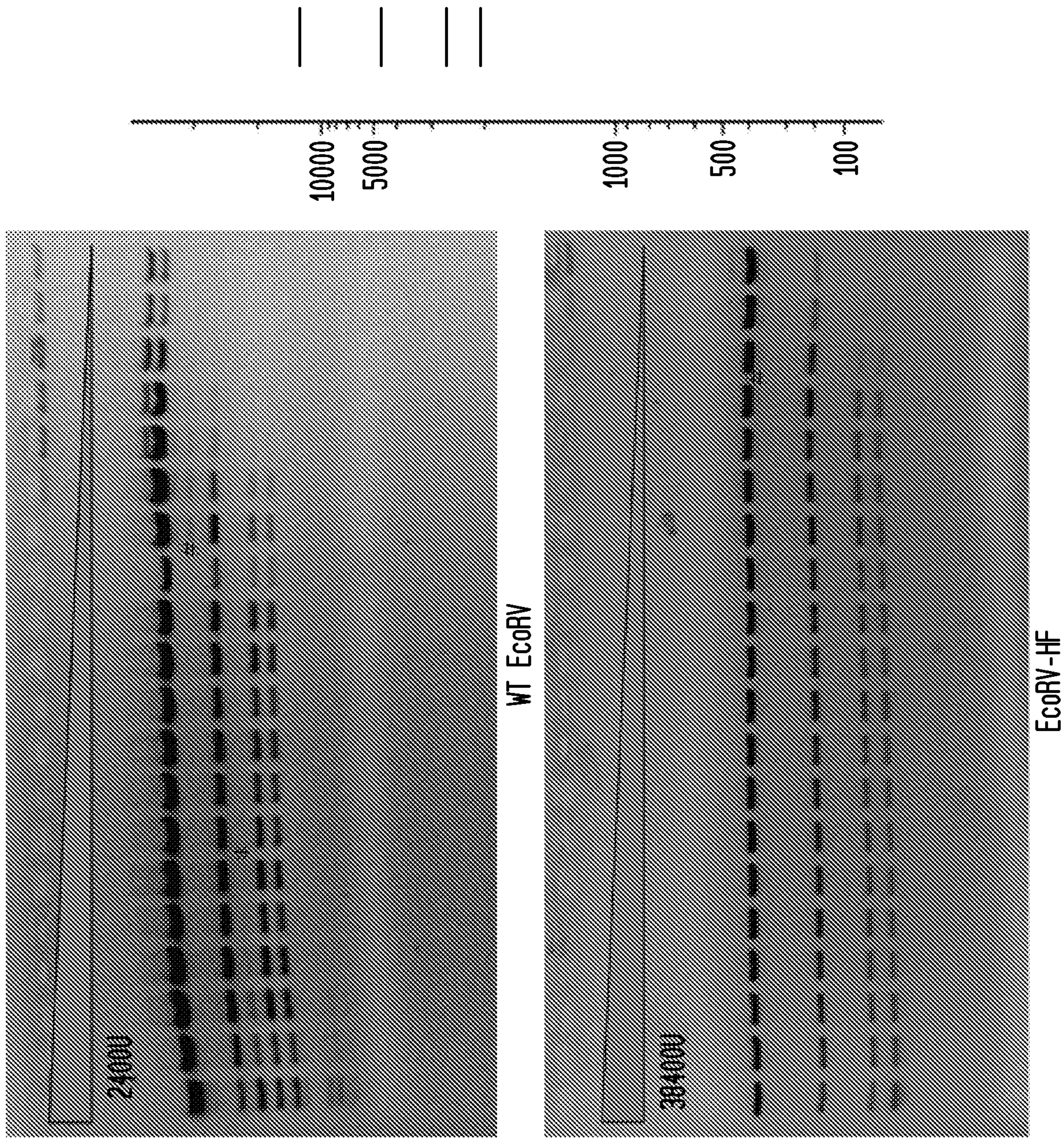

FIGS. 24A-B show cleavage of 1.2 μl pXba DNA substrate in a two-fold serial dilution using diluent A of EcoRV-HF (starting concentration: 38,400 U) and WT EcoRV (starting concentration: 2400 U) in NEB4 buffer.

FIG. 24A shows cleavage by WT EcoRV.

FIG. 24B shows cleavage by EcoRV-HF.

FIGS. 25A-B show cleavage of 1.2 μl T7 DNA substrate in a two-fold serial dilution using diluent A of AvrII-HF (starting concentration: 1,200 U) and WT AvrII (starting concentration: 1,200 U) in NEB4 buffer.

FIG. 25A shows cleavage by WT AvrII.

FIG. 25B shows cleavage by AvrII-HF.

Figures 26A, 26B:
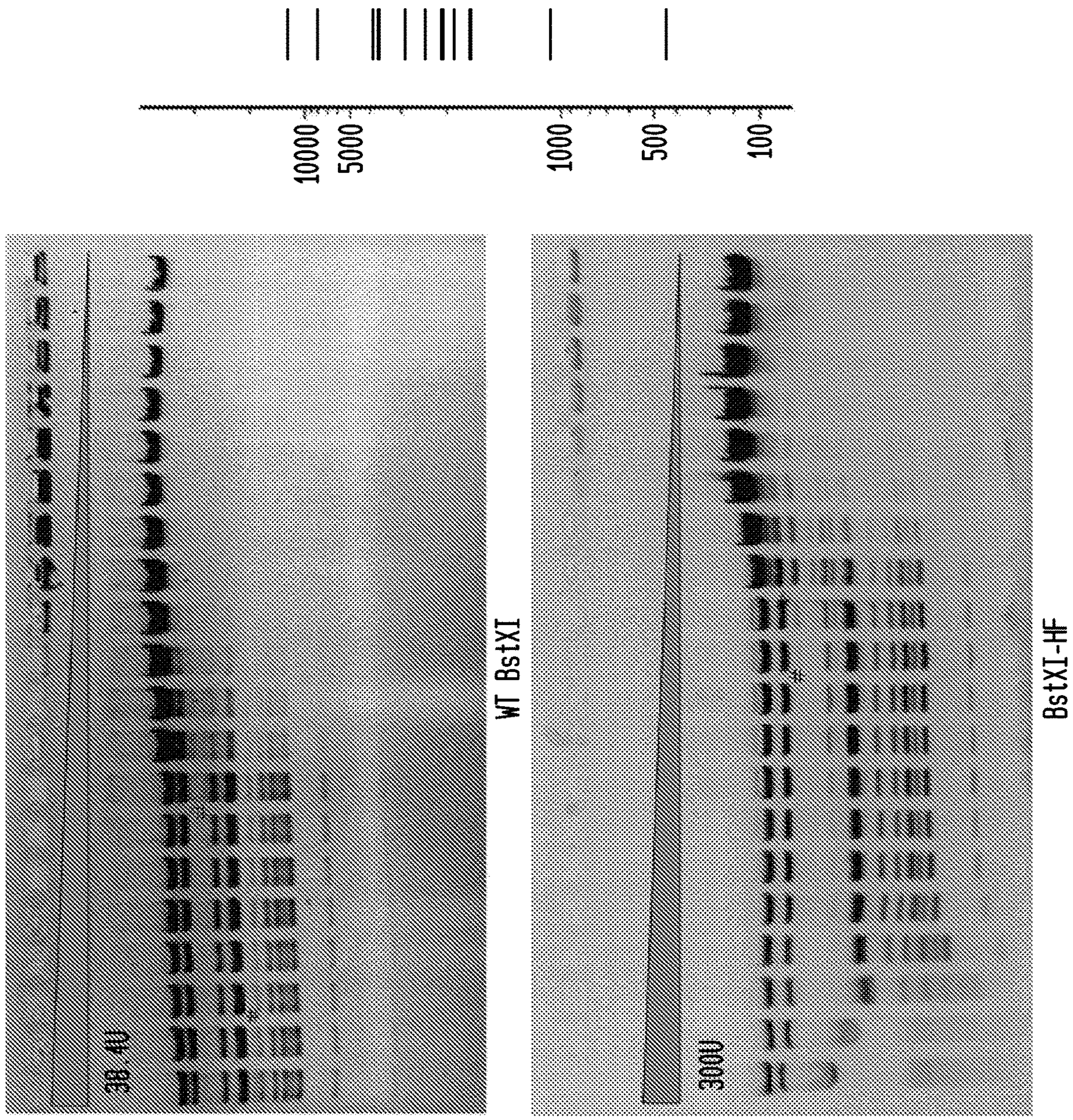

FIGS. 26A-B show cleavage of 1.2 μl lambda DNA substrate by a two-fold serial dilution in diluent A of BstXI-HF (starting concentration: 300 U) and WT BstXI (starting concentration: 38.4 U) in NEB4 buffer. The reaction was performed at 55° C.

FIG. 26A shows cleavage by WT BstXI.

FIG. 26B shows cleavage by BstXI-HF.

FIGS. 27A-B show cleavage of 1.2 μl pXba DNA substrate in a two-fold serial dilution using diluent A of PciI-HF (starting concentration: 600 U) and WT PciI (starting concentration 300 U) in NEB4 buffer.

FIG. 27A shows cleavage by WT PMiI.

FIG. 27B shows cleavage by PciI-HF.

Figures 28A, 28B:
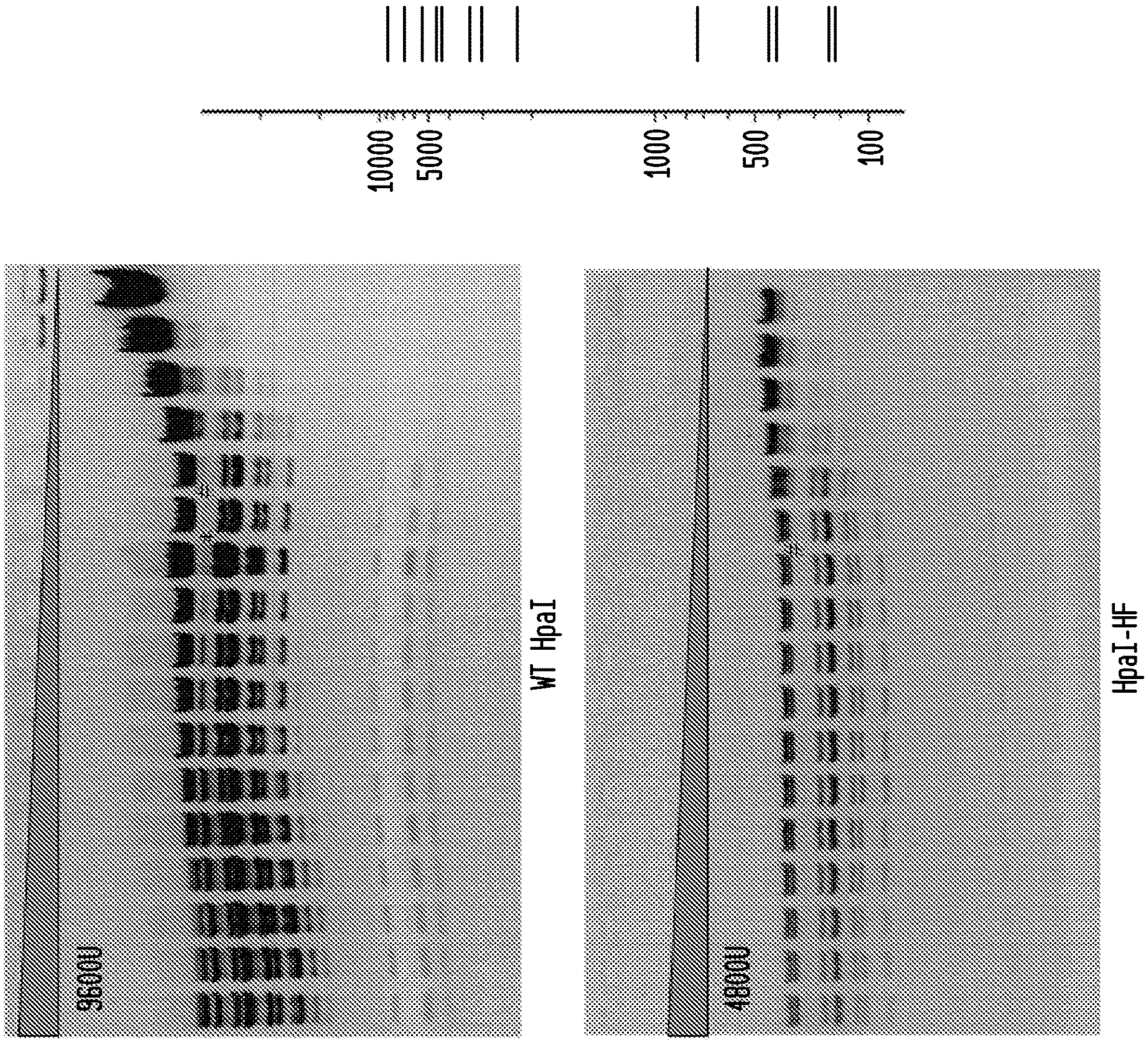

FIGS. 28A-B show cleavage of 1.2 μl lambda DNA substrate in a two-fold serial dilution using diluent A of HpaI-HF (starting concentration: 4,800 U) and WT HpaI (starting concentration 9,600 U) in NEB2 buffer.

FIG. 28A shows cleavage by WT HpaI.

FIG. 28B shows cleavage by HpaI-HF.

FIGS. 29A-B show cleavage of 1.2 μl pXba DNA substrate in a two-fold serial dilution of AgeI-HF using diluent C (starting concentration: 600 U) and WT AgeI (starting concentration 600 U) in NEB4 buffer.

FIG. 29A shows cleavage by WT AgeI.

FIG. 29B shows cleavage by AgeI-HF.

Figures 30A, 30B:
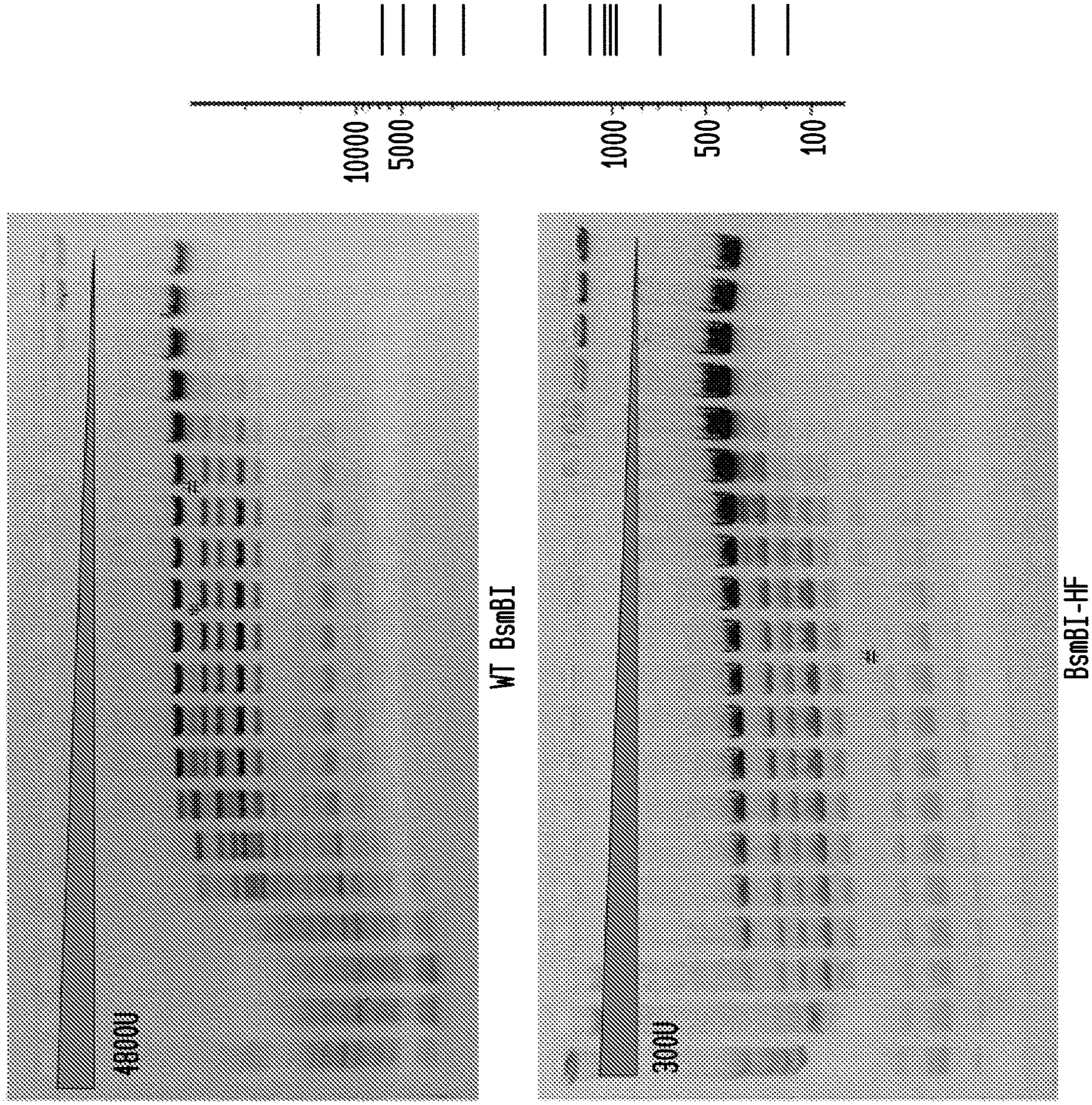

FIGS. 30A-B show cleavage of 1.2 μl lambda DNA substrate in a two-fold serial dilution using diluent A of BsmBI-HF (starting concentration: 300 U) and WT BsmBI (starting concentration 4,800 U) in NEB4 buffer. The reaction is at 55° C.

FIG. 30A shows cleavage by WT BsmBI.

FIG. 30B shows cleavage by BsmBI-HF.

FIGS. 31A-B show the DNA sequence (SEQ ID NO:1) and protein sequence (SEQ ID NO:2) of MluCIM, respectively, for expression of EcoRI and MfeI.

FIG. 32 shows the DNA sequence (SEQ ID NO:3) of Hpy166IIM for expression of SalI.

FIGS. 33A-B show the DNA sequence (SEQ ID NO:4) and protein sequence (SEQ ID NO:5) of MfeI, respectively.

FIGS. 34A-B show the DNA sequence (SEQ ID NO:6) and protein sequence (SEQ ID NO:7) of BstXI, respectively.

FIGS. 35A-B show the DNA sequence (SEQ ID NO:8) and protein sequence (SEQ ID NO:9 of M.BstXI, respectively.

FIGS. 36A-B show the DNA sequence (SEQ ID NO:10) and protein sequence (SEQ ID NO: 11) of S.BstXI, respectively.

FIGS. 37A-B show the DNA sequence (SEQ ID NO:12) and protein sequence (SEQ ID NO:13) of PciI, respectively.

FIGS. 38A-B show the DNA sequence (SEQ ID NO:14) and protein sequence (SEQ ID NO:15) of M.PciI, respectively.

FIG. 39 shows the DNA sequence (SEQ ID NO:17) encoding MI.EarI that recognizes CTCTTC and methylates at N4 cytosine or N6 adenine for cloning SapI and BspQI.

FIG. 40 shows the DNA sequence (SEQ ID NO:18) encoding M2.EarI that recognizes CTCTTC and methylates at N4 cytosine or N6 adenine for cloning SapI and BspQI.

Figure 41A:
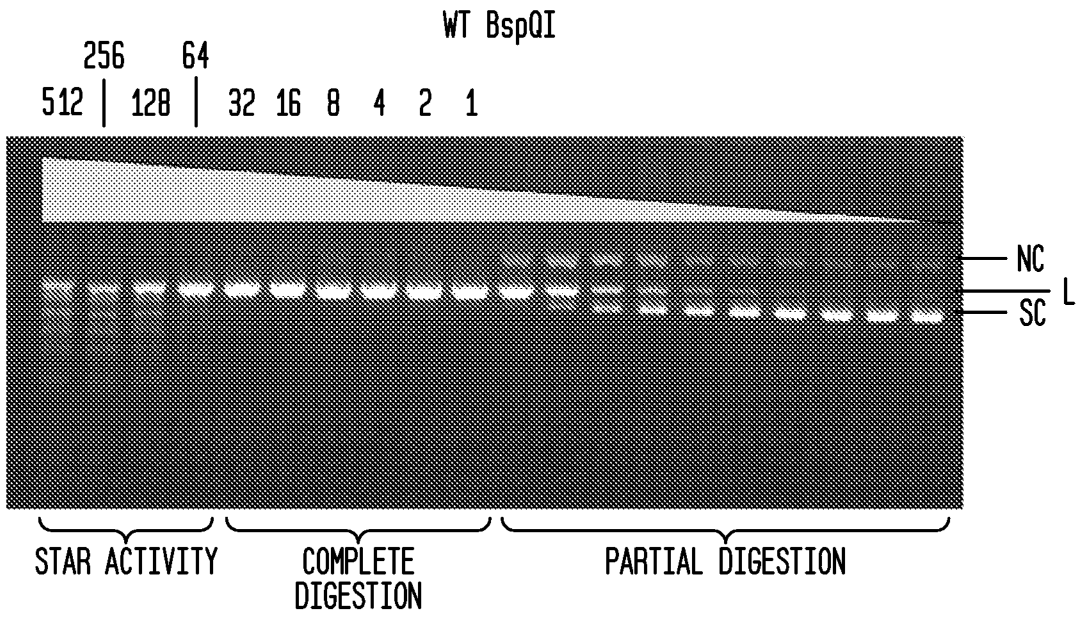
Figure 41B:
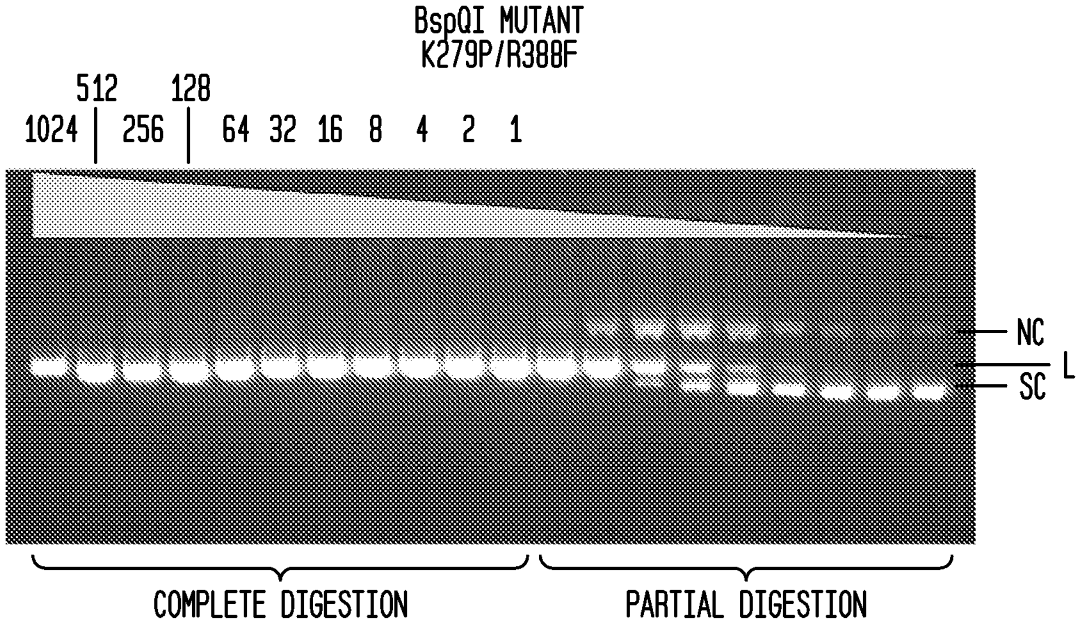

FIGS. 41A-B show agarose gels to determine the FI of 1 μl WT BspQI and 1 μl mutant (K279P/R388F) BspQI (starting concentrations 512 U and 1,024 U, respectively) by cleaving 1 μl pUC19 DNA substrate in a two-fold serial dilution using diluent A and NEB1 buffer plus 10% glycerol. The reaction was conducted at 50° C.

Figure 42:
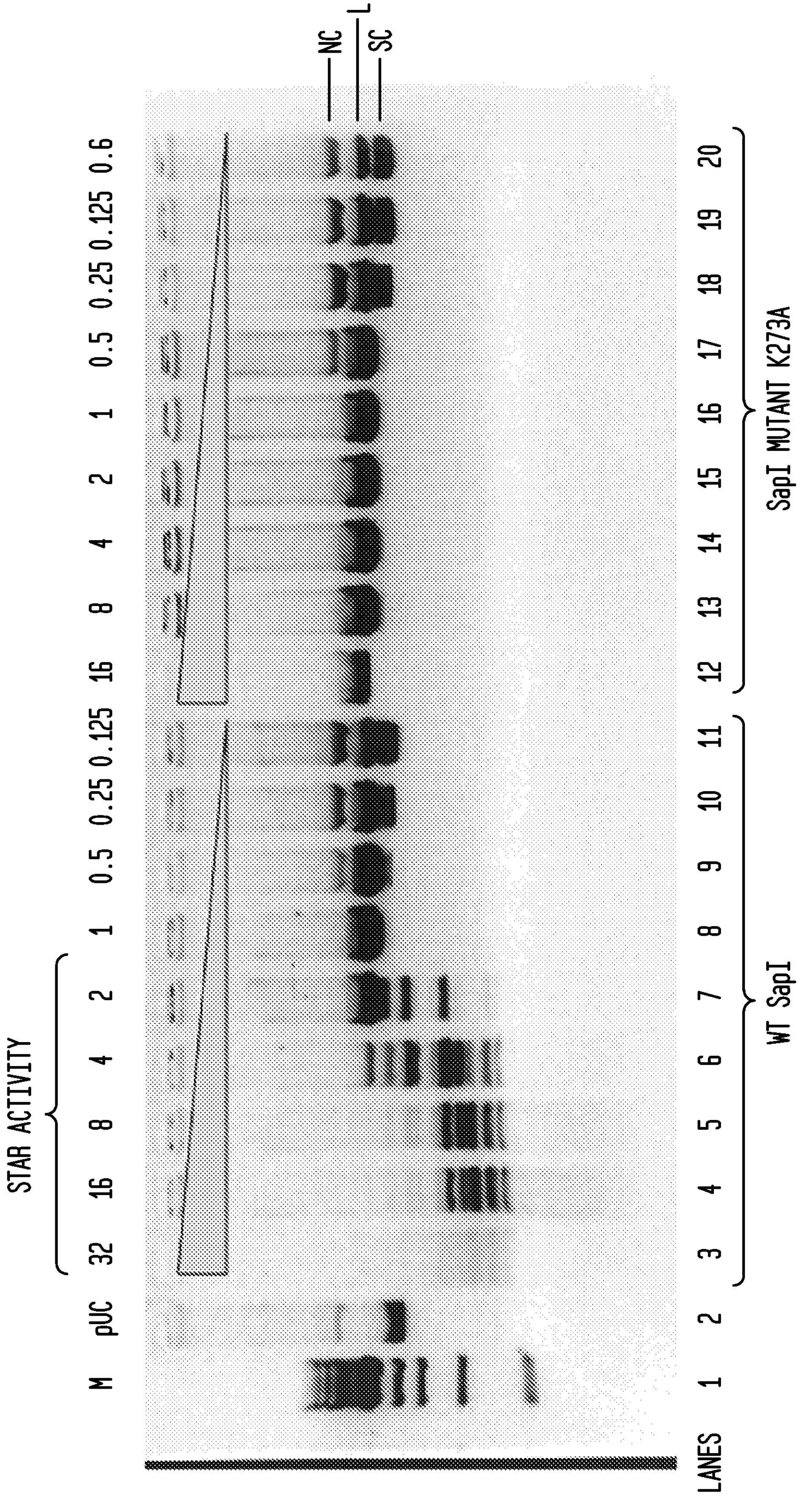

FIG. 42 shows agarose gels to determine the FI of 5 μl WT SapI and 5 μl mutant (K273A) SapI (starting concentrations 32 U and 16 U, respectively) by cleaving pUC19 DNA substrate in a two-fold serial dilution using diluent A and NEB2 buffer plus 25% DMSO.

Figure 43A:
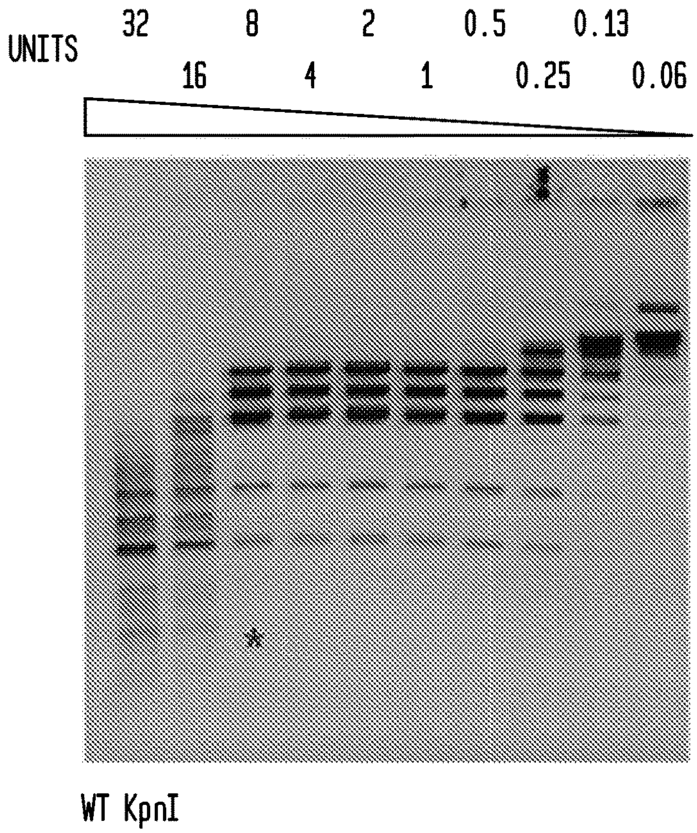
Figure 43B:
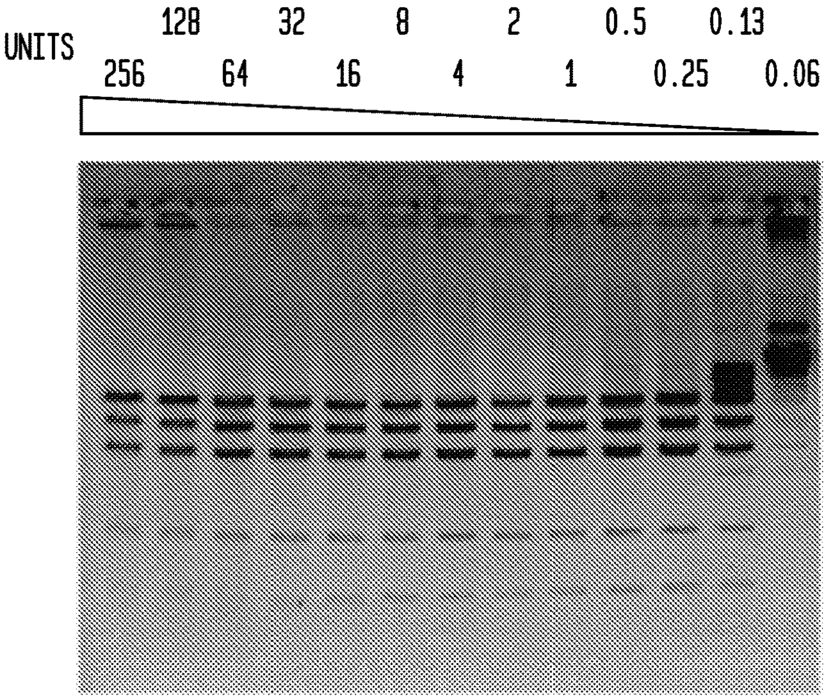

FIGS. 43A-B show catalytic and star activity of pXba by 5 μl WT KpnI and 5 μl D16N/E132A/D148E KpnI (initial concentrations 32 U and 256 U, respectively). The enzyme digested 2 μl pXba DNA substrate (0.5 μg) in a 2-fold serial dilution in NEB2 buffer using a diluent containing 10 mM Tris-HCl, pH 7.4, 50 mM KCl, 0.1 mM EDTA, 1 mM DTT and 50% glycerol with the total volume made up to 50 μl with water.

FIG. 43A shows the cleavage results of KpnI.

FIG. 43B shows the cleavage results of D16N/E132A/D148E KpnI.

FIG. 44A-D show the amino acid sequences of the enzymes in Table 1 and the DNA sequences of the enzymes in Table 1 that have not been previously disclosed.

DETAILED DESCRIPTION OF THE EMBODIMENTS

Embodiments of the invention provide a general method for selecting for restriction endonucleases with desired characteristics. The general method relies on a suitable assay for determining whether the desired restriction endonuclease has been created. In particular an embodiment of the general method provides a systematic screening method with a set of steps. This method has been deduced by performing many hundreds of reactions using many restriction endonucleases. The majority of the examples provided herein relate to identifying restriction endonucleases with reduced star activity but with cleavage activity that is at least similar to the WT restriction endonuclease. However, it is expected that the same methodology can be applied successfully to modifying other properties of the restriction endonucleases relating, for example, to improved cleavage activity in desired buffers, thermostability, rate of reaction in defined conditions, etc.

As discussed above, an end point of interest is to transform restriction endonucleases with star activity into high fidelity restriction endonucleases with significantly reduced star activity. Star activity refers to promiscuity in cleavage specificity by individual restriction endonucleases. The terms “reduction in star activity” and “increase in fidelity” are used interchangeably here. Although restriction endonucleases are characterized by their property of cleaving DNA at specific sequences, some restriction endonucleases additionally cleave DNA inefficiently at secondary sites in the DNA. This secondary cleavage may occur consistently or may arise only under certain conditions such as any of: increased concentrations, certain buffers, temperature, substrate type, storage, and incubation time.

It is generally acknowledged that little is known about the complex environment generated by the hundreds of amino acids that constitute a protein and determine specificity. One approach in the prior art has been to utilize crystallography to identify contact points between an enzyme and its substrate. Nonetheless, crystallography has limitations with respect to freezing a structure in time in an unnatural chemical environment.

The rules that determine the contribution of amino acids at any site in the protein and the role played by the structure of the substrate molecule has proved elusive using existing analytical techniques. For example, it is shown here that mutating an amino acid in a restriction endonuclease can cause all or partial loss of activity.

In this context, no structural explanation has been put forward to explain why star activity could increase with high glycerol concentration (>5% v/v), high enzyme to DNA ratio (usually >100 units of enzyme per μg of DNA), low ionic strength (<25 mM salt), high pH (>8.0), presence of organic solvent (such as DMSO, ethanol), and substitution of $Mg^{2+}$ with other divalent cations ($Mn^{2+}$, $Co^{2+}$). It was here recognized that because of the diversity of factors affecting star activity, it would be necessary to conduct comparisons of WT and mutant star activity under the same reaction conditions and in the same predetermined buffer and to develop a standard reaction condition in which any high fidelity enzyme must be capable of showing the described characteristics even if these characteristics were also observed in other reaction conditions.

Present embodiments of the invention are directed to generating modified restriction endonucleases with specific improved properties, namely enhanced cleavage fidelity without significant reduction in overall cleavage activity or significant loss of yield from the host cells that make the protein. The methods that have been developed here for finding mutants with improved properties have resulted from exhaustive experimentation and the properties of the resultant enzymes have been defined in the context of specified conditions. The methods described herein may be used for altering the enzymatic properties of any restriction endonuclease under predetermined conditions, but are not limited to the specific defined conditions.

| Restriction Endonuclease | Steps Used to Generate a High Fidelity Restriction Endonuclease |
|---|---|
| BamHI (Ex. 1) | Comparison of isochizomer<br>Targeted 22 residues to mutate to Ala. 14 mutants obtained, 3 had improved fidelity<br>Saturation mutagenesis on 2 residues-K30 and E86<br>Recovered E86P as preferred mutant with greatest reduced star activity in selected buffers. Added mutations to E86P.<br>Second round of mutation (Arg, Lys, His, Asp, Glu, Ser, Thr) to Ala and Tyr to Phe. Selected E167 and Y165 for saturation mutagenesis and selected E167T and Y165F.<br>E163A/E167T was selected as preferred high fidelity mutant (BamHI-HF). |
| EcoRI (Ex. 2) | Comparison of isoschizomer<br>Targeted 42 charged residues to mutate to Ala. No high fidelity mutants<br>Second round mutations: Target additional 32 charged residues to mutate to Ala. Identified K62A.<br>Saturation mutagenesis on K62A. EcoRI( K62E) was selected as a preferred high fidelity mutant (EcoRI-HF). |
| ScaI (Ex. 3) | Comparison of isochizomers.<br>Targeted 58 charged residues to mutate to Ala. Identify 4 mutants<br>Preferred mutant of 4 is (H193A/S201F). This is selected as a preferred high fidelity mutant (ScaI-HF) |
| SalI (Ex. 4) | Targeted 86 charged residues and mutate to Ala. SalI (R107A) was preferentially selected as a preferred high fidelity mutant SalI-HF). |
| SphI (Ex. 5) | Target 71 charged residues and mutate to Ala. SphI (K100A) was preferentially selected as a preferred high fidelity mutant (SphI-HF) |
| PstI (Ex. 6) | Target 92 charged amino acids and mutate to Ala. PstI (D91A) was preferentially selected as a preferred high fidelity mutant (PstI-HF) |
| NcoI (Ex. 7) | Target 66 charged residues and mutate to Ala. NcoI (A2T/R31A) was preferentially selected as a preferred high fidelity mutant (NcoI-HF). |
| NheI (Ex. 8) | Target 92 charged residues and mutate to Ala. NheI (E77A) was preferentially selected as a preferred high fidelity mutant (NheI-HF) |
| SspI (Ex. 9) | Target 81 charged residues and mutate to Ala. No preferential mutants obtained.<br>Target 95 residues to additional charged residues and hydroxylated residues to Ala except Tyr. Tyr mutated to Phe.<br>SspI (Y98F) was preferentially selected as a preferred high fidelity mutant (SspI-HF) |
| NotI (Ex. 10) | Target 97 charged residues and mutate to Ala. K150A was preferentially selected as a preferred high fidelity mutant (NotIHF) |
| SacI (Ex. 11) | Target 101 charged residues and mutate to Ala. SacI (Q117H/R200A) was preferentially selected as a preferred high fidelity mutant (SacI-HF) where Q117H was a carry over mutation from template with no affect on activity |
| PvuII (Ex. 12) | Target 47 charged residues and mutate to Ala. No preferred mutants obtained<br>Target 19 hydroxylated residues-Ser/Thr and Tyr. Selected T46A for further improvement<br>Saturation mutagensis results in a preferred mutant T46G, T46H, T64K, T46Y. PvuII(T46G) was preferentially selected as a preferred high fidelity mutant (PvuII-HF) |
| MfeI (Ex. 13) | Target 60 charged residues and mutant to Ala. No preferred mutants obtained<br>Target 26 hydroxylated residues and mutate to Ala except for Tyr which was changed to Phe.<br>Target 38 residues (Cys, Phe, Met, Asn, Gln, Trp) and mutate to Ala<br>Identify Mfe (Q13A/F35Y) as a preferred high fidelity mutant (MfeI-HF) where F35Y is carried from the template |
| HindIII (Ex. 14) | Target 88 charged residues and mutate to Ala. No preferred mutants obtained.<br>Target 103 residues (Cys Met Asn, Gln, Ser Thr Trp) and mutate to Ala and Tyr changed to Phe.<br>Identify HindIII (K198A) as a preferred high fidelity mutant (hindIII-HF) |
| SbfI (Ex. 15) | Target 78 charged residues mutated to Ala<br>Target 41 residues (Ser Thr) mutated to Ala/Tyr to Phe<br>Target 55 residues of Cys, Phe, Met, Asn, Gln. Trp to Ala<br>SbfI (K251A) was selected as a preferred high fidelity mutant (SbfI-HF) |

-continued

| Restriction Endonuclease | Steps Used to Generate a High Fidelity Restriction Endonuclease |
|---|---|
| EagI (Ex. 16) | Target 152 residues (Asp, Glu, His, Lys, Arg, Ser, thr, Asn, and Gln changed to Ala and Tyr changed to Phe).<br>EagI H43A was selected as a preferred high fidelity mutant (EagIHF) |
| EcoRV (Ex. 17) | Target 162 residues (Cys, Asp, Glu, Phe, his, Lys, Met, Asn, Gln, Arg, Ser, Thr, to Ala and Trp to Phe)<br>EcoRV (D19A/E27A) was selected as a preferred high fidelity mutant (EcoRV-HF) |
| AvrII (Ex. 18) | Target 210 residues (Cys, Asp, Glu, Phe, his, Lys, Met, Asn, Gln, Arg, Ser, Thr, to Ala and Trp to Phe)<br>AvrII (Y104F) was selected as a preferred high fidelity mutant (AvrII-HF) |
| BstXI (Ex. 19) | Target 237 residues (Cys, Asp, Glu, Phe, his, Lys, Met, Asn, Gln, Arg, Ser, Thr, to Ala and Trp to Phe)<br>BstXI (N65A) was selected as a preferred high fidelity mutant (BstXI-HF) |
| PciI (Ex. 20) | Target 151 residues (Cys, Asp, Glu, Phe, his, Lys, Met, Asn, Gln, Arg, Ser, Thr, to Ala and Trp to Phe)<br>PciI (E78A/S133A) was selected as a preferred high fidelity mutant. (PciI-HF) This was spontaneous and not one of the 151 separate mutations. |
| HpaI (Ex. 21) | Target 156 residues (Cys, Asp, Glu, Phe, his, Lys, Met, Asn, Gln, Arg, Ser, Thr, to Ala and Trp to Phe)<br>HpaI (E56A) was selected as a preferred high fidelity mutant (HpaI-HF) |
| AgeI (Ex. 22) | Target 149 residues (Cys, Asp, Glu, Phe, his, Lys, Met, Asn, Gln, Arg, Ser, Thr, to Ala and Trp to Phe)<br>AgrI (R139A) was selected as a preferred high fidelity mutant (AgeI-HF) |
| BsmBI (Ex. 23) | Target 358 residues (Cys, Asp, Glu, Phe, his, Lys, Met, Asn, Gln, Arg, Ser, Thr, to Ala and Trp to Phe)<br>BsmBI(N185Y/R232A) was selected as a preferred high fidelity mutant (BsmBI (HF) |
| BspQI (Ex. 24) | Target 122 residues (Arg, Lys, His, Glu, Asp, Gln, Asn, Cys)<br>Replace R at position 279 with Phe, Pro, Tyr, Glu, Asp or Leu.<br>Preferred mutations were R388F and K279P.<br>Created a double mutant BspQI(K279P/R388F) as preferred high fidelity mutant (BspQI-HI) |
| SapI (Ex. 25) | Find K273 and R380 in SapI corresponding to R388 and K279 in BspQI.<br>SapI (K273P/R380F) was selected as a preferred high fidelity mutant (SapI-HF) |
| KpnI (Ex. 26) | Target all residues (Asp, Glu, Arg, Lys, His, Thr, Tyr, Asn, Gln, Phe, Trp, Cys, Met) to Ala.<br>More mutation was done on site D16 and D148.<br>A combined D16N/E132A/D148E was selected as a preferred high fidelity mutant (KpnI-HF). |
| BsaI (Ex. 27) | Find 11 amino acids corresponding to the site in BsmBI.<br>BsaI (Y231F) was selected as a preferred high fidelity mutant (BasI-HF). |

The method follows from the realization that amino acids responsible for cognate activity and star activity are different. The engineering of high fidelity restriction endonucleases described herein demonstrates that cognate activity and star activity can be separated and there are different critical amino acid residues that affect these different activities. The locations of amino acids that are here found to affect star activity are not necessarily found within the active site of the protein. The cleavage properties of any restriction endonuclease has been determined here for the first time by developing a criterion of success in the form of determining a FI (see also Wei et al. *Nucleic Acid Res.,* 36, 9, e50 (2008)) and an overall fidelity index improvement factor.

An "overall fidelity index improvement factor" refers to the highest FI for a mutant with maximum cleavage activity divided by the highest FI of the corresponding WT endonuclease with maximum cleavage activity within a selected set of buffers. The selected, set may be of any size greater than one but practically will contain less than 10 different buffers and more preferably contains 4 buffers. The set may also include less than 4 buffers. The overall FI improvement factor of at least two should preferably be applicable for any mutant restriction endonuclease in the claimed invention additionally but not exclusively to the set of buffers consisting of NEB1, NEB2, NEB3 and NEB4.

A "similar cleavage activity" can be measured by reacting the same amount of enzyme with the same amount and type of substrate under the same conditions and visually comparing the cleavage profiles on a gel after electrophoresis such that the amount of cleavage product appears to be the same within a standard margin of error and wherein the quantitative similarity is more than 10%.

"Artificial" refers to "man-made".

"Standard conditions" refers to an overall FI improvement factor calculated from results obtained in NEB1-4 buffers.

The general method described herein has been exemplified with 27 restriction endonucleases: AgeI, AvrII, BamHI, BsaI, BsmBI, BspQI, BstXI, EagI, EcoRI, EcoRV, HindIII, HpaI, KpnI, MfeI, NcoI, NheI, NotI, PciI, PstI, PvuII, SacI, SalI, SapI, SbfI, ScaI, SphI and SspI restriction endonucleases. However, as mentioned above, the method is expected to be effective for the engineering of any restriction endonuclease that has significant star activity.

Embodiments of the method utilize a general approach to create mutant restriction endonucleases with reduced star activity. For certain enzymes, it has proven useful to mutate charged residues that are determined to be conserved between two isoschizomers (see for example SapI in Example 25). In general, however, the method involves a first step of identifying all the charged and polar residues in a protein sequence for the endonuclease. For example, charged amino acids and polar residues include the acidic residues Glu and Asp, the basic residues His, Lys and Arg, the amide residues Asn and Gln, the aromatic residues Phe, Tyr and Trp and the nucleophilic residue Cys. Individual residues are targeted and mutated to an Ala and the products of these targeted mutations are screened for the desired properties of increased fidelity. If none of the mutants obtained provide a satisfactory result, the next step is to target mutations to all the hydroxylated amino acids, namely, Ser, Thr and Tyr, the preferred mutation being Ser and Thr to Ala and Tyr to Phe. It is also possible to target mutations to both classes of residues at one time as was done for Examples 16-23. The mutation to Ala may be substituted by mutations to Val, Leu or Ile.

After these analyses, if one or more of the preferred mutants generatedin the above steps still have substandard performance under the selected tests, these mutants can be selected and mutated again to each of the additional possible 18 amino acids. This is called saturation mutagenesis. Saturation mutagenesis provided the preferred high fidelity mutants for EcoRI (Example 2), BamHI in part (Example 1) and PvuII (Example 12). Depending on the results of saturation mutagenesis, the next step would be to introduce additional mutations either targeted or random or both into the restriction endonuclease. In Example 11, SacI-HF includes a random mutation generated fortuitously during inverse PCR. In Example 20, PciI-HF resulted from a random mutation and not from targeted mutations. In Example 26, BspQI-HF contains two mutations that were found to act synergistically in enhancing fidelity.

The use of various methods of targeted mutagenesis such as inverse PCR may involve the introduction of non-target mutations at secondary sites in the protein. These secondary mutations may fortuitously provide the desired properties (see Example 20). It is desirable to examine those mutated enzymes with multiple mutations to establish whether all the mutations are required for the observed effect. In Example 11, Q117H in the double mutant had no effect on activity. In Example 20, the additional spontaneous mutation appears to be solely responsible for the observed improved fidelity, whereas in Example 24, the individual mutations acted synergistically.

In some cases, a mutation may provide an additional advantage other than improved fidelity (see for example BamHI in which either E163A or P173A causes the enzyme to become more thermolabile).

The high fidelity/reduced star activity properties of the mutants provided in the Examples were selected according to their function in a set of standard buffers. Other mutations may be preferable if different buffer compositions were selected. However, the same methodology for finding mutants would apply. Table 4 lists mutations which apply to each restriction endonuclease and provide an overall FI improvement factor in the standard buffer.

The engineering of the high fidelity restriction endonucleases to provide an overall FI improvement factor of at least 2 involves one or more of the following steps:

1. Assessment of the Star Activity of the WT Restriction Endonuclease

In an embodiment of the invention, the extent of star activity of a restriction, endonuclease is tested by means of the following protocol: the endonuclease activity is determined for an appropriate substrate using a high initial concentration of a stock endonuclease and serial dilutions thereof (for example, two-fold or three-fold dilutions). The initial concentration of restriction endonuclease is not important as long as it is sufficient to permit an observation of star activity in at least one concentration such that on dilution, the star activity is no longer detected.

An appropriate substrate contains nucleotide sequences that are cleaved by cognate endonuclease activity and where star activity can be observed. This substrate may be the vector containing the gene for the restriction endonuclease or a second DNA substrate. Examples of substrates used in Table 2 are pBC4, pXba, T7, lambda, and pBR322.

The concentration of stock restriction endonuclease is initially selected so that the star activity can be readily recognized and assayed in WT and mutated restriction endonucleases. Appropriate dilution buffers such as NEB diluent A, B or C is selected for performing the serial dilutions according to guidelines in the 2007-08 NEB catalog. The serially diluted restriction endonuclease is reacted with a predetermined concentration of the appropriate substrate in a total reaction volume that is determined by the size of the reaction vessel. For example, it is convenient to perform multiple reactions in microtiter plates where a 30 μl reaction mixture is an appropriate volume for each well. Hence, the examples generally utilize 0.6 μg of substrate in 30 μl, which is equivalent to 1 μg of substrate in 50 μl. The amount of substrate in the reaction mixture is not critical, but it is preferred that it be constant between reactions. The cleavage reaction occurs at a predetermined temperature (for example 25° C., 30° C., 37° C., 50° C., 55° C. or 65° C.) for a standard-time such as one hour. The cleavage products can be determined by any standard technique, for example, by 0.8% agarose gel electrophoresis to determine the fidelity indices as defined above.

Not all restriction endonucleases have significant star activity as determined from their FI. However, if an endonuclease has a highest FI of no more than about 250 and a lowest FI of less than 100, the restriction endonuclease is classified as having significant star activity. Such endonucleases are selected as a target of enzyme engineering to increase fidelity for a single substrate. In some cases, the restriction endonucleases with both FT over about 500 and FI less than about 100 are also engineered for better cleavage activity.

Table 2 below lists the FI of some engineered restriction endonucleases before engineering. All samples were analyzed on 0.8% agarose gel.

TABLE 2

| Enzyme | Diluent (NEB) *** | Substrate * | Temp ° C. | FI-1 ** | FI-2 ** | FI-3 ** | FI-4 ** |
|---|---|---|---|---|---|---|---|
| AgeI | C | pXba | 37 | 16 (1) | 8 (1/2) | 64 (1/8) | 8 (1/2) |
| AvrII | B | T7 | 37 | 64 (1) | 8 (1) | 32 (1/4) | 32 (1) |
| BamHI | A | λ | 37 | 4 (1/2) | 4 (1) | 32 (1) | 4 (1/2) |
| BsaI | B | pBC4 | 50 | 8 (1/4) | 120 (1) | 16 (1/4) | 32 (1) |
| BsmBI | B | λ | 55 | 1 (1/8) | 8 (1/2) | 120 (1) | 4 (1/4) |
| BspQI | B | λ | 50 | 2 (1/8) | 16 (1) | 32 (1) | 4 (1/2) |
| BstXI | B | λ | 55 | 2 (1/2) | 2 (1/2) | 2 (1/8) | 4 (1) |
| EagI | B | pXba | 37 | 4 (1/4) | 8 (1/2) | 250 (1) | 16 (1) |
| EcoRI | C | λ | 37 | 250 (1/2) | 4 (1) | 250 (1) | 4 (1) |
| EcoRV | A | pXba | 37 | 32 (1/16) | 120 (1/2) | 1000 (1) | 64 (1/4) |
| HindIII | B | λ | 37 | 32 (1/4) | 250 (1) | 4000 (1/4) | 32 (1/2) |
| HpaI | A | λ | 37 | 32 (1/16) | 1 (1/4) | 2 (1/8) | 16 (1) |
| KpnI | A | pXba | 37 | 16 (1) | 16 (1/4) | 8 (1/16) | 4 (1/2) |
| MfeI | A | λ | 37 | 32 (1) | 16 (1/8) | 8 (1/16) | 32 (1) |
| NcoI | A | λ | 37 | 120 (1) | 32 (1) | 120 (1/4) | 32 (1) |
| NheI | C | pXba | 37 | 32 (1) | 120 (1/4) | 120 (1/8) | 32 (1) |
| NotI | C | pXba | 37 | ≥32000 (1/16) | 64 (1) | 500 (1) | 32 (1/4) |
| PciI | A | pXba | 37 | 2000 (1/2) | 16 (1/4) | 120 (1) | 8 (1/8) |
| PstI | C | λ | 37 | 64 (1) | 32 (1) | 120 (1) | 8 (1/2) |
| PvuII | A | pBR322 | 37 | 250 (1) | 16 (1/4) | 8 (1/32) | 1/4 (1) |
| SacI | A | pXba | 37 | 120 (1) | 120 (1/2) | 120 (1/32) | 32 (1/2) |
| SalI | A | λ (H3) | 37 | 8 (1/500) | 1 (1/16) | 32 (1) | 1 (1/120) |
| SapI | C | λ | 37 | 16 (1/4) | 64 (1/2) | 32 (1/4) | 16 (1) |
| SbfI | A | λ | 37 | 32 (1) | 8 (1/4) | 8 (1/16) | 8 (1/2) |
| ScaI | A | λ | 37 | 1/16 (1/32) | 1/8 (1) | 4 (1/2) | 1/64 (1/16) |
| SphI | B | λ | 37 | 64 (1) | 32 (1) | 64 (1/4) | 16 (1/2) |
| SspI | C | λ | 37 | 64 (1) | 16 (1) | 32 (1/4) | 16 (1) |

* Substrate: λ is lambda phage DNA; λ (H3) is HindIII-digested lambda phage DNA; pXba is pUC19 with XbaI-digested fragment of Adeno Virus; pBC4: a shorter version of pXba; T7: T7 DNA

** FI-1 to FI-4: fidelity index of the enzyme in NEBuffer 1, 2, 3 and 4. The number in parenthesis is a value for relative cleavage activity of the mutant restriction endonuclease in a specified buffer in a set of buffers compared with the "best" cleavage activity of the same mutant restriction endonuclease in any of the buffers in the set of buffers.

The compositions of NEB buffers follow:

NEB1: 10 mM Bis Tris Propane-HCl, 10 mM $MgCl_2$, 1 mM dithiothreitol (pH 7.0 at 25° C.);

NEB2: 50 mM NaCl, 10 mM Tris-HCl, 10 mM $MgCl_2$, 1 mM dithiothreitol (pH 7.9 at 25° C.);

NEB3: 100 mM NaCl, 50 mM Tris-HCl, 10 mM $MgCl_2$, 1 mM dithiothreitol (pH 7.9 at 25° C.);

NEB4: 50 mM potassium acetate, 20 mM Tris-acetate, 10 mM magnesium acetate, 1 mM dithiothreitol (pH 7.9 at 25° C.).

*** The compositions of NEB diluents follow. (Using diluents in the dilution instead of water will keep the glycerol concentration in the reaction as a constant.)

Diluent A: 50 mM KCl, 10 mM Tris-HCl, 0.1 mM EDTA, 1 mM dithiothreitol, 200 mg/ml BSA. 50% glycerol (pH 7.4 at 25° C.);

Diluent B: 300 mM NaCl, 10 mM Tris-HCl, 0.1 mM EDTA, 1 mM dithiothreitol, 500 mg/ml BSA, 50% glycerol (pH 7.4 at 25° C.);

Diluent C: 250 mM NaCl, 10 mM Tris-HCl, 0.1 mM EDTA, 1 mM dithiothreitol, 0.15% Triton X-100, 200 mg/ml BSA, 50% glycerol (pH 7.4 at 25° C.).

2. Construction of High Expression Host Cell Strains

It is convenient if a host cell is capable of over-expressing the mutant restriction endonuclease for which reduced star activity is sought. If the restriction enzyme is highly expressed in *E. coli*, the star activity can be readily detected in the crude extract, which simplifies the screening for the high fidelity restriction endonuclease. However, the mutated restriction endonuclease can be expressed in any host cell providing that the host cell is protected in some way from toxicity arising from enzyme cleavage. This might include: the presence of a methylase; production in a compartment of the cell which provides a barrier to access to the genome (such as an inclusion body or the periplasm); in vitro synthesis; production in an emulsion (see U.S. patent application Ser. No. 12/035,872) absence of cleavage sites in the host genome; manufacture of the enzyme in component parts subject to intein mediated ligation (see U.S. Pat. No. 6,849,428), etc.

Over-expression of the mutated restriction endonucleases for purposes of production can be achieved using standard techniques of cloning, for example, use of an *E. coli* host, insertion of the endonuclease into a pUC19-derived expression vector, which is a high copy, and use of a relatively small plasmid that is capable of constant expression of recombinant protein. The vector may preferably contain a suitable promoter such as the lac promoter and a multicopy insertion site placed adjacent to the promoter. Alternatively, a promoter can be selected that requires IPTG induction of gene expression. If the activity in the crude extract is not sufficient, a column purification step for the restriction endonuclease in crude extract may be performed.

3. Mutagenesis of Restriction Endonuclease

DNA encoding each charged or polar group in the restriction endonuclease may be individually targeted and the mutated DNA cloned and prepared for testing. Multiple mutations may be introduced into individual restriction endonuclease genes. Targeted mutagenesis of restriction endonucleases may be achieved by any method known in the art. A convenient method used here is inverse PCR. In this approach, a pair of complementary primers that contains the targeted codon plus a plurality of nucleotides (for Example 18 nt) on both the 5' and 3' side of the codon is synthesized. The selection of suitable primers can be readily achieved by reviewing the gene sequence of the endonuclease of interest around the amino acid residue of interest. Access to gene sequences is provided through REBASE and GenBank. The sequences for the endonucleases described herein in the Examples are provided in FIGS. 31 to 38 and 44. The template for PCR is a plasmid containing the restriction endonuclease gene. The polymerase is preferably a high fidelity polymerase such as Vent® or Deep Vent™ DNA polymerase. By varying the annealing temperature and $Mg^{2+}$ concentration, successful introduction of most mutations can be achieved. The PCR amplification product is then purified and preferably digested by DpnI. In an embodiment of the invention, the digested product was transformed into competent host cells (for example, *E. coli*), which have been pre-modified with a corresponding methylase. Colonies from each mutant were picked and grown under similar conditions to those in which the WT is grown (for example, using similar growth medium, drug selection, and temperature). The resulting restriction endonucleases were screened for reduced star activity.

4. Screening for Mutant Restriction Endonucleases with Reduced Star Activity

Conditions such as buffer composition, temperature and diluent should be defined for determining star activity in a mutant restriction endonuclease. Tables 2 and 3 show the FI of recombinant endonucleases before and after mutation in four different buffers using three different diluents at 37° C. Accordingly, it is possible to determine which mutants have an overall desirable improved fidelity index factor of at least 2, more than 10, at least 50 or more than 500 and to select enzymes as preferred high fidelity mutants.

In an embodiment of the invention, the mutant restriction endonucleases were screened for activity in normal buffer conditions (no more than 5% glycerol) first. For those mutants with at least about 10% of activity of WT restriction endonuclease, activity was also determined in star activity promotion conditions that promoted star activity, for example, high glycerol concentration and optionally high pH. Preferably, the mutant with the least star activity but with acceptable cognate activity in normal buffers is selected. Plasmid can then be extracted and sequenced for the confirmation of the mutant. In some cases, the star activity is not easily measured, even with high glycerol and high pH conditions. Instead, the activity in different buffers is measured and compared, and the one with the highest cleavage activity ratio in NEB4 compared with NEB3 can be tested further for star activity improvement.

5. Saturation Mutagenesis on One Single Residue

As described in the previous section, the first step is to mutate a target amino acid in the restriction endonuclease to Ala. If the results are not satisfactory, saturation mutagenesis is performed. This is preferably performed by one of two methods. One method is to change the intended codon into NNN. After mutagenesis, multiple colonies are assayed under normal conditions and under conditions that promote star activity. Alternatively, a different codon can be selected for mutagenesis of each of the targeted amino acids for example: Ala: GCT; Cys: TGC; Asp: GAC; Glu: GAA; His: CAC; Ile: ATC; Lys: AAA; Leu: CTG; Met: ATG; Asn: AAC; Pro: CCG; Gln: CAG; Arg: CGT; Ser: TCC; Thr: ACC; Val: GTT; Trp: TGG and Tyr: TAC 6. Combination More than one mutation can be introduced into the restriction endonuclease gene if a single mutation does not sufficiently reduce the star activity. Mutation combination and saturation mutagenesis can be performed in any order.

7. Mutant Purification and Assessment of the Improvement

The high fidelity mutants may be purified in a variety of ways including use of different chromatography columns. For normal quality assessment, one FPLC heparin column is enough to eliminate the DNA and non-specific nucleases from the preparation. Multiple columns including ion exchange, hydrophobic, size exclusion and affinity columns can be used for further purification.

Purified high fidelity restriction endonucleases are measured for FI in four NEB buffers and compared with the FIs of the WT restriction endonuclease. The ratio of FI for the high fidelity restriction endonuclease in its optimal buffer to that of WT is the overall improvement factor.

TABLE 3

FI* for exemplified restriction endonucleases

| Enzyme | Diluent (NEB) | Substrate * | Temp ° C. | FI-1 ** | FI-2 ** | FI-3 ** | FI-4 ** |
|---|---|---|---|---|---|---|---|
| AgeI-HF | C | pXba | 37 | ≥500 (1) | ≥250 (1/2) | ≥16 (1/16) | ≥250 (1) |
| AvrII-HF | B | T7 | 37 | 500 (1) | ≥500 (1/2) | ≥16 (1/64) | ≥1000 (1) |
| BamHI-HF | A | λ | 37 | ≥4000 (1) | ≥4000 (1) | ≥250 (1/16) | ≥4000 (1) |
| BsaI | B | pBC4 | 50 | ≥4000 (1/2) | ≥8000 (1) | 120 (1) | ≥8000 (1) |
| BsmBI | B | λ | 55 | 2 (1) | ≥500 (1) | ≥64 (1/8) | ≥500 (1) |
| BspQI-HF | A | pUC19 | 50 | ≥1000 (1/4) | ≥1000 (1/4) | ≥64 (1/64) | ≥4000 (1) |
| BstXI-HF | A | λ | 55 | ≥120 (1/2) | ≥250 (1) | ≥16 (1/16) | ≥250 (1) |
| EagI-HF | C | pXba | 37 | 250 (1/2) | 250 (1) | 250 (1/2) | 500 (1) |
| EcoRI-HF | C | λ | 37 | 2000 (1/8) | 4000 (1/4) | 250 (1/250) | 16000 (1) |
| EcoRV-HF | A | pXba | 37 | ≥16000 (1/4) | ≥64000 (1) | ≥32000 (1/2) | ≥64000 (1) |
| HindIII-HF | B | λ | 37 | ≥16000 (1/4) | ≥64000 (1) | ≥16000 (1/4) | ≥32000 (1/2) |
| HpaI-HF | A | λ | 37 | ≥32 (1/32) | ≥2000 (1) | 2 (1/8) | ≥2000 (1/2) |
| KpnI-HF | A | pXba | 37 | ≥4000 (1) | ≥1000 (1/4) | ≥64 (1/64) | ≥4000 (1) |
| MfeI-HF | A | λ | 37 | ≥1000 (1) | ≥250 (1/4) | ≥16 (1/64) | ≥500 (1/2) |
| NcoI-HF | A | λ | 37 | ≥4000 (1/4) | ≥4000 (1/4) | ≥1000 (1/16) | ≥64000 (1) |
| NheI-HF | C | pXba | 37 | ≥128000 (1) | ≥4000 (1/32) | ≥32 (1/2000) | ≥32000 (1/2) |
| NotI-HF | C | pXba | 37 | ≥8000 (1/16) | ≥128000 (1) | ≥4000 (1/64) | ≥64000 (1/2) |
| PciI-HF | A | pXba | 37 | NC | ≥2000 (1) | ≥2000 (1) | ≥1000 (1) |
| PstI-HF | C | λ | 37 | 1000 (1/8) | 4000 (1/2) | 4000 (1/4) | 4000 (1) |
| PvuII-HF | A | pBR322 | 37 | ≥250 (1/120) | ≥2000 (1/16) | ≥250 (1/120) | 500 (1) |
| SacI-HF | A | pXba | 37 | ≥32000 (1) | ≥16000 (1/2) | ≥500 (1/64) | ≥32000 (1) |
| SalI-HF | A | λ (H3) | 37 | ≥8000 (1/8) | ≥64000 (1) | ≥4000 (1/16) | ≥32000 (1/2) |
| SbfI-HF | C | λ | 37 | 1000 (1) | 120 (1/2) | 8 (1/32) | 250 (1) |
| ScaI-HF | A | λ | 37 | 4000 (1/8) | 1000 (1) | 2000 (1/32) | 1000 (1) |
| SphI-HF | B | λ | 37 | 4000 (1/8) | 2000 (1/16) | 250 (1/250) | 8000 (1) |
| SspI-HF | C | λ | 37 | ≥4000 (1/2) | 120 (1/2) | ≥32 (1/128) | 500 (1) |

* The FI is a ratio of the highest concentration that does not show star activity to the lowest concentration that completes digestion of the substrate.

** The number in parenthesis is a value for relative cleavage activity of the mutant restriction endonuclease in a specified buffer in a set of buffers compared with the greatest cleavage activity of the same mutant restriction endonuclease in any of the buffers in the set of buffers.

TABLE 4

| Mutations providing restriction endonucleases with high fidelity | |
|---|---|
| Restriction Endonuclease | Examples of mutants with overall improved FI factor ≥2 |
| AgeI | R139A; S201A* |
| AvrII | Y104F; M29A; E96A; K106A; S127A; F142A |
| BamHI | E163A/E167T; K30A; E86A; E86P; K87A; K87E; K87V; K87N; P144A; Y165F; E167A; E167R; E167K; E167L; E167I K30A/E86A; E86A/K106A; K30A/E86A/K106A; K30A/K87A; E86P/K87E; E86A/Y165F; K30A/E167A; E163S/E170T/P173A; E1663S/E170T/P173A; E86P/K87T/K88N/E163S/E170T/P173A; E86P/K87R/K88G/E163S/E170T/P173A; E86P/K87P/K88R/ E163S/E170T/P173A/E211K; E86P/K87T/K88R/E163S/E170T/P173A/N158S; E86P/K87S/K88P/E163S/E170T/P173A; E86P/K87G/K88S/E163S/E170T/P173A; E86P/K87R/K88Q/E163S/E170T/P173A; E86P/K87W/K88V; E86P/P173A |
| BsaI | Y231F |
| BsmBI | N185Y/R232A; H230A; D231A; R232A; |
| BspQI | K279P/R388F; K279A; K279F; K279P; K279Y; K279E; K279D R388A; R388F; R388Y; R388L; K279P/R388F; K279A/R388A; D244A |
| BstXI | N65A; Y57F; E75A; N76A; K199A; |
| EagI | H43A |
| EcoRI | K62A; K62S; K62L; R9A; K15A; R123A; K130A; R131A; R183A; S2Y; D135A; R187A; K62E |
| EcoRV | D19A; E27A; D19A/E27A |
| HindIII | S188P/E190A; K198A |
| HpaI | Y29F; E56A |
| KpnI | D148E; D16N/R119A/D148E; D2A/D16N/D148E; D16N/E134A/D148E; D16N/E132A/D148E |
| MfeI | Y173F; Q13A/F35Y |
| NcoI | D56A; H143A; E166A; R212A; D268A; A2T/R31A |
| NheI | E77A |
| NotI | K176A; R177A; R253A; K150A |
| PciI | E78A/S133A |
| PstI | E204G; K228A; K228A/A289V; D91A |
| PvuII | T46A; T46H; T46K; T46Y; T46G |
| SacI | Q117H/R154A/L284P; Q117H/R200A |
| SalI | R82A; K93A; K101A; R107A |
| SapI | K273P; R380A; K273P/R380A |
| SbfI | K251A |
| ScaI | R18A; R112A; E119A; H193A; S201F; H193A/S201F |
| SphI | D91A; D139A; D164A; K100A |
| SspI | H65A; K74A; E78A; E85A; E89A; K109A; E118A; R177A; K197A; Y98F |

The mutations for each enzyme are separated by a semicolon.

All references cited above and below, as well as U.S. provisional application Ser. No. 60/959,203, are incorporated by reference.

EXAMPLES

Where amino acids are referred to by a single letter code, this is intended to be standard nomenclature. The key to the code is provided for example in the NEB catalog 2007/2008 on page 280.

Plasmids used for cloning and as substrates have sequences as follows:

µLaczz2 (SEQ ID NO:102), pSyx20-lacIq (SEQ ID NO:105), pBC4 (SEQ ID NO:103), pXba (SEQ ID. NO:104) and pAGR3

(SEQ ID NO:106). pACYC is described in GenBank XO 6403, T7 in GenBank NC001604, pUC18 in GenBank L09136, and pRRS in Skoglund et al. *Gene,* 88:1-5 (1990. pSX33 was constructed by inserting lac gene into µLG339 at EcoRI site. µLG339 is described in Stoker, et al. *Gene* 19, 335-341 (1982).

All buffers identified as NEB buffers used herein are obtainable from New England Biolabs, Inc. (NEB), Ipswich, MA.

Example 1: Engineering of High Fidelity BamHI

1. Extraction of Plasmids Containing BamHI Methylase and BamHI endonuclease

Competent *E. coli* host cells were transformed with pUC18-BamHIR and pACYC184-BamHIM and BamHIR was extracted by a standard Qiagen Mini-prep method using standard miniprep techniques (Qiagen, Valencia, CA).

2. Selection of Mutagenesis Target

BamHI and related restriction endonuclease OkrAI were cloned and sequenced. OkrAI was found to have significant star activity if the reaction occurred at 37° C. in NEB buffers (1, 2 and 4). The present analysis tested the assumption that the amino acid residue(s) responsible for the star activity were similar between BamHI and OkrAI endonuclease.

The complete protein sequence of BamHI (SEQ ID NO:19) is:

1 MEVEKEFITD EAKELLSKDK LIQQAYNEVK TSICSPIWPA TSKTFTINNT

51 EKNCNGVVPI KELCYTLLED TYNWYREKPL DILKLEKKKG GPIDVYKEFI

101 ENSELKRVGM EFETGNISSA HRSMNKLLLG LKHGEIDLAI ILMPIKQLAY

151 YLTDRVTNFE ELEPYFELTE GQPFIFIGFN AEAYNSNVPL IPKGSDGMSK

201 RSIKKWKDKV ENK

The complete protein sequence of OkrAI (SEQ ID NO:20) is:

1 MKIKRIEVLI NNGSVPGIPM ILNEIQDAIK TVSWPEGNNS FVINPVRKGN

51 GVKPIKNSCM RHLHQKGWAL EHPVRIKAEM RPGPLDAVKM IGGKAFALEW

101 ETGNISSSHR AINKMVMGML ERVIIGGVLI LPSRDMYNYL TDRVGNFREL

151 EPYFSVWRQF NLKDAYLAIV EIEHDSVDAQ VSLIPKGTDG RAIR

A "Bestfit" similarity analysis done by GCG for the protein sequence of BamHI and OkrAI endonuclease showed the following result where the upper protein sequence is BamHI and the bottom protein sequence is OkrAI:

-continued

```
(SEQ ID NO: 29)
5'AACGGTGTAGTACCAATTGCAGAACTATGTTACACCTTA3'

(SEQ ID NO: 30)
5'TAAGGTGTAACATAGTTCTGCAATTGGTACTACACCGTT3'

K84A
```

```
bamhir.pep x okrair.pep
      .    .    .    .    .
 22 IQQAYNEVKTSICSPIWPATSKTFTINNTEKNCNGVVPIKELCYTLLEDT 71
  |  ||:. .| . || ..| ||  |  ||| ||| |  |
 18 IPMILNEIQDAIKTVSWPEGNNSFVINPVRKG.NGVKPIKNSCMRHLHQK 66

      .    .    .    .    .
 72 YNWYREKPLDILKLEKKKGGPIDVYKEFIENSELKRVGMEFETGNISSAH 121
   |  | |. | | | : ||:|  |  |   |  :|.||||||||.|
 67 .GWALEHPVRI.KAEMRP.GPLDAVK.MIGG...KAFALEWETGNISSSH 109

     .    .    .    .    .
122 RSMNKLLLGLKHGEIDLAIILMPIKQLAYYLTDRVTNFEELEPYFEL... 168
  |..||:.:|:  | ::::| : : |||||| || |||||| .
110 RAINKMVMGMLERVIIGGVLILPSRDMYNYLTDRVGNFRELEPYFSVWRQ 159

       .    .    .
169 ..TEGQPFIFIGFNAEAYNSNVPLIPKGSDGMSKR 201 (SEQ ID NO: 21)
         .   :  :.  ..| |||||.|| . |
160 FNLKDAYLAIVEIEHDSVDAQVSLIPKGTDGRAIR 194 (SEQ ID NO: 22)
```

The similar charged residues (D, E, H, K, R) in BamHI were found to be E28, K30, K52, K61, E77, K84, E86, K88, D94, K97, K106, E111, E113, H121, R122, K126, K146, D154, R155, E161, E163, E170, E182, K193, D196 and R201. These residues are underlined in the above comparison. Known mutants E77K, D94N, E111K and E113K were previously reported to be inactive (Xu, Shuang-yong et al. *J. Bacteriol.* 266: 4425-4429 (1991)) so they were excluded. The initial mutagenesis selection targeted 22 shared charged amino acid residue for mutation to Alanine: E28A, K30A, K52A, K61A, K84A, E86A, K88A, K97A, K106A, H121A, R122A, K126A, K146A, D154A, R155A, E161A, E163A, E170A, E182A, K193A, D196A and R201A.

3. Mutagenesis of BamHI

The point mutagenesis of the selected mutations was done by inverse PCR. The corresponding codons were all changed to GCA (alanine). The following primers were used for mutagenesis:

```
E28A
(SEQ ID NO: 23)
5'ATTCAACAAGCATACAATGCAGTTAAAACATCTATTGT3'

(SEQ ID NO: 24)
5'ACAAATAGATGTTTTAACTGCATTGTATGCTTGTTGAAT3'

K30A
(SEQ ID NO: 25)
5'CAAGCATACAATGAAGTTGCAACATCTATTTGTTCACCT3'

(SEQ ID NO: 26)
5'AGGTGAACAAATAGATGTTGCAACTTCATTGTATGCTTG3'

K52A
(SEQ ID NO: 27)
5'ACGATTAACAACACCGAAGCAAATTGTAACGGTGTAGTA3'

(SEQ ID NO: 28)
5'TACTACACCGTTACAATTTGCTTCGGTGTTGTTAATCGT3'

K61A
```

-continued

```
(SEQ ID NO: 31)
5'AACCCCCTTGATATACTTGCACTTGAAAAGAAAAAAGGT3'

(SEQ ID NO: 32)
5'ACCTTTTTTCTTTTCAAGTGCAAGTATATCAAGGGGTTT3'

E86A
(SEQ ID NO: 33)
5'GATATACTTAAACTTGCAAAGAAAAAAGGTGGTCCG3'

(SEQ ID NO: 34)
5'CGGACCACCTTTTTTCTTTGCAAGTTTAAGTATATCAAG3'

K88A
(SEQ ID NO: 35)
5'ATACTTAAACTTGAAAAGGCAAAAGGTGGTCCGATTGAT3'

(SEQ ID NO: 36)
5'ATCAATCGGACCACCTTTTGCCTTTTTCAAGTTTAAGTAT3'

K97A
(SEQ ID NO: 37)
5'GGTCCGATTGATGTTTATGCAGAGTTCATAGAAAACAGT3'

(SEQ ID NO: 38)
5'ACTGTTTTCTATGAACTCTGCATAAACATCAATCGGACC3'

K106A
(SEQ ID NO: 39)
5'ATAGAAAAACAGTGAACTTGCACGTGTAGGTATGGAA3'

(SEQ ID NO: 40)
5'AAATTCCATACCTACACGTGCAAGTTCACTGTTTTCTAT3'

H121A
(SEQ ID NO: 41)
5'GGAAATATTAGTTCTGCCGCACGTTCAATGAACAAACTT3'

(SEQ ID NO: 42)
5'AAGTTTGTTCATTGAAACGTGCGGCAGAACTAATATTCC3'

R122A
(SEQ ID NO: 43)
5'AATATTAGTTCTGCCCACGCATCAATGAACAAACTTCTA3'
```

-continued (SEQ ID NO: 44)
5'TAGAAGTTTGTTCATTGATGCGTGGGCAGAACTAATATT3'

K126A (SEQ ID NO: 45)
5'GCCCACCGTTCAATGAACGCACTTCTATTAGGATTAAAACAT3'

(SEQ ID NO: 46)
5'ATGTTTTAATCCTAATAGAAGTGCGGTCATTGAACGGTGGGC3'

K146A (SEQ ID NO: 47)
5'ATTATCCTTATGCCTATTGCACAATTGGCCTATTATCTT3'

(SEQ ID NO: 48)
5'AAGATAATAGGCCAATTGTGCAATAGGCATAAGGATAAT3'

D154A (SEQ ID NO: 49)
5'TTGGCCTATTATCTTACAGCACGTGTTACCAATTTCGAG3'

(SEQ ID NO: 50)
5'CTCGAAATTGGTAACACGTGCTGTAAGATAATAGGCCAA3'

R155A (SEQ ID NO: 51)
5'GCCTATTATCTTACAGATGCAGTTACCAATTTCGAGGAA3'

(SEQ ID NO: 52)
5'TTCCTCGAAATTGGTAACTGCATCTGTAAGATAATAGGC3'

E161A (SEQ ID NO: 53)
5'CGTGTTACCAATTTCGAGGCATTAGAACCTTATTTTGAA3'

(SEQ ID NO: 54)
5'TTCAAAATAAGGTTCTAATGCCTCGAAATTGGTAACACG3'

E163A (SEQ ID NO: 55)
5'ACCAATTTCGAGGAATTAGCACCTTATTTTGAACTTACT3'

(SEQ ID NO: 56)
5'AGTAAGTTCAAAATAAGGTGCTAATTCCTCGAAATTGGT3'

E170A (SEQ ID NO: 57)
5'CCTTATTTTGAACTTACTGCAGGACAACCATTTATTTTTATT3'

(SEQ ID NO: 58)
5'AATAAAAATAAATGGTTGTGCTGCAGTAAGTTCAAAATAAGG3'

E182A (SEQ ID NO: 59)
5'TTTATTTTTATTGGATTTAATGCTGCAGCTTATAATTCTAATGTC3'

(SEQ ID NO: 60)
5'GACATTAGAATTATAAGCTGCAGCATTAAATCCAATAAAAATAAA3'

K193A (SEQ ID NO: 61)
5'AATGTCCCTTTAATTCCCGCAGGTTCTGACGGTATGTCA3'

(SEQ ID NO: 62)
5'TGACATACCGTCAGAACCTGCGGGAATTAAAGGGACATT3'

D196A (SEQ ID NO: 63)
5'TTAATTCCCAAAGGTTCTGCAGGTATGTCAAAACGCTCA3'

(SEQ ID NO: 64)
5'TGAGCGTTTTGACATACCTGCAGAACCTTTGGGAATTAA3'

R201A (SEQ ID NO: 65)
5'TCTGACGGTATGTCAAAAGCATCAATTAAGAAATGGAAA3'

(SEQ ID NO: 66)
5'TTTCCATTTCTTAATTGATGCTTTTGACATACCGTCAGA3'

The PCR reaction in a reaction volume of 100 μl, contained 2 μl of each PCR primer, 1 μl pUC18-bamhiR, 400 μM dNTP, 4 units of Deep Vent™ DNA polymerase, and 10 μl 10× Thermopol buffer containing 0, 2, or 6 μl $MgSO_4$ with additional water.

The PCR reaction conditions were 94° C. for 5 min, followed by 25 cycles of 94° C. 30 sec, 55° C. 30 sec, 72° C. 4 min and a final extension time at 72° C. for 7 mins. The PCR product was, purified on a standard Qiagen spin column (Qiagen, Valencia, CA). Six to sixteen μl of PCR product was digested by 20 units of DpnI for 1 hour. The digested product was transformed into *E. coli* (pACYC-bamHIM).

After six PCR reactions, 14 out of the engineered 22 mutations were obtained: E28A, K30A, K61A, E86A, K97A, H121A, K126A, K146A, E161A, E163A, E170A, E182A, and R201A. Mutant proteins were extracted from cell lysates in an overnight culture and the activity was compared to WT BamHI. Normal enzyme activity was assayed in NEB2 buffer with or without 5% glycerol, while star activity was determined in NEB2 with 39.2% glycerol, though initially, lower percentage glycerol could be used. The substrate used for different reactions was pBR322, pUC19 or lambda DNA. The cleavage reaction was performed at 37° C. for 30 min or 1 hour. It was found that mutants K97A, H121A, K126A, E161A, E182A, R201A were inactive (less than 1% of the WT BamHI activity) while E28A, K146A, E163A, E170A mutants had a similar level of activity including star activity to that of WT enzyme. Three mutants K30A, E86A and K126A were found to have significantly reduced star activity compared with WT BamHI. It was also found that K30A and E86A had similar overall cleavage activity to the WT enzyme while showing significant reduction in star activity. In contrast, K126A had only 25% of the overall cleavage activity of the WT enzyme and less significant improvement on star activity than observed for K30A an E86A.

A recheck on the pUC18-bamHIR plasmid revealed that the normal high copy plasmid had mutated to a low copy plasmid. A pair of primers was designed to transfer the bamHIR gene into the high copy plasmid:

(SEQ ID NO: 67)
5'GGTGGTGCATGCGGAGGTAAATAAATGGAAGTAGAAAAAGAGTTTATT
ACTGAT3'

(SEQ ID NO: 68)
5'GGTGGTGGTACCCTATTTGTTTTCAACTTTATCTTTCCATTTCTTAAT
TGA3'

The template was pUC18-bamhIR WT, with mutations at K30A, E86A or K126A. The PCR composition contained: 5 μl template, 2 μl primers each, 400 μM dNTP, 10 μl 10×Thermopol buffer, 4 units 2 μl Deep Vent™ polymerase, 72 μl $H_2O$ with 0, 2, 6 μl $MgSO_4$. The PCR conditions were 94° C. for 5 min, followed by 25 cycles of 94° C. at 30 sec, 55° C. at sec and 72° C. at 40 sec and a final extension period of 7 min. The PCR product was digested with SphI and KpnI and was ligated to pUC19 with the same pair of enzyme digestion. The ligated product was transformed into competent *E. coli*-containing pACYC-bamHIM. 26 colonies that contained the pUC19 version of BamHIR K30A and 12 of those that contained E86A were identified and grown. The activity of BamHI from these cultures was checked. All of them were active. Plasmids from five colonies of each mutation were extracted and the BamHIR plasmids from three of each mutation were sequenced. The identity of plasmids pUC19-BamHI(K30A) and pUC19-BamHI (E86A) were confirmed.

Those mutations that were unsuccessful in pUC18-BamHIR were repeated using the pUC19-BamHI(K30A) vector. The PCR mixture contained: 1 μl template and an amplification mixture containing 2 μl primers each, 400 μM dNTP, 10 μl 10×Thermopol buffer, 4 units 2 μl Deep Vent™ polymerase, 76 μl $H_2O$ with 0, 2, 6 μl 100 μM $MgSO_4$. The PCR condition was 94° C. for 5 min, followed by 25 cycles of 94° C. for 30 sec, 55° C. for 30 sec and 72° C. for 3 min and 30 sec and a final extension period of 7 min. The PCR products were digested by DpnI and transformed to competent *E. coli* transformed with pACYC-BamHIM. The enzyme activities were checked on pUC19 substrate. The reaction composition was: 3 μl cell extract, 3 μl NEB2, 3 μl 50% glycerol, 0.5 μl 0.5 μg pUC19, 20.5 μl $H_2O$. Reaction was at 37° C. for 1 hour. K30A/R122A, K30A/R155A and K30A/K193A were inactive. K30A/K52A and K30A/K88A were about 1/10 of the K30A activity. The normal activity of K30A/K106A, K30A/D154A and K30A/D196A were similar to that of K30A BamHI. The comparison of star activity of these three mutants with K30A at the high concentration glycerol (39.2%) showed that K30A/D196A had similar star activity as K30A, K30A/D154A even has more star activity than K30A, and K30A/K106A had less star activity than K30A. Attempts to isolate the K106A mutation of BamHI in the pUC19 vector failed because of cytotoxicity.

The mutation on the K30, E86 and K106 sites was combined using the inverse PCR: K30A/E86A, E86A/K106A, K30A/K106A and K30A/E86A/K106A. K30A/E86A appeared to be the preferred mutant. After purification, the FI was found to be improved for the BamHI mutant by 25% in all NEB buffers.

Further mutagenesis was done on the site of K30 and E86 randomly:

```
For K30:
                                        (SEQ ID NO: 69)
5'CAAGCATACAATGAAGTTNNNACATCTATTTGTTCACCT3'

                                        (SEQ ID NO: 70)
5'AGGTGAACAAATAGATGTNNNAACTTCATTGTATGCTTG3'

For E86:
                                        (SEQ ID NO: 71)
5'GATATACTTAAACTTNNNAAGAAAAAAAGGTGGTCCG3'

                                        (SEQ ID NO: 72)
5'CGGACCACCTTTTTTCTTNNNAAGTTTAAGTATATCAAG3'
```

The PCR composition was: 1 μl template (pUC19-BamHIR(K30A) or pUC19-BamHIR(E86A)) and the amplification mixture as described above was used. The PCR was performed at 94° C. 5 min, followed by 25 cycles of 94° C. 30 sec, 55° C. 30 sec and 72° C. 3 min and 30 sec and a final extension period of 7 min. The PCR products were digested by DpnI and transformed into *E. coli* (pACYC-BamHIM).

Total of 155 colonies were picked on K30 random mutations, and 158 colonies on E86 site. The colonies were grown overnight and made into cell extract. 0.5 μg pUC19 was digested with 1 μl cell extract in NEB 2 buffer with 42.5% glycerol, 37° C. 1 hour. The cell extract with apparent less star activity was re-assayed under 1, 4, 16 fold dilution on 0.5 g pUC19 in NEB 2 buffer with 39.2% glycerol, 37° C. 30 min. For those mutants observed to have reduced star activity, the corresponding plasmids were extracted and sequenced to confirm the mutation. A total of 3 clones (#12, #66 and #82) contained the K30 mutation, and a total of 33 clones (#5, #15, #16, #19, #29, #47, #51, #55, #56, #58, #61, #69, #71, #73, #76, #82, #86, #88, #93, #94, #97, #98, #100, #104, #107, #113, #117, #118, #129, #132, #136, #139 and #151) were sequenced. After sequencing, #12 and #66 were found to contain the K30G mutation, and #82 the K30N mutation. Surprisingly, all 33 mutations are E86P mutation, just in different codons (CCA, CCT, CCC, CCG). Among these codons, the CCG occurred at the highest frequency in *E. coli* (clones #98, #136 and #139).

The cell extracts corresponding to K30G, K30N and K30A were serially diluted as 1, 2, 4, 8, 16 and 32 folds, while E86P and E86A were serially diluted 1, 2, 4, 8, 16, 32, 64, 128 and 256 fold. The serially diluted extracts were reacted with 0.5 μg pUC19 in NEB2 with 39.2% glycerol, 37° C. 30 min. Under extreme conditions, E86P appeared to be much superior to other mutants. At up to 32 times fold digestion, there was no significant star activity band. The difference between E86P and the K30 mutants (K30G, K30N and K30A) was so large that it was not additionally necessary to combine any of these mutations in the E86P mutant.

The activity of BamHI(E86P) was determined for 1 μg lambda DNA, substrate (also used for WT BamHI activity determination). The assay was performed in NEB1 buffer at 37° C. for 1 hour.

4. Detailed Comparison of BamHI(E86P) and WT BamHI

A. The Activity of BamHI(E86P) in Different NEB Buffers

The activity of purified BamHI(E86P) was determined in NEB1, NEB2, NEB3, NEB4 and NEB BamHI buffer, using lambda DNA substrate at 37° C. for 1 hour. BamHI(E86P) was most active in NEB1 buffer and NEB2, while having 50%, 50% and 25% activity levels in NEB3, NEB4, and BamHI buffer.

B. a Comparison of Cleavage Activity of BamHI(E86P) and WT BamHI on pUC19

There is one GGATCC site (BamHI site) and 6 AGATCC sites (BamHI star activity site) in pUC19 so that pUC19 was selected as a preferred substrate for comparison of the BamHI(E86P) and WT BamHI.

0.5 mg pUC19 was digested by WT BamHI and BamHI (E86P) in a serial dilution of 1, 3, 9, 27, 81, 243, 729, 2181, 6561, and 19683 folds with NEB dilution buffer A, in different buffers. WT BamHI showed star activity in every NEB normal buffer, while BamHI(E86P) showed no star activity bands at all (FIGS. 2-5). This demonstrated that BamHI(E86P) had greatly reduced star activity while retaining the cognate cleavage activity.

C. A Comparison of Cleavage Activity of BamHI(E86P) and WT BamHI on Lambda DNA Substrate To calculate the Fidelity Index, the restriction enzyme was diluted with dilution buffer, and the glycerol concentration was kept constantly at 5%. In the standard reaction condition used here, lambda DNA substrate concentration was 1 μg and the total reaction volume was 50 μl. In order to keep the enzyme volume at 10%, the enzyme was added in a volume of 5 μl. This is equivalent to 0.6 μg of substrate digested by 3 μl of restriction enzyme in a total volume of 30 μl. 0.6 mg lambda DNA was digested by 3 μl WT BamHI and BamHI (E86P) in a 1:2 serial dilution from 1 to 32768, in NEB1, NEB2, NEB3, NEB4 and NEB BamHI buffer at 37° C. for 1 hour.

TABLE 5

Fidelity Indices for WT and mutant BamHI in various buffers

| | BamHI(E86P) | | WT BamHI | | |
|---|---|---|---|---|---|
| Buffer | Activity | Fidelity Index | Activity | Fidelity Index | Improvement Factor |
| NEB1 | 100% | ≥4000 | 50% | 4 | ≥1000 |
| NEB2 | 100% | ≥4000 | 100% | 16 | ≥250 |
| NEB3 | 50% | ≥4000 | 100% | 32 | ≥125 |
| NEB4 | 50% | ≥4000 | 50% | 4 | ≥1000 |
| BamHI buffer | 25% | ≥2000 | 50% | 32 | ≥125 |

5. Further Improvement of BamHI for High Fidelity Mutants

At one hour level, the BamHI(E86P) appeared to be a good high fidelity BamHI mutant. However, when the reaction time was extended (e.g. overnight, or 14 hours), star activity bands appeared even though the star activity of E86P was not detected at one hour. (FIG. 3) The search for improved high fidelity BamHI was continued.

6. Mutations of Other Charged and Polar Residues

The other charged residues (Arg, Lys, His, Asp, Glu) were mutated to Ala at the positions of 2, 4, 5, 6, 10, 11, 13, 14, 18, 19, 20, 43, 51, 62, 69, 70, 76, 77, 78, 81, 87, 89, 94, 98, 101, 104, 107, 111, 113, 132, 133, 135, 137, 160, 167, 200, 204, 205, 207, 208, 209, 211, 213 in SEQ ID NO:19. The mutations were done on the template of pUC19-BamHI (K30A).

Other polar residues (Ser, Thr and Tyr) were mutated to Ala while Tyr was mutated to Phe at the positions of 9, 17, 26, 32, 36, 41, 42, 44, 46, 50, 65, 66, 71, 72, 75, 96, 103, 114, 118, 119, 123, 150, 151, 153, 157, 165, 169, 184, 186, 195, 199, 202 in SEQ ID NO:19.

By using similar mutation and screen methods, the following mutations were discovered to have reduced star activity, K30A/K87A, E86P/K87E, E86A/Y165F, and K30A/E167A. E86P/K87E was identified as a mutant with improved properties in the presence of additional DMSO. However, the activity of this mutant in normal reaction buffer was much lower than that of WT BamHI.

The following combination of mutations was made: E86P/Y165F, E86P/E167A, E86P/Y165F/E167A, K30A/Y165F/E167A, K30G/Y165F/E167A, K30A/Y165F/E167A, E86A/Y165F/E167A. All had low activity.

Up to this point, it was found that E167A and Y165F had a strong effect, K87A had medium effect, and K30A and E86A had weak effect on the BamHI star activity. E86P is a special mutation that reduces star activity at 1 hour level but not overnight.

7. Mutation of E167 and Y165 to all Other Residues

E167 was mutated to all other residues in pUC19-BamHI by changing the codon to GCA for Ala, TGC for Cys, GAC for Asp, TTC for Phe, GGT for Gly, CAC for His, ATC for Ile, AAA for Lys, CTG for Leu, ATG for Met, AAC for Asn, CCG for Pro, CAG for Gln, CGT for Arg, TCC for Ser, ACC for Thr, GTT for Val, TGG for Trp, and TAC for Tyr.

After comparison of all the mutants, the E167T mutation was preferred, while E167R, E167K, E167L and E1671 mutations showed improvement in reduced star activity compared with E167A.

Y165 was also mutated to all other amino acid residues by changing the corresponding codon to GCT for Ala, TGC for Cys, GAC for Asp, GAA for Glu, GGT for Gly, CAC for His, ATC for Ile, AAA for Lys, CTG for Leu, ATG for Met, AAC for Asn, CCG for Pro, CAG for Gln, CGT for Arg, TCC for Ser, ACC for Thr, GTT for Val, TGG for Trp.

After comparison of all the mutants, the presence of Y165F resulted in significant cleavage activity while other mutations of listed immediately above showed low activity or no cleavage activity.

8. Further Mutations on BamHI(E167T)

All charged and polar residues were mutated to Ala, on the template of puc19-BamHI(E167T), as the same procedure as above.

E163A/E167T as the preferred mutation was identified as BamHI-HF.

9. Comparison of BamHI-HF to WT BamHI

Introduction of a mutation at E163 resulted in reduced thermostability of the BamHI mutant, as did mutation P173A when added to other mutations responsible for reducing star activity.

BamHI-HF, unlike the BamHI(E86P), had no significant star activity in an overnight reaction in NEB1-4 buffers. FIG. 4 shows the results in NEB1 and NEB2. Hence BamHI (E163A/E167T) was selected as the preferred high fidelity BamHI.

The fidelity indices of BamHI-HF were measured in all of the four NEB buffers on lambda DNA substrate, with diluent A, at 37° C. and compared with the WT enzyme.

TABLE 6

Comparison of BamHI-HF and WT BamHI

| | BamHI-HF | | WT BamHI | | |
|---|---|---|---|---|---|
| Buffer | Activity | Fidelity Index | Activity | Fidelity Index | Improvement Factor |
| NEB1 | 100% | ≥8000 | 50% | 4 | ≥1000 |
| NEB2 | 50% | ≥4000 | 100% | 16 | ≥250 |
| NEB3 | 12.5% | ≥250 | 100% | 32 | ≥8 |
| NEB4 | 50% | ≥4000 | 50% | 4 | ≥1000 |

BamHI-HF has a highest activity in NEB1, the fidelity index is 8000, WT BamHI has the highest activity in NEB2 and NEB3, and the highest FI is 32. The overall FI improvement factor, which is the ratio of the FI in the best buffer for each of the mutant and the WT enzyme, is ≥8000/32=250 fold.

10. Additional Mutations of BamHI

E163A/E167T/P173A was predicted to have a preferred reduction in star activity and additionally to be thermolabile.

(E86P/K87S/K88P/E163S/E170T/P173A) was tested. This mutant displayed 10-fold reduction in specific activity but had a compensating increased yield of protein from host cells.

Other BamHI mutants that shared reduced thermostability, reduced star activity and acceptable specific activity include:

E86P/K87R/K88G/E163S/E170T/P173A

E86P/K87P/K88R/E163S/E170T/P173A/E211K

E86P/K87T/K88R/E163S/E170T/P173A/N158S

E86P/K87S/K88P/E163S/E170T/P173A

E86P/K87G/K88S/E163S/E170T/P173A

E86P/K87R/K88Q/E163S/E170T/P173A

Example 2: Preparation of a High Fidelity EcoRI

1. Expression of EcoRI

PCR on EcoRI used the following primers:

```
                                    (SEQ ID NO: 73)
GGTGGTGCATGCGGAGGTAAATAAATGTCTAATAAAAAACAGTCAAATAG

GCTA

                                    (SEQ ID NO: 74)
GGTGGTGGTACCTCACTTAGATCTAAGCTGTTCAAACAA
```

The PCR product was then digested with a second pair of restriction endonucleases—SphI and Acc65I, and ligated into the pUC19 digested with the same second pair of restriction endonucleases. The ligated plasmid was then be transformed into competent *E. coli* premodified with pACYC-MiucIM.

2. Mutagenesis of EcoRI

Initial selection of target amino acid residues resulted from a comparison of EcoRI with its isoschizomer RsrI, which is also known for its star activity.

```
EcoRI vs. RsrI
           .    .    .    .    .
  4 KKQSNRLTEQHKLSQGVIGIFGDYAKAHDLAVGEVSKLVKKALSNEYPQL  53
    | |. ||  | .|  | : |||. |  |||.: ||.  |   |. ::| |
 10 KGQALRLGIQQELGGGPLSIFGAAAQKHDLSIREVTAGVLTKLAEDFPNL  59

           .    .    .    .    .
 54 SFRYRDSIKKTEINEALKKIDPDLGGTLFVSNSSIKPDGGIVEVKDDYGE 103
    |. | |: | ||| |: || || ||| ..||:|||||| ||| :|
 60 EFQLRTSLTKKAINEKLRSFDPRLGQALFVESASIRPDGGITEVKDRHGN 109

          .    .    .    .    .
104 WRVVLVAEAKHQGKDIINIRNGLLVGKRGDQDLMAAGNAIERSHKNISEI 153
    |||:|| |.|||| |: | |.| || ||| ||||||||| |||: |:
110 WRVILVGESKHQGNDVEKILAGVLQGKAKDQDFMAAGNAIERMHKNVLEL 159

          .    .    .    .    .
154 ANFMLSESHFPYVLFLEGSNFLTENISITRPDGRVVNLEYNSGILNRLDR 203
     |:|| | |||||.||:|||| ||. :|||||||| : :.||.|||:||
160 RNYMLDEKHFPYVVFLQGSNFATESFEVTRPDGRVVKIVHDSGMLNRIDR 209

          .    .    .    .    .
204 LTAANYGMPINSNLCINKFVNHKDKSIMLQAASIYTQGDGREWDSKIMFE 253
    .||..  || | | | |   | | ||:| .  | . | |
210 VTASSLSREINQNYCENIVVRAGSFDHMFQIASLYCK..AAPWTAGEMAE 257

254 IMFDISTTSLRVLGRDL 270 (SEQ ID NO: 75)
     | :. ||||:: ||
258 AMLAVAKTSLRIIADDL 274 (SEQ ID NO: 76)
```

Except for D91, E111 and K113, which were known active center residues, the 42 charged residues were identical or similar in the two endonucleases. The charged residues were as follows: K4, R9, K15, K29, H31, D32, E37, E49, R56, R58, K63, E68, K71, D74, K89, E96, K98, K99, R105, H114, D118, K130, D133, D135, E144, R145, H147, K148, E152, E160, H162, E170, E177, R183, D185, R200, D202, R203, E253, R264, D269.

All of these charged residues were mutated to Ala (codon GCA, GCT, GCC or GCG) and the mutated genes amplified and cloned as follows:

The amplification mixture was the same as used in Example 1 (2 μl PCR primers each, 400 mM dNTP, 4 units of Deep Vent DNA polymerase, 10 μl 10×Thermopol buffer with additional 0, 2, 6 μl $MgSO_4$, and the total reaction volume was 100 μl) and was added to 1 μl pUC19-EcoRI).

The PCR reaction conditions was 94° C. for 5 min, followed by 25 cycles of 94° C. for sec, 55° C. for 30 sec, 72° C. for 3 min and 30 sec and a final extension time at 72° C. for 7 min. After PCR, the product was purified by the standard Qiagen spin column (Qiagen, Valencia, CA). 16 μl PCR product was digested by 20 units of DpnI for 1 hour. The digested product was transformed into a methylase protected competent *E. coli* preparation.

3. Screening EcoRI High Fidelity Mutants

Three colonies each were picked for each mutation and grown in LB with Ampicillin and Chloramphenicol for overnight. The activity assay was performed on pBR322 and lambda DNA to ensure the mutant had at least similar activity to WT EcoRI. Then these mutants were tested using 3 μl of cell extract in 2-fold serial dilution, 12 μl 50% glycerol, 3 μl of NEB1 buffer, 0.5 μl pBR322 and 11.5 μl water, reacted at 37° C. for one hour. However, none of the mutations improved the performance of star activity.

From this result, it was concluded that an effective mutation could not always be recognized as a homologous residue between isoschizomers.

4. Repeat Mutagenesis on the Rest of 32 Charged Residues

All remaining 32 charged residues were mutated into Ala as described in step 2 by targeting amino acid residues 5, 12, 14, 26, 40, 43, 44, 59, 62, 65, 72, 76, 100, 103, 117, 123, 131, 192, 221, 225, 226, 227, 228, 242, 244, 245, 247, 249, 257, 268, 272 and 277.

The numbers above correspond to amino acid positions in the EcoRI protein sequence (SEQ ID NO:83).

5. Repeat Selection

Four colonies were picked from each sample containing a different type of mutation and grown in 4 ml LB with CAM. After sonication, cell extracts were tested on lambda DNA substrate in normal glycerol condition in NEB1 buffer. Those extracts with similar activity were tested again on pUC19 substrate by adding 3 μl of cell extract in two-fold serial dilutions, in 3 μl of NEB2 buffer to 0.5 μl of pUC19 and 23.5 μl 50% glycerol to provide a final concentration of 39.2% glycerol in the reaction mixture.

Among all of these mutants, K62A was found to be the mutation with the least star activity and a high FI. R9A, K15A, R123A, K130A, R131A, R183A mutants all showed partial reduction in star activity. Interestingly, one clone containing the targeted mutation K5A showed a partial improvement. Additionally, a secondary mutation, S2Y was found after sequencing. Separation of these two mutations revealed that the effective mutation for this isolate was S2Y. D135A and R187A EcoRI also had much less star activity. However, the cleavage activity of these mutants was not optimal.

6. Comparison of EcoRI(K62A) with WT EcoRI

A side-by-side comparison was performed in a 3-fold serial dilution using NEB dilution buffer C, by digesting 0.6 μg of lambda DNA in four different NEB buffers (FIG. 6). EcoRI(K62A) had substantially less star activity than the WT EcoRI.

A more quantitative comparison was done by determining the Fidelity Index measurement for EcoRI(K62A) and WT EcoRI. The conditions for the fidelity index measurement was the same as for Table 2 using lambda DNA as substrate and, dilution buffer C. The reaction was incubated at 37° C. for 1 hour and the digestion products analyzed on an 0.8% agarose gel.

TABLE 7

Fidelity Index for EcoRI(K62A) and WT EcoRI

| | EcoRI(K62A) | | WT EcoRI | | |
|---|---|---|---|---|---|
| Buffer | Activity | Fidelity Index | Activity | Fidelity Index | Improvement Factor |
| NEB1 | 50% | 32000 | 50% | 250 | 128 |
| NEB2 | 50% | 8000 | 100% | 4 | 2000 |
| NEB3 | 12.5% | 4000 | 100% | 250 | 16 |
| NEB4 | 100% | 32000 | 100% | 4 | 8000 |
| EcoRI buffer | 12.5% | 4000 | 100% | 250 | 16 |

7. Further Mutation of EcoRI

Though it was not apparent that the EcoRI(K62A) had star activity on lambda DNA substrate, star activity was observed using Litmus28 substrate after a 10 hours digestion. EcoRI(K62A) in NEB4 had significantly reduced star activity compared with WT EcoRI in EcoRI buffer (FIG. 7).

Further improvements were investigated. EcoRI(K62) was mutated to all other amino acid residues by changing K to the corresponding codons as in the example 1. K62S and K62L were similar as K62A. EcoRI(K62E) had a ≥100 fold overall fidelity index improvement factor when compared with EcoRI(K62A) as shown in FIG. 6. EcoRI(K62E) was named EcoRI-HF.

8. Comparison of EcoRI-HF and WT EcoRI

A quantitative comparison was done by the FI measurement on EcoRI-HF and WT EcoRI in diluent C. The conditions for the FI measurement were the same as in Table 2 using lambda DNA as substrate. The reaction conditions were 37° C. for 1 hour and the results analyzed on a 0.8% agarose gel (FIG. 8).

TABLE 8

Comparison of EcoRI-HF and WT EcoRI

| | EcoRI-HF | | WT EcoRI | | |
|---|---|---|---|---|---|
| Buffer | Activity | Fidelity Index | Activity | Fidelity Index | Improvement Factor |
| NEB1 | 12.5% | 2000 | 50% | 250 | 8 |
| NEB2 | 100% | 4000 | 100% | 4 | 1000 |

TABLE 8-continued

Comparison of EcoRI-HF and WT EcoRI

| | EcoRI-HF | | WT EcoRI | | |
|---|---|---|---|---|---|
| Buffer | Activity | Fidelity Index | Activity | Fidelity Index | Improvement Factor |
| NEB3 | 0.4% | 250 | 100% | 250 | 1 |
| NEB4 | 100% | 16000 | 100% | 4 | 4000 |
| EcoRI buffer | 0.4% | 250 | 100% | 250 | 1 |

The overall fidelity index improvement factor was found to be 64 fold (16000 in NEB4 for EcoRI-HF to 250 of WT EcoRI in NEB3).

Example 3: Engineering a High Fidelity ScaI

1. Expression of ScaI

The sequence for ScaI restriction endonuclease and methylase are described in REBASE and in GenBank and is presented in FIG. 44 (SEQ ID NO:97). The genes expressing these enzymes were inserted into plasmids to produce pRRS-ScaI and pACYC184-ScaIM respectively. pACYC184-ScaIM was then transformed into competent *E. coli* host cells. The pRRS vector was derived from pUC19 and differs only in the presence of multiple cloning sites. pRRS-ScaIR was transformed into *E. coli* (pACYC-ScaIM) to make an expression strain. Plating and cell culture were performed at 30° C.

2. Mutagenesis of ScaI

ScaI has two sequenced isoschizomers: LlaDI and NmeSI. However, there was no known information on the star activity of LlaDI or NmeSI nor was there any information on the active site of these enzymes. Therefore all 58 charged residues were initially selected for targeted mutation at positions 4, 8, 11, 12, 14, 18, 25, 27, 30, 37, 39, 40, 43, 46, 51, 57, 61, 68, 72, 74, 80, 86, 97, 103, 108, 112, 114, 119, 120, 121, 127, 128, 129, 133, 135, 139, 140, 141, 147, 152, 156, 158, 159, 161, 162, 171, 172, 175, 179, 182, 184, 187, 172, 175, 192, 193, 195, 200, 222, 227 in the protein.

The numbers above correspond to amino acid positions in the ScaI protein sequence (SEQ ID NO:97).

The method of primer design and PCR is similar to that described in Example 1 for BamHI and Example 2 for EcoRI. Mutagenesis was achieved by varying annealing temperature and DNA polymerases. The PCR product was digested with DpnI and transformed into competent *E. coli* (pACYC184-ScaIM).

3. Selection of ScaI High Fidelity Mutants

Four colonies from each mutant of ScaI mutant were picked and grown in 4 ml LB with 100 μg/ml Amp and 33 μg/ml Cam at 30° C. overnight. Each cell culture was sonicated and the activity tested on lambda DNA in NEB2 buffer. Those that were apparently active were retested in 10, 100, and 1000 fold dilutions. Since ScaI has very significant star activity, the star activity bands were easily compared for the mutants versus the WT restriction endonuclease. Those with reduced star activity were retested with a two-fold serial dilution with NEB dilution buffer A. The FI was measured for each of the mutants. The FI was ⅛ for WT ScaI in NEB 2 buffer. Four mutants with similar activity levels were found to have greatly reduced star activity compared with WT ScaI. Mutant #6-3 ScaI had two fold more activity and the FI was 4 or 32 times better than WT ScaI. #26-2 ScaI has two fold more activity and an FI which was 8 or 64 times better than WT; #28-2 ScaI has 2 fold more activity and FI to be 120 or 1000 times better than WT, #54-3 has same activity as WT and FT to be 250 or 2000 times better than WT.

Four mutants: #6-3, #26-2, #28-2 and #54-3 ScaI were further tested in the presence of 36.7% glycerol for digestion of lambda DNA substrate. #54-3 showed a greater improvement in reduced star activity than the other three mutants.

After the plasmid was extracted, #6-3 was sequenced and found to have a mutation at Ri8A. #26-2 was sequenced and found to have a mutation at R112A. #28-2 was sequenced and found to have a mutation at E119A. These mutations were predicted. However, the #54-3 was found to have a double mutant- H193A/S20IF. The S201F was a spontaneously secondary mutation that occurred during PCR, and was located outside the primer region of the H193A mutation.

To understand which residue was primarily responsible for the reduction in star activity a single mutation (S201F) was introduced into ScaI using the following primers:

```
                                          (SEQ ID NO: 77)
5'-GATTGGGTGGCGCAGAAATTTCAAACGGGCCAGCAGTCG-3'

                                          (SEQ ID NO: 78)
5'-CGACTGCTGGCCCGTTTGAAATTTCTGCGCCACCCAATC-3'.
```

The sequences for ScaI(H193A), ScaI(S201F) and ScaI (H193A/S201F) were confirmed. The three mutants and the WT ScaI were compared at the glycerol level of 5% and 37% (FIG. 9). S201F contributed significantly to the FI in contrast to H193A, which only contributed weakly. However, these two mutations appeared to be additive in improving the FI. S201F did not show star activity in 5% glycerol, but did show some star activity in 37% glycerol. H193A had some star activity in 5% glycerol, and significant star activity in 37% glycerol. However, with the combination of these two mutations, no star activity was detected in either 5% or 37% glycerol. This finding not only shows that the amino acids with hydroxyl group can be major active residue for star activity, but also that the right combination of the mutations can push the improvement in fidelity to a very high level. If mutations of charged residues fail to improve star activity, it is here observed that mutations on Ser, Thr and Tyr can be successful in improving the fidelity index. The ScaI(H193A/S201F) was labelled ScaI-HF.

4. Comparison of ScaI-HF and WT ScaI

ScaI-HF and WT ScaI were compared at a 2.5 fold serial dilution with NEB dilution buffer A in different NEB buffers on 1 μg lambda DNA in four different NEB buffers, 37° C., 1 hour (FIG. 10).

TABLE 9

Comparison of Fidelity Index for ScaI-HF and WT ScaI

| | ScaI-HF | | WT ScaI | | |
|---|---|---|---|---|---|
| Buffer | Activity | Fidelity Index | Activity | Fidelity Index | Improvement Factor |
| NEB1 | 12% | 250 | 6% | 1/64 | 16000 |
| NEB2 | 100% | 120 | 100% | 1/8 | 2000 |
| NEB3 | 3% | 2000 | 25% | 4 | 500 |
| NEB4 | 100% | 250 | 1% | 1/32 | 8000 |

ScaI-HF performed best in NEB2 and NEB4 buffers, in which the best FI was 250; WT ScaI performed best in NEB2 buffer, in which the FI was 1/8. The overall FI improvement factor was 250/(1/8)=4000.

Example 4: Engineering of High Fidelity SalI

1. Expression of SalI

SalI was expressed in *E. coli* transformed with placzz1-SalIR and pACYC-Hpy166IIM where placzz1 is a pUC19 μlasmid which utilizes the lac promoter to express the restriction endonuclease gene that is inserted into an adjacent multi-copy site. Hpy166I1M protects the outside four bases of SalI.

2. Mutagenesis of SalI 86 charged residues of SalI were mutated to Ala using the similar PCR methods in the previous examples: 5, 6, 8, 9, 12, 13, 19, 27, 31, 34, 35, 37, 42, 43, 45, 50, 60, 63, 65, 67, 73, 82, 83, 84, 90, 93, 97, 100, 101, 103, 107, 109, 111, 114, 116, 119, 126, 129, 131, 134, 140, 143, 145, 147, 148, 156, 157, 164, 168, 172, 173, 174, 180, 181, 186, 190, 191, 193, 210, 218, 226, 232, 235, 237, 238, 244, 246, 250, 25.6, 257, 258, 259, 260, 261, 264, 266, 271, 275, 297, 300, 304, 305, 306, 308, 309, 311.

The numbers above correspond to amino acid positions in the SalI protein sequence (SEQ ID NO:94).

The mutants were grown in LB with Amp and Cam at 30° C. overnight.

3. Selection of SalI-HF

The selection of SalI-HF was performed as described in the previous examples. The major difference was that the star activity of SalI could not be easily assayed in the crude extract, either in 5% glycerol or high glycerol concentration. Glycerol not only promoted the star activity of SalI, but also greatly inhibited the cognate activity.

Active mutants were assayed in both 5% glycerol and 37% glycerol on HindIII digested lambda DNA. The mutants #22, #26, #29, #31, #43 and #51 were tested for cleavage activity in all four NEB buffers. After several rounds of comparison in different conditions and substrates, #31, SalI(R107A) was found to be the preferred mutant, retaining high cleavage high activity, but displaying substantially reduced star activity. SalI(R107A) was labeled SalI-HF.

4. Comparison of SalI-HF and WT SalI

The FI of SalI-HF and WT SalI were determined (FIG. 11). The results are shown as Table 10 (below):

TABLE 10

Comparison of SalI-HF and WT SalI

| | SalI-HF | | WT SalI | | |
|---|---|---|---|---|---|
| Buffer | Activity | Fidelity Index | Activity | Fidelity Index | Improvement Factor |
| NEB1 | 50% | ≥1000 | 0.2% | 8 | 16000 |
| NEB2 | 100% | ≥2000 | 6% | 1/8 | 2000 |
| NEB3 | 25% | ≥500 | 100% | 4 | 500 |
| NEB4 | 100% | ≥2000 | 0.8% | 1/32 | 8000 |

SalI-HF performed best in NEB 2 and NEB 4 buffers, in which both FIs are 2000; WT SalI performed best in NEB 3 buffer, in which the FI was 4. The overall FI improvement factor was ≥2000/4=≥500.

Example 5: Engineering of High Fidelity SphI

1. Expression of SphI

SphI was expressed in *E. coli* (placzz1-SphIR, pACYCI84-CviAIIM). CviAIIM protects the internal four bases of SphI. The transformed cells were grown in LB with Amp and Cam at 37° C. overnight.

2. Mutagenesis of SphI

All charged residues in SphI were mutated to Ala using the methods described in the Example 1 to Example 4. A total of 71 mutations were made: 3, 5, 12, 18, 21, 24, 25, 30, 31, 35, 43, 46, 51, 54, 57, 58, 60, 61, 72, 75, 77, 78, 87, 90, 91, 95, 100, 104, 107, 108, 110, 113, 120, 123, 124, 125, 129, 130, 131, 139, 140, 142, 146, 147, 155, 157, 159, 164, 170, 172, 173, 175, 178, 184, 186, 190, 194, 196, 197, 198, 206, 207, 209, 212, 215, 221, 227, 230, 231, 232, 235.

The numbers above correspond to amino acid positions in the SphI protein.sequence (SEQ ID NO:98).

3. Selection of SphI-HF

Four colonies of each mutation were grown up in LB with Amp and Cam at 37° C. overnight. The activity selection was mainly on pBR322 in 5% glycerol and 30% glycerol in NEB2. With the experience of previous examples, the selection of high fidelity SphI was straightforward. SphI mutants D91A, K100A, D139A and D164A were found to significantly reduce star activity in SphI. Among them, K100A was the preferred mutation with the least star activity. SphI (K100A) was named as SphI-HF.

4. Comparison of SphI-HF and WT SphI

The comparison of SphI-HF and WT SphI was done side by side in their respective preferred buffers. SphI-HF was 2-fold serial diluted with NEB dilution buffer A and reacted in NEB4, and WT SphI was 2-fold serial diluted with NEB dilution buffer B. The digestion on lambda DNA is compared in FIG. 12.

TABLE 11

FI comparison of SphI-HF and WT SphI

| | SphI-HF | | WT SphI | | |
|---|---|---|---|---|---|
| Buffer | Activity | Fidelity Index | Activity | Fidelity Index | Improvement Factor |
| NEB1 | 50% | ≥1000 | 100% | 64 | ≥16 |
| NEB2 | 50% | ≥1000 | 100% | 32 | ≥32 |
| NEB3 | 3% | ≥120 | 25% | 64 | ≥2 |
| NEB4 | 100% | ≥2000 | 50% | 16 | ≥64 |

SphI-HF performed best in NEB4, in which FI is ≥2000; WT SphI performed best in NEB1 or NEB2, in which the preferred FI is 64. The overall FI improvement factor was ≥32.

Example 6: Engineering of High Fidelity PstI

1. Expression of PstI

PstI was expressed from *E. coli*(pACYC-HpyCH4VM, pPR594-PstIR). HpyCH4VM protects the internal four bases of PstI. pPR594 is a expression vector with Amp resistance and ptac promoter. The cell was grown in LB with Amp and Cam at 30° C., the culture was then induced by IPTG overnight.

2. Mutagenesis of PstI 92 charged residues were mutated to Ala using the method described in the previous examples. These were: 8, 0.10, 11, 14, 25, 26, 38, 40, 41, 44, 45, 47, 58, 61, 63, 66, 67, 69, 73, 74, 77, 78, 82, 85, 88, 91, 92, 94, 95, 99, 104, 105, 116, 119, 127, 128, 136, 142, 145, 146, 150, 151, 152, 156, 159, 169, 170, 174, 176, 179, 180, 184, 188, 191, 197, 202, 204, 207, 212, 214, 217, 218, 226, 227, 228, 231, 236, 237, 238, 239, 240, 246, 251, 257, 258, 261, 263, 273, 282, 284, 286, 287, 295, 297, 302, 305, 306, 309, 313, 314, 319 and 320.

The numbers above correspond to amino acid positions in the PstI protein sequence (SEQ ID NO:91).

After the PCR products were digested with DpnI, the samples were transformed into competent *E. coli*(pACYC-HpyCH4VM) and grown on LB plate with Amp and Cam.

3. Selection of PstI-HF

The selection of PstI-HF was similar to the previous samples. The normal activity enzyme activity was tested on lambda DNA with 5% glycerol, and the star activity was tested on pBR322 substrate in the condition of NEB4 buffer and 20% DMSO. DMSO enhanced the star activity more significantly than the same concentration glycerol. During the selection, #26, #56 and #65 had reduced star activity compared to the WT. When each was sequenced, the mutations were found to be D91A, E204G and K228A/A289V. Mutant #26 PstI(D91A) was labeled PstI-HF.

4. Comparison of PstI-HF and WT PstI

The FI of PstI-HF and WT PstI were measured separately on lambda DNA substrate in NEB1-4 buffers. The dilution buffer is NEB dilution buffer C. The comparison is shown as in the FIG. 13, and the result is listed in Table 12 (below).

TABLE 12

Comparison of PstI-HF and WT PstI

| | PstI-HF | | WT PstI | | |
|---|---|---|---|---|---|
| Buffer | Activity | Fidelity Index | Activity | Fidelity Index | Improvement Factor |
| NEB1 | 12.5% | ≥250 | 50% | 32 | ≥8 |
| NEB2 | 100% | ≥2000 | 25% | 16 | ≥125 |
| NEB3 | 25% | ≥500 | 100% | 120 | ≥2 |
| NEB4 | 100% | ≥2000 | 50% | 8 | ≥250 |

PstI-HF performed best in NEB2 and NEB4, in which the preferred FI is ≥2000; WT PstI performed best in NEB3, in which the FI was 120. The overall FI improvement factor was ≥2000/120=16 times.

Example 7: Engineering of High Fidelity NcoI

1. Expression of NcoI

Expression of NcoI was achieved in *E. coli* (pSYX20-NcoIM, pRRS-NcoIR). pRRS is a pUC19 derivative plasmid, and pSYX20 is a compatible low copy number plasmid with pRRS vector. The cells were grown at 30° C. overnight in the LB with Amp and Kanamycin (Kan).

2. Mutagenesis of NcoI

All 66 charged residues in NcoI were mutated to Ala. These residues were: 7, 8, 19, 22, 27, 30, 31, 32, 33, 37, 39, 42, 46, 55, 56, 61, 62, 64, 68, 69, 75, 84, 88, 89, 92, 93, 95, 97, 100, 116, 136, 144, 146, 162, 166, 170, 178, 183, 185, 187, 188, 189, 196, 199, 202, 204, 209, 211, 212, 213, 216, 219, 227, 229, 237, 241, 244, 250, 251, 257, 259, 261, 268, 279, 282, 285.

The numbers above correspond to amino acid positions in the NcoI protein sequence (SEQ ID NO:88).

The methods were the same as in the previous examples using inverse PCR followed by DpnI digestion. The treated product was then transformed into *E. coli* (pSYX20-NcoIM).

3. Selection of NcoI-HF

The selection of NcoI-HF was similar to that of PstI-HF. The activity was assayed as described above using lambda DNA as substrate with 5% glycerol. Star activity was determined using pBR322 or lambda in 19% DMSO. The following mutations were found to improve star activity:

A2T/R31A, D56A, H143A, E166A, R212A and D268A. Among these mutants, NcoI(A2T/R31A) was selected as the NcoI-HF.

4. Comparison of NcoI-HF and WT NcoI

The FIs of NcoI-HF and WT NcoI were determined separately on lambda DNA in NEB1-4 buffers. The comparison is shown in FIG. 14, and the results listed in Table 13 (below).

TABLE 13

Comparison of NcoI-HF with WT NcoI

| Buffer | NcoI-HF Activity | NcoI-HF Fidelity Index | WT NcoI Activity | WT NcoI Fidelity Index | Improvement Factor |
|---|---|---|---|---|---|
| NEB1 | 25% | ≥4000 | 100% | 120 | ≥32 |
| NEB2 | 25% | ≥4000 | 100% | 32 | ≥125 |
| NEB3 | 6.3% | ≥1000 | 25% | 120 | ≥8 |
| NEB4 | 100% | ≥16000 | 100% | 32 | ≥500 |

NcoI-HF showed the greatest reduction in star activity in NEB4, in which the preferred FI was 16000; WT NcoI performed best in NEB1, NEB2 and NEB4, in which the preferred FI was 120. The overall FI improvement factor was ≥16000/120=125.

Example 8: Engineering of High Fidelity NheI

1. Expression of NheI

NheI was expressed in *E. coli* transformed with pACYC-NheIM, and placzz1-NheIR. placzz1 is a pUC19 derivative plasmid. The cell was grown at 30° C. for overnight in the LB with Amp and Cam.

2. Mutagenesis of NheI

All 92 charged residues in NheI were mutated to Ala as the following residues: 5, 6, 7, 14, 17, 19, 22, 25, 28, 31, 38, 39, 42, 47, 49, 52, 56, 58, 59, 60, 64, 74, 75, 76, 77, 80, 91, 93, 104, 105, 110, 112, 116, 117, 123, 126, 130, 131, 133, 135, 137, 147, 149, 152, 159, 160, 165, 167, 170, 171, 174, 179, 183, 195, 202, 205, 207, 209, 210, 211, 214, 216, 218, 221, 225, 231, 241, 243, 244, 250, 252, 256, 257, 259, 264, 266, 267, 281, 285, 287, 288, 289, 291, 297, 300, 307, 313, 315, 318, 321, 324, 325.

The numbers above correspond to amino acid positions in the NheI protein sequence (SEQ ID NO:89).

The methods were the same as in the previous examples using inverse PCR followed by DpnI digestion. The treated product was then transformed into *E. coli* (pACYC-NheIM).

3. Selection of NheI-HF

Selection of NheI-HF was performed according to the previous examples. The standard and star activity assays contained pBR322 as a substrate in NEB4 buffer and 5% glycerol and 39% glycerol, respectively. Only one mutation was found to be significant in improving the NheI. This was E77A. NheI(E77A) was selected as the NheI-HF.

4. Comparison of NheI-HF and WT NheI

The FIs of NheI-HF and WT NheI were determined separately on pXba, a plasmid substrate containing the XbaI digested piece from Adeno virus in each of NEB1-4 buffers. The comparison is shown in FIG. 15, and the result is listed in Table 14 (below).

TABLE 14

Comparison of NheI-HF and WT NheI

| Buffer | NheI-HF Activity | NheI-HF Fidelity Index | WT NheI Activity | WT NheI Fidelity Index | Improvement Factor |
|---|---|---|---|---|---|
| NEB1 | 100% | ≥128000 | 100% | 32 | ≥4000 |
| NEB2 | 3% | ≥4000 | 25% | 120 | ≥32 |
| NEB3 | 0.05% | ≥32 | 12.5% | 120 | ≥0.25 |
| NEB4 | 50% | ≥32000 | 100% | 32 | ≥1000 |

NheI-HF showed optimal activity in NEB1 buffer where its FI is ≥128,000. WT NheI has maximum activity in NEB1 and NEB4 buffers, where its best FI is 32. so, the overall FI improvement factor is ≥128.000/32=≥4000.

Example 9: Engineering of High Fidelity SspI

1. Expression of SspI

SspI was expressed from *E. coli* transformed with pACYC-SspIM, and placzz1-SspIR. placzz1 is a pUC19 derivative plasmid. The cells were grown at 30° C. overnight in LB with Amp and Cam.

2. Mutagenesis of SspI

All 81 charged residues in SspI were mutated to Ala: These were: 3, 8, 12, 13, 18, 19, 20, 35, 40, 42, 44, 47, 52, 60, 62, 65, 68, 69, 72, 74, 76, 77, 78, 79, 83, 85, 88, 89, 90, 96, 100, 108, 109, 118, 119, 127, 128, 129, 131, 132, 137, 144, 153, 154, 155, 156, 158, 165, 168, 170, 172, 177, 178, 179, 181, 185, 186, 187, 191, 194, 195, 197, 202, 204, 215, 222, 229, 237, 240, 246, 250, 256, 257, 259, 260, 264, 265, 267, 268, 269, 274.

The numbers above correspond to amino acid positions in the SspI protein sequence (SEQ ID NO:99).

The methods were the same as in the previous examples using inverse PCR followed by DpnI digestion. The treated product was then transformed into *E. coli* (pACYC-SspIM).

3. Selection of SspI High Fidelity Mutants

The standard cognate and star activity assays of NheI were performed using (DX174 substrate in NEB 4 buffer and 5% glycerol and 39% glycerol respectively. Mutants #16 (H65A), #20(K74A), #23(E78A), #26(E85A), #28(E89A), #33(K109A), #34(E118A), #52(R177A), #62(K197A), #67 (D229A) all showed reduced star activity. K109A showed the greatest reduction in star activity. It was decided to seek further improvements in star activity.

4. Further Mutations

All residues originally identified as Tyr were mutated to Phe, while other residues Cys, Phe, Met, Asn, Gln, Ser, Thr, and Trp were mutated to Ala. This group included 95 residue mutations at the following positions: 2, 6, 7, 9, 10, 13, 22, 25, 26, 27, 29, 30, 32, 33, 34, 39, 41, 51, 53, 55, 56, 57, 58, 59, 61, 63, 71, 75, 81, 84, 87, 91, 94, 98, 104, 106, 107, 110, 111, 113, 114, 123, 125, 134, 136, 139, 140, 141, 142, 143, 146, 152, 157, 159, 160, 164, 173, 175, 180, 183, 190, 192, 193, 196, 198, 199, 201, 205, 207, 211, 214, 218, 219, 220, 221, 223, 225, 226, 227, 228, 230, 232, 233, 235, 238, 239, 241, 249, 254, 255, 272, 275, 276, 277, 280.

The numbers above correspond to amino acid positions in the SspI protein sequence (SEQ ID NO:113).

The PCRs and the selections were done by the same procedure as above. Among these mutants, it was found that Y98F had least star activity, and it was better than SspI (K109A) in this respect. The SspI(Y98F) was labelled SspI-HF and was deposited as the production strain.

5. Comparison of SspI-HF and WT SspI

The FIs of SspI-HF and WT SspI were determined separately using lambda DNA substrate in NEB1-4 buffers. The diluent was NEBC. The comparison is shown in FIG. 16, and the result is listed in Table 15 (below).

TABLE 15

Comparison of SspI-HF and WT SspI

| | SspI-HF | | WT SspI | | |
|---|---|---|---|---|---|
| Buffer | Activity | Fidelity Index | Activity | Fidelity Index | Improvement Factor |
| NEB1 | 50% | ≥4000 | 100% | 64 | ≥64 |
| NEB2 | 50% | 120 | 100% | 16 | ≥8 |
| NEB3 | 0.6% | ≥32 | 25% | 32 | ≥1 |
| NEB4 | 100% | 500 | 100% | 16 | ≥32 |

SspI-HF performed best in NEB4, in which the preferred FI was 500; WT SspI performed best in NEB1, NEB2 and NEB4, in which the preferred FI was 64. The overall FI improvement factor was ≥500/64=8.

Example 10: Engineering of High Fidelity NotI

1. Expression of NotI

NotI has significant star activity in NEB4 buffer and less in NEB3 buffer. NotI was engineered to reduce star activity in any NEB buffer. NotI was expressed in competent *E. coli* transformed with pACYC184-EagIM and placzz2-NotIR. The cells were grown at 37° C. for overnight in the LB with Amp and Cam.

2. Mutagenesis of NotI

All 97 charged residues in NotI were mutated to Ala as the following residues: 2, 4, 8, 10, 17, 21, 22, 26, 31, 34, 35, 36, 49, 52, 57, 59, 62, 72, 74, 75, 77, 84, 87, 96, 97, 105, 117, 121, 122, 125, 126, 129, 130, 133, 140, 141, 145, 150, 152, 156, 160, 165, 167, 174, 176, 177, 182, 187, 189, 193, 194, 200, 205, 208, 210, 219, 224, 225, 227, 236, 237, 245, 251, 253, 267, 271, 272, 280, 283, 290, 292, 294, 296, 304, 306, 308, 310, 314, 319, 321, 323, 327, 331, 335, 336, 339, 353, 354, 356, 358, 361, 365, 367, 368, 369, 370, 378, 382.

The numbers above correspond to amino acid positions in the NotI protein sequence (SEQ ID NO:90).

The method for introducing mutants into the enzyme was the same as in the previous examples using inverse PCR followed by DpnI digestion. The treated product was then transformed into

*E. coli* containing pACYC-EagIM.

3. Selection of NotI-HF

Selection of NotI-HF was performed as described in the previous examples. The standard cognate and star activity assays used pXba substrate in NEB 4 buffer and 5% glycerol and NEB ExoI buffer (67 mM Glycine-KOH, pH 9.5, 6.7 mM $MgCl_2$, 10 mM 2-mercaptoethanol) and 37% glycerol respectively. #37(K150A), #44(K176A), #45(R177A), #63 (R253A) all showed reduced star activity. K150A was the preferred mutation to reduce star activity. NotI(K150A) was selected as the NotI-HF.

4. Comparison of NotI-HF and WT NotI

The FIs of NotI-HF and WT NotI were determined separately using pXba substrate in NEB1-4 buffers. The comparison is shown in FIG. 17, and the results are listed in Table 16 (below).

TABLE 16

Comparison of NotI-HF and WT NotI

| | NotI-HF | | WT NotI | | |
|---|---|---|---|---|---|
| Buffer | Activity | Fidelity Index | Activity | Fidelity Index | Improvement Factor |
| NEB1 | 6% | ≥8000 | 6% | ≥8000 | ND |
| NEB2 | 100% | ≥128000 | 50% | 250 | ≥512 |
| NEB3 | 1.6% | ≥4000 | 100% | 4000 | ≥1 |
| NEB4 | 50% | ≥64000 | 12.5% | 32 | ≥2000 |

ND: Not determinable, for that both FI is an uncertain number over limit.

NotI-HF performed best in NEB2, in which the preferred FI was 128000; WT NheI performed best in NEB3, in which the preferred FI was 4000. The overall fidelity index improvement factor was ≥128000/4000=≥32. Engineering NotI not only further improved the FI of NotI, but also changed the optimal buffer.

Example 11: Engineering of High Fidelity SacI

1. Expression of SacI

SacI was expressed in *E. coli* transformed with μLG-SacIM and pRRS-SacIR. pRRS is a pUC19 derivative plasmid, μLG is a low copy compatible plasmid. The cells were grown at 30° C. overnight in-LB with Amp and Kan.

2. Mutagenesis of SacI

All 101 charged residues in SacI were mutated to Ala as the following residues: 6, 7, 11, 15, 16, 19, 24, 25, 29, 30, 39, 40, 42, 45, 58, 61, 62, 63, 65, 67, 70, 71, 72, 74, 75, 76, 81, 85, 94, 98, 104, 105, 114, 116, 120, 123, 127, 129, 133, 134, 141, 143, 144, 145, 146, 150, 151, 154, 169, 170, 172, 181, 187, 196, 197, 200, 201, 211, 216, 220, 221, 224, 227, 228, 232, 238, 240, 246, 248, 250, 258, 270, 271, 277, 281, 288, 289, 295, 296, 297, 299, 303, 306, 313, 314, 321, 322, 324, 332, 336, 337, 340, 342, 344, 345, 347, 349, 350, 353, 357.

The numbers above correspond to amino acid positions in the SacI protein sequence (SEQ ID NO:93).

The methods were the same as in the previous examples using inverse PCR followed by DpnI digestion. The treated product was then transformed into *E. coli* (μLG-SacIM).

3. Selection of SacI-HF

Selection of SacI-HF was achieved using a method that was similar to the previous examples. The standard activity check used pUC19 with 5% glycerol in NEB4 and the star activity check was on pUC19 in NEB4 buffer with 39% glycerol. #52 SacI (Q17H/R154A/L284P) and #60 SacI (Q117H/R200A) both had reduced star activity, and SacI QI 17H/R200A proved to be the preferred mutation. The Q117H was a carry over mutation from the template, which did not affect the activity of SacI. SacI(Q117H/R200A) was selected as the SacI-HF.

4. Comparison of SacI-HF and WT SacI

The FIs of SacI-HF and WT SacI were determined separately on pXba substrate in NEB1-4 buffers. The comparison is shown in FIG. 18, and the result is listed in Table 17 (below).

TABLE 17

| Comparison of SacI-HF and WT SacI | | | | | |
|---|---|---|---|---|---|
| | SacI-HF | | WT SacI | | |
| Buffer | Activity | Fidelity Index | Activity | Fidelity Index | Improvement Factor |
| NEB1 | 25% | ≥2000 | 100% | 120 | ≥16 |
| NEB2 | 12.5% | ≥120 | 50% | 120 | ≥1 |
| NEB3 | 0.8% | ≥120 | 3% | 120 | ≥1 |
| NEB4 | 100% | 4000 | 100% | 32 | 120 |

SacI-HF performed best in NEB4, in which the FI was 4000; WT SacI performed best in NEB1 and NEB4, in which the preferred FI was 120. The overall FI improvement factor was 4000/120=32.

Example 12: Engineering of High Fidelity PvuII

1. Expression of PvuII

PvuII was expressed in *E. coli* transformed with pACYC-PvuIIM and placzz2-PvuIIR. Placzz2 is a pUC19 derivative plasmid; pACYC is a low copy compatible plasmid. The cells were grown at 30° C. overnight in LB with Amp and Cam.

2. Mutagenesis of PvuII

All 47 charged residues in PvuII were mutated to Ala as the following residues: 3, 5, 8, 11, 15, 18, 21, 25, 26, 30, 34, 38, 54, 55, 58, 61, 66, 68, 70, 75, 78, 83, 84, 85, 93, 95, 105, 110, 114, 116, 118, 119, 121, 125, 126, 128, 129, 130, 134, 136, 137, 138, 143, 147, 151, 152, and 155.

The numbers above correspond to amino acid positions in the PvuII protein sequence (SEQ ID NO:92).

The methods were the same as in the previous examples using inverse PCR followed by DpnI digestion. The treated product was then transformed into *E. coli* (pACYC-PvuIIM).

3. Selection of PvuII High Fidelity Mutants

Selection of PvuII-HF was similar to the previous examples. The standard activity check used lambda DNA substrate with 5% glycerol in NEB4 and the star activity check was on pBR322 in NEB4 buffer with 39% glycerol. None of the mutants were qualified as high fidelity PvuII.

4. Additional Mutagenesis Steps

An additional mutagenesis step was mutation of all of the Ser, Thr into Ala, and Tyr to Phe in PvuII. The mutated positions were: 2, 19, 46, 49, 67, 71, 77, 81, 82, 94, 104, 113, 123, 124, 132, 133, 148, 154 and 157.

The methods were the same as in the previous examples using inverse PCR followed by DpnI digestion. The treated product was then transformed into *E. coli* (pACYC-PvuIIM).

The PvuII(T46A) apped to have less star activity than the WT PvuII, however, further improvement was desired.

T46 was mutated to all other amino acid residues, by changing the codons to the corresponding amino acids. Among all these mutations, T46H, T46K, T46Y, T46G were all better than T46A. T46G is selected as the PvuII-HF.

5. Comparison of PvuII-HF and WT PvuII

The FIs of PvuII-HF and WT PvuII were determined separately on pBR322, with diluent A in NEB1-4 buffers. The comparison is shown in FIG. 19, and the result is listed in Table 18 (below).

TABLE 18

| Comparison of PvuII-HF and WT PvuII | | | | | |
|---|---|---|---|---|---|
| | PvuII-HF | | WT PvuII | | |
| Buffer | Activity | Fidelity Index | Activity | Fidelity Index | Improvement Factor |
| NEB1 | 3.1% | ≥250 | 100% | 250 | ≥1 |
| NEB2 | 12.5% | ≥1000 | 25% | 16 | ≥64 |
| NEB3 | 0.4% | ≥32 | 3.1% | 8 | ≥4 |
| NEB4 | 100% | 500 | 100% | ¼ | 2000 |

PvuII-HF performed best in NEB4, in which the FI was 500; WT PvuII performed best in NEB1 and NEB4, in which the preferred FI was 250. The overall FI improvement factor was ≥500/250=2. Though the overall FI improvement factor is not high for PvuII, the FI improved 2000 times in NEB4.

Example 13: Engineering of High Fidelity MfeI

1. Expression of MfeI

MfeI was expressed in *E. coli* transformed with pACYC-MluCIM and pRRS-MfeIR. pRRS is a pUC19 derivative plasmid, pACYC is a low copy compatible plasmid. MluCIM methylate AATT, which is the inner four nucleic acid sequence of the MfeI. The cells were grown at 37° C. overnight in LB with Amp and Cam.

2. Mutagenesis of MfeI

The mutagenesis of MfeI was done in three batches. The first batch is all of the charged residues, mutated into Ala as the following amino acid positions: 3, 5, 9, 19, 24, 36, 39, 44, 45, 47, 48, 50, 60, 61, 64, 65, 72, 83, 87, 90, 92, 93, 98, 100, 101, 103, 107, 109, 110, 115, 119, 120, 121, 124, 132, 135, 142, 143, 144, 153, 155, 158, 159, 161, 162, 164, 165, 171, 172, 175, 181, 184, 187, 188, 192, 195, 196, 198, 199, 200; The second batch is all of the residues with hydroxyl group: Ser, Thr and Tyr, with Ser and Thr changed into Ala and Tyr changed into Phe. The residues are at: 4, 7, 21, 28, 38, 40, 43, 53, 74, 75, 76, 81, 89, 91, 112, 122, 127, 134, 136, 157, 167, 170, 173, 177, 185, and 200. The third batch is the residues of Cys, Phe, Met, Asn, Gln, Trp all changed into Ala, the residues are at: 10, 12, 13, 25, 26, 29, 31, 32, 35, 51, 55, 67, 68, 77, 78, 84, 88, 96, 102, 105, 117, 123, 126, 141, 148, 149, 152, 168, 169, 174, 176, 178, 179, 180, 183, 191, 193, 194.

The numbers above correspond to amino acid positions in the MfeI protein sequence (SEQ ID NO:5).

The methods were the same as in the previous examples using inverse PCR followed by DpnI digestion. The treated product was then transformed into *E. coli* (pACYC-MluCIM).

3. Selection of MfeI-HF

Selection of MfeI-HF was achieved using a method that was similar to the previous examples. Cleavage activity was determined using ΦX174 substrate with 5% glycerol in NEB4 and star activity was determined using ΦX174 substrate in NEB4 buffer with 39% glycerol. A significant difficulty for this enzyme was that many mutations improved cleavage activity of the enzyme with reduced star activity, but required higher glycerol concentrations than the WT enzyme. MfeI(K50A) is one example, having reduced star activity and high cleavage activity in high concentration glycerol, while in lower glycerol concentrations, the activity was low. MfeI(Y173A) also reduced star activity. The preferred mutation was Q13A/F35Y. The mutation of F35Y was from the template, and Q13A was a targeted mutation. MfeI(Q13A/F35Y) was labelled MfeI-HF.

4. Comparison of MfeI-HF and WT MfeI

The FIs of MfeI-HF and WT MfeI were determined separately on lambda DNA substrate, with the dilution in NEB diluent A in NEB1-4 buffers. The comparison is shown in FIG. 20, and the result is listed in Table 19 (below).

TABLE 19

Comparison of MfeI-HF and WT MfeI

| Buffer | MfeI-HF Activity | MfeI-HF Fidelity Index | WT MfeI Activity | WT MfeI Fidelity Index | Improvement Factor |
|---|---|---|---|---|---|
| NEB1 | 100% | ≥1000 | 100% | 32 | ≥32 |
| NEB2 | 25% | ≥250 | 12.5% | 16 | ≥16 |
| NEB3 | 1.3% | ≥16 | 6.3% | 8 | ≥2 |
| NEB4 | 100% | ≥500 | 100% | 32 | ≥16 |

MfeI-HF performed best in NEB1 and NEB4, in which the preferred FI was ≥1000; WT MfeI performed best in NEB1 and NEB4, in which the preferred FI was 32. The overall FI improvement factor was ≥1000/32=32 fold.

Example 14: Engineering of High Fidelity HindIII

1. Expression of HindIII

HindIII was expressed in *E. coli* transformed with pUC19-HindIIIRM, which contains both HindIII endonuclease and methylase genes. The cells were grown at 30° C. overnight in LB with Amp.

2. Mutagenesis of HindIII 88 charged residues in HindIII were mutated to Ala. These were: 2, 3, 7, 8, 14, 20, 22, 34, 37, 39, 42, 45, 52, 55, 61, 62, 66, 69, 74, 84, 87, 89, 94, 100, 101, 109, 111, 114, 117, 120, 123, 124, 126, 128, 132, 134, 135, 136, 137, 138, 153, 158, 162, 163, 171, 172, 180, 182, 183, 190, 197, 198, 201, 202, 207, 209, 214, 215, 218, 222, 225, 227, 228, 229, 237, 238, 243, 244, 245, 249, 250, 251, 254, 255, 261, 265, 266, 267, 270, 274, 275, 281, 283, 286, 290, 293, 296, 297.

All residues Cys, Met, Asn, Gln, Ser, Thr, Trp were changed to Ala while Tyr was changed to Phe at the positions of 4, 11, 15, 17, 18, 19, 21, 23, 26, 27, 30, 31, 36, 38, 46, 57, 58, 59, 60, 63, 64, 76, 77, 80, 82, 83, 88, 91, 99, 102, 103, 104, 112, 113, 116, 118, 121, 122, 125, 131, 133, 139, 143, 146, 147, 148, 149, 151, 152, 154, 155, 157, 159, 160, 164, 168, 169, 170, 178, 184, 185, 187, 188, 189, 191, 193, 194, 195, 199, 200, 203, 204, 206, 210, 211, 212, 213, 216, 217, 219, 220, 221, 224, 230, 232, 233, 236, 240, 241, 246, 252, 253, 256, 258, 262, 263, 264, 277, 278, 279, 280, 284, 287, 288, 294, 295, 299.

The numbers above correspond to amino acid positions in the HindIII protein sequence (SEQ ID NO:85).

The methods were the same as in the previous examples using inverse PCR followed by DpnI digestion. The treated product was then transformed into *E. coli* strain ER3081.

3. Selection of HindIII-HF

Selection of HindIII-HF was achieved using a method that was similar to the previous examples. The standard activity check used lambda DNA with 5% glycerol in NEB4 and star activity was measured using lambda DNA substrate in NEB4 buffer with 39% glycerol. 2 mutants of HindIII were found to have reduced star activity. These were HindIII (K198A) and S188P/E190A. HindIII(K198A) was labelled HindIII-HF.

4. Comparison of HindIII-HF and WT HindIII

The FIs of HindIII-HF and WT HindIII were determined separately using lambda DNA substrate in each of NEB1-4 buffers with diluent B. The comparison is shown in FIG. 21, and the result is listed in Table 20 (below).

TABLE 20

Comparison of HindIII-HF and WT HindIII

| Buffer | HindIII-HF Activity | HindIII-HF Fidelity Index | WT HindIII Activity | WT HindIII Fidelity Index | Improvement Factor |
|---|---|---|---|---|---|
| NEB1 | 25% | ≥16000 | 25% | 32 | ≥500 |
| NEB2 | 100% | ≥64000 | 100% | 250 | ≥250 |
| NEB3 | 12.5% | ≥16000 | 25% | 4000 | ≥4 |
| NEB4 | 50% | ≥32000 | 50% | 32 | ≥1000 |

HindIII-HF performed best in NEB2, in which the preferred FI was ≥64000; WT HindIII performed best in NEB2, in which the preferred FI was 250. The overall FI improvement factor was 4000/120=32.

Example 15: Engineering of High Fidelity SbfI

1. Expression of SbfI

SbfI was expressed in *E. coli* transformed with pUC19-SbfIRM. The cells were grown at 30° C. overnight in LB with Amp.

2. Mutagenesis of SbfI 78 charged residues in SbfI were mutated to Ala. These were: 5, 8, 15, 18, 23, 27, 30, 34, 46, 49, 50, 53, 58, 63, 66, 70, 71, 74, 81, 82, 83, 85, 86, 87, 90, 94, 103, 115, 120, 121, 127, 132, 135, 136, 143, 144, 147, 150, 152, 154, 164, 169, 170, 183, 184, 187, 188, 192, 196, 204, 206, 208, 213, 214, 215, 218, 219, 226, 228, 230, 233, 237, 238, 239, 241, 248, 251, 253, 257, 258, 259, 260, 262, 266, 282, 284, 285, 288, 293, 297, 299, 304, 305, 307, 311, 316, and 322.

The residues of Ser and Thr in SbfI were also mutated into Ala. Tyr was mutated into Phe. The following positions were targeted: 3, 4, 5, 10, 13, 16, 31, 35, 38, 54, 55, 56, 68, 76, 78, 80, 88, 109, 111, 116, 119, 129, 131, 137, 146, 162, 174, 197, 198, 201, 205, 210, 224, 252, 263, 270, 272, 286, 298, 315, 321.

Another 55 residues of Cys, Phe, Met, Asn, Gln, Trp were also mutated to Ala at positions of: 2, 24, 26, 29, 32, 51, 62, 65, 67, 72, 84, 91, 92, 95, 97, 101, 104, 106, 110, 112, 114, 117, 124, 134, 140, 157, 160, 171, 178, 179, 185, 189, 193, 212, 217, 225, 231, 243, 245, 247, 256, 265, 268, 277, 279, 280, 281, 283, 287, 289, 290, 296, 301, 313 and 317.

The numbers above correspond to amino acid positions in the SbfI protein sequence (SEQ ID NO:96).

The methods were the same as in the previous examples using inverse PCR followed by DpnI digestion. The mutated products were transformed into *E. coli* strain ER2984.

3. Selection of SbfI-HF

Selection of SbfI-HF was achieved as described in previous examples. The standard activity check used lambda DNA with 5% glycerol in NEB4 and the star activity check was on lambda DNA in Exonuclease I buffer. SbfI(K251A) was labelled SbfI-HF.

4. Comparison of SbfI-HF and WT SbfI

The FIs of SbfI-HF and WT SbfI were determined separately on lambda DNA in NEB1-4 buffers with diluent C. The comparison is shown in FIG. 22, and the result is listed in Table 21 (below).

TABLE 21

Comparison of SbfI-HF and WT SbfI

| Buffer | SbfI-HF Activity | SbfI-HF Fidelity Index | WT SbfI Activity | WT SbfI Fidelity Index | Improvement Factor |
|---|---|---|---|---|---|
| NEB1 | 100% | 1000 | 100% | 16 | 64 |
| NEB2 | 50% | 120 | 50% | 32 | 4 |
| NEB3 | 3.5% | 8 | 25% | 120 | 1/16 |
| NEB4 | 100% | 250 | 12.5% | 8 | 32 |

SbfI-HF performed best in NEB1 and NEB4, in which the preferred FI was 1000; WT SbfI performed best in NEB1, in which the preferred FI was 8. The overall FI improvement factor was 1000/8=125 fold.

Example 16: Engineering of High Fidelity EagI

1. Expression of EagI

EagI was expressed in *E. coli* transformed with pBR322-EagIRM. The cells were grown at 30° C. overnight in LB with 20 μg/ml Tetracycline.

2. Mutagenesis of EagI

Asp, Glu, His, Lys, Arg, Ser, Thr, Asn and Gln residues were mutated to Ala. Tyr was mutated to Phe. These were the following residues: 2, 3, 4, 5, 6, 9, 13, 14, 17, 19, 21, 23, 27, 35, 36, 37, 40, 42, 43, 44, 45, 46, 49, 51, 53, 55, 56, 58, 60, 66, 67, 69, 71, 72, 73, 74, 75, 77, 78, 80, 82, 86, 87, 92, 93, 94, 95, 98, 99, 100, 102, 103, 104, 105, 112, 113, 114, 116, 117, 119, 122, 125, 127, 132, 134, 135, 137, 139, 140, 141, 145, 147, 148, 150, 152, 154, 155, 156, 157, 160, 162, 163, 164, 166, 169, 172, 173, 176, 177, 178, 179, 182, 185, 187, 188, 189, 193, 196, 197, 201, 202, 203, 204, 205, 206, 208, 209, 212, 217, 220, 221, 222, 224, 225, 230, 235, 236, 237, 238, 239, 240, 241, 243, 245, 246, 247, 248, 251, 255, 257, 258, 259, 260, 263, 264, 265, 266, 270, 272, 273, 275, 276, 277, 279, 280, 283, 286, 288, 289, 291, 295, 296.

The numbers above correspond to amino acid positions in the EagI protein sequence (SEQ ID NO:82).

The methods were the same as in the previous examples using inverse PCR followed by DpnI digestion. The treated product was then transformed into *E. coli* strain ER 3081 and grown on the LB agar plate with Tetracycline.

3. Selection of EagI-HF

Selection of EagI-HF was achieved using a method that was different to the previous examples which used high concentration of glycerol, high concentration of DMSO or high pH. Since the expression was too low to show the star activity in the crude extract, it would be very tedious to purify each of the mutants to check the star activity. From the previous examples, it was deduced that HF endonucleases tended to have increased cleavage activity in NEB4 compared to NEB3. Hence, the activity of EagI in the crude extract was measured in both NEB3 and NEB4; the one with highest ratio of NEB4/NEB3 was selected. EagI(H43A) was labelled EagI-HF.

4. Comparison of EagI-HF and WT EagI

The FIs of EagI-HF and WT EagI were determined separately on pXba substrate in each of NEB1-4 buffers. The comparison is shown in FIG. 23, and the result is listed in Table 22 (below).

TABLE 22

Comparison of EagI-HF and WT EagI

| Buffer | EagI-HF Activity | EagI-HF Fidelity Index | WT EagI Activity | WT EagI Fidelity Index | Improvement Factor |
|---|---|---|---|---|---|
| NEB1 | 50% | 250 | 25% | 4 | 64 |
| NEB2 | 100% | 250 | 50% | 8 | 32 |
| NEB3 | 50% | 250 | 100% | 250 | 1 |
| NEB4 | 100% | 500 | 100% | 16 | 16 |

EagI-HF performed best in NEB2 and NEB4, in which the preferred FI was 500; WT EagI performed best in NEB3 and NEB4, in which the preferred FI was 250. The overall FI improvement factor was ≥500/250=2.

Example 17: Engineering of High Fidelity EcoRV

1. Expression of EcoRV

EcoRV was expressed in *E. coli* strain transformed with pACYC-EcoRVM and placzz1-EcoRV. Placzz1 is a pUC19 derivative plasmid and pACYC is a low copy compatible plasmid. The cells were grown at 37° C. overnight in LB with Amp and Cam.

2. Mutagenesis of EcoRV

Cys, Asp, Glu, Phe, His, Lys, Met, Asn, Gln, Arg, Ser, Thr, and Trp residues were changed to Ala. Tyr was changed to Phe. These were: 2, 4, 5, 6, 9, 12, 13, 14, 15, 16, 17, 18, 19, 21, 25, 27, 29, 31, 35, 36, 37, 38, 41, 42, 44, 45, 47, 48, 49, 53, 54, 57, 58, 59, 61, 64, 65, 67, 68, 69, 70, 71, 72, 74, 75, 76, 78, 79, 81, 82, 84, 85, 86, 90, 92, 93, 94, 95, 96, 97, 98, 99, 100, 101, 102, 104, 105, 106,110, 111, 112, 113, 114, 115, 116, 117, 118, 119, 120, 123, 125, 126, 127, 128, 131, 132, 136, 138, 139, 140, 143, 144, 145, 146, 147, 149, 150, 151, 152, 154, 155, 157, 158, 161, 163, 164, 167, 169, 171, 172, 173, 174, 179, 183, 185, 186, 187, 188, 191, 193, 195, 196, 197, 198, 199, 201, 203, 206, 207, 208, 209, 210, 211, 212, 214, 215, 216, 217, 218, 219, 220, 221, 222, 223, 224, 226, 227, 228, 229, 230, 231, 232, 234, 235, 236, 237, 238, 239, 241, 242, 244, and 245.

The numbers above correspond to amino acid positions in the EcoRV protein sequence (SEQ ID NO:84).

The methods were the same as in the previous examples using inverse PCR followed by DpnI digestion. The treated product was then transformed into *E. coli* (pACYC-EcoRVM).

3. Selection of EcoRV-HF

Selection of EcoRV-HF was achieved using a method that was similar to the previous examples. The standard activity check used pXba with 5% glycerol in NEB4 and the star activity check was on pXba in Exonuclease I buffer with 39% glycerol.

EcoRV(D19A/E27A) was found to have reduced star activity compared with WT EcoRV. This mutant was labeled EcoRV-HF. For this mutant, the E27A was the targeted mutation, and D19A was a spontaneous mutation. The double mutant had greater reduction in star activity than either the D19A and E27A single mutant.

4. Comparison of EcoRV-HF and WT EcoRV

The FIs of EcoRV-HF and WT EcoRV were determined separately on pXba substrate in each of NEB1-4 buffers. The comparison is shown in FIG. 24, and the result is listed in Table 23 (below).

TABLE 23

| Comparison of EcoRV-HF and WT EcoRV | | | | | |
|---|---|---|---|---|---|
| | EcoRV-HF | | WT EcoRV | | |
| Buffer | Activity | Fidelity Index | Activity | Fidelity Index | Improvement Factor |
| NEB1 | 25% | ≥16000 | 6.3% | 32 | ≥500 |
| NEB2 | 100% | ≥64000 | 50% | 120 | ≥500 |
| NEB3 | 50% | ≥32000 | 100% | 1000 | ≥32 |
| NEB4 | 100% | ≥64000 | 25% | 64 | ≥1000 |

EcoRV-HF performed best in NEB2 and NEB4, in which the preferred FI was ≥64000; WT EcoRV performed best in NEB3, in which the preferred FI was 1000. The overall FI improvement factor was ≥64000/1000=64.

Example 18: Engineering of High Fidelity AvrII

1. Expression of AvrII

AvrII was expressed in *E. coli* transformed with pUC19-AvrIIRM. The cells were grown at 30° C. overnight in LB with Amp.

2. Mutagenesis of AvrII

Cys, Asp, Glu, Phe, His, Lys, Met, Asn, Gln, Arg, Ser, Thr, and Trp residues were mutated to Ala. Tyr was changed to Phe. These were: 2, 3, 4, 6, 8, 9, 10, 12, 15, 17, 19, 20, 22, 23, 27, 29, 30, 31, 32, 34, 36, 40, 41, 42, 43, 44, 46, 47, 48, 50, 51, 53, 55, 56, 57, 58, 59, 60, 65, 68, 70, 72, 74, 75, 76, 77, 79, 80, 82, 83, 84, 86, 87, 88, 94, 95, 96, 97, 100, 104, 105, 106, 107, 108, 110, 112, 113, 116, 117, 119 120, 121, 122, 123, 124, 126, 127, 129, 130, 131, 132, 134, 136, 139, 142, 143, 144, 145, 150, 151, 152, 153, 154, 156, 157, 158, 161, 163, 164, 165, 166, 168, 169, 173, 174, 177, 178, 181, 182, 184, 186, 187, 188, 189, 190, 191, 192, 195, 198, 200, 202, 206, 207, 211, 215, 216, 220, 223, 224, 226, 229, 230, 231, 232, 233, 234, 235, 236, 237, 239, 243, 244, 245, 246, 248, 249, 253, 255, 256, 260, 262, 264, 265, 266, 267, 268, 269, 270, 272, 274, 276, 277, 278, 279, 280, 281, 284, 285, 286, 288, 289, 290, 291, 299, 302, 303, 304, 305, 306, 308, 310, 312, 314, 315, 316, 318, 321, 322, 324, 325, 328, 331, 333, 335, 337, 338, 339, 340, 342, 343, 346, 347, 348, 350, 351, 353, 354, 355, 356, 358.

The numbers above correspond to amino acid positions in the AvrII protein sequence (SEQ ID NO:80).

The methods were the same as in the previous examples using inverse PCR followed by DpnI digestion. The treated product was then transformed into *E. coli* expression strain ER2984.

3. Selection of AvrII-HF

Selection of AvrII-HF was achieved using a method that was similar to the previous examples. The cleavage activity was determined using pBC4 with 5% glycerol in NEB4 and the star activity was measured using pBC4 in ExoI buffer with 39% glycerol. Mutants #16 (M29A), #57(E96A), #60 (Y104F), #62(K106A), #154(S127A), #170(F142A) all showed improvement. AvrII(Y104F) was labelled AvrII-HF.

4. Comparison of AvrII-HF and WT AvrII

The FIs of AvrII-HF and WT AvrII were determined separately on T7 DNA substrate with diluent B in each of NEB1-4 buffers. The comparison is shown in FIG. 25, and the result is listed in Table 24 (below).

TABLE 24

| Comparison of AvrII-HF and WT AvrII | | | | | |
|---|---|---|---|---|---|
| | AvrII-HF | | WT AvrII | | |
| Buffer | Activity | Fidelity Index | Activity | Fidelity Index | Improvement factor |
| NEB1 | 100% | 500 | 100% | 64 | ≥8 |
| NEB2 | 50% | ≥500 | 100% | 8 | ≥64 |
| NEB3 | 3.1% | ≥16 | 25% | 32 | ≥0.5 |
| NEB4 | 100% | 1000 | 100% | 32 | 32 |

AvrII-HF performed best in NEB1 and NEB4, in which the preferred FI was 1000; WT AvrII performed best in NEB1 and NEB4, in which the preferred FI was 64. The overall FI improvement factor was 1000/64=16.

Example 19: Engineering of High Fidelity BstXI

1. Expression of BstXI

BstXI was expressed in *E. coli* transformed with pACYCBstXIMS and pUC19-BstXIR. pACYC is a low copy compatible plasmid. The BstXI has to have both Methylase gene and the specificity gene to have a methylase function. The cells were grown at 37° C. overnight in LB with Amp and Cam.

2. Mutagenesis of BstXI 237 amino acid mutations were made in BstXI as follows. Cys, Asp, Glu, Phe, His, Lys, Met, Asn, Gln, Arg, Ser, Thr, Trp were mutated to Ala. Try was mutated to Phe. These were: 4, 6, 7, 9, 11, 12, 14, 15, 17, 18, 20, 21, 22, 23, 24, 26, 27, 29, 30, 31, 32, 33, 34, 35, 36, 37, 39, 40, 42, 43, 46, 48, 50, 53, 54, 57, 58, 59, 60, 62, 63, 64, 65, 66, 71, 72, 73, 75, 76, 78, 80, 81, 82, 83, 84, 86, 89, 91, 93, 94, 95, 96, 97, 98, 103. 105, 106, 108, 110, 111, 112, 114, 117, 118, 120, 123, 124, 125, 126, 127, 128, 129, 130, 131, 137, 138, 139, 141, 142, 144, 145, 146, 148, 151, 152, 153, 154, 155, 156, 159, 162, 163, 166, 168, 169, 171, 172, 173, 174, 175, 176, 177, 178, 182, 185, 188, 189, 191, 193, 194, 195, 196, 198, 199, 201, 204, 208, 209, 210, 211, 212, 214, 215, 216, 217, 218, 219, 220, 221, 223, 228, 229, 230, 233, 235, 236, 238, 239, 240, 244, 245, 248, 249, 250, 253, 254, 255, 258, 259, 260, 261, 263, 264, 265, 267, 268, 269, 272, 276, 277, 278, 279, 280, 282, 285, 286, 287, 288, 289, 291, 293, 294, 295, 300, 301, 302, 304, 305, 306, 308, 309, 312, 314, 317, 318, 319, 320, 323, 324, 325, 326, 330, 331, 333, 334, 335, 337, 343, 344, 345, 346, 347, 349, 353, 355, 356, 357, 358, 359, 360, 362, 363, 364, 365, 367, 369, 371, 373, 374, 376, 377, 378, 379, 380, 381, 382, and 383.

The numbers above correspond to amino acid positions in the BstXI protein sequence (SEQ ID NO:7).

The methods were the same as in the previous examples using inverse PCR followed by DpnI digestion. The treated product was then transformed into *E. coli* (pACYC-BstX-IMS).

3. Selection of BstXI-HF

Selection of BstXI-HF was achieved using a method that was similar to the previous examples. The cleavage activity was determined using pBC4 with 5% glycerol in NEB4 and the star activity was determined using pBC4 DNA substrate in NEB4 buffer with 39% glycerol. Mutants #36(Y57F), #44(N65A), #48(E75A), #49(N76A), and #124(K199A) all had reduced star activity. The BstXI(N65A) was labelled BstXI-HF.

4. Comparison of BstXI-HF and WT BstXI

The FIs of BstXI-HF and WT BstXI were determined separately on lambda DNA substrate with diluent A in each of NEB1-4 buffers. The comparison is shown in FIG. 26, and the result is listed in Table 25 (below).

TABLE 25

Comparison of BstXI-HF and WT BstXI

| | BstXI-HF | | WT BstXI | | |
|---|---|---|---|---|---|
| Buffer | Activity | Fidelity Index | Activity | Fidelity Index | Improvement Factor |
| NEB1 | 50% | ≥120 | 6.3% | 4 | ≥32 |
| NEB2 | 100% | ≥250 | 100% | 32 | ≥8 |
| NEB3 | 6.3% | ≥16 | 100% | 2 | ≥8 |
| NEB4 | 100% | ≥250 | 100% | 32 | ≥32 |

BstXI-HF performed best in NEB2 and NEB4, in which the preferred FI was ≥250; WT BstXI performed best in NEB2, NEB3 and NEB4, in which the preferred FI was 32. The overall FI improvement factor was 250/32=8.

Example 20: Engineering of High Fidelity PciI

1. Expression of PciI

PciI was expressed in *E. coli* transformed with pACYC-PciIM and placzz1-PciIR. placzz1 is a pUC19 derivative plasmid, pACYC is a low copy compatible plasmid. The cells were grown at 37° C. overnight in LB with Amp and Cam.

2. Mutagenesis of PciI 151 amino acid residues in PciI were mutated with Cys, Asp, Glu, Phe, His, Lys, Met, Asn, Gln, Arg, Ser, Thr. Trp was changed to Ala and Tyr to Phe. These were: 2, 3, 4, 6, 8, 9, 10, 11, 12, 14, 17, 18, 19, 21, 24, 25, 26, 28, 29, 30, 31, 33, 34, 35, 36, 38, 39, 41, 44, 46, 47, 49, 50, 51, 54, 55, 56, 58, 59, 60, 63, 67, 68, 69, 71, 74, 75, 78, 80, 81, 82, 85, 86, 91, 92, 95, 97, 98, 101, 103, 104, 107, 109, 113, 114, 115, 118, 119, 120, 121, 122, 124, 126, 127, 129, 130, 131, 132, 133, 135, 136, 137, 138, 143, 145, 146, 147, 148, 149, 151, 152, 153, 154, 155, 157, 158, 159, 161, 164, 165, 167, 172, 175, 178, 179, 180, 182, 184, 185, 186, 190, 192, 193, 196, 197, 198, 199, 200, 202, 203, 206, 207, 209, 210, 215, 218, 221, 222, 228, 229, 230, 231, 232, 233, 234, 235, 237, 238, 239, 241, 242, 243, 244, 246, 247, 248, 253, 254, 255, 256.

The numbers above correspond to amino acid positions in the PciI protein sequence (SEQ ID NO:15).

The methods were the same as in the previous examples using inverse PCR followed by DpnI digestion. The treated product was then transformed into *E. coli* (pACYC-PciIM).

3. Selection of PciI-HF

Selection of PciI-HF was achieved using a method that was similar to the previous examples. The cleavage activity was determined using SalI-cut pBR322 with 5% glycerol in NEB4 and the star activity was determined using SalI-cut pBR322 in ExoI buffer with 39% glycerol. A double mutant PciI(E78A/S133A) had reduced star activity and strong cleavage activity. This mutant was not one of the targeted mutations described above, but was a fortuitous random event.

4. Comparison of PciI-HF and WT PciI

The FIs of PciI-HF and WT PciI were determined separately on pXba substrate with diluent A in each of NEB1-4 buffers. The comparison is shown in FIG. 27, and the result is listed in Table 26 (below).

TABLE 26

Comparison of PciI-HF and WT PciI

| | PciI-HF | | WT PciI | | |
|---|---|---|---|---|---|
| Buffer | Activity | Fidelity Index | Activity | Fidelity Index | Improvement Factor |
| NEB1 | NC | NC | 50% | 2000 | N/A |
| NEB2 | 100% | ≥2000 | 25% | 16 | ≥120 |
| NEB3 | 100% | ≥2000 | 100% | 120 | ≥16 |
| NEB4 | 100% | ≥1000 | 12.5% | 8 | ≥120 |

PciI-HF performed best in NEB2, NEB3 and NEB4, in which the preferred FI was ≥2000; WT PciI performed best in NEB3, in which the preferred FI was 120. The overall FI improvement factor was ≥2000/120=16.

Example 21: Engineering of High Fidelity HpaI

1. Expression of HpaI

HpaI was expressed in *E. coli* transformed with pACYC-MseIM and placzz1-HpaIR. placzz1 is a pUC19 derivative plasmid, pACYC is a low copy-compatible plasmid. The cells were grown at 37° C. overnight in LB with Amp and Cam.

2. Mutagenesis of HpaI 156 amino acid residues in HpaI were mutated with Cys, Asp, Glu, Phe, His, Lys, Met, Asn, Gln, Arg, Ser, and Thr. Trp was changed to Ala and Tyr to Phe. These were: 7, 8, 9, 13, 14, 16, 17, 19, 20, 21, 22, 23, 26, 27, 29, 30, 33, 34, 35, 36, 37, 38, 40, 41, 42, 46, 47, 48, 50, 51, 56, 57, 59, 60, 65, 67, 69, 71, 72, 74, 75, 78, 79, 80, 81, 82, 83, 84, 85, 86, 89, 91, 93, 94, 95, 99, 100, 104, 105, 106, 108, 109, 110, 113, 115, 117, 119, 121, 122, 123, 124, 127, 128, 130, 131, 133, 135, 136, 137, 138, 139, 141, 142, 146, 147, 149, 150, 152, 156, 158, 159, 160, 162, 164, 165, 166, 167, 168, 169, 170, 172, 173, 176, 177, 180, 181, 182, 184, 185, 187, 188, 190, 191, 192, 193, 195, 196, 197, 202, 204, 206, 208, 209, 211, 212, 214, 215, 216, 217, 218, 219, 220, 221, 222, 223, 224, 225, 228, 230, 231, 233, 234, 235, 236, 237, 238, 240, 241, 242, 243, 244, 245, 247, 248, 249.

The numbers above correspond to amino acid positions in the HpaI protein sequence (SEQ ID NO:86).

The methods were the same as in the previous examples using inverse PCR followed by DpnI digestion. The treated product was then transformed into *E. coli* (pACYC-MseIM).

3. Selection of HpaI-HF

Selection of HpaI-HF was achieved using a method that was different to the previous examples. The cleavage activity and star activity were determined using lambda DNA substrate in NEB2 buffer. This HpaI has much more star activity in NEB2 than NEB4, and could be clearly observed in 5% glycerol.

HpaI(Y29F) and HpaI(E56A) were both preferred mutations with reduced star activity. HpaI(E56A) was labelled HpaI-HF.

4. Comparison of HpaI-HF and WT HpaI

The FIs of HpaI-HF and WT HpaI were determined separately on lambda DNA substrate with diluent A in each of NEB1-4 buffers. The comparison is shown in FIG. 28, and the result is listed in Table 27 (below).

TABLE 27

Comparison of HpaI-HF and WT HpaI

| Buffer | HpaI-HF Activity | HpaI-HF Fidelity Index | WT HpaI Activity | WT HpaI Fidelity Index | Improvement Factor |
|---|---|---|---|---|---|
| NEB1 | 3.1% | ≥32 | 6.3% | 32 | ≥1 |
| NEB2 | 100% | ≥2000 | 25% | 1 | ≥2000 |
| NEB3 | 12.5% | 2 | 12.5% | 2 | 1 |
| NEB4 | 50% | ≥2000 | 100% | 16 | ≥120 |

HpaI-HF performed best in NEB2, in which the preferred FI was ≥2000; WT PciI performed best in NEB4, in which the preferred FI was 16. The overall FI improvement factor was ≥2000/16=120.

Example 22: Engineering of High Fidelity AgeI

1. Expression of AgeI

AgeI was expressed in *E. coli* transformed with pRRS-AgeIRM and psyx20-lacIq. pRRS is a pUC19 derivative plasmid, psyx20-lacIq is a low copy compatible plasmid with lac expressed under lacIq promoter. The cells were grown at 37° C. in LB with Amp and Kan to 200 Klett units, and then induced at 25° C. with 0.5 mM IPTG overnight. The expression of AgeI was extremely difficult to achieve because it was unstable.

2. Mutagenesis of AgeI 149 amino acid residues in AgeI were mutated with Cys, Asp, Glu, Phe, His, Lys, Met, Asn, Gln, Arg, Ser, and Thr. Trp was changed to Ala and Tyr to Phe. These were: 2, 4, 6, 7, 9, 14, 16, 18, 19, 21, 22, 23, 24, 25, 26, 27, 29, 30, 31, 32, 37, 38, 40, 42, 43, 44, 45, 49, 51, 53, 55, 56, 58, 60, 62, 64, 65, 67, 68, 69, 72, 73, 75, 77, 78, 79, 82, 83, 85, 86, 87, 88, 90, 91, 92, 94, 96, 97, 102, 103, 104, 105, 110, 111, 114,116, 119, 120, 122, 123, 128, 129, 130, 134, 135, 138, 139, 140, 142, 144, 146, 147, 148, 152, 153, 155, 157, 159, 166, 168, 170, 173, 174, 176, 177, 178, 182, 183, 185, 186, 188, 192, 195, 198, 200, 201, 206, 211, 212, 214, 217, 219, 220, 222, 223, 224, 225, 226, 227, 229, 231, 233, 234, 235, 237, 238, 239, 240, 241, 243, 245, 247, 248, 250, 251, 253, 255, 256, 258, 260, 262, 265, 266, 267, 268, 269, 271, 272 The methods were the same as in the previous examples using inverse PCR followed by DpnI digestion. The treated product was then transformed into *E. coli* (psyx20-lacIq).

The numbers above correspond to amino acid positions in the AgeI protein sequence (SEQ ID NO:79).

3. Selection of AgeI-HF

Selection of AgeI-HF was achieved using a method that was similar to the previous examples. The standard activity check used pXba with 5% glycerol in NEB4 and the star activity check was on pXba in NEB4 buffer with 39% glycerol. Because of the difficulty of the expression system, this selection was repeated eight times before meaningful mutants were obtained. Two mutants, S201A and R139A had reduced star activity and R139A was labelled AgeI-HF.

4. Comparison of AgeI-HF and WT AgeI

The FIs of AgeI-HF and WT AgeI were determined separately on pXba substrate with diluent A in each of NEB1-4 buffers. The comparison is shown in FIG. 29, and the result is listed in Table 28 (below).

TABLE 28

Comparison of AgeI-HF and WT AgeI

| Buffer | AgeI-HF Activity | AgeI-HF Fidelity Index | WT AgeI Activity | WT AgeI Fidelity Index | Improvement Factor |
|---|---|---|---|---|---|
| NEB1 | 100% | ≥500 | 100% | 16 | ≥32 |
| NEB2 | 50% | ≥250 | 50% | 8 | ≥32 |
| NEB3 | 6.3% | ≥16 | 12.5% | 64 | ≥0.25 |
| NEB4 | 100% | ≥250 | 50% | 8 | ≥32 |

AgeI-HF performed best in NEB1, and NEB4, in which the preferred FI was ≥500; WT AgeI performed best in NEB3, in which the preferred FI was 16. The overall FI improvement factor was ≥500/16=32.

Example 23: Engineering of High Fidelity BsmBI

1. Expression of BsmBI

BsmBI was expressed in *E. coli* transformed with pACYC-BsmAIM, ptaczz2-BsmBIR and psyx20-lacIq. Ptaczz2 is a pUC19 derivative plasmid which carries a inducible ptac promoter, pACYC is a low copy compatible plasmid. BsmAIM (GTCTC) covers BsmBI (CGTCTC) specificity. The psyx20-lacIq is a low copy vector with strong express of lacI. The cells were grown at 37° C. then induced in LB with Amp, Cam and Kan.

2. Mutagenesis of BsmBI 358 amino acid residues in BsmBI were mutated with Cys, Asp, Glu, Phe, His, Lys, Met, Asn, Gln, Arg, Ser, and Thr. Trp was changed to Ala and Tyr to Phe. These were: 8, 9, 12, 13, 14, 15, 17, 18, 19, 20, 21, 24, 25, 26, 27, 28, 29, 31, 33, 37, 38, 40, 42, 43, 44, 46, 47, 49, 50, 51, 52, 53, 54, 55, 56, 57, 58, 60, 61, 62, 63, 64, 65, 66, 67, 69, 70, 72, 76, 78, 79, 80, 81, 82, 83, 84, 88, 91, 93, 95, 96, 98, 99, 101, 103, 104, 105, 106, 109, 110, 111, 113, 114, 115, 117, 118, 119, 120, 121, 122, 124, 126, 127, 128, 130, 131, 132, 133, 134, 135, 138, 141, 143, 144, 145, 147, 149, 150, 154, 155, 157, 158, 160, 162, 163, 164, 165, 166, 167, 168, 169, 172, 174, 175, 176, 177, 179, 180, 181, 182, 184, 185, 186, 188, 189, 191, 194, 195, 197, 200, 201, 203, 205, 206, 207, 208, 211, 212, 213, 214, 215, 216, 217, 220, 221, 222, 223, 224, 225, 226, 228, 229, 230, 231, 232, 233, 235, 236, 237, 238, 239, 240, 242, 243, 247, 250, 251, 252, 257, 258, 260, 262, 263, 264, 265, 266, 268, 269, 271, 273, 274, 279, 280, 282, 283, 284, 287, 288, 289, 292, 294, 295, 296, 297, 299, 300, 301, 302, 303, 304, 305, 306, 307, 309, 310, 313, 314, 315, 316, 317, 318, 320, 321, 324, 325, 326, 328, 331, 332, 333, 334, 335, 336, 339, 340, 341, 342, 343, 344, 345, 348, 349, 351, 352, 353, 355, 356, 357, 358, 360, 361, 363, 364, 366, 367, 368, 370, 372, 375, 376, 377, 379, 381, 382, 384, 385, 386, 388, 389, 390, 393, 394, 395, 396, 398, 399, 400, 401, 402, 403, 404, 405, 406, 407, 408, 409, 410, 411, 412, 413, 414, 418, 421, 424, 425, 426, 428, 430, 431, 432, 433, 434, 436, 437, 438, 439, 442, 443, 444, 445, 446, 446, 448, 449, 450, 451, 452, 453, 454, 457, 458, 460, 461, 462, 464, 466, 467, 468, 470, 471, 472, 473, 474, 477, 478, 479, 480, 482, 483, 484, 485, 486, 487, 488, 489, 491, 492, 495, 496, 497, 498, 499, 500, 502, 503, 504, 505, 506, 507, 510, 511, 515, 516, 517, 518, 519, 522, 523.

The numbers above correspond to amino acid positions in the BsmBI protein sequence (SEQ ID NO:81).

The methods were the same as in the previous examples using inverse PCR followed by DpnI digestion. The treated product was then transformed into *E. coli* (pACYC-BsmAIM, psyx20-lacIq).

3. Selection of BsmBI-HF

Selection of BsmBI-HF was achieved using a method that was similar to the previous examples. The cleavage was determined using lambda DNA with 5% glycerol in NEB4 and the star activity was determined using Litmus28i in NEB4 buffer with 39% glycerol. Preferred mutants included H230A, D231A and N185Y/R232A. N185Y/R232A was labeled BsmBI-HF.

4. Comparison of BsmBI-HF and WT BsmBI

The FIs of BsmBI-HF and WT BsmBI were determined separately on lambda DNA substrate with diluent A in each of NEB1-4 buffers. The comparison is shown in FIG. 30, and the result is listed in Table 29 (below).

TABLE 29

Comparison of BsmBI-HF and WT BsmBI

| Buffer | BsmBI-HF Activity | BsmBI-HF Fidelity Index | WT BsmBI Activity | WT BsmBI Fidelity Index | Improvement Factor |
|---|---|---|---|---|---|
| NEB1 | 100% | 32 | 12.5% | 1 | 32 |
| NEB2 | 100% | ≥500 | 50% | 8 | ≥64 |
| NEB3 | 12.5% | ≥64 | 100% | 120 | ≥0.5 |
| NEB4 | 100% | ≥500 | 25% | 4 | ≥120 |

BsmBI-HF performed best in NEB1, NEB2 and NEB4, in which the preferred FI was ≥500; WT BsmBI performed best in NEB3, in which the preferred FI was 120. The overall FI improvement factor was ≥500/120=4.

Example 24: Engineering BspQI Variants with Reduced Star Activity

1. Site-Directed Mutagenesis of BspQI Restriction Endonuclease

*E. coli* was transformed with pSX33-EarIM1M2 and pZZlacI-PspQI that was $Km^R$ and $Amp^R$). M.EarI (CTCTTC) also modifies BspQI site (GCTCTTC) and therefore pSX33-earIM1M2 (FIGS. 17 and 18) was used to co-transform and modify the *E. coli* chromosome. The WT amino acid sequence is shown in FIG. 16.

122 charged or non-charged amino acid residues in BspQI (Arg, Lys, His, Glu, Asp, Gln, Asn, Cys) were changed to Ala by site-directed mutagenesis. PCR was carried out under the following conditions: DNA denaturation, 98° C. for 30 sec, 1 cycle; DNA denaturation/primer annealing/extension, 98° C. for 10 sec, 55° C. to 65° C. for 30 sec, 72° C. for 2 min, for PCR 18 cycles; 72° C. for 15 min, 1 cycle. In 100 µl reactions, 2 units of Phusion™ DNA polymerase (NEB, Ipswich, MA), 1 mM dNTP, 10 ng to 100 ng template DNA, 20 µl 5× reaction buffer, 0.04 µM primers, sterile water to 100 µl total volume.

PCR DNA was digested with DpnI to destroy template DNA (Dam methylated) and co-transformed with pSX33-earIMlM2 into *E. coli*. Individual transformants were cultured overnight (5 ml LB, 50 µg/ml $Km^R$ and 100 µg/ml $Amp^R$) and split into two parts. One part (1.5 ml) was harvested by centrifugation and lysed by sonication in a sonication buffer (20 mM Tris-HCl, pH 7.5, 0.1 mM DTT, 50 mM NaCl, 10% glycerol). The cell extract was heated at 50° C. for 1 h and denatured *E. coli* proteins were removed by centrifugation. The clarified lysate was assayed for restriction activity and star activity on pUC19 DNA.

BspQI star activity assay condition: 1 µg pUC19 DNA, 5 µl of 10×NEB buffer 1, 25% DMSO, 2.5 µl clarified cell extract, sterile deionized water to 50 µl total volume and incubated at 50° C. for 1 h. Digested DNA was resolved by electrophoresis in 0.8 to 1% agarose gel.

The second part of the cell culture (uninduced) was harvested and plasmid DNA was prepared by Qiagen spin column purification procedure (Qiagen, Valencia, CA). The bspQIR alleles were sequenced by Big-dye dideoxy-terminator sequencing method to confirm the desired mutations. After identification of reduced star activity mutants, fresh transformants were obtained and IPTG-induced cultures were made. Restriction and star activity was assayed again to confirm the reduced star activity in comparison with the WT enzyme in all four buffers.

Among the 122 BspQI mutants constructed by site-directed mutagenesis, two BspQI variants, R388A and K279A, display reduced star activity. The star activity of R388A was reduced approximately 16-fold in buffer 1 and 10% glycerol. However, R388A still displayed star activity at high enzyme concentration. BspQI variant K279A also displayed reduced star activity (>8-fold improvement in reduced star activity).

To further reduce star activity at high enzyme concentration, R388 and K279 were substituted for Phe, Pro, Tyr, Glu, Asp, or Leu. IPTG-induced cell extracts of various R388X, and K279X mutants were assayed for restriction and star activity. It was found that R388F or K279P displayed the minimal star activity in either cell extracts or purified enzyme. The specific activity was not affected by the amino acid substitutions.

To still further reduce BspQI star activity, the two amino acid substitutions were combined into one mutant enzyme (double mutant, K279P/R388F) by site-directed mutagenesis. This double mutant lacks star activity in buffer 1 and buffer 2 with 10% glycerol (FIG. 41B).

TABLE 30

BspQI-HF vs WT BspQI

| Buffer | BspQI-HF Activity | BspQI-HF Fidelity Index | WT BspQI Activity | WT BspQI Fidelity Index | Improvement Factor |
|---|---|---|---|---|---|
| NEB1 | 25% | ≥1000 | 12.5% | 2 | ≥1000 |
| NEB2 | 25% | ≥1000 | 100% | 16 | ≥64 |
| NEB3 | 1.3% | ≥64 | 100% | 32 | ≥2 |
| NEB4 | 100% | ≥4000 | 50% | 4 | ≥1000 |

Example 25: Engineering SapI Variants with Reduced Star Activity

The conserved K279 and R388 amino acid residues were found in BspQI where corresponding positions are K273 and R380 in SapI. A 6xHis tagged SapI expression clone was first constructed in pUC19. The SapI expression strain was *E. coli* transformed with pSX33-earIM1M2 and pUC-SapI that was $Km^R$ and $Amp^R$. Lys273 to Pro (K273P) and Arg 380 to Phe (R380F) amino acid substitutions were introduced into SapI by site-directed mutagenesis. SapI single mutant R380A was also constructed. Both SapI variants R380A and K273P/R380F showed reduced star activity when restriction activity and star activity reactions were performed (FIG. 42).

PCR, transformation, plasmid DNA preparation, and enzyme activity assay were carried out as described for BspQI, except that SapI activity was determined at 37° C. The 6×His-tagged SapI variant K273P/R380F was purified through Ni-NTA column chromatography and shown to display diminished star activity in the presence of 25% DMSO or 5% glycerol.

Example 26: Engineering KpnI High Fidelity Mutants

KpnI, which contains two activities, has been changed into a mutant with lower star activity (International Publication No. WO 07/027464). The example below describes novel mutants with improved star activity and similar cleavage activity to the wild-type.

Charged amino acid residues except the catalytic residues, (Asp, Glu, Arg, Lys and His) or polar amino acids (Ser, Thr, Tyr, Asn, Gln, Phe, Trp, Cys and Met) were individually mutated to Alanine.

Mutagenesis was carried out by inverse PCR using primers bearing the desired mutations. In general, inverse PCR was performed using 0.4 mM of each of the 4 dNTP, 1× ThermoPol Buffer (NEB), 20 ng of template DNA, 40 mol of each of the primers and 4 U of Vent DNA polymerase (NEB) in a final volume of 100 μL.

Plasmids pUC19 or pAGR3 containing the KpnIR under the control of Plac or Ptac promoter, respectively, were used as template. PCRs were done with a temperature scheme of 94° C. for 4 minutes followed by 25 cycles of 94° C. for 30 seconds for denaturation, 55° C. for seconds for annealing and 72° C. for 5 minutes for extension. The cycles were followed by incubation at 72° C. for 7 minutes before the reactions were treated by 20 U of DpnI (NEB) at 37° C. for 1 hour to degrade the template DNA. After inactivating DpnI at 80° C. for 20 minutes, 2 μl of the reaction was used to transform 50 μL of chemically competent NEB5alpha (NEB) pre-transformed by pSYX20-KpnIM. The transformed bacteria were plated out onto LB plates containing 100 μg/ml of ampicillin and 30 μg/ml of kanamycin, and incubated at 37° C. for 12 to 15 hours. Three to four colonies of each construct were cultured in 1 ml of LB containing 100 μg/ml of ampicillin and 30 g/ml of kanamycin at 37° C. for 12 to 15 hours with shaking of 200 rpm. The cultures were spun down and resuspended in 0.2 ml of sonication buffer (20 mM Tris-HCl, pH 8.3, 50 mM NaCl, 1 mM EDTA, 1 mM PMSF.) The resuspended cells were sonicated for 20 seconds, followed by centrifugation at 13,000 rpm at 4° C. for 5 min. Dilutions of the supernatant were made and 5 μL of which were assayed for KpnI cleavage activity.

For the screening of the mutants, an activity assay reaction was performed using 5 μL of 10- or 100-fold dilutions of the lysate supernatant, 0.5 ug of pXba DNA (NEB) and 1× NEBuffer 4 in a total volume of 50 μL. After incubating at 37° C. for 1 hour, the assay reactions were stopped by adding 10 μl of 6×DNA loading dye and analyzed by electrophoresis through 0.8% agarose gels in 1×TBE. Mutants that showed increased overall cleavage activity compared with the parent enzyme (KpnI D148E) were assayed for reduced star activity in a buffer containing 25% DMSO.

The assay was performed using 5 μL of dilutions of the enzymes incubated with 1 μg of pXba DNA (NEB) in the presence of 5% glycerol and 0.2 mg/ml of BSA in 1×NEBuffer 4 (total volume=50 μL). After incubation at 37° C. for 1 hour, the reactions were treated by 20 g of proteinase K (NEB) at 37° C. for 15 minutes and then analyzed by electrophoresis through 0.8% agarose gels in 1×TBE. Divalent metal-dependent assays were carried out at 37° C. for 1 hour, using 50 U of enzyme and 1 μg of pXba DNA in a buffer containing 20 mM Tris HCl, 50 mM NaCl, pH 7.9, 1 mM DTT and increasing concentration of MgSO4/CaCl2)/MnCl2, followed by electrophoresis through 0.8% agarose gels in 1×TBE. The total reaction volume is 50 μL.

The result of random mutagenesis, was a preferred mutant, KpnI D148E, which showed lower star activity than the wild-type enzyme and KpnI D1631/K165A mutant described previously (International Publication No. WO 07/027464). However, KpnI D148E displayed star activity at high enzyme concentration. Double and triple mutants were constructed in D148E background to reduce this observed star activity. KpnI (D16N/E132A/D148E) was found to have lower star activity and higher specificity activity than mutant D148E. Amino acid substitutions D148 to E and E132 to A were introduced by site-directed mutagenesis. The D16 to N mutation was introduced by PCR. In standard reaction condition, one-hour incubation of purified enzymes with substrate DNA pXba (containing 6 KpnI sites) at 37° C.), resulted in the reduced star activity shown in Table 31.

TABLE 31

Fidelity indices for KpnI mutants

| | KpnI-HF | | WT KpnI | | |
|---|---|---|---|---|---|
| Buffer | Activity | Fidelity Index | Activity | Fidelity Index | Improvement Factor |
| NEB1 | 100% | ≥4000 | 100% | 16 | ≥250 |
| NEB2 | 50% | ≥2000 | 25% | 16 | ≥64 |
| NEB3 | 6.3% | ≥250 | 6.3% | 8 | ≥32 |
| NEB4 | 100% | ≥4000 | 50% | 4 | ≥1000 |

No star activity of pXba was observed for mutant D16N/E132A/D148E up to 4000U. Star activity observed for pBR322 substrate, which bears no KpnI site, was also diminished when cleaved with KpnI D148E and D16N/E132A/D148E.

Example 27: Engineering of High Fidelity BsaI

1. Expression of BsaI

BsaI was expressed in *E. coli* transformed with pACYC-BsmAIM, pUC19-BsaIR and psyx20-lacIq. pACYC is a low copy compatible plasmid. BsmAIM(GTCTC) covers BsmBI specificity(CGTCTC). The psyx20-lacIq is a low copy vector with strong express of lacI. The cells were grown at 37° C. then induced in LB with Amp, Cam and Kan.

2. Mutagenesis of BsaI

The amino acid of BsaI is similar to that of BsmBI. 11 amino acids around and at the corresponding previous effective site is mutated as R229A, S230A, Y231F, T232A, T233A, D234A, R235A, R236A, F238A, E239A, Y240F.

The methods were the same as in the previous examples using inverse PCR followed by DpnI digestion. The treated product was then transformed into *E. coli* (pACYC-BsmAIM, psyx20-lacIq).

3. Selection of BsaI-HF

Selection of BsaI-HF was achieved using a method that was similar to the previous examples. The standard activity check used lambda DNA with 5% glycerol in NEB4 and the star activity check was litmus28i in NEB4 buffer with 39% glycerol. One mutant, Y231F, out of the 11 designed ones, reduced star activity and labeled as BsaI-HF.

4. Comparison of BsaI-HF and WT BsaI

The FIs of BsaI-HF and WT BsaI were determined separately on lambda DNA with diluent A in NEB1-4 buffers. The result is listed in Table 32 (below).

TABLE 32

| Comparison of BsaI-HF and WT BsaI | | | | | |
|---|---|---|---|---|---|
| | BsaI-HF | | WT BsaI | | |
| Buffer | Activity | Fidelity Index | Activity | Fidelity Index | Improvement Factor |
| NEB1 | 50% | ≥4000 | 25% | 8 | ≥500 |
| NEB2 | 100% | ≥8000 | 100% | 120 | ≥64 |
| NEB3 | 100% | 120 | 25% | 16 | 8 |
| NEB4 | 100% | ≥8000 | 100% | 32 | ≥250 |

BsaI-HF performed best in NEB2, NEB3 and NEB4, in which the best FI was ≥8000; WT BsaI performed best in NEB2 and NEB4, in which the best FI was 120. So the overall FI improvement factor was ≥8000/120=64.

What is claimed is:

1. A composition comprising a variant SbfI restriction endonuclease having reduced star activity, when compared to the wildtype enzyme, wherein the variant SbfI restriction endonuclease comprises an amino acid sequence that differs from the amino acid sequence of the parent SbfI restriction endonuclease by having a substitution at a position corresponding to 251 in SEQ ID NO: 96.

2. A composition according to claim 1, wherein the substitution corresponding to position 251 is K251A.

3. A composition comprising a variant Sbf1 restriction endonuclease, wherein the amino acid sequence of the variant Sbf1 restriction endonuclease is identical to the wild type Sbf1 restriction endonuclease except for an amino acid substitution at position 251 of the wild type Sbf1 restriction endonuclease.

4. The composition of claim 3, wherein the amino acid substitution is K251A.

* * * * *